United States Patent
Ichihara et al.

(10) Patent No.: US 9,005,681 B2
(45) Date of Patent: Apr. 14, 2015

(54) FOOD PRODUCT CONTAINING STARCH GEL, STARCH GRANULE, PRODUCTION METHOD AND USE THEREOF

(75) Inventors: Takashi Ichihara, Osaka (JP); Junya Fukuda, Osaka (JP); Masakazu Kimura, Osaka (JP); Kenichi Kurita, Osaka (JP)

(73) Assignee: Glico Nutrition Co., Ltd., Osaka (JP)

( * ) Notice: Subject to any disclaimer, the term of this patent is extended or adjusted under 35 U.S.C. 154(b) by 0 days.

(21) Appl. No.: 13/383,060

(22) PCT Filed: Aug. 11, 2010

(86) PCT No.: PCT/JP2010/005046
§ 371 (c)(1),
(2), (4) Date: Sep. 24, 2012

(87) PCT Pub. No.: WO2011/021372
PCT Pub. Date: Feb. 24, 2011

(65) Prior Publication Data
US 2013/0022711 A1 Jan. 24, 2013

(30) Foreign Application Priority Data
Aug. 18, 2009 (JP) ................................. 2009-189567

(51) Int. Cl.
| | | |
|---|---|---|
| A23L 1/0522 | (2006.01) | |
| A21D 2/18 | (2006.01) | |
| A23G 3/42 | (2006.01) | |
| A23G 9/34 | (2006.01) | |
| A23L 1/16 | (2006.01) | |
| A23L 1/31 | (2006.01) | |
| A23L 1/314 | (2006.01) | |
| A23L 1/317 | (2006.01) | |
| C12N 9/44 | (2006.01) | |
| A23L 1/00 | (2006.01) | |
| A23L 1/187 | (2006.01) | |
| A23L 1/212 | (2006.01) | |
| A23L 1/24 | (2006.01) | |
| A21D 8/04 | (2006.01) | |
| A23L 1/325 | (2006.01) | |

(52) U.S. Cl.
CPC *A21D 2/186* (2013.01); *A23G 3/42* (2013.01); *A23G 9/34* (2013.01); *A23L 1/0522* (2013.01); *A23L 1/16* (2013.01); *A23L 1/31* (2013.01); *A23L 1/31409* (2013.01); *A23L 1/31418* (2013.01); *A23L 1/317* (2013.01); *C12N 9/2451* (2013.01); *C12N 9/246* (2013.01); *C12Y 302/01033* (2013.01); *C12Y 302/01068* (2013.01); *A23L 1/3175* (2013.01); *A23L 1/005* (2013.01); *A23L 1/1875* (2013.01); *A23L 1/2128* (2013.01); *A23L 1/24* (2013.01); *A21D 8/042* (2013.01); *A23L 1/325* (2013.01); *A23L 1/05223* (2013.01)

(58) Field of Classification Search
CPC .............................. A23L 1/0522; A23L 1/095
USPC ............................................ 426/48, 578, 549
See application file for complete search history.

(56) References Cited

U.S. PATENT DOCUMENTS

| | | | |
|---|---|---|---|
| 5,445,950 A | 8/1995 | Kobayashi et al. | |
| 6,461,656 B1 * | 10/2002 | Bindzus et al. | ............... 426/242 |
| 2005/0204425 A1 | 9/2005 | Myers et al. | |
| 2007/0110847 A1 | 5/2007 | Okamoto et al. | |

FOREIGN PATENT DOCUMENTS

| | | | | |
|---|---|---|---|---|
| CN | 101028101 A | 9/2007 | | |
| JP | 59196072 | * 11/1984 | ............. | A23L 1/325 |
| JP | 1-159047 A | 6/1989 | | |
| JP | 5-112469 A | 5/1993 | | |
| JP | 06-269291 A | 9/1994 | | |
| JP | 11-255802 A | 9/1994 | | |
| JP | 7-063324 B | 7/1995 | | |
| JP | 8-277230 A | 10/1996 | | |
| JP | 10-215795 A | 8/1998 | | |
| JP | 11-192052 | 7/1999 | | |
| JP | 2001-103991 A | 4/2001 | | |
| JP | 3312225 | 8/2002 | | |
| JP | 2003-219813 A | 8/2003 | | |
| JP | 3723860 B2 | 12/2005 | | |
| JP | 2007-302767 A | 11/2007 | | |
| JP | 4170062 | 10/2008 | | |
| WO | 96/03513 A2 | 2/1996 | | |
| WO | 2005/096839 A1 | 10/2005 | | |
| WO | 2006/065579 A2 | 6/2006 | | |
| WO | 2008/059992 A1 | 5/2008 | | |

OTHER PUBLICATIONS

JP-59-196072-Official Translation.*
Protein Search—Result-1—ID AAB84206 (May 7, 2013).*
Protein Search—Result-1—ID AAY77741 (5-7-20130.*
Chinese Office Action for corresponding Chinese Application No. 201080036978.3 issued Jan. 15, 2013 and English translation.

(Continued)

*Primary Examiner* — Hamid R Badr
(74) *Attorney, Agent, or Firm* — Renner, Otto, Boisselle & Sklar, LLP

(57) ABSTRACT

Here is provided a method of producing a starch gel-containing food, the method comprising the steps of: treating starch granules with an enzyme at a temperature of about 10° C. or higher and about 70° C. or lower to obtain an enzyme-treated starch; mixing a food material, the enzyme-treated starch and water to obtain a mixture; heating the mixture thereby gelatinizing the enzyme-treated starch in the mixture; and cooling the mixture containing the gelatinized enzyme-treated starch thereby gelling the starch to obtain a starch gel-containing food, wherein the enzyme is selected from the group consisting of amyloglucosidase, isoamylase, α-glucosidase, α-amylase having a characteristic capable of improving a gel forming ability of a starch, and cyclodextrin glucanotransferase.

36 Claims, No Drawings

(56) References Cited

OTHER PUBLICATIONS

"Study on physic-chemical characteristics of potato gelatin starch", China Academic Journal Electronic Publishing House. vol. 23, No. 8 77, Dec. 31, 2002 and English translation.

International Search Report and Written Opinion for corresponding International Application No. PCT/JP2010/005046 mailed Nov. 30, 2010.

Form PCT/ISA/237 for corresponding International Application No. PCT/JP2010/005046 dated Nov. 30, 2010.

Japanese Office Action for corresponding Japanese Application No. 2011-508150 dated Apr. 20, 2011.

Fukai et al., "Koso Shori ni yoru Kakushu Denpunryu no Tokusei Kaihen (the 1st report) Characteristic Change of Rice Starch Granules by Enzymatic Treatment", Journal of starch and its related carbohydrates and enzymes, 1993, vol. 40, No. 3, pp. 263-269.

Fukai et al., "Changes in Three Kinds of Starch Granules after Enzymatic Treatment, part II", Journal of the Agricultural Chemical Society of Japan, 1994, vol. 68, No. 4, p. 793-800.

Absar et al., Enzymatic hydrolysis of potato starches containing different amounts of phosphorus, Food Chem., Jan. 1, 2009, Vo. 112, No. 1, p. 57-62.

Karim et al., "Dual Modification of Starch via Partial Enzymatic Hydrolysis in the Granular State and Subsequent Hydroxypropylation", J. Agric Food Chem, 2008, Vo. 56, No. 22, p. 10901-10907.

Machida et al, "Genome sequencing and analysis of *Aspergillus oryzae*", Nature (Lond), 2005, vol. 438, No. 7071, p. 1157-1161.

Nunberg et al., Molecular cloning and characterization of the glucoamylase gene of *Aspergillus awamori*, Mol Cell Biol. 1984, vol. 4, No. 11, p. 2306-15.

Krohn et al., "An isoamylase with neutral pH optimum from a *Flavobacterium* species: cloning, characterization and expression of the *iam* gene", Mol Gen Genet, 1997, vol. 254, No. 5, p. 469-478.

Pel et al., "Genome sequencing and analysis of the versatile cell factory *Aspergillus niger* CBS 513.88", Nat Biotechnol, 2007, vol. 25, No. 2, p. 221-231.

Japanese Office Action for corresponding Japanese Application No. 2011-508150 dated Apr. 20, 2011 (English translation provided herewith).

Chinese Office Action for corresponding Chinese Application No. 201080036978.3 issued Oct. 11, 2013 and English translation.

Chinese Office Action for corresponding Chinese Application No. 201080036978.3 issued Jul. 2, 2014 and English translation.

Chinese Office Action for corresponding Chinese Application No. 201080036978.3 issued Jan. 4, 2015 and partial English translation.

\* cited by examiner

FOOD PRODUCT CONTAINING STARCH GEL, STARCH GRANULE, PRODUCTION METHOD AND USE THEREOF

TECHNICAL FIELD

The present invention relates to a starch gel-containing food, a starch having a high viscosity and a gel forming ability, a food containing the starch, and a method of producing thereof. More particularly, the present invention relates to a method of producing a starch gel-containing food using an enzyme capable of improving a gel forming ability of a starch.

BACKGROUND ART

With diversification of foods, foods having various shapes, physical properties and textures have been required. Particularly, intense interest has recently been shown towards melt in mouth and texture as important physical properties for the purpose of designing foods. Also in the fields related to deglutition and care toward which intense interest has recently been shown, texture has been studied as important physical properties.

In the case of designing processed foods, utilization of a gelling agent is important so as to improve texture and physical properties, and it is possible to develop various products according to how to use.

For the purpose of altering physical properties of foods, various gelling agents have hitherto been added to food materials in the case of preparing foods.

In food processing, natural macromolecules such as agar, gelatin, gellan gum, xanthan gum, locust bean gum, carrageenan, pectin, sodium alginate, Tamarind seed gum, psyllium seed gum, microcrystalline cellulose, curdlan, and starch; or synthetic macromolecules such as carboxymethyl cellulose (CMC) or methyl cellulose are commonly used as gelling agents.

In the case of using these gelling agents, gelling agents may be sometimes used alone, however, in order to form gels having more various characteristics, for example, use of two or more kinds of gelling agents such as native gellan gum and guar gum in combination is studied and utilized (Patent Document 1).

However, there are few combinations which can synergistically change the gel strength of foods. Even if it is possible to synergistically change the gel strength, the gel obtained thereby does not have nice physical properties. Mixing of two or more kinds of gelling agents is a defect due to being complicated and that many materials are very expensive.

Furthermore, there is such a restriction on use in food processing that, for example, a gelatin is inferior in resistance to an acid and an alkali, and also an agar is inferior in resistance to an acid.

Starches have successfully produced various physical properties by adding not only raw starches but also a processed starch obtained by chemically modifying starches (also referred to as a chemically modified starch) such as starch acetate and monostarch phosphate as a gelling agent to food materials. For example, Patent Documents 2, 3 and 4 indicate examples in which a crosslinked starch is utilized in a white table bread, confectioneries or noodles. However, in the case where a crosslinked starch having a high crosslinking degree is added to a food, the hardness and the viscosity of a gel can be enhanced, but there is such a drawback that a final product has powdery texture and also is inferior in flavor. Also, in the case where a starch having a low crosslinking degree is added to a food, since a large amount of the starch needs to be used so as to obtain the desired hardness, the obtained food has increased powdery texture, thus causing deterioration of quality of a final product. Therefore, there is a limit on the use amount of the starch having a low crosslinking degree. In addition, processing of the starch utilizing a chemical reaction also has such problems that there is a strict legal restriction on a processing method and a processing degree so as to secure safety, and that it is not necessarily suited to needs of consumers who require security and safety.

For the purpose of deigning these processed foods, it is urgently necessary to develop a processing technique to obtain a processed starch which exhibits various physical properties and has high safety.

As a result of intensive studies, we have found that a food with rich elasticity, crispy sensation and the like can be prepared by adopting the steps of treating starch granules with a starch hydrolase or a glycosyltransferase in advance; then mixing the resultant with a food material and water; and heating the mixture.

A starch is a material utilized for various purposes and the most important function thereof is the thickening function and the gel forming function. Particularly in the food industry, the thickening function and the gel forming function of the starch are widely utilized for forming the shape, physical properties and texture of a food. The structure of a starch delicately varies depending on plant from which the starch derived (for example, corn, potato, wheat, and cassava). As a result, the thickening function and gel forming function also vary depending on the plant from which the starch derived. Therefore, those skilled in the art have been selected a native starch to be used for a long time depending on the purpose. For example, a wheat starch has often been used in a fish paste product for a long time. The reason is that the wheat starch is excellent in gel forming function. For example, a cassava starch is commonly utilized in a food which has high transparency and requires sticky texture. However, with the advancement of characteristics required in the current food industry, it becomes impossible to cope with the advancement only by changing a native starch to be used. Therefore, there arises the need to alter the thickening function or the gel forming function of a starch.

Means which are used most commonly to alter the thickening function or the gel forming function of a starch is a chemical modification of a starch. Above all, techniques of applying a chemical treatment, such as a technique of introducing a new crosslinking point between starch molecules using a suitable chemical crosslinking agent and a technique of introducing a suitable functional group have widely been utilized so as to remarkably alter the thickening function or the gel forming function. However, a starch subjected to such a chemical treatment has been specified as a food additive from October, 2008 in Japan, and thus restricted by law. Therefore, there has been required a technique in which the thickening function or the gel forming function of a starch is altered without a chemical treatment.

The technique of altering a starch without a chemical treatment includes a technique of an enzymatic treatment of a starch. Since an enzyme commonly acts on a substrate dissolved in water, an enzymatic treatment is usually carried out after completely dissolving a starch in water. A hydrolytic enzyme or a glycosyltransferase is allowed to act on a starch dissolved in water to cleave the starch, thereby producing molecules having a lower molecular weight such as dextrin, starch syrup, maltooligosaccharide, maltose, and glucose. However, in the enzymatic treatment with a hydrolytic enzyme or a glycosyltransferase, a starch molecule is cleaved to form low-molecular weight molecules. Therefore, it has been commonly considered that the thickening function and the gel forming function of the obtained molecule deteriorate as compared with the thickening function and the gel forming function of the starch, or are lost.

Also, Patent Document 5 discloses, as a method of altering physical properties of a starch, a technique in which an enzyme is allowed to act on a starch in the form of starch granules in water without dissolving them in water. Patent Document 5 discloses that although a starch has conventionally been dissolved in water before an enzymatic treatment in the case of subjecting the starch to the enzymatic treatment, it is not necessarily required to dissolve the starch in water before the enzymatic treatment, and it is possible to subject starch granules, which are not dissolved in water but suspended in water, to the enzymatic treatment. Specifically, it is disclosed that a hydrolytic enzyme such as α-amylase or glucoamylase can act on starch granules, which are not dissolved in water but suspended in water, and thus a reducing sugar can be produced. Patent Document 5 also discloses as a result of this that the viscosity of the starch subjected to the enzymatic treatment is lower than that of the starch which is not subjected to the enzymatic treatment. However, Patent Document 5 neither suggests nor discloses that a starch having improved thickening function or gel forming function as compared with the starch, which is not subjected to the enzymatic treatment, is obtained by allowing a hydrolytic enzyme or a glycosyltransferase to act on starch granules.

Patent Documents 6 to 10 also disclose a technique of allowing a hydrolytic enzyme to act on insoluble starch granules. These inventions disclose a technique in which the action of a hydrolytic enzyme on starch granules opens pores on the surfaces of starch granules to make porous starch granules, and the porous starch granules are utilized as a powdered base material or a porous carrier. However, Patent Documents 6 to 10 neither suggests nor discloses that a starch having improved thickening function and gel forming function is obtained by allowing a hydrolytic enzyme or a glycosyltransferase to act on starch granules. An object of the present invention is not to open pores on the surfaces of enzyme-treated starch granules, and there is not any relationship between an improvement in thickening function and gel forming function, and whether or not pores are opened on the surfaces of enzyme-treated starch granules. If a heated food is produced using the enzyme-treated starch of the present invention, the enzyme-treated starch forms a hard gel in the heated food. The enzyme-treated starch of the present invention is usable in the heated food. On the other hand, in the prior art, it is important that pores are present on the surfaces of starch granules. If starch granules after subjected to the enzymatic treatment and water are mixed and then heated, starch granules are collapsed and pore-opened states thereof are lost. Therefore, those skilled in the art did not consider to use a pore-opened starch of the prior art in the heated food. In the present invention, it is possible to adjust the hardness of a gel to be formed using an enzyme-treated starch by adjusting the degree of the enzymatic treatment. The hardness of the gel exerts an influence on texture, chewiness, and the like of the food. Therefore, use of the method of the present invention can exert an influence on texture of the food. As described above, the enzyme-treated starch granules of the prior art and the enzyme-treated starch granules used in the present application quite differ in application and usage.

As described above, it was conventionally impossible to provide a starch excellent in thickening function or gel forming function without utilizing a chemical modification of a starch.

Also, in the prior art, no attention was paid at all whether or not an enzyme has characteristics capable of improving a gel forming ability of a starch. It was not also found at all whether or not industrial advantages are exerted by characteristics of an enzyme capable of improving a gel forming ability of a starch.

PRIOR ART DOCUMENTS

Patent Documents

Patent Document 1: Japanese Laid-open Patent Publication No. 10-215795
Patent Document 2: Japanese Patent Gazette No. 3,723,860
Patent Document 3: Japanese Patent Gazette No. 3,312,225
Patent Document 4: Japanese Patent Publication for Opposition No. 7-63324
Patent Document 5: Japanese Laid-open Patent Publication No. 6-269291
Patent Document 6: Japanese Laid-open Patent Publication No. 2003-219813
Patent Document 7: Japanese Patent Gazette No. 4,170,062
Patent Document 8: Japanese Laid-open Patent Publication No. 1-159047
Patent Document 9: Japanese Laid-open Patent Publication No. 5-112469
Patent Document 10: Japanese Laid-open Patent Publication No. 8-277230

SUMMARY OF THE INVENTION

Problems to be Solved by the Invention

The present invention is intended to solve the above problems, and it is an object of the invention to provide a food containing a starch gel having the desired degree of hardness and a method of producing the same. In a specific embodiment of the present invention, objects are to provide a starch excellent in thickening function or gel forming function without utilizing a chemical modification of a starch; a food containing the starch; and a method of producing the starch and food.

Means for Solving the Problems

The present inventors have intensively studied so as to solve the above problems and have found that a starch excellent in thickening function and gel forming function is obtained by allowing a specific hydrolytic enzyme or glycosyltransferase having characteristics capable of improving a gel forming ability of a starch to act on starch granules under the condition where a starch is not dissolved, and thus have completed the present invention based on this finding. It is commonly considered that when a hydrolytic enzyme or a glycosyltransferase is allowed to act on a starch, the starch is cleaved to form smaller molecules, and therefore the viscosity and the gel forming ability of the obtained molecules deteriorate as compared with the viscosity and gel forming ability of the starch before being subjected to the enzymatic treatment, or are lost. Actually, when the same hydrolytic enzyme or glycosyltransferase as the hydrolytic enzyme or glycosyltransferase capable of producing such an excellent starch when being allowed to act on starch granules under the condition where a starch is not dissolved in water is allowed to act on a starch after dissolving the starch in water, the starch viscosity decreases, and thus a starch excellent in thickening function or gel forming function cannot be obtained. As described above, the present invention cannot be conceived from the conventionally general knowledge and technical common sense possessed by those skilled in the art.

The conditions of an enzymatic treatment of starch granules can vary depending on the specificity of the enzyme and the origin of starch granules. For example, first, starch granules are suspended in ion-exchange water or a buffer solution to prepare a starch suspension. In the case where the pH adjustment of the starch suspension is required, the pH is adjusted to the optimum pH of the enzyme. While warming this starch suspension at the temperature at which starch granules are not degraded (preferably from about 10° C. to about 70° C.), the enzyme is added and the reaction can be carried out, for example, within about 24 hours (preferably from about for 1 hour to about 20 hours). Then, the enzyme and a carbohydrate eluted by enzymatic hydrolysis are removed by the washing and dehydration steps which are a conventional method of preparing a starch, followed by the drying step, and thus the objective enzyme-treated starch granules can be obtained.

The present invention is, for example, as follows:

(Item 1) A method of producing a starch gel-containing food, the method comprising the steps of:

treating starch granules with an enzyme at a temperature of about 10° C. or higher and about 70° C. or lower to obtain an enzyme-treated starch;

mixing a food material, the enzyme-treated starch and water to obtain a mixture;

heating the mixture thereby gelatinizing the enzyme-treated starch in the mixture; and cooling the mixture containing the gelatinized enzyme-treated starch thereby gelling the starch to obtain a starch gel-containing food, wherein the enzyme is selected from the group consisting of amyloglucosidase, isoamylase, α-glucosidase, α-amylase having a characteristic capable of improving a gel forming ability of a starch, and cyclodextrin glucanotransferase.

(Item 2) The method according to Item 1, wherein the enzyme is selected from the group consisting of amyloglucosidase, isoamylase, α-glucosidase, α-amylase derived from the genus *Aspergillus*, and cyclodextrin glucanotransferase.

(Item 3) The method according to Item 1, wherein the enzyme is selected from the group consisting of amyloglucosidase, isoamylase, α-glucosidase, α-amylase derived from *Aspergillus oryzae*, α-amylase derived from *Aspergillus niger*, and cyclodextrin glucanotransferase.

(Item 4) The method according to Item 1, wherein the enzyme is selected from the group consisting of amyloglucosidase derived from *Aspergillus niger* commercially available from Novozyme as AMG, amyloglucosidase derived from *Aspergillus niger* commercially available from Genencor as OPTIDEX L-400, amyloglucosidase derived from *Aspergillus niger* commercially available from DANISCO as DIAZYME X4NP, amyloglucosidase derived from *Aspergillus niger* commercially available from Amano Enzyme as glucoamylase "Amano" SD, amyloglucosidase derived from *Rhizopus niveus* commercially available from Amano Enzyme as Gluczyme AF6, amyloglucosidase derived from *Rhizopus oryzae* commercially available from SHIN NIHON CHEMICALS Corporation as Sumizyme, α-glucosidase derived from *Aspergillus niger* commercially available from Amano Enzyme as transglucosidase L "Amano", α-glucosidase derived from *Aspergillus niger* commercially available from Genencor as Transglucosidase L-500, α-amylase derived from *Aspergillus oryzae* commercially available from Amano Enzyme as Biozyme A, α-amylase derived from *Aspergillus oryzae* commercially available from SHIN NIHON CHEMICALS Corporation as Sumizyme L, α-amylase derived from *Aspergillus niger* commercially available from Danisco as AMYLEX A3, α-amylase derived from *Aspergillus niger* commercially available from SHIN NIHON CHEMICALS Corporation as Sumizyme AS, isoamylase derived from *Pseudomonas amyloderamosa* commercially available from Sigma as isoamylase, cyclodextrin glucanotransferase derived from *Bacillus licheniformis* commercially available from Novozyme as Toruzyme, and cyclodextrin glucanotransferase derived from *Paenibacillus macerans* (*Bacillus macerans*) commercially available from Amano Enzyme as Cyclodextrin glucanotransferase "Amano".

(Item 5) The method according to Item 1, wherein:
(1) the enzyme is encoded by a nucleic acid molecule which is capable of hybridizing under stringent conditions with a nucleic acid molecule consisting of a base sequence complementary to a base sequence of SEQ ID NO: 1, 3, 5, 7, 9 or 11, and has a starch hydrolysis activity; or
(2) the enzyme is encoded by a nucleic acid molecule which is capable of hybridizing under stringent conditions with a nucleic acid molecule consisting of a base sequence complementary to a base sequence of SEQ ID NO: 13, and has a transglycosylation activity; wherein the stringent conditions are hybridization in a solution containing 50% formamide, 5×SSC (750 mM NaCl, 75 mM trisodium citrate), 50 mM sodium phosphate (pH 7.6), 5×Denhardt's solution (0.2% BSA, 0.2% Ficoll 400 and 0.2% polyvinylpyrrolidone), 10% dextran sulfate and 20 µg/ml denatured sheared salmon sperm DNA at 65° C., and subsequent washing under the condition of 65° C. using an SSC solution having a 0.1 to 2-fold concentration (a composition of an SSC solution having a 1-fold concentration is 150 mM sodium chloride and 15 mM sodium citrate).

(Item 6) The method according to Item 1, wherein:
(1) the enzyme has an amino acid sequence having at least 95% or more of homology with an amino acid sequence of SEQ ID NO: 2, 4, 6, 8, 10 or 12, and has a starch hydrolysis activity; or
(2) the enzyme has an amino acid sequence having at least 95% or more of homology with an amino acid sequence of SEQ ID NO: 14, and has a transglycosylation activity.

(Item 7) The method according to Item 1, wherein the starch granules are starch granules of an untreated starch, a physically treated starch or a chemically modified starch.

(Item 8) The method according to Item 1, wherein the starch granules are starch granules of an untreated starch, and the starch granules have been neither chemically modified nor physically treated in any stage until the starch gel-containing food is obtained by the method.

(Item 9) The method according to Item 1, wherein the starch granules are starch granules of an untreated starch or a physically treated starch, the method further comprises the step of chemically modifying the enzyme-treated starch, and the chemically modified enzyme-treated starch is mixed with the food material and water.

(Item 10) The method according to Item 1, wherein the starch granules are starch granules of an untreated starch or a chemically modified starch, the method further comprises the step of physically treating the enzyme-treated starch, and the physically treated enzyme-treated starch is mixed with the food material and water.

(Item 11) A starch gel-containing food produced by the method according to Item 1.

(Item 12) The food according to Item 11, wherein the food is a high moisture content type food and the amount of moisture of the food is more than 40 g and less than 95 g per 100 g of the edible portion.

(Item 13) The food according to Item 11, wherein the food is selected from the group consisting of traditional Japanese-style confectioneries, fat- or oil-containing foods, gelatinous foods, fish meat and animal meat processed foods, salsa and sauces, and noodles.

(Item 14) The food according to Item 11, wherein the food is a low moisture content type food and the amount of moisture of the food is 1 g or more and 40 g or less per 100 g of the edible portion.

(Item 15) The food according to Item 11, wherein the food is selected from the group consisting of bakeries, Western-style confectioneries, and fried foods.

(Item 16) The food according to Item 11, wherein the enzyme is selected from the group consisting of amyloglucosidase, isoamylase, α-glucosidase, α-amylase derived from the genus *Aspergillus*, and cyclodextrin glucanotransferase.

(Item 17) The food according to Item 11, wherein the enzyme is selected from the group consisting of amyloglucosidase, isoamylase, α-glucosidase, α-amylase derived from *Aspergillus oryzae*, α-amylase derived from *Aspergillus niger*, and cyclodextrin glucanotransferase.

(Item 18) The food according to Item 11, wherein the starch is derived from cassava, corn or wheat.

In a specific embodiment, the present invention is, for example, as follows:

(Item 1A) A heat-cooked starch-containing food containing an enzyme-treated starch having high viscosity and gel-forming ability, the starch-containing food is a food produced by a method comprising the steps of mixing a food material and the enzyme-treated starch and then heating them, the enzyme-treated starch is a starch obtained by treating starch granules of untreated starch with a starch hydrolase under the condition where the starch granules are not dissolved, the enzyme-treated starch is not modified on hydroxyl groups at the positions 2, 3 and 6 of the glucose residues, the enzyme-treated starch can form a gel having a Young's modulus higher than that of the untreated starch or a rupture stress higher than that of the untreated starch, when measured by a rheometer.

(Item 2A) The food according to Item 1A, wherein the untreated starch is a untreated wheat starch, the enzyme-treated starch is a enzyme-treated wheat starch, and the enzyme-treated wheat starch is capable of forming a gel having a Young's modulus which accounts for 110% or more and 500% or less (110% or more and 330% or less in an embodiment) of the Young's modulus of the untreated wheat starch, or a rupture stress which accounts for 110% or more and 300% or less of the rupture stress of the untreated wheat starch, when measured by a rheometer.

(Item 3A) The food according to Item 1A, wherein the untreated starch is a untreated cassava starch, the enzyme-treated starch is a enzyme-treated cassava starch, and the enzyme-treated cassava starch is capable of forming a gel having a Young's modulus which accounts for 110% or more and 500% or less (110% or more and 330% or less in an embodiment) of the Young's modulus of the untreated cassava starch, or a rupture stress which accounts for 110% or more and 300% or less of the rupture stress of the untreated cassava starch, when measured by a rheometer.

(Item 4A) The food according to Item 1A, wherein the untreated starch is a untreated corn starch, the enzyme-treated starch is a enzyme-treated corn starch, and the enzyme-treated corn starch is capable of forming a gel having a Young's modulus which accounts for 110% or more and 500% or less (110% or more and 330% or less in an embodiment) of the Young's modulus of the untreated corn starch, or a rupture stress which accounts for 110% or more and 300% or less of the rupture stress of the untreated corn starch, when measured by a rheometer.

(Item 5A) A heat-cooked starch-containing food containing an enzyme-treated wheat starch having high viscosity and gel-forming ability, the starch-containing food is a food produced by a method comprising the steps of mixing a food material and the enzyme-treated wheat starch and then heating them, the enzyme-treated wheat starch is a starch obtained by treating starch granules of untreated wheat starch with a starch hydrolase under the condition where the starch granules are not dissolved, the enzyme-treated wheat starch is not modified on hydroxyl groups at the positions 2, 3 and 6 of the glucose residues, the enzyme-treated wheat starch can form a gel having a Young's modulus of $5.0 \times 10^6$ dyn/cm$^2$ or more and $8.0 \times 10^6$ dyn/cm$^2$ or less, or a rupture stress of 150 g or more and 450 g or less, when measured by a rheometer.

(Item 6A) A heat-cooked starch-containing food containing an enzyme-treated cassava starch having high viscosity and gel-forming ability, the starch-containing food is a food produced by a method comprising the steps of mixing a food material and the enzyme-treated cassava starch and then heating them, the enzyme-treated cassava starch is a starch obtained by treating starch granules of untreated cassava starch with an starch hydrolase under the condition where the starch granules are not dissolved, the enzyme-treated cassava starch is not modified on hydroxyl groups at the positions 2, 3 and 6 of the glucose residues, the enzyme-treated cassava starch can form a gel having a Young's modulus of $5.2 \times 10^5$ dyn/cm$^2$ or more and $2.7 \times 10^6$ dyn/cm$^2$ or less ($5.2 \times 10^5$ dyn/cm$^2$ or more and $1.6 \times 10^6$ dyn/cm$^2$ or less in one embodiment), or a rupture stress of 55 g or more and 150 g or less, when measured by a rheometer.

(Item 7A) A heat-cooked starch-containing food containing an enzyme-treated corn starch having high viscosity and gel-forming ability, the starch-containing food is a food produced by a method comprising the steps of mixing a food material and the enzyme-treated corn starch and then heating them, the enzyme-treated corn starch is a starch obtained by treating starch granules of untreated corn starch with an starch hydrolase under the condition where the starch granules are not dissolved, the enzyme-treated corn starch is not modified on hydroxyl groups at the positions 2, 3 and 6 of the glucose residues, the enzyme-treated corn starch can form a gel having a Young's modulus of $6.0 \times 10^6$ dyn/cm$^2$ or more and $9.0 \times 10^6$ dyn/cm$^2$ or less, or a rupture stress of 210 g or more and 450 g or less (220 g or more and 450 g or less in one embodiment), when measured by a rheometer.

(Item 8A) The food according to any one of Items 1A to 7A, wherein the starch is forming a gel in the food.

(Item 9A) The food according to any one of Items 1A to 8A, wherein the food is a high moisture content type food and the amount of moisture of the food is more than 40 g and less than 95 g per 100 g of the edible portion.

(Item 10A) The food according to any one of Items 1A to 9A, wherein the food is selected from the group consisting of traditional Japanese-style confectioneries, fat- or oil-containing foods, gelatinous foods, fish meat and animal meat processed foods, salsa and sauces, and noodles.

(Item 11A) The food according to any one of Items 1A to 8A, wherein the food is a low moisture content type food and the amount of moisture of the food is 1 g or more and 40 g or less per 100 g of the edible portion.

(Item 12A) The food according to any one of Items 1A to 8A and 11A, wherein the food is selected from the group consisting of bakeries, Western-style confectioneries, and fried foods.

(Item 13A) The food according to any one of Items 1A to 12A, wherein the starch hydrolase is selected from the group consisting of amyloglucosidase, isoamylase, α-glucosidase, and α-amylase having characteristics capable of improving a gel-forming ability of a starch.

(Item 14A) The food according to Item 13A, wherein the starch hydrolase is selected from the group consisting of amyloglucosidase, isoamylase, α-glucosidase, and α-amylase derived from the genus *Aspergillus*.

(Item 15A) The food according to Item 13A, wherein the starch hydrolase is selected from the group consisting of amyloglucosidase, isoamylase, α-glucosidase, α-amylase derived from *Aspergillus oryzae*, and α-amylase derived from *Aspergillus niger*.

(Item 16A) A method of producing a starch-containing food, the method comprising the steps of:
adding and mixing an enzyme-treated starch to a food material; and
heat-cooking the mixture;
the enzyme-treated starch is a starch obtained by treating starch granules of untreated starch with a starch hydrolase under the condition where the starch granules are not dissolved;
the enzyme-treated starch is not modified on hydroxyl groups at the positions 2, 3 and 6 of the glucose residues,
the enzyme-treated starch can form a gel having a Young's modulus higher than that of the untreated starch or a rupture stress higher than that of the untreated starch, when measured by a rheometer.

(Item 17A) An enzyme-treated starch having high viscosity and gel-forming ability,
the enzyme-treated starch is a starch obtained by treating starch granules of untreated starch with an starch hydrolase under the condition where the starch granules are not dissolved,
the enzyme-treated starch is not modified on hydroxyl groups at the positions 2, 3 and 6 of the glucose residues,
the enzyme-treated starch can form a gel having a Young's modulus higher than that of the untreated starch or a rupture stress higher than that of the untreated starch, when measured by a rheometer.

(Item 18A) The starch according to Item 17A, wherein the untreated starch is a untreated wheat starch, the enzyme-treated starch is a enzyme-treated wheat starch, and
the enzyme-treated wheat starch is capable of forming a gel having a Young's modulus which accounts for 110% or more and 500% or less (110% or more and 330% or less in an embodiment) of the Young's modulus of the untreated wheat starch, or a rupture stress which accounts for 110% or more and 300% or less of the rupture stress of the untreated wheat starch, when measured by a rheometer.

(Item 19A) The starch according to Item 17A, wherein the untreated starch is a untreated cassava starch, the enzyme-treated starch is a enzyme-treated cassava starch, and
the enzyme-treated cassava starch is capable of forming a gel having a Young's modulus which accounts for 110% or more and 500% or less (110% or more and 330% or less in an embodiment) of the Young's modulus of the untreated cassava starch, or a rupture stress which accounts for 110% or more and 300% or less of the rupture stress of the untreated cassava starch, when measured by a rheometer.

(Item 20A) The starch according to Item 17A, wherein the untreated starch is a untreated corn starch, the enzyme-treated starch is a enzyme-treated corn starch, and
the enzyme-treated corn starch is capable of forming a gel having a Young's modulus which accounts for 110% or more and 500% or less (110% or more and 330% or less in an embodiment) of the Young's modulus of the untreated corn starch, or a rupture stress which accounts for 110% or more and 300% or less of the rupture stress of the untreated corn starch, when measured by a rheometer.

(Item 21A) An enzyme-treated wheat starch having high viscosity and gel-forming ability,
the enzyme-treated wheat starch is a starch obtained by treating starch granules of untreated wheat starch with an starch hydrolase under the condition where the starch granules are not dissolved,
the enzyme-treated wheat starch is not modified on hydroxyl groups at the positions 2, 3 and 6 of the glucose residues,
the enzyme-treated wheat starch can form a gel having a Young's modulus of $5.0 \times 10^6$ dyn/cm$^2$ or more and $8.0 \times 10^6$ dyn/cm$^2$ or less, or a rupture stress of 150 g or more and 450 g or less, when measured by a rheometer.

(Item 22A) An enzyme-treated cassava starch having high viscosity and gel-forming ability,
the enzyme-treated cassava starch is a starch obtained by treating starch granules of untreated cassava starch with an starch hydrolase under the condition where the starch granules are not dissolved,
the enzyme-treated cassava starch is not modified on hydroxyl groups at the positions 2, 3 and 6 of the glucose residues,
the enzyme-treated cassava starch can form a gel having a Young's modulus of $5.2 \times 10^5$ dyn/cm$^2$ or more and $2.7 \times 10^6$ dyn/cm$^2$ or less ($5.2 \times 10^5$ dyn/cm$^2$ or more and $1.6 \times 10^6$ dyn/cm$^2$ or less in one embodiment), or a rupture stress of 55 g or more and 150 g or less, when measured by a rheometer.

(Item 23A) An enzyme-treated corn starch having high viscosity and gel-forming ability,
the enzyme-treated corn starch is a starch obtained by treating starch granules of untreated corn starch with an starch hydrolase under the condition where the starch granules are not dissolved,
the enzyme-treated corn starch is not modified on hydroxyl groups at the positions 2, 3 and 6 of the glucose residues,
the enzyme-treated corn starch can form a gel having a Young's modulus of $6.0 \times 10^6$ dyn/cm$^2$ or more and $9.0 \times 10^6$ dyn/cm$^2$ or less, or a rupture stress of 210 g or more and 450 g or less (220 g or more and 450 g or less in one embodiment), when measured by a rheometer.

(Item 24A) The starch according to any one of Items 18A to 23A, wherein the starch hydrolase is selected from the group consisting of amyloglucosidase, isoamylase, α-glucosidase, and α-amylase having characteristics capable of improving a gel-forming ability of a starch.

(Item 25A) The starch according to Item 24A, wherein the starch hydrolase is selected from the group consisting of amyloglucosidase, isoamylase, α-glucosidase, and α-amylase derived from the genus *Aspergillus*.

(Item 26A) The starch according to Item 24A, wherein the starch hydrolase is selected from the group consisting of amyloglucosidase, isoamylase, α-glucosidase, α-amylase derived from *Aspergillus oryzae*, and α-amylase derived from *Aspergillus niger*.

(Item 27A) A method of producing an enzyme-treated starch having high viscosity and gel-forming ability, the method comprising the step of:

treating starch granules of untreated starch with a starch hydrolase at a temperature of 10° C. or higher and 70° C. or lower;

the starch hydrolase is selected from the group consisting of amyloglucosidase, isoamylase, α-glucosidase, and α-amylase having a characteristic capable of improving a gel forming ability of a starch.

(Item 28A) The method according to Item 27A, wherein the starch hydrolase is selected from the group consisting of amyloglucosidase, isoamylase, α-glucosidase, and α-amylase derived from the genus *Aspergillus*.

(Item 29A) The method according to Item 27A or 28A, wherein the starch hydrolase is selected from the group consisting of amyloglucosidase, isoamylase, α-glucosidase, α-amylase derived from *Aspergillus oryzae*, and α-amylase derived from *Aspergillus niger*.

(Item 30A) The method according to any one of Items 27A to 29A, wherein the starch hydrolase is selected from the group consisting of amyloglucosidase derived from *Aspergillus niger* commercially available from Novozyme as AMG, amyloglucosidase derived from *Aspergillus niger* commercially available from Genencor as OPTIDEX L-400, amyloglucosidase derived from *Aspergillus niger* commercially available from DANISCO as DIAZYME X4NP, amyloglucosidase derived from *Aspergillus niger* commercially available from Amano Enzyme as glucoamylase "Amano" SD, amyloglucosidase derived from *Rhizopus niveus* commercially available from Amano Enzyme as Gluczyme AF6, amyloglucosidase derived from *Rhizopus oryzae* commercially available from SHIN NIHON CHEMICALS Corporation as Sumizyme, α-glucosidase derived from *Aspergillus niger* commercially available from Amano Enzyme as transglucosidase L "Amano", α-glucosidase derived from *Aspergillus niger* commercially available from Genencor as Transglucosidase L-50, α-amylase derived from *Aspergillus oryzae* commercially available from Amano Enzyme as Biozyme A, α-amylase derived from *Aspergillus oryzae* commercially available from SHIN NIHON CHEMICALS Corporation as Sumizyme L, α-amylase derived from *Aspergillus niger* commercially available from Danisco as AMYLEX A3, α-amylase derived from *Aspergillus niger* commercially available from SHIN NIHON CHEMICALS Corporation as Sumizyme AS, and isoamylase derived from *Pseudomonas amyloderamosa* commercially available from Sigma as isoamylase.

(Item 31A) The method according to any one of Items 27A to 30A, wherein the starch hydrolase is encoded by a nucleic acid molecule which is capable of hybridizing under stringent conditions with a nucleic acid molecule having a complementary sequence of the base sequence of SEQ ID NO: 1, 3, 5, 7, 9 or 11, and has a starch hydrolysis activity; wherein the stringent conditions are hybridization in a solution containing 50% formamide, 5×SSC (750 mM NaCl, 75 mM trisodium citrate), 50 mM sodium phosphate (pH 7.6), 5×Denhardt's solution (0.2% BSA, 0.2% Ficoll 400 and 0.2% polyvinylpyrrolidone), 10% dextran sulfate and 20 µg/ml denatured sheared salmon sperm DNA at 65° C., and subsequent washing under the condition of 65° C. using an SSC solution having a 0.1 to 2-fold concentration (a composition of an SSC solution having a 1-fold concentration is 150 mM sodium chloride and 15 mM sodium citrate).

(Item 32A) The method according to any one of Items 27A to 30A, wherein the starch hydrolase has an amino acid sequence having at least 95% or more of homology with an amino acid sequence of SEQ ID NO: 2, 4, 6, 8, 10 or 12, and has a starch hydrolysis activity.

(Item 33A) An enzyme-treated starch having high viscosity and gel-forming ability, the enzyme-treated starch is a starch obtained by treating starch granules of untreated starch with a starch hydrolase under the condition where the starch granules are not dissolved;

the enzyme-treated starch is not modified on hydroxyl groups at the positions 2, 3 and 6 of the glucose residues, the starch hydrolase is selected from the group consisting of amyloglucosidase derived from *Aspergillus niger* commercially available from Novozyme as AMG, amyloglucosidase derived from *Aspergillus niger* commercially available from Genencor as OPTIDEX L-400, amyloglucosidase derived from *Aspergillus niger* commercially available from DANISCO as DIAZYME X4NP, amyloglucosidase derived from *Aspergillus niger* commercially available from Amano Enzyme as glucoamylase "Amano" SD, amyloglucosidase derived from *Rhizopus niveus* commercially available from Amano Enzyme as Gluczyme AF6, amyloglucosidase derived from *Rhizopus oryzae* commercially available from SHIN NIHON CHEMICALS Corporation as Sumizyme, α-glucosidase derived from *Aspergillus niger* commercially available from Amano Enzyme as transglucosidase L "Amano", α-glucosidase derived from *Aspergillus niger* commercially available from Genencor as Transglucosidase L-50, α-amylase derived from *Aspergillus oryzae* commercially available from Amano Enzyme as Biozyme A, α-amylase derived from *Aspergillus oryzae* commercially available from SHIN NIHON CHEMICALS Corporation as Sumizyme L, α-amylase derived from *Aspergillus niger* commercially available from Danisco as AMYLEX A3, α-amylase derived from *Aspergillus niger* commercially available from SHIN NIHON CHEMICALS Corporation as Sumizyme AS, and isoamylase derived from *Pseudomonas amyloderamosa* commercially available from Sigma as isoamylase.

(Item 34A) An enzyme-treated starch having high viscosity and gel-forming ability, the enzyme-treated starch is a starch obtained by treating starch granules of untreated starch with a starch hydrolase under the condition where the starch granules are not dissolved;

the enzyme-treated starch is not modified on hydroxyl groups at the positions 2, 3 and 6 of the glucose residues, the starch hydrolase is encoded by a nucleic acid molecule which is capable of hybridizing under stringent conditions with a nucleic acid molecule having a complementary sequence of the base sequence of SEQ ID NO: 1, 3, 5, 7, 9 or 11, and has a starch hydrolysis activity; wherein the stringent conditions are hybridization in a solution containing 50% formamide, 5×SSC (750 mM NaCl, 75 mM trisodium citrate), 50 mM sodium phosphate (pH 7.6), 5×Denhardt's solution (0.2% BSA, 0.2% Ficoll 400 and 0.2% polyvinylpyrrolidone), 10% dextran sulfate and 20 µg/ml denatured sheared salmon sperm DNA at 65° C., and subsequent washing under the condition of 65° C. using an SSC solution having a 0.1 to 2-fold concentration (a composition of an SSC solution having a 1-fold concentration is 150 mM sodium chloride and 15 mM sodium citrate).

(Item 35A) An enzyme-treated starch having high viscosity and gel-forming ability, the enzyme-treated starch is a starch obtained by treating starch granules of untreated starch with a starch hydrolase under the condition where the starch granules are not dissolved;

the enzyme-treated starch is not modified on hydroxyl groups at the positions 2, 3 and 6 of the glucose residues, the starch hydrolase has an amino acid sequence having at least 95% or more of homology with an amino acid sequence of SEQ ID NO: 2, 4, 6, 8, 10 or 12, and has a starch hydrolysis activity.

Effects of the Invention

According to the present invention, a starch "having a strong gel forming ability and a high viscosity" which have never been achieved by a conventional starch has been successfully developed by using an enzyme having characteristics capable of improving a gel forming ability of a starch.

Since a conventional starch having a strong gel forming ability cannot sufficiently undergo swelling and gelatinization in a usual heating temperature zone, powderiness is likely to be left when added to a food. In order to sufficiently swell and gelatinize the conventional starch having a strong gel forming ability, heating at higher temperature than usual heating temperature zone of a food is required. As for a starch subjected to an acid treatment and a starch having enriched in amylose fraction, they are excellent in gel forming ability, however they do not exhibit viscosity or hardly exhibit viscosity, and thus the application of them has been limited. Even in the case of such a starch subjected to an acid treatment, the gel forming ability can be improved as compared to the prior art by the enzymatic treatment according to the method of the present invention while maintaining a certain degree of viscosity.

Furthermore, although a chemically treated starch is often used for a bracken-starch dumpling (Warabimochi), it is necessary to use an acetylation treatment and a phosphate crosslinking treatment in combination.

The starch developed in this time is a starch in which these defects have been improved. In the case where an untreated starch, a physically treated starch, or a bleached starch is used as a raw material, and the starch developed in this time is produced under the condition where a chemical treatment is not applied in any stage of the production process, the addition to a usual food, or the application in a food containing a starch as a main raw material is not limited, and the starch can be used in all foods "dealt as a food".

In the case where an untreated starch, a physically treated starch or a bleached starch is used as a raw material and the enzyme-treated starch of the present invention is produced under the condition where a chemical treatment is not applied in any stage of the production process, the enzyme-treated starch of the present invention prepared by using a starch hydrolase or a glycosyltransferase does not correspond to a processed starch obtained by a chemical modification in a food additive. Therefore, it is possible to prepare a food without the addition of a food additive if the enzyme-treated starch of the present invention prepared by using a starch hydrolase or a glycosyltransferase is used.

In the case where an untreated starch is used as a raw material and an enzyme-treated starch is produced under the condition where neither a chemical treatment nor a physical treatment is applied in any stage of the production process, since the enzyme-treated starch used in the present invention has a higher gel forming ability than that of the untreated starch and is free from a forcible bond, the starch can sufficiently undergo gelatinization even at usual heating temperature and can exhibit viscosity. Furthermore, the obtained starch paste has less spinnability regardless of being sufficiently gelatinized. The gel obtained by using a high concentration of the starch of the present invention is very rich in elasticity. That is, in the case where the starch of the present invention is added to a high moisture content type food, a body can be imparted and also natural elasticity can be imparted by a strong gel forming ability. On the other hand, in the case where the starch of the present invention is added to a low moisture content type food, texture with nice melt in mouth can be imparted to a food. Furthermore, there is less restriction even in the operation step due from the viewpoint of gelatinization characteristics of them.

Even in the case where a processed starch or a physically treated starch is used as a raw material or a food is produced under the condition where a chemical modification or a physical treatment is applied in any stage of the production process of a food, a food of the present invention has a harder gel and has different texture as compared with the case where a food is produced using a corresponding starch produced without being subjected to an enzymatic treatment. Therefore, according to the present invention, it is possible to provide a food having texture which is different from that of the prior art.

MODE FOR CARRYING OUT THE INVENTION

Hereinafter, the present invention will be described in detail.

(1. Materials)

(1.1 Starch Granules)

In the present description, the term "starch granules" refers to starch molecules in a crystalline state. The starch granules may be untreated starch granules, or may be starch granules obtained by a chemical modification or a physical treatment of untreated starch granules. In the case where an enzyme-treated starch classified as a food is preferably used, starch granules to be used are untreated starch granules obtained from plants. Plants store starch molecules as granules (i.e., as a large crystal) in amyloplasts. The granules are called starch granules. In the starch granules, starch molecules are mutually bonded through a hydrogen bond or the like. Therefore, starch granules are not easily dissolved in water as they are, and are not also easily digested. When the starch granules are heated together with water, they are swollen and molecules are disentangled to form a colloid. This change is called "gelatinization". The size and shape of the starch granules vary depending on plants from which the starch granules are obtained. For example, an average granule size of corn starch granules (corn starch) is from about 12 μm to about 15 μm and is slightly smaller, and the size is relatively uniform, than that of other starch granules. Starch granules of wheat and barley are classified into two kinds in size: large-sized starch granules having a granule size of about 20 μm to about 40 μm, and small-sized starch granules having a granule size of several μm. Rice has a compound starch granule structure in which many small angular starch granules having a diameter of several μm are accumulated in amyloplast. The average granule size of potato starch granules is about 40 μm and is the largest among those which are commonly used as a starch raw material. In the present invention, commercially available various starch granules can be used. Starch granules may be prepared by the method of, for example, purifying starch granules from plants and used in the present invention.

In a state of starch granules, the enzyme hardly acts on starch granules since starch molecules are strongly bonded to each other. In a specific embodiment for obtaining an enzyme-treated starch to be treated as a food, the starch granules used in the present invention are isolated or purified from plants, but are not subjected to an acid treatment, a chemical modification treatment and a heat treatment. In the present description, the term "untreated" starch granules refer to starch granules which are naturally produced and are not subjected to a treatment other than treatments required to separate starch granules from other components (for example, protein and lipid) coexisting in a natural state. Accordingly, the respective steps in the method of preparing starch granules, such as the step of removing impurities from plants or the like to purify a starch is not encompassed in a treatment of starch granules in the present description. It is possible to use, as starch granules, any starch granules as long as they are usually commercially available starch granules.

In another specific embodiment, the starch granules used in the present invention may be starch granules treated by subjecting untreated starch granules to a chemical modification or a physical treatment. Examples of the chemically modified starch granules include an acetylated distarch adipate, an acetylated oxidized starch, an acetylated distarch phosphate, a starch sodium octenyl succinate, a starch acetate, an oxidized starch, a bleached starch, a hydroxypropyl distarch phosphate, a hydroxypropyl starch, a distarch phosphate, a monostarch phosphate, and a phosphated distarch phosphate. The "acetylated distarch adipate" refers to those obtained by esterifying a starch with acetic anhydride and adipic anhydride. The "acetylated oxidized starch" refers to those obtained by treating a starch with sodium hypochlorite and then esterifying it with acetic anhydride. The "acetylated distarch phosphate" refers to those obtained by esterifying a starch with sodium trimetaphosphate or phosphorus oxychloride and acetic anhydride or vinyl acetate. The "starch sodium octenyl succinate" refers to those obtained by esterifying a starch with octenyl succinic anhydride. The "starch acetate" refers to those obtained by esterifying a starch with acetic anhydride or vinyl acetate. The "oxidized starch" refers to those obtained by treating a starch with sodium hypochlorite, wherein the content of carboxyl groups is 1.1% or less when carboxyl groups (also referred to as carboxyl groups) in a sample starch are analyzed in accordance with the method for the purity test described in Ministry of Health and Welfare Notification No. 485. Provided that, even when the amount of a carboxyl group is within the above range, the "bleached starch" is not included in the definition of the "oxidized starch". The "bleached starch" refers to those obtained by treating a starch with sodium hypochlorite, wherein the content of carboxyl groups is 0.1% or less when carboxyl groups in a sample starch are analyzed in accordance with the method for the purity test described in Ministry of Health and Welfare Notification No. 485, and wherein the test results of "Confirmation test (3)" of the oxidized starch described in Ministry of Health and Welfare Notification No. 485 are negative and wherein it can be reasonably explained that a change in properties, such as viscosity, of the starch is not caused by oxidation. Those in which, even if the amount of carboxyl groups is 0.1% or less, properties such as viscosity of the starch change from those of the native starch are classified as the oxidized starch, and are not dealt as a food in Japan but dealt as food additives. The "hydroxypropyl distarch phosphate" refers to those obtained by esterifying a starch with sodium trimetaphosphate or phosphorus oxychloride and etherifying it with propylene oxide. The "hydroxypropyl starch" refers to those obtained by etherifying a starch with propylene oxide. The "distarch phosphate" refers to those obtained by esterifying a starch with sodium trimetaphosphate or phosphorus oxychloride. The "monostarch phosphate" refers to those obtained by esterifying a starch with orthophosphoric acid, a potassium salt or a sodium salt thereof, or sodium tripolyphosphate. The "phosphated distarch phosphate" refers to those obtained by esterifying a starch with orthophosphoric acid, a potassium salt or a sodium salt thereof, or sodium tripolyphosphate, and esterifying it with sodium trimetaphosphate or phosphorus oxychloride.

Examples of the types of the physically treated starch granules include a heat-moisture-treated starch and a thermally inhibited starch.

The starch granules used in the present invention may be either a aboveground starch or a underground starch. Examples of the underground starch include a cassava starch, a potato starch, a sweet potato starch, and a kudzu starch. Examples of the aboveground starch include a wheat starch, a corn starch (for example, a high amylose corn starch, a usual corn starch, and a waxy corn starch), a rice starch (for example, a glutinous rice starch and a nonglutinous rice starch), a bean starch (for example, a green gram starch, a pea starch, an adzuki bean starch, and a fava bean starch), and an *Amaranthus* starch. The starch granules used in the present invention are preferably starches derived from cassava, corn, or wheat. In the case where the untreated starch is used as the starch granules, an untreated cassava starch, an untreated corn starch or an untreated wheat starch is preferably used. In the case where the chemically modified starch is used as the starch granules, it is preferred to use an acetylated distarch adipate, an acetylated oxidized starch, an acetylated distarch phosphate, a starch sodium octenyl succinate, a starch acetate, an oxidized starch, a bleached starch, a hydroxypropyl distarch phosphate, a hydroxypropyl starch, a distarch phosphate, a monostarch phosphate or a phosphated distarch phosphate of a cassava starch, a corn starch or a wheat starch. In the case where the physically treated starch is used, it is preferred to use a heat-moisture-treated starch or a thermally inhibited starch of a cassava starch, a corn starch or a wheat starch.

Since the structure of the starch delicately varies depending on the origin, features of physical properties vary depending on the origin. For example, although the untreated wheat starch has a high gel forming ability, the starch paste thereof has a low viscosity and the starch paste is opaque. Although the untreated cassava starch has a low gel forming ability, the starch paste thereof has a high viscosity and the starch paste has high transparency and the degree of retrogradation is a middle degree. Particularly, although the untreated cassava starch is inexpensive, the starch paste thereof is transparent, and it therefore has a merit of being easily added, the application thereof is limited because of their low gel forming ability. Furthermore, the untreated native wheat starch could not be used in the application where viscosity is required because of a low viscosity of the starch paste. Although the untreated corn starch has a high gel forming ability, the starch paste thereof has slightly low viscosity, and the starch paste is opaque and has high retrogradation property.

The chemical modification alters physical properties of the untreated starch granules. Commonly, crosslinking such as phosphate crosslinking or adipate crosslinking often makes the gel formed by using the obtained starch granules harder and higher turbidity than the gel formed by using the untreated starch granules. Generally, hydroxypropylation, acetylation and oxidation treatments often improve transparency and make softer the gel formed by using the obtained starch granules as compared with the gel formed by using the untreated starch granules. Commonly, the treatment with octenyl succinic acid can make it possible for the gel formed using the obtained starch granules to contain oil.

The physical treatment also alters physical properties of the untreated starch granules. For example, commonly, the heat-moisture treatment often makes the gel formed by using the obtained starch granule harder and the viscosity of the starch paste lower than those of the gel formed by using the untreated starch granules. For example, commonly, the thermal inhibition treatment often makes the gel formed by using the obtained starch granules harder than the gel formed by using the untreated starch granules. Also, when the time of the dry heat treatment is long, the obtained starch often exhibits low viscosity of the starch paste like a highly crosslinked starch.

It is preferred that the starch granules used in the present invention contain impurities as low as possible. The content of impurities in the starch granules is preferably about 10% by weight or less, more preferably about 5% by weight or less, and still more preferably about 1% by weight or less.

(1.2 Enzyme)

The enzyme usable in the present invention is a starch hydrolase or a glycosyltransferase. The starch hydrolase is roughly classified into α-amylase, β-amylase, amyloglucosidase, isoamylase, pullulanase, and α-glucosidase. However, even in the enzymes classified as the same enzyme (for example, α-amylase), if the microorganisms producing the enzyme are different, it is considered that features such as reaction specificity and substrate specificity of the enzymes are different. Since these starch hydrolases and glycosyltransferase are very widely distributed in animals, microorganisms and plants, it can be said that there are infinite kinds of starch hydrolases and glycosyltransferases.

The starch hydrolase usable in the production of the starch of the present invention is a starch hydrolase selected from the group consisting of amyloglucosidase, isoamylase, α-glucosidase, and α-amylase having characteristics capable of improving a gel forming ability of a starch. In the present description, the "α-amylase having characteristics capable of improving a gel forming ability of a starch" is α-amylase wherein the Young's modulus or rupture stress of the starch after the treatment with the enzyme is 10% or more higher than the Young's modulus or rupture stress of the starch before the treatment with the enzyme, when measured by the judgment method described below. The starch hydrolase used in the present invention is preferably an enzyme classified as α-amylase, amyloglucosidase, isoamylase, or α-glucosidase. The enzyme classified as β-amylase or pullulanase is not preferable. It is considered that the enzyme classified as amyloglucosidase, isoamylase or α-glucosidase can produce an enzyme-treated starch having a high viscosity and a gel forming ability if these enzymes are allowed to act on starch granules. However, in the case of the enzyme classified as α-amylase, not all enzymes can be suitably utilized and α-amylase having characteristics capable of improving a gel forming ability of a starch needs to be selected, and the starch of the present invention cannot be produced even if an α-amylase not having this activity is used.

It is possible to judge whether or not the enzyme classified as α-amylase is α-amylase having characteristics capable of improving a gel forming ability of a starch, by the following judgment method.

Examples of the glycosyltransferase usable in the production of the starch of the present invention include cyclodextrin glucanotransferase.

(1.2.1 Method of Judging α-Amylase Having Characteristics Capable of Improving Gel Forming Ability of Starch)

The α-amylase having characteristics capable of improving a gel forming ability of a starch can be judged by the following method. To 400 g of a wheat starch, 900 g of ion-exchange water is added thereby suspending the wheat starch, and each enzyme is added thereto. The amount of a reducing sugar released in the suspension by the reaction is measured to determine a degradation ratio. When the degradation ratio reaches 15%, starch granules are recovered by filtration, washed with water and then dried. Using the enzyme-treated starch thus obtained, a Young's modulus and a rupture stress are determined by rheometer analysis. In the case where the Young's modulus or rupture stress of the starch after treatment with the enzyme increases by 10% or more as compared with the Young's modulus or rupture stress of the starch before treatment with the enzyme, the enzyme is judged as α-amylase having characteristics capable of improving a gel forming ability of the starch. As an example, the judgment results of various starch hydrolases are shown in Table 1A below.

TABLE 1A

| Name of enzyme group | Origin | Product name (Selling agency) | Rupture stress | | Young's modulus | | |
|---|---|---|---|---|---|---|---|
| | | | Measured value (g) | Relative %[*1] | Measured value (dyn/cm$^2$) | Relative %[*2] | Judgment |
| Before treatment with enzyme | — | — | 141 | 100 | 4,601,665 | 100 | Reference |
| α-amylase | *Aspergillus oryzae* | Biozyme A (Amano Enzyme) | 197 | 140 | 5,518,329 | 120 | Usable |
| α-amylase | *Aspergillus niger* | AMYLEX A3 (DANISCO) | 211 | 150 | 5,465,779 | 119 | Usable |
| α-amylase | *Bacillus subtilis* | Novamyl (Novo) | Not measurable since gel is not formed because of being too soft | | | | Not usable |
| α-amylase | *Bacillus amyloliquefaciens* | α-amylase (Reagent) (Sigma) | Not measurable since gel is not formed because of being too soft | | | | Not usable |
| α-amylase | *Bacillus* sp. | Maltogenase L (Novo) | Not measurable since gel is not formed because of being too soft | | | | Not usable |
| α-amylase | *Bacillus licheniformis* | Termamyl 120L (Novo) | Not measurable since gel is not formed because of being too soft | | | | Not usable |

[*1] Relative rupture stress = {(rupture stress for after treatment with enzyme)/(rupture stress for before treatment with enzyme)} × 100
[*2] Relative Young's modulus = {(Young's modulus for after treatment with enzyme)/(Young's modulus for before treatment with enzyme)} × 100

As described above, it is possible to easily decide whether or not various α-amylases have characteristics capable of improving a gel forming ability of a starch. It is noted that a specific method of rheometer analysis is as described in 1.2.2 below.

(1.2.2 Specific Method of Rheometer Analysis)

A starch paste is prepared so that the concentration of the starch is 20% by weight on the dry matter basis, and then filled in a Krehalon casing having a folding width of 45 mm. This starch paste filled in the casing is heated to 90° C. at 1° C./min and maintained at 90° C. for 30 minutes. Then the starch paste is left to cool in a constant-temperature water bath at 20° C. for 30 minutes and then cooled to 5° C. in a refrigerator. After cooling, it is refrigeration stored at 5° C. for 16 hours, then it is left at room temperature (about 25° C.) for 4 hours to return the temperature of it to room temperature, and then measurements by a rheometer (RT-2010J-CW) manufactured by Rheotech Inc. is performed. The measurement is carried out under the measurement conditions of the rheometer: a test item: a rupture test; a height of a sample: 25 mm; and a movement rate (rupture rate) of a sample: 6 cm/min, using an adapter of a spherical jig for measurement viscosity (25 (diameter: 5 mm, area: 19.635 $mm^2$). At the measurement, the hardness of the starch gel is evaluated by a rupture stress (g) and a Young's modulus ($dyn/cm^2$).

(1.2.3: Preferred Example Used in Present Application)

In order to produce the starch of the invention, an enzyme selected from the group consisting of amyloglucosidase, isoamylase, α-glucosidase, α-amylase having characteristics capable of improving a gel forming ability of a starch, and cyclodextrin glucanotransferase is used.

In a specific embodiment, the enzyme is selected from the group consisting of amyloglucosidase, isoamylase, α-glucosidase, α-amylase derived from the genus *Aspergillus*, and cyclodextrin glucanotransferase.

In a specific embodiment, the enzyme is selected from the group consisting of amyloglucosidase, isoamylase, α-glucosidase, α-amylase derived from *Aspergillus oryzae*, α-amylase derived from *Aspergillus niger*, and cyclodextrin glucanotransferase.

In a preferred embodiment, the enzyme is selected from the group consisting of amyloglucosidase derived from *Aspergillus niger* commercially available from Novozyme as AMG, amyloglucosidase derived from *Aspergillus niger* commercially available from Genencor as OPTIDEX L-400, amyloglucosidase derived from *Aspergillus niger* commercially available from DANISCO as DIAZYME X4NP, amyloglucosidase derived from *Aspergillus niger* commercially available from Amano Enzyme as glucoamylase "Amano" SD, amyloglucosidase derived from *Rhizopus niveus* commercially available from Amano Enzyme as Gluczyme AF6, amyloglucosidase derived from *Rhizopus oryzae* commercially available from SHIN NIHON CHEMICALS Corporation as Sumizyme, α-glucosidase derived from *Aspergillus niger* commercially available from Amano Enzyme as transglucosidase L "Amano", α-glucosidase derived from *Aspergillus niger* commercially available from Genencor as Transglucosidase L-50, α-amylase derived from *Aspergillus oryzae* commercially available from Amano Enzyme as Biozyme A, α-amylase derived from *Aspergillus oryzae* commercially available from SHIN NIHON CHEMICALS Corporation as Sumizyme L, α-amylase derived from *Aspergillus niger* commercially available from Danisco as AMYLEX A3, α-amylase derived from *Aspergillus niger* commercially available from SHIN NIHON CHEMICALS Corporation as Sumizyme AS, isoamylase derived from *Pseudomonas amyloderamosa* commercially available from Sigma as isoamylase, cyclodextrin glucanotransferase derived from *Bacillus licheniformis* commercially available from Novozyme as Toruzyme, and cyclodextrin glucanotransferase derived from *Paenibacillus macerans* (*Bacillus macerans*) commercially available from Amano Enzyme as Cyclodextrin glucanotransferase "Amano".

In a specific preferred embodiment, the enzyme is a starch hydrolase, and the starch hydrolase is encoded by a nucleic acid molecule which is capable of hybridizing under stringent conditions with a nucleic acid molecule having a complementary sequence to the base sequence of SEQ ID NO: 1, 3, 5, 7, 9 or 11 and has a starch hydrolysis activity; wherein the stringent conditions are hybridization in a solution containing 50% formamide, 5×SSC (750 mM NaCl, 75 mM trisodium citrate), 50 mM sodium phosphate (pH 7.6), 5×Denhardt's solution (0.2% BSA, 0.2% Ficoll 400 and 0.2% polyvinylpyrrolidone), 10% dextran sulfate and 20 μg/ml denatured sheared salmon sperm DNA at 65° C., and subsequent washing under the condition of 65° C. using an SSC solution having a 0.1 to 2-fold concentration (a composition of an SSC solution having a 1-fold concentration is 150 mM sodium chloride and 15 mM sodium citrate).

In a preferred embodiment, the starch hydrolase has an amino acid sequence having at least 95% or more of homology with an amino acid sequence of SEQ ID NO: 2, 4, 6, 8, 10 or 12, and has a starch hydrolysis activity (1.2.4. α-Amylase)

α-Amylases exist in many microorganisms, animals and plants. Examples of microorganisms which produce an α-amylase include those of genus *Aspergillus* (for example, *Aspergillus oryzae, Aspergillus niger, Aspergillus awamori, Aspergillus flavus, Aspergillus kawachii, Aspergillus sclerotiorum* and the like); those of genus *Bacillus* (for example, *Bacillus subtilis, Bacillus acidocaldarius, Bacillus amyloliquefaciens, Bacillus stearothermophilus, Bacillus cereus, Bacillus licheniformis* and the like); those of genus *Geobacillus* (for example, *Geobacillus stearothermophilus, Geobacillus thermodenitrificans, Geobacillus thermodenitrificans* and the like); those of genus *Lactobacillus* (for example, *Lactobacillus amylovorus, Lactobacillus cellobioses, Lactobacillus manihotivorans* and the like); further more, *Pseudomonas* sp., *Pyrococcus furiosus, Rhizopus microsporus, Thermotoga maritima, Vibrio* sp. and the like. Furthermore, it is confirmed that the α-amylase derived from animals exist in human pancreas, human saliva, human urine, porcine pancreas, bovine pancreas, carp intestinal tract and the like, and that the α-amylase derived from plants exist in barley, rice, wheat, oat, rye, soybean, and fava bean. The organisms that produce an α-amylase are not limited to them.

α-Amylase may be commercially available one or may be prepared from these organisms by a method known in the art, or may be prepared by a genetic recombination method based on an amino acid sequence or a base sequence of α-amylase of these organisms, or may be chemically synthesized. Any α-amylase known in the art can be used as long as it has properties of cleaving an α-1,4-glucoside bond in the end type.

An α-amylase used in the present invention is preferably an α-amylase from genus *Aspergillus*, and most preferably an α-amylase derived from *Aspergillus oryzae* or *Aspergillus niger*.

A nucleotide sequence encoding typical α-amylase derived from *Aspergillus oryzae* is shown in SEQ ID NO: 1, and its amino acid sequence is shown in SEQ ID NO: 2. A nucleotide sequence encoding typical α-amylase derived from *Aspergillus niger* is shown in SEQ ID NO: 3, and its amino acid sequence is shown in SEQ ID NO: 4. It is considered that α-amylases of closely related species have a very high homology and exhibit the similar enzyme activities. Therefore, it is considered that α-amylases derived from *Aspergillus oryzae* have amino acid sequences having a very high homology to SEQ ID NO: 2 and exhibit the similar enzyme activities. Since it is shown that a commercially available α-amylase derived from *Aspergillus oryzae* has characteristics capable of improving a gel forming ability of a starch, it is considered that α-amylase having an amino acid sequence of SEQ ID NO: 2 and α-amylase having an amino acid sequence which has a high homology thereto also have characteristics capable of improving a gel forming ability of a starch. Similarly, since it is shown that a commercially available α-amylase derived from *Aspergillus niger* has characteristics capable of improving a gel forming ability of a starch, it is considered that α-amylase having an amino acid sequence of SEQ ID NO: 2 and α-amylase having an amino acid sequence which have a high homology thereto also have characteristics capable of improving a gel forming ability of a starch.

The α-amylase used in the present invention is not an amylase derived from *Bacillus amyloliquefaciens*. The reason is that the amylase derived from *Bacillus amyloliquefaciens* cannot produce a starch having a high viscosity and a gel forming ability.

A lot of α-amylase is commercially available. Examples of the commercially available α-amylase are described below: Biozyme F1OSD (origin: *Aspergillus oryzae*; Amano Enzyme Inc.), Biozyme A (origin: *Aspergillus oryzae*; Amano Enzyme Inc.), Kokulase (origin: *Aspergillus oryzae*; Mitsubishi-Kagaku Foods Corporation), Sumizyme L (origin: *Aspergillus oryzae*; SHIN NIHON CHEMICALS Corporation), AMYLEX A3 (origin: *Aspergillus niger*; Danisco Japan Ltd.), GRINDAMYLA (origin: *Aspergillus oryzae*; Danisco Japan Ltd.), VERON AX (origin: *Aspergillus oryzae*; HIGUCHI INC.), VERON GX (origin: *Aspergillus oryzae*; HIGUCHI INC.), VERON M4 (origin: *Aspergillus oryzae*; HIGUCHI INC.), VERON ELS (origin: *Aspergillus oryzae*; HIGUCHI INC.), Sumizyme AS (origin: *Aspergillus niger*; SHIN NIHON CHEMICALS Corporation), Bakezyme P500 (origin: *Aspergillus oryzae*; Nihon Siber Hegner K.K.), and α-Amylase (origin: *Aspergillus oryzae*; Sigma-Aldrich Corporation).

Such commercially available α-amylase is subjected to amino acid analysis to determine the amino acid sequence thereof, and a DNA sequence is designed based on the amino acid sequence, and then the DNA sequence is introduced into *E. coli* or the like, and thus α-amylase having the same amino acid sequence as that of the commercially available α-amylase can be produced.

(1.2.5 Amyloglucosidase)

Amyloglucosidase refers to an enzyme capable of producing β-D-glucose by hydrolyzing a 1,4-α bond at a non-reducing terminal of a carbohydrate chain of a starch or the like. The amyloglucosidase hydrolyzes an α-1,4-glucoside chain from a non-reducing terminal, and also an α-1,6-glucoside chain, although the degradation rate is low. A systematic name of the amyloglucosidase is glucan 1,4-α-glucosidase. Another name of the amyloglucosidase is exo-1,4-α-D-glucosidase, 1,4-α-D-glucan glucohydrolase, glucoamylase, γ-amylase, lysosomal α-glucosidase, or acidic maltase. The amyloglucosidase is classified as EC 3.2.1.3.

Amyloglucosidases exist in many microorganisms, animals and plants. Examples of microorganisms which produce an amyloglucosidase include those of genus *Aspergillus* (for example, *Aspergillus niger, Aspergillus oryzae, Aspergillus candidus, Aspergillus terreus, Aspergillus awamori, Aspergillus phoenicis, Aspergillus saitoi* and the like); those of genus *Candida* (for example, *Candida antarctica, Candida tsukubaensis* and the like); those of genus *Rhizopus* (for example, *Rhizopus delemar, Rhizopus delmar, Rhizopus javanicus, Rhizopusniveus, Rhizopusniveus, Rhizopus oligosporus, Rhizopus oryzae* and the like); those of genus *Saccharomyces* (for example, *Saccharomyces cerevisiae, Saccharomyces diastaticus, Saccharomyces diastaticus, Saccharomyces fibuligera*); further more, *Clostridium thermoamylolyticum, Cladosporium resinae, Lentinus edodes, Mucor rouxianus, Magnaporthe grisea, Monascus kaoliang, Paecilomyces varioti, Penicillium oxalicum, Thermomyces lanuginosus, Trichoderma reesei* and the like. Furthermore, it is confirmed that an amyloglucosidase derived from animals exists in mucosa membrane of small intestine of human, rat and mice, and that an amyloglucosidase derived from plants exists in beet and the like. The organisms that produce an amyloglucosidase are not limited to them.

Amyloglucosidase may be commercially available one or may be prepared from these organisms by a method known in the art, or may be prepared by a genetic recombination method based on an amino acid sequence or a base sequence of amyloglucosidase of these organisms, or may be chemically synthesized. Any amyloglucosidase known in the art can be used as long as it has properties of cleaving an α-1,4-glucoside bond and an α-1,6-glucoside bond in an exo type from a non-reducing terminal side in a glucose unit to produce β-glucose.

An amyloglucosidase used in the present invention is preferably an amyloglucosidase from genus *Aspergillus* or an amyloglucosidase from genus *Rizopus*, and most preferably an amyloglucosidase derived from *Aspergillus niger* or an amyloglucosidase derived from *Rizopus niveus*.

A nucleotide sequence encoding typical amyloglucosidase derived from *Aspergillus niger* is shown in SEQ ID NO: 5, and its amino acid sequence is shown in SEQ ID NO: 6. It is considered that amyloglucosidase of closely related species have a very high homology and exhibit the similar enzyme activities. Therefore, it is considered that amyloglucosidase derived from *Aspergillus niger* have amino acid sequences having a very high homology to SEQ ID NO: 6 and exhibit the similar enzyme activities. Since it is shown that a commercially available amyloglucosidase derived from *Aspergillus niger* has starch hydrolysis activity, it is considered that amyloglucosidase having an amino acid sequence of SEQ ID NO: 6 and amyloglucosidase having an amino acid sequence which has a high homology thereto also have starch hydrolysis activity.

The amyloglucosidase used in the present invention is not an amyloglucosidase derived from *Candida tsukubaensis*. The reason is that the amyloglucosidase derived from *Candida tsukubaensis* cannot produce a starch having a high viscosity and a gel forming ability.

A lot of amyloglucosidase is commercially available. Examples of the commercially available amyloglucosidase are described below: GlucS G (origin: *Rhizopus niveus*; Amano Enzyme Inc.), Gluczyme AF6 (origin: *Rhizopus niveus*; Amano Enzyme Inc.), Gluczyme NL4.2 (origin: *Aspergillus niger*; Amano Enzyme Inc.), Brewing glucoamylase "Amano" SD (origin: *Aspergillus niger*; Amano Enzyme Inc.), GODO-ANGH (origin: *Aspergillus niger*; GODO SHUSEI CO., LTD.), OPTIDEX L-400 (origin: *Aspergillus niger*; Genencor Kyowa), OPTIDEX L (origin: *Aspergillus niger*; Genencor Kyowa), Sumizyme (origin: *Rhizopus oryzae*; SHINNIHON CHEMICALS Corporation), Sumizyme SG (origin: *Rhizopus* sp.; SHIN NIHON CHEMICALS Corporation), Sumizyme HG (origin: *Rhizopus*

*oryzae*; SHIN NIHON CHEMICALS Corporation), GLU-COZYME #20000 (origin: *Rhizopus* sp.; Nagase Chemtex Corporation), AMG (origin: *Aspergillus niger*; Novozymes Japan Ltd.), GLUTASEAN (origin: *Aspergillus niger*; HBI Enzymes Ltd.), UNIASE K, 2K (origin: *Rhizopus* sp.; YAKULT PHARMACEUTICAL INDUSTRY CO., LTD.), UNIASE 30 (origin: *Rhizopus* sp.; YAKULT PHARMACEUTICAL INDUSTRY CO., LTD.), UNIASE 60F (origin: *Rhizopus* sp.; YAKULT PHARMACEUTICAL INDUSTRY CO., LTD.), MAGNUX JW-201 (origin: *Rhizopus* sp.; Rakuto Kasei Industrial Co., Ltd.), GRINDAMYL AG (origin *Aspergillus* sp.; Danisco Japan Ltd.), DIAZYME X4NP (origin: *Aspergillus niger*; Danisco Japan Ltd.), Bakezyme AG800 (origin: *Aspergillus niger*; Nihon Siber Hegner K.K.), Amyloglucosidase (origin: *Aspergillus niger*; Sigma-Aldrich Corporation), Amyloglucosidase (origin: *Rhizopus* sp.; Sigma-Aldrich Corporation), and Glucoamylase (origin: *Rhizopus* sp.; Toyobo Co., Ltd.).

Such commercially available amyloglucosidase is subjected to amino acid analysis to determine the amino acid sequence thereof, and a DNA sequence is designed based on the amino acid sequence, and then the DNA sequence is introduced into *E. coli* or the like, and thus amyloglucosidase having the same amino acid sequence as that of the commercially available amyloglucosidase can be produced.

(1.2.6 Isoamylase)

Isoamylase refers to an enzyme which cleaves an α-1,6-glucoside bond of at a branched point of amylopectin, glycogen, or the like to produce amylose-like linear polysaccharides. Another name of the isoamylase is glycogen 6-glucanohydrolase. The isoamylase is classified as EC3.2.1.68. The isoamylase can be derived from any organism capable of producing isoamylase.

Isoamylases exist in many microorganisms, animals and plants. Examples of microorganisms which produce an isoamylase include *Flavobacterium* sp.; *Bacillus* sp.; furthermore, *Pseudomonas amyloderamosa*, *Sulfolobus solfataricus* and the like. Furthermore, it is confirmed that an isoamylase derived from animals exists in human pancreas and the like, and that an isoamylase derived from plants exists in *Oryza sativa*, potato (*Solanum tuberosum*) tuber, *Arabidopsis thaliana* and the like. The organisms that produce an isoamylase are not limited to them.

Isoamylase may be commercially available or may be prepared from these organisms by a method known in the art, or may be prepared by a genetic recombination method based on an amino acid sequence or a base sequence of isoamylase of these organisms, or may be chemically synthesized. Any isoamylase known in the art can be used as long as it has properties of cleaving an α-1,6-glucoside bond of amylopectin in the end type.

An isoamylase used in the present invention is preferably an isoamylase from genus *Flavobacterium* or genus *Pseudomonas*, and more preferably an isoamylase derived from *Flavobacterium* sp. or an isoamylase derived from *Pseudomonas amyloderamosa*.

A nucleotide sequence encoding typical isoamylase derived from *Flavobacterium* sp. is shown in SEQ ID NO: 7, and its amino acid sequence is shown in SEQ ID NO: 8. A nucleotide sequence encoding typical isoamylase derived from *Pseudomonas amyloderamosa* is shown in SEQ ID NO: 9, and its amino acid sequence is shown in SEQ ID NO: 10. It is considered that isoamylase of closely related species have a very high homology and exhibit the similar enzyme activities. Therefore, it is considered that isoamylase derived from *Flavobacterium* sp. have amino acid sequences having a very high homology to SEQ ID NO: 8 and exhibit the similar enzyme activities. Since it is shown that a commercially available isoamylase derived from *Flavobacterium* sp. has starch hydrolysis activity, it is considered that isoamylase having an amino acid sequence of SEQ ID NO: 8 and isoamylase having an amino acid sequence which has a high homology thereto also have starch hydrolysis activity. Similarly, since it is shown that a commercially available isoamylase derived from *Pseudomonas amyloderamosa* has starch hydrolysis activity, it is considered that isoamylase having an amino acid sequence of SEQ ID NO: 10 and isoamylase having an amino acid sequence which has a high homology thereto also have starch hydrolysis activity.

A lot of isoamylase is commercially available. Examples of the commercially available isoamylase are described below: GODO-FIA (origin: *Flavobacterium odoratum*; GODO SHUSEI CO., LTD.), and Isoamylase (origin: *Pseudomonas* sp.; Sigma-Aldrich Corporation).

Such commercially available isoamylase is subjected to amino acid analysis to determine an amino acid sequence thereof, and a DNA sequence is designed based on the amino acid sequence, and then the DNA sequence is introduced into *E. coli* or the like, and thus isoamylase having the same amino acid sequence as that of the commercially available isoamylase can be produced.

(1.2.7 α-Glucosidase)

α-Glucosidase refers to an enzyme which hydrolyzes an α-1,4-glucoside bond at a non-reducing terminal to produce α-glucose. Systematic name of the α-glucosidase is α-D-glucoside glucohydrolase. Another name of the α-glucosidase is maltase, glucoinvertase, or glucoside sucrase. The α-D-glucosidase is classified as EC 3.2.1.20.

α-Glucosidases exist in many microorganisms, animals and plants. Examples of microorganisms which produce an α-glucosidase include those of genus *Aspergillus* (for example, *Aspergillus oryzae*, *Aspergillus niger*, *Aspergillus awamori*, *Aspergillus fumigatus*, *Aspergillus nidulans* and the like); those of genus *Bacillus* (for example, *Bacillus amyloliquefaciens*, *Bacillus amylolyticus*, *Bacillus caldovelox*, *Bacillus cereus*, *Bacillus licheniformis*, *Bacillus thermoglucosidius*, *Bacillus* sp., *Bacillus subtilis*, *Bacillus brevis*, *Bacillus stearothermophilus*; those of genus *Lactobacillus* (*Lactobacillus acidophilus*, *Lactobacillus brevis* and the like); those of genus *Penicillium* (*Penicillium brevicompactum*, *Penicilliumcitrinum*, *Penicilliumoxalicum*, *Penicillium purpurogenum*); those of genus *Pyrococcus* (*Pyrococcus furiosus*, *Pyrococcus woesei* and the like), those of genus *Saccharomyces* (*Saccharomyces carlsbergensis*, *Saccharomyces cerevisiae*, *Saccharomyces fibuligera*, *Saccharomyces oviformis*, *Saccharomyces carlsbergensis*, *Saccharomyces logos* and the like); furthermore, *Candida tropicalis*, *Schizosaccharomyces pombe*, *Sulfolobus solfataricus*, *Thermotoga maritima*, *Escherichia coli* and the like. It is confirmed that the α-glucosidase derived from animals widely exist within a range from invertebrate animals such as mollusks, crustaceans, and insects to vertebrate animals such as fishes, amphibians, reptiles, birds, and mammalians, and the α-glucosidase derived from plants exist in beans, rice, buckwheat, corn, beet seeds and the like. It is noted that organisms capable of producing α-glucosidase are not limited to them.

α-Glucosidase may be commercially available one or may be prepared from these organisms by a method known in the art, or may be prepared by a genetic recombination method based on an amino acid sequence or a base sequence of α-glucosidase of these organisms, or may be chemically synthesized. Any α-glucosidase known in the art can be used as long as it has properties of cleaving an α-1,4-glucoside bond and an α-1,6-glucoside bond in an exo type from a non-reducing terminal side in a glucose unit to produce α-glucose.

An α-glucosidase used in the present invention is preferably an α-glucosidase from genus *Aspergillus*, and more preferably an α-glucosidase derived from *Aspergillus niger*.

A nucleotide sequence encoding typical α-glucosidase derived from *Aspergillus niger* is shown in SEQ ID NO: 11, and its amino acid sequence is shown in SEQ ID NO: 12. It is considered that α-glucosidase of closely related species have a very high homology and exhibit the similar enzyme activities. Therefore, it is considered that α-glucosidase derived from *Aspergillus niger* have amino acid sequences having a very high homology to SEQ ID NO: 12 and exhibit the similar enzyme activities. Since it is shown that a commercially available α-glucosidase derived from *Aspergillus niger* has starch hydrolysis activity, it is considered that α-glucosidase having an amino acid sequence of SEQ ID NO: 12 and α-glucosidase having an amino acid sequence which has a high homology thereto also have starch hydrolysis activity.

A lot of α-glucosidase is commercially available. Examples of the commercially available α-glucosidase are described below: Transglucosidase L 500 (origin: *Aspergillus*; Genencor Kyowa), Transglucosidase L "Amano" (origin: *Aspergillus niger*; Amano Enzyme Inc.), α-Glucosidase (origin: *Bacillus stearothermophilus*; Sigma-Aldrich Corporation), α-Glucosidase (origin: rice; Sigma-Aldrich Corporation), α-Glucosidase (origin: *Saccharomyces cerevisiae*; Sigma-Aldrich Corporation), α-Glucosidase (origin: *Aspergillus niger*; Sigma-Aldrich Corporation), and α-Glucosidase (origin: Microorganism; Toyobo Co., Ltd.).

Such commercially available α-glucosidase is subjected to amino acid analysis to determine the amino acid sequence thereof, and a DNA sequence is designed based on the amino acid sequence, and then the DNA sequence is introduced into *E. coli* or the like, and thus α-glucosidase having the same amino acid sequence as that of the commercially available α-glucosidase can be produced.

(1.2.8 Cyclodextrin Glucanotransferase)

Cyclodextrin glucanotransferase is also called CGTase and is classified as EC2.4.1.19. CGTase is an enzyme capable of catalyzing a transglycosylation reaction (i.e., disproportionation reaction) of maltooligosaccharide. CGTase is an enzyme which performs a transfer reaction so as to recognize 6 to 8 glucose-chain at a non-reducing terminal of donor molecules thereby cyclizing this portion to produce cyclodextrin having a degree of polymerization of 6 to 8 and noncyclic limit dextrin. As an example of CGTase usable in the present invention, CGTase derived from well-known microorganisms or a commercially available CGTase can be used. CGTase is preferably selected from the group consisting of cyclodextrin glucanotransferase derived from *Bacillus licheniformis* commercially available from Novozyme as Toruzyme, and cyclodextrin glucanotransferase (optimum pH 6.0) derived from *Paenibacillus macerans* (also classified as *Bacillus macerans*) commercially available from Amano Enzyme as Cyclodextrin glucanotransferase "Amano".

CGTase may be commercially available or may be prepared from CGTase producing organisms by a method known in the art, or may be prepared by a genetic recombination method based on an amino acid sequence or a base sequence of CGTase of CGTase producing organisms, or may be chemically synthesized. Any CGTase known in the art can be used as long as it has a transglycosylation activity, and an activity capable of improving a gel forming ability of a starch.

(1.2.9 Use of Enzymes in Combination)

In the case of producing the starch of the present invention, multiple kinds of starch hydrolases or glycosyltransferases may be allowed to act on in combination. Particularly, since α-glucosidase alone does not easily react with starch granules, it is preferred to use in combination with α-amylase.

(1.2.10 Common Explanation about Enzymes)

In the present description, the fact that the enzyme is "derived" from certain organisms means not only the fact that the enzyme is directly isolated from the organisms, but also the fact that an enzyme having the same amino acid sequence is produced from another organisms based on an amino acid sequence of the enzyme possessed by the organisms, or a base sequence encoding the amino acid sequence. For example, also in the case of introducing a gene encoding the enzyme obtained from the organisms into *E. coli* and isolating the enzyme from the *E. coli*, it is said that the enzyme is "derived" from the organisms.

In the present description, a large excess amount of the enzyme is added to starch granules. Therefore, the amount of the enzyme is represented by % by weight. It is not necessary to represent it by the unit (U).

Many α-amylases, amyloglucosidases, isoamylases, α-glucosidases and cyclodextrin glucanotransferases are known, and, therefore, many natural base sequences and amino acid sequences of these enzymes are known. It is known that variants (so-called allele variants) having a slightly different sequence from the natural sequences can occur naturally. Such naturally occurring variants and variants created by artificially mutating the natural enzymes, in addition to the enzymes exemplified above, can be used in the method of the present invention insofar as they have a desired activity. Variant enzymes preferably have activity equal to, or higher than, that of the enzyme before modification. For example, the amino acid sequence of a starch hydrolase used in the present invention, in a certain embodiment, may be identical with (that is, 100% identical with) an amino acid sequence (that is, a reference amino acid sequence) of the starch hydrolase used in the Examples of the present application, or the amino acid sequence of SEQ ID NO: 2, SEQ ID NO: 4, SEQ ID NO: 6, SEQ ID NO: 8, SEQ ID NO: 10, or SEQ ID NO: 12; or this amino acid sequence may, in another embodiment, be altered in up to a certain number of amino acids compared with a reference amino acid sequence. Such alterations can be selected from the group consisting of a deletion, a substitution (including conservative and non-conservative substitution), or an insertion of at least 1 (preferably 1 or several; there is no specific upper limit, for example, about 50 or less, about 40 or less, about 30 or less, about 20 or less, about 10 or less, or the like) amino acids. This alteration may occur at a position of an amino terminus or a carboxyl terminus of a reference amino acid sequence, or may occur at any position other than these termini. Alteration of an amino acid residue may be interspersed with one residue, or a few residues may be contiguous. Those skilled in the art can easily select a objective enzyme having a desired property. Alternatively, a gene encoding the objective enzyme may be directly chemically synthesized. Methods for such chemical synthesis are well-known in the art.

Modification to enzyme can be carried out using a method well-known in the art, for example, by carrying out site-directed mutagenesis, mutagenesis with a mutagen (treatment of a subject gene with a mutagenic agent such as nitrite, or treatment with UV rays), or error-prone PCR. It is preferable to use site-directed mutagenesis from the viewpoint that the objective mutation is easily obtained, because the objective modification can be introduced at an objective site when site-directed mutagenesis is used. Alternatively, a nucleic acid molecule having an objective sequence may be directly synthesized. Such chemical synthesis methods are well-known in the art. Techniques of site-directed mutagenesis are described in, for example, Nucl. Acid Research, Vol. 10, pp. 6487-6500 (1982).

Upon design of the aforementioned modification, the hydrophobicity index of an amino acid can be considered. Significance of a hydrophobic amino acid index upon impartation interacting biological function to a protein is generally recognized in the art (Kyte. J and Doolittle, R. F., J. Mol. Biol. 157 (1): 105-132, 1982). The hydrophobic nature of an amino acid contributes to the secondary structure of a produced protein and, then, defines interaction between the protein and other molecule (e.g. starch hydrolase or glycosyltransferase, substrate, receptor, DNA, antibody, antigen and the like). An amino acid is assigned a hydrophobicity index based on hydrophobicity and a nature of a charge thereof. They are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamic acid (−3.5); glutamine (−3.5); aspartic acid (−3.5); asparagine (−3.5); lysine (−3.9); and arginine (−4.5).

It is well-known in the art to substitute a certain amino acid with another amino acid having a similar hydrophobicity index, thereby, a protein still having substantially similar biological functions (e.g. protein substantially equivalent in enzyme activity) can be produced. In such an amino acid substitution, a hydrophobicity index is preferably within ±2, more preferably within ±1, further preferably within ±0.5. It is understood in the art that such the substitution of an amino acid based on hydrophobicity is efficient. As described in U.S. Pat. No. 4,554,101, the following hydrophilicity index is assigned to amino acid residues: arginine (+3.0); lysine (+3.0); aspartic acid (+3.0±1); glutamic acid (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); and tryptophan (−3.4). It is understood that an amino acid can be substituted with another amino acid which has a similar hydrophilicity index, and can still provide a biological equivalent. In such the amino acid substitution, the hydrophilicity index is preferably within ±2, more preferably within ±1, and further preferably within ±0.5.

In the present invention, "conservative substitution" refers to substitution in which a hydrophilicity index or/and a hydrophobicity index are similar, as described above, between the original amino acid and an amino acid to be substituted, in amino acid substitution. Examples of conservative substitution are well-known to those skilled in the art, and include, but are not limited to substitution among the following each group, for example: arginine and lysine; glutamic acid and aspartic acid; serine and threonine; glutamine and asparagines; and valine, leucine, and isoleucine.

The enzyme used in the method of the present invention may be isolated from naturally occurring microorganisms producing the above-mentioned enzyme of interest. For example, firstly, a microorganism producing the enzyme of interest is inoculated into a suitable medium (for example, L broth (1% Bacto-Tryptone (Difco Laboratories, Detroit, Mich., USA), 0.5% Bacto-Yeast Extract (Difco), 0.5% NaCl, pH 7.3) and cultured at appropriate temperature (for example, about 30° C. to about 40° C.) overnight with shaking. Then, this culture is centrifuged to precipitate the microbial cells and then obtained a culture supernatant. The obtained culture supernatant is concentrated with UF membrane to obtain an enzyme liquid of interest. When further purification is necessary, a solution containing a purified enzyme of interest can be obtained by combining fractionation with ion-exchange chromatography on Q-Sepharose or the like, fractionation with gel filtration chromatography on Sephacryl S-200HR (manufactured by Pharmacia) or the like and fractionation with hydrophobic chromatography on Phenyl-TOYOPEARL 650M (manufactured by Tosoh Corporation) or the like, if necessary.

Alternatively, the enzyme used in the method of the present invention can be obtained by introducing a nucleic acid molecule containing a base sequence encoding enzyme of interest into a suitable host cell, to express the enzyme, and purifying the expressed enzyme from the host cell or its culture liquid.

Purified enzyme obtained resultingly is treated with trypsin, the resulting trypsin treated fragment is separated by HPLC, and the amino acid sequence of the N-terminus of any of the separated peptide fragments is determined using a peptide sequencer. Then, using synthetic oligonucleotide probes prepared based on the identified amino acid sequence, a suitable genome library or a cDNA library is screened, thereby, a nucleic acid molecule (also referred to as a gene) comprising a base sequence encoding natural enzyme can be obtained. Fundamental strategies for preparing the oligonucleotide probes and DNA libraries, and screening them by hybridization of nucleic acids, are well-known to those skilled in the art. For example, see Sambrook et al., *Molecular Cloning: A Laboratory Manual* (1989); *DNA Cloning*, Volumes I and II (edited by D. N. Glover, 1985); *Oligonucleotide Synthesis* (edited by M. J. Gait, 1984); and Nucleic Acid Hybridization (edited by B. D. Hames & S. J. Higgins, 1984).

Alternatively, based on homology to a base sequence of a certain enzyme gene for which a base sequence encoding enzyme is known, screening can be conducted by hybridization using nucleic acid probes containing at least a part of this base sequence, thereby, a nucleic acid molecule containing another kind of the enzyme gene may be acquired. Such methods are known in the art.

Alternatively, degenerate primers corresponding to a region which is conserved in the amino acid sequence of various enzymes are prepared, and PCR is performed, and the base sequence of the enzyme may be acquired. Such methods are known in the art.

When a genome library is screened, the resulting nucleic acid molecule can be subcloned using methods well-known to those skilled in the art. For example, by mixing λ phage containing an objective gene, suitable *Escherichia coli* and suitable helper phage, a plasmid containing an objective gene can be easily obtained. Thereafter, by transforming suitable *Escherichia coli* using a solution containing the plasmid, an objective gene can be subcloned. By culturing the resulting transformant, a plasmid DNA may be obtained, for example, by an alkaline SDS method, and the base sequence of the objective gene can be determined. A method of determining a base sequence is well-known to those skilled in the art. Further, using primers synthesized based on a base sequence of a DNA fragment, and using a polymerase chain reaction (PCR) employing, for example, the genomic DNA of *Aquifex aeolicus, Rhodothermus obamensis, Bacillus stearothermophilus, Bacillus caldovelox, Bacillus thermocatenulatus, Bacillus caldolyticus* or the like as a template, an enzyme gene may be directly amplified.

Alternatively, the enzyme gene can be chemically synthesized based on a known base sequence.

A base sequence encoding an amino acid sequence of the enzyme used in the method of the present invention may be altered in up to certain number of nucleotides as compared with the nucleotide sequence (that is, the reference nucleotide sequence) encoding the reference amino acid sequence described above. Such alterations can be selected from the group consisting of a deletion of at least one nucleotide, substitution with at least one nucleotide, including transition and transversion, or an insertion of at least one nucleotide. This alteration may occur at a position of the 5' terminus or the 3' terminus of a reference nucleotide sequence, or may occur at any position other than these termini. Alteration of a base may be interspersed with one base, or a few bases may be contiguous.

A nucleotide alteration can generate a nonsense, missense or frame shift mutation in a code sequence, and thus alteration of the enzyme encoded by such a altered base sequence can be effected.

In the case where the enzyme used in the present invention is a starch hydrolase, it is preferred that this enzyme has at least about 20%, preferably at least about 30%, more preferably at least about 40%, still more preferably at least about 50%, and particularly preferably at least about 60%, about 70%, about 80%, about 90%, about 95%, about 96%, about 97%, about 98% or about 99% of identity against an amino acid sequence of a starch hydrolase used in Examples, or an amino acid sequence of SEQ ID NO: 2, 4, 6, 8, 10 or 12, and has a starch hydrolysis activity (characteristics capable of improving a gel forming ability of a starch in a specific case).

In the case where the enzyme used in the present invention is a glycosyltransferase, it is preferred that this enzyme has at least about 20%, preferably at least about 30%, more preferably at least about 40%, still more preferably at least about 50%, and particularly preferably at least about 60%, about 70%, about 80%, about 90%, about 95%, about 96%, about 97%, about 98% or about 99% of identity against an amino acid sequence of a glycosyltransferase used in Examples, or an amino acid sequence of SEQ ID NO: 14, and has a transglycosylation activity (characteristics capable of improving a gel forming ability of a starch in a specific case).

In the present specification, the identity of sequences is calculated using maximum matching of GENETYX-WIN Ver. 4.0 (Genetics Co., Ltd.). This program aligns sequence data to be analyzed, and sequence data to be compared so that amino acid pairs matched between sequences become greatest while substitution and deletion are considered, and thereupon, gives a score to each of Matches, Mismatches, and Gaps, calculates a sum, outputs alignment at the smallest sum, and calculates identity thereupon (Reference: Takashi, K., and Gotoh, O. 1984. Sequence Relationships among Various 4.5 S RNA Species J. Biochem. 92:1173-1177). In the present specification, the percentage identity of sequences is calculated using maximum matching of GENETYX-WIN Ver. 4.0 under the condition of Matches=−1; Mismatches=1; Gaps=1; *N+=2.

As a natural enzyme or nucleic acid molecule, an enzyme or nucleic acid molecule having a sequence that is not identical with, but is homologous to, the amino acid sequence of the enzyme or the base sequence encoding the amino acid sequence of the enzyme can also be used. Such an enzyme or nucleic acid molecule having homology with the natural enzyme or nucleic acid molecule includes, but are not limited to, in the case of a nucleic acid, nucleic acid molecules containing a base sequence having at least about 30%, about 35%, about 40%, about 45%, about 50%, about 55%, about 60%, about 65%, about 70%, about 75%, about 80%, about 85%, about 90%, about 95%, or about 99% identity with a comparison subject sequence, and, in the case of an enzyme, includes, but are not limited to, enzymes having an amino acid sequence having at least about 40%, about 45%, about 50%, about 55%, about 60%, about 65%, about 70%, about 75%, about 80%, about 85%, about 90%, about 95%, or about 99% identity with a comparison subject sequence, when compared in maximum matching in for example GENETYX-WIN Ver. 4.0 under the conditions described above.

A starch hydrolase, which is encoded by a nucleic acid molecule which is capable of hybridizing under stringent conditions with a nucleic acid molecule having a complementary sequence of a base sequence (for example, SEQ ID NO: 1, 3, 5, 7, 9 or 11) encoding a natural known starch hydrolase, can be used in the method of the present invention as long as it has a starch hydrolysis activity (characteristics of improving a gel forming ability of a starch in a specific case). A starch hydrolase, which is encoded by a nucleic acid molecule containing an altered base sequence obtained by altering a nucleic acid molecule which is capable of hybridizing under stringent conditions with a nucleic acid molecule having a complementary sequence of a base sequence encoding a natural known starch hydrolase can also be used in the method of the present invention as long as it has an ability capable of producing a high viscosity starch having a gel forming ability. Those skilled in the art can easily select a desired starch hydrolase gene.

A transglycosylase, which is encoded by a nucleic acid molecule which is capable of hybridizing under stringent conditions with a nucleic acid molecule having a complementary sequence of a base sequence (for example, SEQ ID NO: 13) encoding a natural known transglycosylase, can be used in the method of the present invention as long as it has a transglycosylase activity (characteristics of improving a gel forming ability of a starch in a specific case). A transglycosylase, which is encoded by a nucleic acid molecule containing an altered base sequence obtained by altering a nucleic acid molecule which is capable of hybridizing under stringent conditions with a nucleic acid molecule having a complementary sequence of a base sequence encoding a natural known transglycosylase can also be used in the method of the present invention as long as it has an ability to produce a high viscosity starch having a gel forming ability. Those skilled in the art can easily select a desired transglycosylase gene.

As used in the present description, the term "stringent conditions" refers to conditions under which a sequence hybridizes with a specific sequence, but not with a non-specific sequence. Selection of appropriate stringent conditions is well-known to those skilled in the art, and is described, for example, in Molecular Cloning (Sambrook, et al., supra). For example, "stringent conditions" are hybridization in a solution containing 50% formamide, 5×SSC (750 mM NaCl, 75 mM trisodium citrate), 50 mM sodium phosphate (pH 7.6), 5×Denhardt's solution (0.2% BSA, 0.2% Ficoll 400 and 0.2% polyvinylpyrrolidone), 10% dextran sulfate and 20 µg/ml denatured sheared salmon sperm DNA at 65° C., and subsequent washing under the condition of 65° C. using an SSC (saline-sodium citrate) solution having a 0.1 to 2-fold concentration (a composition of an SSC solution having a 1-fold concentration is 150 mM sodium chloride and 15 mM sodium citrate). Therefore, for example, a polynucleotide being capable to hybridize under stringent conditions means, specifically, a polynucleotide which can be identified using the conditions under which hybridization is performed at 65° C. in a solution containing 50% formamide, 5×SSC (750 mM NaCl, 75 mM trisodium citrate), 50 mM sodium phosphate (pH 7.6), 5×Denhardt's solution (0.2% BSA, 0.2% Ficoll 400 and 0.2% polyvinyl pyrrolidone), 10% dextran sulfate, and 20 µg/ml denatured sheared salmon sperm DNA using a filter on which a DNA derived from a colony or a plaque has been immobilized, and a filter is washed under the condition of 65° C. using an SSC (saline-sodium citrate) solution having a 0.1 to 2-fold concentration (a composition of an SSC solution having a 1-fold concentration is 150 mM sodium chloride, 15 mM sodium citrate).

Specifically, the conditions mean, for example, that

A nucleic acid molecule used for producing an enzyme used in the present method may be a nucleic acid molecule which was conservatively modified relative to a nucleic acid molecule comprising a base sequence encoding a natural enzyme. The "nucleic acid molecule which was conservatively modified relative to a nucleic acid molecule comprising a base sequence encoding natural enzyme" refers to a nucleic acid molecule comprising a base sequence encoding an amino acid sequence which is the same or essentially the same as an amino acid sequence of the natural enzyme. The "amino acid sequence which is essentially the same as an amino acid sequence of the natural enzyme" refers to an amino acid sequence having essentially the same enzyme activity as that of the natural enzyme. Due to the degeneracy of the genetic code, many functionally equivalent base sequences encode any prescribed amino acid sequence. For example, codons GCA, GCC, GCG and GCU all encode the amino acid alanine. Therefore, at all positions where alanine is specified by a GCA codon, the codon can be changed to GCC, GCG or GCU without changing the encoded alanine. Similarly, regarding an amino acid which can be encoded by a plurality of codons, at all positions where the amino acid is specified by a codon, the codon can be changed to any another codon encoding the amino acid without changing the particular amino acid coded. Such a variation in a base sequence is a "silent mutation" which is one kind of conservatively modified mutation. All base sequences in the present specification which encode a polypeptide also include all possible silent mutations of the nucleic acid. Silent mutation includes "silent substitution" in which a coded amino acid is not changed, and the case where a nucleic acid does not originally encode an amino acid (for example, a mutation at an intron portion, a mutation at other untranslated region and the like). When a certain nucleic acid encodes an amino acid, silent mutation has the same meaning as that of silent substitution. In the present specification, "silent substitution" refers to substitution of a base sequence encoding a certain amino acid with another base sequence encoding the same amino acid, in a base sequence. Based on the phenomenon of degeneracy in the genetic code, in the case where there are a plurality of base sequences encoding a certain amino acid (for example, glycine and the like), such silent substitution is possible. Therefore, a polypeptide having an amino acid sequence encoded by a base sequence produced by silent substitution has the same amino acid sequence as that of the original polypeptide. In the art, it is understood that each codon in a nucleic acid (except for AUG which is the only codon usually encoding methionine, and TGG which is the only codon usually encoding tryptophan) can be modified in order to produce functionally the same molecule. Therefore, each silent mutation of a nucleic acid encoding a polypeptide is implicitly included in each described sequence. Preferably, such a modification can be performed so that substitution of cysteine, which is an amino acid that greatly influences the conformation of a polypeptide, is avoided.

A base sequence encoding enzyme used in the present invention can be changed in conformity with a codon usage in an organism into which the sequence is introduced for expression. Codon usage reflects the usage in a gene which is highly expressed in the organism. For example, when expression is intended in *Escherichia coli*, the sequence can be made to be optimal for expression in *Escherichia coli* according to the published codon usage table (for example, Sharp, et al., Nucleic Acids Research 16, No. 17, p. 8207 (1988)).

An expression vector can be made using a nucleic acid molecule comprising the base sequence modified as described above. A method for preparing an expression vector using a particular nucleic acid sequence is well-known to those skilled in the art.

When a nucleic acid molecule is referred to in the present specification, a "vector" refers to a nucleic acid molecule which can transfer an objective base sequence into an objective cell. Examples of such vectors include a vector which can autonomously replicate in an objective cell, or can be incorporated into a chromosome of an objective cell, and has a promoter at a position suitable for transcribing a modified base sequence. In the present specification, the vector may be a plasmid.

As used in the present description, an "expression vector" refers to a vector which can express a modified base sequence (i.e. base sequence encoding modified enzyme) in an objective cell. An expression vector contains, in addition to a modified base sequence, various regulation elements such as a promoter regulating expression thereof and, if necessary, factors necessary for replication in an objective cell and selection of a recombinant (e.g. origin of replication (ori), and a selectable marker such as a drug resistant gene). In an expression vector, a modified base sequence is operably linked so that it is transcribed and translated. Regulation elements include a promoter, a terminator and an enhancer. In addition, when secretion of an expressed enzyme outside a cell is intended, a base sequence encoding a secretion signal peptide is linked upstream of a modified base sequence in the correct reading frame. It is well-known to those skilled in the art that both the type of an expression vector used for introduction into a particular organism (e.g. bacterium), and the kind of a regulation element and other factors used in the expression vector, can vary depending on an objective cell.

As used in the present description, a "terminator" is a sequence which is situated downstream of a protein coding region, and is involved in termination of transcription upon transcription of a base sequence into an mRNA, and in the addition of a poly A sequence. It is known that a terminator influences the expression level of a gene by involving the stability of an mRNA.

As used in the present description, a "promoter" refers to a region on a DNA which determines a transcription initiation site of a gene, and directly regulates the transcription frequency, and is a base sequence to which a RNA polymerase binds, thereby, initiating transcription. Since the region of a promoter is usually a region about 2 kbp or less upstream of a first exon of a putative protein coding region in many cases, when a protein coding region in a genome base sequence is predicted using a DNA analyzing software, a promoter region can be putative. A putative promoter region varies with every structural gene, and is usually upstream of a structural gene without limitation, and may be downstream of a structural gene. Preferably, a putative promoter region is present about 2 kbp or less upstream of a first exon translation initiation point.

As used in the present description, an "enhancer" can be used for enhancing the expression efficiency of an objective gene. Such an enhancer is well-known in the art. A plurality of enhancers can be used, or only one may be used, or may not be used at all.

As used in the present description, "operably linked" refers to when a desired base sequence is placed under the control of a transcription and translation regulating sequence (e.g. promoter, enhancer and the like) or a translation regulating sequence which effect expression (i.e. operation). In order that a promoter is operably linked to a gene, usually, a promoter is disposed immediately upstream of the gene, but it is not necessary that the promoter is disposed adjacent to the gene.

In order to operably link a modified nucleic acid sequence to the aforementioned regulation element, an enzyme gene should be processed in some cases. Examples include the case where the distance between a promoter and a coding region is too long, and reduction in a transcription efficiency is predicted, the case where the distance between a ribosome binding site and a translation initiation codon is not suitable, and the like. Examples of processing mean include digestion with a restriction enzyme, digestion with an exonuclease such as Bal31 and ExoIII, or introduction of site-directed mutation using a single-stranded DNA such as M13 or PCR.

Then, the expression vector prepared as described above is introduced into a cell, thereby, the objective enzyme is expressed.

As used in the present description, "expression" of an enzyme refers to in vivo or in vitro transcription and translation of a base sequence encoding the enzyme, and production of the encoded enzyme.

A cell into which an expression vector is introduced (also referred to as a host) includes prokaryotes and eukaryotes. A cell into which an expression vector is introduced can be easily selected, taking various conditions such as ease of expression of objective enzyme, ease of culturing, growth rate, and safety into consideration. Examples of such cells include microorganisms such as bacteria and fungi. Examples of more preferable cells include mesophilic microorganisms (e.g. yeast, mold, *Escherichia coli, Bacillus subtilis*). A cell may be a microorganism cell, or may be a plant or animal cell. Depending on the cell to be used, a starch hydrolase can be an enzyme which has undergone post-translational processing.

In the method of the present invention, the technique of introducing an expression vector into a cell may be any technique known in the art. Examples of such techniques include, for example, transformation, transduction, and transfection. Such techniques of introducing a nucleic acid molecule are well-known in the art, and are conventional, and are described, for example, in Ausubel F. A., et al. ed. (1988), Current Protocols in Molecular Biology, Wiley, New York, N.Y.; Sambrook J, et al. (1987) Molecular Cloning: A Laboratory Manual, 2nd Ed., Cold Spring Harbor Laboratory Press, Cold Spring Harbor, N.Y., and Bessatsu Jikken-igaku "Idenshidounyu & Hatsugen kaiseki jikkenhou", Yodosha, 1997.

(1.3 Other Materials)

In the production of enzyme-treated starch granules, any material used usually in an enzymatic treatment can be used as long as it does not obstruct an action of the enzyme. Examples of such other material include salts and buffer agents. Since it is commonly known that a rate of an enzyme reaction can be drastically improved by adding a specific salt suitable to each enzyme, it is preferred to add such a specific salt. It is possible to shorten the treatment time by adding such a suitable salt to each enzyme. Examples of the combination of the enzyme and the salt include a combination of amyloglucosidase and a metal ion (for example, sodium ion, potassium ion, calcium ion, or magnesium ion). As a result of a test by the present inventors, for example, in the case of treating an untreated native cassava starch with amyloglucosidase (for example, "OPTIDEX L-400" derived from *Aspergillus niger*, manufactured by Genencor), a degradation rate of the starch in the system, in which 100 ppm (in terms of a metal ion) of sodium chloride, or sodium sulfate, or potassium chloride, or calcium chloride, or magnesium chloride is added, increased by 1.5 to 2 times as compared with the system in which no metal ion is added.

(2. Method for Producing Enzyme-Treated Starch Granule)

Enzyme-treated starch granules are produced by treating starch granules with a starch hydrolase or a glycosyltransferase. Details of each step will be described below.

(2.1 Preparation of Suspension)

In the production method of the present invention, for example, starch granules, a starch hydrolase or a glycosyltransferase, a buffer agent, and a solvent dissolving them are used as main materials. Although all of these materials are usually added at the time of initiation of a reaction, any material among these materials may be further added during the reaction. The solvent used in the production method of the present invention can be any solvent as long as it is a solvent which does not impair an enzyme activity of the enzyme to be used. The typical solvent is water (for example, ion-exchange water, purified water, and tap water). The solvent may be moisture of a crushed cell liquid obtained in association with the enzyme upon preparing the enzyme.

In the production method of the present invention, first, a reaction solution is prepared. The reaction solution can be obtained, for example, by adding starch granules and a starch hydrolase or a glycosyltransferase to a suitable solvent. For example, the enzyme may be added after preparing a starch suspension by suspending starch granules in the solvent (for example, water or buffer solution). Alternatively, the reaction solution may be prepared by mixing a suspension containing starch granules with a solution containing an enzyme. To this reaction solution, any buffer agent may be optionally added for the purpose of adjusting the pH as long as it does not inhibit the enzyme reaction. It is noted that although starch granules are not dissolved but suspended in the reaction solution, it is called as reaction solution, since other components such as an enzyme are dissolved therein.

The pH of the reaction solution can be arbitrarily set as long as it is the pH at which the enzyme to be used can exert an activity. The pH of the reaction solution is preferably around the optimum pH of the enzyme to be used. The pH of the reaction solution is typically about 2 or more, preferably about 3 or more, still more preferably about 4 or more, particularly preferably about 5 or more, particularly preferably about 6 or more, and most preferably about 7 or more. The pH of the reaction solution is typically about 13 or less, preferably about 12 or less, still more preferably about 11 or less, particularly preferably about 10 or less, particularly preferably about 9 or less, and most preferably about 8 or less. In an embodiment, the pH of the reaction solution is typically within the optimum pH ±3, preferably within the optimum pH ±2, still more preferably within the optimum pH ±1, and most preferably within the optimum pH ±0.5, of the enzyme to be used.

The amount of the starch granules in the reaction solution can be arbitrarily set as long as it is the amount which enables the enzyme reaction. The amount of the starch granules in the reaction solution is preferably about 5% by weight or more, more preferably about 10% by weight or more, still more preferably about 20% by weight or more, and most preferably about 30% by weight or more. The amount of the starch granules in the reaction solution is preferably about 60% by weight or less, more preferably about 50% by weight or less, still more preferably about 40% by weight or less, and most preferably about 35% by weight or less.

The amount of the enzyme in the reaction solution can be arbitrarily set as long as it is the amount which enables the enzyme reaction. The amount of the enzyme is preferably the amount enough to carryout the reaction within a reasonable time. As the amount of the enzyme increases, the time required to the reaction becomes shorter. As the amount of the enzyme decreases, the time required to the reaction becomes longer. When the amount of the enzyme is too large, the cost increases too much and the enzyme may be sometimes aggregated to form a precipitate. Therefore, it is preferred to appropriately set the amount of the enzyme.

The amount of the enzyme in the reaction solution is preferably about 0.01% by weight or more, more preferably about 0.05% by weight or more, and still more preferably about 0.1% by weight or more, based on the solid content of the starch granules. The amount of the enzyme in the reaction solution is preferably about 10% by weight or less, more preferably about 5% by weight or less, and still more preferably about 1% by weight or less, based on the solid content of the starch granules. The amount of the enzyme in the reaction solution may be the amount enough to enable proceeding of the enzyme reaction. Therefore, it is not necessary to examine in detail about an activity (number of units) of the enzyme.

(2.2 Enzyme Reaction)

Next, the reaction solution is reacted optionally by heating using a method known in the art. The solution temperature in the reaction step can be any temperature as long as it is the temperature at which the starch granules are not substantially collapsed. The reaction temperature is preferably the temperature at which an enzyme to be used can sufficiently exert an activity and sufficiently retain an activity (that is, less likely to be inactivated). The temperature of the solution in this reaction step is preferably the temperature at which about 50% or more, and more preferably about 80% or more of the activity of the enzyme contained in this solution before the reaction remains after a predetermined reaction time. For example, this temperature can be an optimum temperature ±10° C., more preferably an optimum temperature ±5, still more preferably an optimum temperature ±1° C., and most preferably an optimum pH ±0.5° C., of the enzyme to be used. The reaction temperature is preferably about 10° C. or higher, more preferably about 10° C. or higher, still more preferably about 15° C. or higher, further more preferably about 20° C. or higher, particularly preferably about 30° C. or higher, and most preferably 40° C. or higher. The reaction temperature is preferably about 70° C. or lower, more preferably about 65° C. or lower, particularly preferably about 60° C. or lower, and most preferably 55° C. or lower.

The reaction time can be arbitrarily set taking the reaction temperature, the amount of the enzyme to starch granules into consideration. The reaction time can be preferably for about 1 hour or more, for example, about 2 hours or more, about 3 hours or more, about 6 hours or more, and about 12 hours or more. Although there is no particular upper limit of the reaction time, the reaction time is preferably about 72 hours or less, more preferably about 48 hours or less, still more preferably about 36 hours or less, particularly preferably about 24 hours or less, and most preferably about 20 hours or less.

(2.3 Post-Treatment)

The starch granules subjected to the enzymatic treatment can be used as they are depending on the application. However, it is preferred that the enzyme used and glucide eluted by enzymatic hydrolysis are removed by washing the starch granules subjected to the enzymatic treatment, and followed by dehydration. Washing and dehydration of the starch granules subjected to the enzymatic treatment can be carried out by any method known in the art. Washing and dehydration of the starch granules are conventional methods used for preparation of a starch, and are commonly carried out. Furthermore, it is preferred to obtain the objective enzyme-treated starch granules by drying the starch after dehydration. Drying of the starch after dehydration can be carried out by any method known in the art.

(2.4 Chemical Modification)

The starch granules subjected to the enzymatic treatment can be subjected to a chemical modification, if desired. Not only in the case where the starch granules used in the enzymatic treatment are untreated starch granules or starch granules subjected to a physical treatment, but also in the case where starch granules of some chemically modified starch are used, it is possible to be subjected to a chemical modification which is different from various chemical modifications applied to the chemically modified starch. Examples of the chemical modification include acetylation, adipate crosslinking, oxidation, bleaching, phosphate crosslinking, treatment with octenyl succinic acid, hydroxypropylation, phosphorylation, and phosphoric acid monoesterification. These chemical modification methods are well known in the art. These chemical modifications can be carried out to any degree as long as they are within the scope permitted by the Food Sanitation Law of Japan. In Japan, in order that the chemically modified starch is approved as a food additive, it is essential that various chemical substances in a sample starch are analyzed in accordance with a method for a purity test described in Ministry of Health and Welfare Notification No. 485 and the obtained analytical results meet the following standards:

(a) Acetylated distarch adipate: the content of adipic acid groups shall be 0.135% or less and the content of acetyl groups shall be 2.5% or less;

(b) Acetylated oxidized starch: the content of acetyl groups shall be 2.5% or less and the content of carboxyl groups shall be 1.3% or less;

(c) Acetylated distarch phosphate: the content of acetyl groups shall be 2.5% or less and the content of phosphorus shall be 0.14% or less in terms of P;

(d) Starch sodium octenyl succinate: the content of octenyl succinic acid groups shall be 3.0% or less;

(e) Starch acetate: the content of acetyl groups shall be 2.5% or less;

(f) Oxidized starch: the content of carboxyl groups shall be 1.1% or less;

(g) Hydroxypropyl distarch phosphate: the content of hydroxypropyl groups shall be 7.0% or less and the content of phosphorus shall be 0.14% or less in terms of P;

(h) Hydroxypropyl starch: the content of hydroxypropyl groups shall be 7.0% or less;

(i) Distarch phosphate: the content of phosphorus shall be 0.5% or less in terms of P;

(j) Monostarch phosphate: the content of phosphorus shall be 0.5% or less in terms of P;

(k) Phosphated distarch phosphate: the content of phosphorus shall be 0.5% or less in terms of P;

(l) Bleached starch; the content of carboxyl groups shall be 0.1% or less, the test results of "Confirmatory test (3)" of the oxidized starch described in Ministry of Health and Welfare Notification No. 485 shall be negative, and it shall be reasonably explained that a change in properties, such as viscosity, of the starch is not caused by oxidation. Regarding the countries other than Japan, any degree of a chemical treatment can be carried out as long as it is within the scope permitted in that country. Some kinds of chemical modifications can be used in combination.

(2.5 Physical Treatment)

The starch granules subjected to the enzymatic treatment can be subjected to a physical treatment, if desired. Not only in the case where the starch granules used in the enzymatic treatment are untreated starch granules or a chemically modified starch, but also in the case where the starch granules subjected to some physical treatment are used, it is possible to be subjected to a physical treatment which is different from the physical treatment. Examples of the physical treatment include a heat-moisture treatment and a thermal inhibition treatment.

The "heat-moisture treatment" refers to heating to a temperature of about 95 to about 125° C. in a low moisture state where a starch is not gelatinized in a closed container under the condition of a relative humidity of about 100%. The "low moisture state where a starch is not gelatinized" indicates, for example, the moisture content of about 50% or less. The low moisture state where a starch is not gelatinized may be, for example, the moisture content of about 35% or less, about 30% or less, about 25% or less, or about 20% or less. The heating time of the heat-moisture treatment can vary depending on the method of the heat-moisture treatment. For example, a heat-moisture treatment is carried out in accordance with the method described in Japanese Laid-open Patent Publication No. 6-145203, a heat treatment is carried out by first decompressing to a pressure of about 0 to 500 torr (about 0 to 66.661 kPa) and then introducing pressurized steam, followed by retention at about 100° C. to about 150° C. for about 2 minutes to about 120 minutes. The heat-moisture treatment is described in various documents and can be carried out in accordance with any heat-moisture treatment method known in the art. The heat-moisture treatment is described, for example, in Japanese Laid-open Patent Publication No. 6-145203, Japanese Laid-open Patent Publication No. 4-130102, A Technical Journal on Food Chemistry & Chemicals 2010-2 (P. 37-42) and the like. The temperature, time and the like of the heat-moisture treatment can be appropriately set depending on the objective starch and physical properties thereof.

The "thermal inhibition treatment" refers to the fact that a crystal structure of starch granules is reinforced by subjecting starch granules dried to extremely low water content to a dry heat treatment. The "starch granules dried to extremely low water content" refers to starch granules whose moisture content is less than about 1%. The moisture content of the starch granules subjected to a thermal inhibition treatment is preferably about 0%. The method of drying starch granules to extremely low water content is described, for example, in JP-A-2008-223032 and can be, for example, a method in which the pH of starch granules is adjusted to the pH of 7.0 or more and then dehydration is carried out until the moisture content reaches less than about 1%. In the case of drying to low water content, the pH is preferably 7 or more, more preferably more than 8, still more preferably from 7.5 to 10.5, and further more preferably from 8 to 9.5. The dehydration may be either thermal dehydration or nonthermal dehydration. In the case of a dry heat treatment, a heat treatment is carried out at a sufficient temperature for the time enough to inhibit a starch. Preferably, a heat treatment is carried out at a sufficient temperature for the time enough to make a starch non-aggregative. The heating temperature for a thermal inhibition treatment is preferably higher than about 100° C. The heat treatment temperature is preferably about 200° C. or lower. The heating temperature for a thermal inhibition treatment is more preferably from about 120° C. to about 180° C., particularly preferably from about 140° C. to about 160° C., and most preferably from about 160° C. The level of inhibition depends on the pH, heating temperature and heating time. As the pH becomes higher, a more highly inhibited starch is obtained. As the temperature of the heat treatment becomes higher, a more highly inhibited starch is obtained. As the time of the heat treatment becomes longer, a more highly inhibited starch is obtained. The thermal treatment time for a thermal inhibition treatment can be, for example, about 3 hours or more, and preferably about 20 hours or less. The thermal inhibition treatment is described in various documents and can be carried out in accordance with any thermal inhibition treatment method known in the art. The thermal inhibition treatment is described, for example, in U.S. Pat. No. 6,221,420, Pamphlet of International Publication No. WO 95/04082, and Japanese Laid-open Patent Publication No. 2008-223032. The temperature, time, and the like of the thermal inhibition treatment can be appropriately set depending on the objective starch and physical properties thereof. The physical treatment can be carried out in accordance with the method well known in the art.

Examples of the heat-moisture-treated starch include, for example, "Delicastar series", "Naturastar series", and "AMYLOGEL" manufactured by SANWA CORNSTARCH CO., LTD.; and "ROADSTER" manufactured by Nihon Shokuhin Kako Co., Ltd. Examples of the thermally inhibited starch include "NOVATION series" manufactured by National Starch Corp.

(3. Characteristics of Enzyme-Treated Starch Granules of the Present Invention)

In a specific embodiment, the enzyme-treated starch of the present invention is an enzyme-treated starch having a high viscosity and a gel forming ability, and the enzyme-treated starch is an enzyme-treated starch obtained by treating starch granules with an enzyme at a temperature of about 10° C. or higher and about 70° C. or lower.

In another specific embodiment, the enzyme-treated starch of the present invention is an enzyme-treated starch having a high viscosity and a gel forming ability; the enzyme-treated starch is a starch obtained by treating starch granules of an untreated starch with a starch hydrolase under the condition where the starch granules are not dissolved; the enzyme-treated starch is not modified on hydroxyl groups at the positions 2, 3 and 6 of the glucose residues; and the enzyme-treated starch can form a gel having a Young's modulus higher than that of the untreated starch or a rupture stress higher than that of the untreated starch, when measured by a rheometer.

(3.1 Viscosity)

It is well known that when a starch is heated together with a predetermined amount or more of water, starch granules generally cause a gelatinization phenomenon such as swelling, an increase in transparency, and an increase in viscosity. The starch granules are collapsed by further heating. In order to measure a change in viscosity associated with a series of these events, an amylograph manufactured by Brabender Inc. is practical and is widely used, although there are some methods. The amylograph is that in which the object is heated at a predetermined rate and a relationship between the temperature and the viscosity of the object is recorded. That is, starch granules undergo swelling with heating, while manifestation of viscosity and an increase in viscosity arise in the amylograph. Then, when the swelling of the starch granules becomes to maximum, the viscosity also reaches a peak. This viscosity is called maximum viscosity. Further heating causes collapse of the starch granules and simultaneously causes a decrease in viscosity. This degree of the decrease in viscosity is called breakdown. A viscosity curve obtained by this amylograph varies depending on the origin and production method of the starch, and is a measuring method showing features of the starch.

For example, the measurement by the amylograph is carried out as follows. A starch suspension is prepared in 450 ml of water so as to obtain a predetermined amount of enzyme-treated starch granules (for example, the concentration of a wheat starch is 8.5% by weight, the concentration of a corn starch is 7.0% by weight, and the concentration of a cassava starch is 6.0% by weight, on the dry matter basis), put in a sample container, and then warmed to 50° C. while rotating them. Then the suspension is heated to 95° C. at 1.5° C./min and maintained at 95° C. for 15 minutes, followed by cooling at 1.5° C./min. The measurement is carried out using an amylograph VISCOGRAPH-E manufactured by Brabender Inc. under the conditions of a rotation number of a sample container of 75 rpm and a measuring cartridge of 700 cmg. Wherein, the viscosity reached to a peak is regarded as a maximum viscosity, and a difference between this maximum viscosity and a viscosity at the point after maintaining at 95° C. for 15 minutes is regarded as breakdown. This difference is also called as a breakdown viscosity. When the difference between the maximum viscosity and the viscosity at the point after maintaining at 95° C. for 15 minutes is less than 100 BU, it is said that the starch has no "breakdown".

In the case where the enzyme-treated starch granules of the present invention are prepared from an untreated starch and have not been subjected to either a chemical modification or a physical treatment, it is preferred that the enzyme-treated starch granules of the present invention have a maximum viscosity which accounts for about 50% or more (more preferably about 60% or more, particularly preferably about 70% or more, and most preferably about 80% or more, about 90% or more, or about 100% or more) of the maximum viscosity of the untreated starch, when measured by an amylograph under the above conditions. There is no particular upper limit of the maximum viscosity of the enzyme-treated starch of the present invention. For example, the maximum viscosity of the enzyme-treated starch of the present invention can be about 300% or less, about 250% or less, about 200% or less, about 150% or less, about 110% or less, and about 100% or less of the maximum viscosity of the untreated starch, when measured by an amylograph under the above conditions. For example, it is preferred that the enzyme-treated wheat starch can form a gel having a viscosity which accounts for 70% or more and 200% or less (more preferably 80% or more and 200% or less) of the viscosity of the untreated wheat starch.

For example, regarding the wheat starch, a maximum viscosity of the native wheat starch when measured by an amylograph under the above conditions is from about 550 BU to about 650 BU. On the other hand, in the case where the enzyme-treated starch granules of the present invention are prepared from an untreated wheat starch and have not been subjected to either a chemical modification or a physical treatment, a maximum viscosity of the enzyme-treated wheat starch granules of the present invention when measured by an amylograph under the above conditions may be preferably about 400 BU or more, more preferably about 420 BU or more, particularly preferably about 450 BU or more, most preferably about 500 BU or more, for example, about 550 BU or more, about 570 BU or more, about 600 BU or more, or about 650 BU or more. In a specific embodiment, it is possible to make the maximum viscosity of the enzyme-treated wheat starch granules of the present invention when measured by an amylograph under the above conditions to about 660 BU or more, about 670 BU or more, or about 700 BU or more. The maximum viscosity of the enzyme-treated wheat starch granules of the present invention when measured by an amylograph under the above conditions can be, for example, about 900 BU or less, about 850 BU or less, about 800 BU or less, or about 750 BU or less.

For example, regarding the corn starch, a maximum viscosity of the native corn starch when measured by an amylograph under the above conditions is from about 400 BU to about 500 BU. On the other hand, in the case where the enzyme-treated starch granules of the present invention are prepared from an untreated corn starch and have not been subjected to either a chemical modification or a physical treatment, a maximum viscosity of the enzyme-treated corn starch granules of the present invention when measured by an amylograph under the above conditions may be preferably about 250 BU or more, more preferably about 270 BU or more, particularly preferably about 300 BU or more, most preferably about 350 BU or more, for example, about 400 BU or more, about 420 BU or more, about 440 BU or more, or about 450 BU or more. The maximum viscosity of the enzyme-treated corn starch granules of the present invention when measured by an amylograph under the above conditions can be, for example, about 600 BU or less, about 550 BU or less, about 520 BU or less, or about 500 BU or less.

For example, regarding the cassava starch, a maximum viscosity of the native cassava starch when measured by an amylograph under the above conditions is from about 700 BU to about 800 BU. On the other hand, in the case where the enzyme-treated starch granules of the present invention are prepared from an untreated cassava starch and have not been subjected to either a chemical modification or a physical treatment, a maximum viscosity of the enzyme-treated cassava starch granules of the present invention when measured by an amylograph under the above conditions may be preferably about 500 BU or more, more preferably about 520 BU or more, particularly preferably about 530 BU or more, most preferably about 550 BU or more, for example, about 600 BU or more, about 620 BU or more, about 630 BU or more, or about 650 BU or more. The maximum viscosity of the enzyme-treated cassava starch granules of the present invention when measured by an amylograph under the above conditions can be, for example, about 900 BU or less, about 850 BU or less, about 800 BU or less, or about 770 BU or less.

In the case where the enzyme-treated starch granules of the present invention are prepared from an untreated starch and have not been subjected to either a chemical modification or a physical treatment, the enzyme-treated starch granules of the present invention have breakdown when measured by an amylograph. Some conventional starches have no breakdown, whereas, the enzyme-treated starch granules of the present invention have breakdown.

For example, in the case where the untreated starch is a wheat starch, a corn starch or a cassava starch and neither a chemical modification nor a physical treatment is carried out, the obtained enzyme-treated starch has a breakdown viscosity of about 100 BU or more.

In the case where the untreated starch is a wheat starch and neither a chemical modification nor a physical treatment is carried out, the breakdown viscosity of the obtained enzyme-treated starch is preferably about 100 BU or more, more preferably about 120 BU or more, still more preferably about 130 BU or more, and most preferably about 150 BU or more. In the case where the untreated starch is a wheat starch and neither a chemical modification nor a physical treatment is carried out, although there is no particular upper limit of the breakdown viscosity of the obtained enzyme-treated starch, the breakdown viscosity of the obtained enzyme-treated starch can be, for example, about 500 BU or less, about 450 BU or less, about 400 BU or less, about 350 BU or less, or about 300 BU or less.

In the case where the untreated starch is a corn starch and neither a chemical modification nor a physical treatment is carried out, the breakdown viscosity of the obtained enzyme-treated starch is preferably about 100 BU or more, more preferably about 110 BU or more, still more preferably about 120 BU or more, and most preferably about 150 BU or more. In the case where the untreated starch is a corn starch and neither a chemical modification nor a physical treatment is carried out, although there is no particular upper limit of the breakdown viscosity of the obtained enzyme-treated starch, the breakdown viscosity of the obtained enzyme-treated starch can be, for example, about 300 BU or less, about 290 BU or less, about 280 BU or less, 200 BU or less, about 190 BU or less, or about 180 BU or less.

In the case where the untreated starch is a cassava starch and neither a chemical modification nor a physical treatment is carried out, the breakdown viscosity of the obtained enzyme-treated starch is preferably about 300 BU or more, more preferably about 320 BU or more, still more preferably about 330 BU or more, and most preferably about 350 BU or more. In the case where the untreated starch is a cassava starch and neither a chemical modification nor a physical treatment is carried out, although there is no particular upper limit of the breakdown viscosity of the obtained enzyme-treated starch, the breakdown viscosity of the obtained enzyme-treated starch can be, for example, about 550 BU or less, about 540 BU or less, about 530 BU or less, about 500 BU or less, about 480 BU or less, or about 470 BU or less.

(3.2 Gel Forming Ability)

It is well known that when the concentration of a starch of a starch paste reaches a predetermined concentration or more, a starch gel is formed by cooling it. Similarly to the viscosity, physical properties of this starch gel vary depending on the origin and production method of the starch, and the starch is used in various foods taking features of this gelling physical properties into consideration. Some methods of measuring physical properties of the gel are practically used, and one of them is a method of measuring using a rheometer. The gel forming ability can be measured by the following method using a rheometer. For example, a starch paste is filled in a casing, heated, and then refrigerated for 16 hours or 21 days (for example, at about 5° C.) and, after returning to room temperature (for example, at about 25° C.), physical properties of the gel are measured by a rheometer.

The specific measuring method using a rheometer is as described in the aforementioned 1.2.2. In the case where the enzyme-treated starch granules of the present invention are prepared from an untreated wheat starch and have not been subjected to either a chemical modification or a physical treatment, it is preferred that the enzyme-treated wheat starch has a rupture stress which accounts for 110% or more and 300% or less of the rupture stress of the untreated wheat starch, or has a Young's modulus which accounts for 110% or more and 500% or less (110% or more and 330% or less in an embodiment) of the Young's modulus of the untreated wheat starch.

In the case where the enzyme-treated starch granules of the present invention are prepared from an untreated corn starch and have not been subjected to either a chemical modification or a physical treatment, it is preferred that the enzyme-treated corn starch has a rupture stress which accounts for 110% or more and 300% or less of the rupture stress of the untreated corn starch, or has a Young's modulus which accounts for 110% or more and 500% or less (330% or less in an embodiment) of the Young's modulus of the untreated corn starch.

In the case where the enzyme-treated starch granules of the present invention are prepared from an untreated cassava starch and have not been subjected to either a chemical modification or a physical treatment, it is preferred that the enzyme-treated cassava starch has a rupture stress which accounts for 110% or more and 300% or less of the rupture stress of the untreated cassava starch, or has a Young's modulus which accounts for 110% or more and 500% or less (330% or less in an embodiment) of the untreated cassava starch.

In the case where the enzyme-treated starch granules of the present invention are prepared from an untreated wheat starch and have not been subjected to either a chemical modification or a physical treatment, and the untreated starch is a wheat starch, the rupture stress of the obtained enzyme-treated starch is preferably about 150 g or more, more preferably about 160 g or more, still more preferably about 170 g or more, particularly preferably about 180 g or more, and most preferably about 200 g or more. In the case where the untreated starch is a wheat starch, although there is no particular upper limit of the rupture stress of the obtained enzyme-treated starch, the rupture stress of the obtained enzyme-treated starch can be, for example, about 450 g or less, about 440 g or less, about 430 g or less, about 420 g or less, about 410 g or less, or about 400 g or less.

In the case where the untreated starch is a corn starch and neither a chemical modification nor a physical treatment is carried out, the rupture stress of the obtained enzyme-treated starch is preferably about 210 g or more, more preferably about 220 g or more, still more preferably about 230 g or more, and most preferably about 240 g or more, and, in one embodiment, is 250 g or more. In the case where the untreated starch is a corn starch and neither a chemical modification nor a physical treatment is carried out, although there is no particular upper limit of the rupture stress of the obtained enzyme-treated starch, the rupture stress of the obtained enzyme-treated starch can be, for example, about 450 g or less, about 440 g or less, about 430 g or less, about 420 g or less, about 410 g or less, or about 400 g or less.

In the case where the untreated starch is a cassava starch and neither a chemical modification nor a physical treatment is carried out, the rupture stress of the obtained enzyme-treated starch is preferably about 55 g or more, more preferably about 60 g or more, still more preferably about 65 g or more, and most preferably about 70 g or more. In the case where the untreated starch is a cassava starch and neither a chemical modification nor a physical treatment is carried out, although there is no particular upper limit of the rupture stress of the obtained enzyme-treated starch, the rupture stress of the obtained enzyme-treated starch can be, for example, about 150 g or less, about 140 g or less, about 130 g or less, about 120 g or less, about 110 g or less, or about 100 g or less.

In the case where the untreated starch is a wheat starch and neither a chemical modification nor a physical treatment is carried out, the Young's modulus of the obtained enzyme-treated starch is preferably about $5.0 \times 10^6$ dyn/cm$^2$ or more, more preferably about $5.2 \times 10^6$ dyn/cm$^2$ or more, still more preferably about $5.4 \times 10^6$ dyn/cm$^2$ or more, and most preferably about $5.6 \times 10^6$ dyn/cm$^2$ or more. In the case where the untreated starch is a wheat starch and neither a chemical modification nor a physical treatment is carried out, although there is no particular upper limit of the Young's modulus of the obtained enzyme-treated starch, the Young's modulus of the obtained enzyme-treated starch can be, for example, about $8.0 \times 10^6$ dyn/cm$^2$ or less, about $7.5 \times 10^6$ dyn/cm$^2$ or less, about $7.0 \times 10^6$ dyn/cm$^2$ or less, about $6.9 \times 10^6$ dyn/cm$^2$ or less, about $6.8 \times 10^6$ dyn/cm$^2$ or less, or about $6.7 \times 10^6$ dyn/cm$^2$ or less.

In the case where the untreated starch is a corn starch and neither a chemical modification nor a physical treatment is carried out, the Young's modulus of the obtained enzyme-treated starch is preferably about $6.0 \times 10^6$ dyn/cm$^2$ or more, more preferably about $6.2 \times 10^6$ dyn/cm$^2$ or more, still more preferably about $6.3 \times 10^6$ dyn/cm$^2$ or more, and most preferably about $6.5 \times 10^6$ dyn/cm$^2$ or more. In the case where the untreated starch is a corn starch and neither a chemical modification nor a physical treatment is carried out, although there is no particular upper limit of the Young's modulus of the obtained enzyme-treated starch, the Young's modulus of the obtained enzyme-treated starch can be, for example, about $9.0 \times 10^6$ dyn/cm$^2$ or less, about $8.9 \times 10^6$ dyn/cm$^2$ or less, about $8.8 \times 10^6$ dyn/cm$^2$ or less, about $8.7 \times 10^6$ dyn/cm$^2$ or less, about $8.6 \times 10^6$ dyn/cm$^2$ or less, or about $8.5 \times 10^6$ dyn/cm$^2$ or less.

In the case where the untreated starch is a cassava starch and neither a chemical modification nor a physical treatment is carried out, the Young's modulus of the obtained enzyme-treated starch is preferably about $5.2 \times 10^5$ dyn/cm$^2$ or more, more preferably about $5.4 \times 10^5$ dyn/cm$^2$ or more, still more preferably about $5.6 \times 10^5$ dyn/cm$^2$ or more, and most preferably about $5.8 \times 10^5$ dyn/cm$^2$ or more. In the case where the untreated starch is a cassava starch and neither a chemical modification nor a physical treatment is carried out, although there is no particular upper limit of the Young's modulus of the obtained enzyme-treated starch, the Young's modulus of the obtained enzyme-treated starch can be, for example, about $2.7 \times 10^6$ dyn/cm$^2$ or less, about $2.5 \times 10^6$ dyn/cm$^2$ or less, about $2.4 \times 10^6$ dyn/cm$^2$ or less, about $2.3 \times 10^6$ dyn/cm$^2$ or less, about $2.2 \times 10^6$ dyn/cm$^2$ or less, about $2.0 \times 10^6$ dyn/cm$^2$ or less, about $1.8 \times 10^6$ dyn/cm$^2$ or less, about $1.6 \times 10^6$ dyn/cm$^2$ or less, about $1.5 \times 10^6$ dyn/cm$^2$ or less, about $1.4 \times 10^6$ dyn/cm$^2$ or less, about $1.3 \times 10^6$ dyn/cm$^2$ or less, about $1.2 \times 10^6$ dyn/cm$^2$ or less, or about $1.1 \times 10^6$ dyn/cm$^2$ or less.

In a specific embodiment, in the case where the untreated starch is a wheat starch and neither a chemical modification nor a physical treatment is carried out, the obtained enzyme-treated starch has breakdown (about 100 BU or more), and a rupture stress of about 150 to about 450 (g) or a Young's modulus of about 5,000,000 to about 8,000,000 (dyn/cm$^2$).

In a specific embodiment, in the case where the untreated starch is a corn starch and neither a chemical modification nor a physical treatment is carried out, the obtained enzyme-treated starch has breakdown (about 100 BU or more), and a rupture stress of about 210 to about 450 (g) (about 220 to about 450 (g) in one embodiment) or a Young's modulus of about 6,000,000 to about 9,000,000 (dyn/cm$^2$).

In a specific embodiment, in the case where the untreated starch is a cassava starch and neither a chemical modification nor a physical treatment is carried out, the obtained enzyme-treated starch has breakdown (about 100 BU or more), and a rupture stress of about 55 to about 150 (g) or a Young's modulus of about 520,000 to about 2,700,000 (dyn/cm$^2$) (about 520,000 to about 1,600,000 (dyn/cm$^2$) in one embodiment).

Also, in the case where a chemically modified starch or a physically treated starch is used as starch granules, or in the case where a chemical modification or a physical treatment is carried out after an enzymatic treatment, an improvement in gel forming ability can be obtained similarly to the above.

(3.3 Enzyme-Treated Starch in which Hydroxyl Groups at Positions 2, 3 and 6 of Glucose Residues are not Modified)

In the case where the enzyme-treated starch granules of the present invention are prepared from an untreated starch, a physically treated starch or a bleached starch and have not been subjected to chemical modification, since the enzyme-treated starch of the present invention is not subjected to an artificial chemical treatment, hydroxyl groups at the positions 2, 3 and 6 of glucose residues are not modified as compared with a native starch (i.e., untreated starch). A starch, in which hydroxyl groups at the positions 2, 3 and 6 of glucose residues are modified, refers to a modified starch (also referred to as a chemically modified starch) subjected to so-called chemical modification by an industrial process. According to the ministerial ordinance to revise a part of the Ordinance For Enforcement of the Food Sanitation Act notified in Ministry of Health and Welfare Notification No. 485 dated Oct. 1, 2008, the following 11 items of modified starches will be dealt as an additive:

acetylated distarch adipate;
acetylated oxidized starch;
acetylated distarch phosphate;
starch sodium octenyl succinate;
starch acetate;
oxidized starch;
hydroxypropyl distarch phosphate;
hydroxypropyl starch;
distarch phosphate;
monostarch phosphate; and
phosphated distarch phosphate. In Ministry of Health and Welfare Notification No. 485, a method for a purity test of these starches is described. Therefore, it is possible to judge that a sample starch is not a starch subjected to a chemical modification, for example, by analyzing various chemical substances in the sample starch, such as adipic acid groups, acetyl groups, and carboxyl groups in accordance with a method for a purity test of the above various modified starches described in Ministry of Health and Welfare Notification No. 485 dated Oct. 1, 2008, comparing with the results of analysis of a raw material native starch carried out for comparison reference, and confirming there is no increase in the content of corresponding various chemical substances. Particularly, it is possible to judge that a sample starch is not a starch subjected to a chemical modification, by measuring the content of adipic acid groups, the content of acetyl groups, the content of carboxyl groups, the content of vinyl acetate, the content of octenyl succinic acid groups, the content of hydroxypropyl groups, and the content of propylene chlorohydrins, and confirming that the contents of them do not increase as compared with those of the raw material native starch. It is preferred to use the content of adipic acid groups, the content of acetyl groups, the content of carboxyl groups, the content of octenyl succinic acid groups, the content of hydroxypropyl groups, and the content of propylene chlorohydrins as evaluation criteria. It is recognized that a bleached starch subjected to a bleaching treatment using sodium hypochlorite is distributed as a food. It is also possible to judge this bleached starch by measuring the content of carboxyl groups using a method for a purity test similar to that in the above oxidized starch. The chemical modified starch other than the above modified starches of 11 items cannot be used in a food since it is not recognized by the Food Sanitation Law of JAPAN. Therefore, the chemically modified starch other than the above 11 items are not basically used in JAPAN and are not distributed. Accordingly, practically, in the case of confirming whether or not hydroxyl groups at the 2-, 3- and 6-positions of a glucose residue of the starch of the invention of the present application are modified, it is not necessary to confirm whether or not a chemical modification other than the above chemical modification has been subjected.

In the present description, in the case where "hydroxyl groups at the positions 2, 3 and 6 of glucose residues are not modified", it is preferred that all hydroxyl groups at the positions 2, 3 and 6 of glucose residues are not modified. However, in the case where hydroxyl groups are subjected to some modification in a natural state, some modifications may be contained. In this case, based on the total number of hydroxyl groups at the positions 2, 3 and 6 of glucose residues, preferably about 70% or more, more preferably about 80% or more, still more preferably about 90% or more, particularly preferably about 95% or more, about 96% or more, about 97% or more, about 98% or more, about 99% or more, or about 99.5%, and most preferably about 100% of hydroxyl groups are not modified.

(4. Food of the Present Invention)

In a specific embodiment, the food of the present invention is a food produced by a method including the steps of treating starch granules with an enzyme at a temperature of about 10° C. or higher and about 70° C. or lower to obtain an enzyme-treated starch; mixing a food material, the enzyme-treated starch and water to obtain a mixture; heating the mixture thereby gelatinizing the enzyme-treated starch in the mixture; and cooling the mixture containing the gelatinized enzyme-treated starch thereby gelling the starch to obtain a starch gel-containing food.

In another specific embodiment, the food of the present invention is a heat cooked starch-containing food containing an enzyme-treated starch having a high viscosity and a gel forming ability. In another specific embodiment, the starch-containing food of the present invention is a food produced by a method including mixing a food material with the enzyme-treated starch, and then heating the mixture.

In the present description, the starch gel-containing food refers to a food containing a starch gel. If the food contains the starch gel, it is not necessary for the food to be entirely in a gel form. For example, in the case of gelatinous foods such as custard pudding; and gel-like traditional Japanese-style confectioneries such as kudzu starch cake and Uiro, entire foods form a gel. In the case of fat or oil-containing foods such as whipping cream and ice cream; and sauces such as meat sauce, foods are not entirely in a gel form but contain a micro starch gel, and are therefore included in the starch gel-containing food of the present invention. Also, bakeries and Western-style confectioneries are included in the starch gel-containing food of the present invention since they contain a starch gel with the decreased water content which was obtained by once forming a gel during the production process, and baking the gel.

In a specific embodiment, the food of the present invention can be prepared by using enzyme-treated starch granules. The starch produced by the method of the present invention can be utilized in the same application as in a conventional starch. By utilizing the enzyme-treated starch of the present invention in a food, physical properties and texture of the food are altered. The enzyme-treated starch of the present invention can be used in almost all of compositions for eating and drinking or compositions for food additives prepared by utilizing a conventional starch.

In the food of the present invention, any material used usually in the objective composition and food can be used as long as an excellent effect obtained by the enzyme-treated starch granules is not impaired. In a preferred embodiment, the starch of the present invention forms a gel in the food of the present invention.

In the case where the enzyme-treated starch of the present invention is utilized in a high moisture content type food, it imparts a body, imparts natural elasticity by a strong gel forming ability, and also imparts appropriate smooth texture in mouth. The high moisture content type food refers to a food in which the amount of moisture per 100 g of the edible portion is more than 40 g in a state at the time of eating. Examples of the high moisture content type food include, for example, traditional Japanese-style confectioneries, fat or oil-containing foods, gelatinous foods, fish meat and animal meat processed foods, salsa and sauces, and noodles.

In the case where the enzyme-treated starch of the present invention is utilized in a low moisture content type food, it is possible to impart smooth texture with nice melt in mouth. The low moisture content type food refers to a food in which the amount of moisture per 100 g of the edible portion is 40 g or less in a state at the time of eating. Examples of the low moisture content type food include, for example, bakeries, Western-style confectioneries, fried foods, and jelly candies.

As described above, the high moisture content type food and the low moisture content type food are classified by the amount of moisture, per 100 g of the edible portion, which is more than 40 g, or 40 g or less. Provided that the food in which the amount of moisture per 100 g of the edible portion is around 40 g (35 to 50 g) may sometimes exhibit contradicting physical properties depending on the form, even in the case of the same amount of moisture. Also, in the case of the fried food, it is judged by the amount of moisture for the coating part in which core food materials have been removed.

The amounts of water per 100 g of the edible portion of various foods are exemplified below (extract from Standard Tables of Food Composition in Japan (Fifth Revised and Enlarged Edition); the number in parenthesis denotes the amount of moisture):

(1) Bakeries: white table bread (38.0 g), hard biscuit (2.6 g), pie pastry (32.0 g), Eisei-boro (4.5 g);
(2) Traditional Japanese-style confectioneries: Uiro (54.5 g), Kudzu-manju (45.0 g), Daifuku-mochi (41.5 g);
(3) Western-style confectioneries: sponge cake (32.0 g), Kasutera (25.6 g), hot cake (40.0 g);
(4) Fat- or oil-containing foods: whipping cream (milk fat type, 42.1 g), whipping cream (vegetable fat type, 41.2 g), ice creams (ice milk: 65.6 g, lactic ice: 60.4 g);
(5) Gelatinous foods: custard pudding (74.1 g);
(6) Fish meat and animal meat processed foods: Sumaki-kamaboko (75.8 g), Yakinuki-kamaboko (72.8 g), Vienna sausage (53.0 g);
(7) Salsa and sauces: worcester sauce (61.7 g), meat sauce (78.8 g), Thousand Island dressing (44.1 g); and
(8) Jelly candies: jelly candy (16 g), jelly beans (9.5 g).

By using the enzyme-treated starch of the present invention in these foods, the following physical properties, for example, are improved as compared with the case of using a conventional starch:

(1) In bakeries, textures with softness and nice melt in mouth is imparted. Examples of bakeries include breads, cookies, biscuits, pizza crusts, pie pastries, corn cups for ice creams, pastries of Monaka, and puff of cream puff.
(2) In traditional Japanese-style confectioneries, appropriate hardness, brittleness, and appropriate viscoelasticity and sticky textures are imparted. Examples of traditional Japanese-style confectioneries include kudzu starch cake, Uiro, and Manju.
(3) In Western-style confectioneries, improvement of volumes by nice puffing after baking as well as soft and nice textures are imparted. Examples of Western-style confectioneries include sponge cake, chiffon cake, Kasutera, Madeleine, financier, pound cake, and Swiss roll.
(4) In fat- or oil-containing foods, while maintaining appropriate body and shape retention, nice melt in mouth and smooth texture is imparted. Examples of the fat- or oil-containing food include custard cream, flour paste, filling, whipping cream, and ice creams (for example, ice milk, lactic ice).
(5) In gelatinous foods, while maintaining sticky and chewy, nice melt in mouth and smooth texture is imparted. Examples of the gelatinous food include jelly, pudding, mousse, yogurt, and goma-dofu.

(6) In fish meat and animal meat processed foods, while having elasticity with nice chewiness, the effect of small change with time is imparted. Examples of fish meat and meat processed foods include kamaboko and sausage.

(7) In salsa and sauces, while having nice body and shape retention, properties of being less likely to cause dropping because of nice adhesion onto a food as well as less stickiness and thread-forming sensation, and smooth textures are imparted. Examples of salsa and sauces include salsa for split and broiled fish, glaze for mitarashi dango, fruit sauce, white sauce, and dressing.

(8) In fried foods, crispy light texture is imparted. Examples of fried foods include tempura and fried prawn.

(9) In noodles, sticky texture rich in chewiness is imparted. Examples of noodles include udon, somen, hiyamugi, Chinese noodles, buckwheat noodles, macaroni, and spaghetti.

(10) In jelly candies, while having appropriate elasticity, nice melt in mouth and smooth texture is imparted. Examples of jelly candies include jelly candy and jellybeans.

In the food of the present invention, the enzyme-treated starch of the present invention can be used in the same amount as that of the starch which has been conventionally used in the food. A conventional starch may be used as a part and the remainder may be replaced by the enzyme-treated starch of the present invention. The enzyme-treated starch of the present invention preferably accounts for about 50% by weight or more, more preferably about 60% by weight or more, still more preferably about 70% by weight or more, further preferably about 80% by weight or more, particularly preferably about 90% by weight or more, and most preferably 100% by weight, of a usual use amount of the starch. In other word, most preferably, the entire amount of a conventional starch is replaced by the enzyme-treated starch of the present invention.

(5. Method for Producing Starch Gel-Containing Food)

In a specific embodiment, the method for producing a starch gel-containing food of the present invention includes the steps of treating starch granules with an enzyme at a temperature of about 10° C. or higher and about 70° C. or lower to obtain an enzyme-treated starch; mixing a food material, the enzyme-treated starch and water to obtain a mixture; heating the mixture thereby gelatinizing the enzyme-treated starch in the mixture; and cooling the mixture containing the gelatinized enzyme-treated starch thereby gelling the starch to obtain a starch gel-containing food. In the production of a conventional food, starch granules are not subjected to an enzymatic treatment during the food production process.

The step of treating starch granules with an enzyme at a temperature of about 10° C. or higher and about 70° C. or lower to obtain an enzyme-treated starch can be carried out as described in detail in the aforementioned "2.2 Enzyme Reaction". As described above, the starch granules can be starch granules of an untreated starch, a physically treated starch or a chemically modified starch. In the case where it is preferable to obtain an enzyme-treated starch which is dealt as a food, starch granules are starch granules of an untreated starch, a physically treated starch or a bleached starch, and the starch granules are not subjected to a chemical modification in any stage until a starch gel-containing food is obtained using the starch granules. In a specific embodiment, the starch granule is a starch granule of an untreated starch or a physically treated starch, the step of chemically modifying the enzyme-treated starch is further included, and the chemically modified enzyme-treated starch is mixed with the food material and water. In another specific embodiment, the starch granules are starch granules of an untreated starch or a chemically modified starch, the step of physically treating the enzyme-treated starch is further included, and the physically treated enzyme-treated starch is mixed with the food material and water.

Next, a mixture is obtained by mixing a food material, the enzyme-treated starch and water. A mixing method and a mixing ratio of the food material, the enzyme-treated starch and water can be a mixing method and a mixing ratio in accordance with a usual method for producing the objective food.

Next, the mixture is heated thereby gelatinizing the enzyme-treated starch in the mixture. The heating can be heat cooking. Heating can be carried out under the same conditions as those of heat cooking in a usual method for producing the objective food.

Next, the mixture containing the gelatinized enzyme-treated starch is cooled, thereby gelling the starch to obtain a starch gel-containing food. Cooling may be carried out by leaving the mixture after heating at room temperature, or carried out in a refrigerator or the like.

In the embodiment in which the enzyme-treated starch of the present invention is used, the food of the present invention can be produced in the same method as in the case of a usual starch, except that the enzyme-treated starch is used. The method for producing the starch-containing food of the present invention includes the steps of adding an enzyme-treated starch to a food material and mixing them; and heat cooking the mixture.

The enzyme-treated starch of the present invention has excellent viscosity and gel forming ability as compared with a conventional untreated starch. Therefore, by adding the enzyme-treated starch of the present invention to the food material, mixing them and heat cooking the mixture, this enzyme-treated starch is gelatinized and then cooled to form a gel. Accordingly, the obtained heat cooked material is provided with excellent physical properties (for example, excellent body, natural elasticity, nice melt in mouth, smooth texture, sticky texture, and soft texture) as compared with the heat cooked material in which a conventional untreated starch is used. In the present description, the food may also be a beverage.

In the present description, "heat cooking" refers to heating of a mixture of a food material and a starch. Preferably, heat cooking can be heating at a collapse temperature or higher of starch granules. For example, the mixture of a food material and a starch can be heated at about 70° C. or higher, about 80° C. or higher, about 90° C. or higher or about 95° C. or higher. Preferably, heat cooking is carried out at a temperature at which excess denaturation of the food material and the starch does not arise. For example, the mixture of a food material and a starch can be heated at about 200° C. or lower, about 150° C. or lower, about 130° C. or lower or about 110° C. or lower. Heat cooking is carried out for a usual heat cooking time of the objective food.

Heat cooking is preferably carried out in the presence of some degree of moisture. Usually, when starch granules are heated in the presence of a predetermined amount or more of water, swelling arises, transparency increases and viscosity increases. When the food material contains too much moisture, it is not necessary to add water to the mixture of a food material and a starch. However, when the food material contains small amount of moisture, it is preferred to add water to the mixture of a food material and a starch. It is noted that in the case of a food which does not contain food materials other than water and a starch, like a sugar-free kuzuyu, water is considered as the food material.

Heat cooking can be a part of the method for producing the objective food. For example, in the case of a gelatinous food such as jelly, it can be heat cooled after cooking at a temperature of, for example, about 5 to 10° C.

(6. Explanation of Sequence)

SEQ ID NO: 1 is a nucleotide sequence encoding α-amylase derived from *Aspergillus oryzae*;

SEQ ID NO: 2 is an amino acid sequence of α-amylase derived from *Aspergillus oryzae*;

SEQ ID NO: 3 is a nucleotide sequence encoding α-amylase derived from *Aspergillus niger*;

SEQ ID NO: 4 is an amino acid sequence of α-amylase derived from *Aspergillus niger*;

SEQ ID NO: 5 is a nucleotide sequence encoding amyloglucosidase derived from *Aspergillus niger*;

SEQ ID NO: 6 is an amino acid sequence of amyloglucosidase derived from *Aspergillus niger*;

SEQ ID NO: 7 is a nucleotide sequence encoding isoamylase derived from *Flavobacterium* sp.;

SEQ ID NO: 8 is an amino acid sequence of isoamylase derived from *Flavobacterium* sp.;

SEQ ID NO: 9 is a nucleotide sequence encoding isoamylase derived from *Pseudomonas amyloderamosa*;

SEQ ID NO: 10 is an amino acid sequence of isoamylase derived from *Pseudomonas amyloderamosa*;

SEQ ID NO: 11 is a nucleotide sequence encoding α-glucosidase derived from *Aspergillus niger*;

SEQ ID NO: 12 is an amino acid sequence of α-glucosidase derived from *Aspergillus niger*;

SEQ ID NO: 13 is a nucleotide sequence encoding cyclodextrin glucanotransferase derived from *Paenibacillus macerans* (also classified as *Bacillus macerans*).

SEQ ID NO: 14 is an amino acid sequence of cyclodextrin glucanotransferase derived from *Paenibacillus macerans* (also classified as *Bacillus macerans*).

EXAMPLES

Next, the present invention will be described in more detail by way of Examples, but the present invention is not limited to these Examples. It is noted that in the Examples, a viscosity was measured by an amylograph from Brabender Inc., and physical properties of a gel were measured by a rheometer from Rheotech Inc.

(1. Method for Measurement of Viscosity)

A viscosity was measured by the following method. A starch suspension was adjusted in 450 ml of water so that the concentration of a wheat starch was 8.5% by weight, the concentration of a corn starch was 7.0% by weight and the concentration of a cassava starch was 6.0% by weight, on the dry matter basis and, put in a sample container, and then warmed to 50° C. while rotating them. Then the suspension was heated to 95° C. at 1.5° C./min, and maintained at 95° C. for 15 minute, followed by cooling at 1.5° C./min. The measurement was carried out using an amylograph VISCO-GRAPH-E manufactured by Brabender Inc. under the conditions of a rotation number of the sample container of 75 rpm and a measuring cartridge of 700 cmg. Wherein, the viscosity reached to a peak was regarded as a maximum viscosity, and a difference between this maximum viscosity and a viscosity soon after maintaining at 95° C. for 15 minutes was regarded as breakdown.

(2. Method for Measurement of Physical Properties of a Gel)

Physical properties of a gel were measured by the following method. A starch paste was prepared so that the concentration of the starch was 20% by weight on the dry matter basis, and then filled in a Krehalon casing having a folding width of 45 mm. This starch paste filled in the casing was heated to 90° C. at 1° C./min and maintained at 90° C. for 30 minutes. Then, the starch paste was left to cool in a constant-temperature water bath at 20° C. for 30 minutes and then cooled to 5° C. in a refrigerator. After cooling, it was refrigeration storaged at 5° C. for 16 hours, then it was left at room temperature (about 25° C.) for 4 hours to return the temperature of it to room temperature, and then physical properties of the gel were measured by a rheometer (RT-2010J-CW) manufactured by Rheotech Inc. The measurement was carried out under the measurement conditions of the rheometer: a test item: a rupture test; a height of a sample: 25 mm; and a movement rate (rupture rate) of a sample: 6 cm/min, using an adapter of a spherical jig for measurement viscosity φ5 (diameter: 5 mm, area: 19.635 mm$^2$). At the measurement, the hardness of the starch gel was evaluated by a rupture stress (g) and a Young's modulus (dyn/cm$^2$).

(3. Method for Measurement of Degradation Ratio of Starch Granules)

A degradation ratio of starch granules was measured by the following method. The amount (g) of released reducing sugars contained in the supernatant obtained by centrifugation (at 3,000 rpm for 5 minutes) of a starch degraded suspension after subjecting to an enzyme reaction was measured by a phenol-sulfuric acid method. The percentage of the amount of the released reducing sugars to the total amount of the starch (g) before subjecting to an enzyme reaction was determined.

$$\text{Degradation ratio (\%) of starch granules} = \{(\text{amount } (g) \text{ of released reducing sugars}) \times 100\}/\{(\text{total amount } (g) \text{ of starch before enzymatic reaction})\} \quad \text{[Equation 1]}$$

Test Example 1

Comparison Between Liquid Reaction and Solid Reaction

1. Liquid Reaction

To 15 g (dry weight) of an untreated native wheat starch, 250 g of ion-exchange water was added and, after adjusting the pH of the mixture to 5.0, the mixture was warmed in a boiled water bath to prepare a starch paste in which a starch was completely dissolved. To this starch paste, 0.1% by weight (based on starch solid content) of α-amylase (origin: *Aspergillus oryzae*) was added to make the total weight to 300 g, and stirred at 50° C. to carry out an enzyme reaction. After 30 minutes, this was left in a boiled water bath for 10 minutes to deactivate the enzyme and thereby obtained a sample 1. Using the obtained sample 1, physical properties of the gel were measured and evaluated by a rupture stress and a Young's modulus.

2. Solid Reaction

To 400 g of an untreated native wheat starch (dry weight), 900 g of ion-exchange water was added to prepare a starch suspension. After adjusting the pH of the suspension to 5.0, 1% by weight (based on starch solid content) of α-amylase (origin: *Aspergillus oryzae*) was added and stirred at 50° C. for 18 hours to carry out an enzyme reaction. After completion of the reaction, an enzyme-treated starch was recovered by centrifugal filtration and blow drying. To 15 g (dry weight) of this enzyme-treated starch, ion-exchange water was added to make the total weight to 300 g. This was warmed in a boiled water bath to prepare a starch paste in which the starch was completely dissolved, as a sample 2. Using the obtained sample 2, physical properties of the gel were measured and evaluated by a rupture stress and a Young's modulus.

TABLE 1

| Physical properties of Gel | Sample 1 (those reacted in a form of liquid) | Sample 2 (those reacted in a form of solid) | Untreated wheat starch |
|---|---|---|---|
| Rupture stress | Not measurable since gel is not formed because of being too soft | 206 g | 141 g |
| Young's modulus | | 5,533,540 dyn/cm$^2$ | 4,601,665 dyn/cm$^2$ |

When an enzyme was allowed to act on the starch after gelling, a remarkable decrease in viscosity was confirmed in the obtained sample 1, and the sample did not retain viscosity physical properties of the starch anymore and thus a gel was not formed. On the other hand, when the enzyme is reacted keeping the starch granules as it is, it was confirmed that the obtained sample 2 retained viscosity physical properties of the starch and a hard gel was formed.

Comparative Example 1

Viscosity characteristics were analyzed by the amylograph and the rheometer without subjecting an untreated native wheat starch to an enzymatic treatment. The results are shown in Table 2-2.

Examples 1-1 and 1-2

To 400 g of an untreated native wheat starch, 900 g of ion-exchange water was added to prepare a starch suspension. After adjusting the pH of the suspension to 5.0, 0.1% by weight (based on starch solid content) of α-amylase ("Biozyme A" derived from *Aspergillus oryzae*, manufactured by Amano Enzyme Inc.; optimum pH of 5.0) was added and stirred at 50° C. for 1 hour to carry out an enzyme reaction and resulted in preparation of a sample having a degradation ratio of about 5% (Example 1-1). Using a similar amount of the enzyme, stirring was carried out at 50° C. for 3 hours to prepare a sample having a degradation ratio of about 10% (Example 1-2). After completion of the reaction, an enzyme-treated starch was recovered by centrifugal filtration and blow drying. Viscosity characteristics of the obtained enzyme-treated starch were analyzed by the amylograph and the rheometer. After completion of the reaction, a degradation ratio was determined using a part of the reaction solution. The results are shown in Table 2-2.

Example 1-3

To 400 g of an untreated native wheat starch, 900 g of ion-exchange water was added to prepare a starch suspension. After adjusting the pH of the suspension to 5.0, 1% by weight (based on starch solid content) of α-amylase ("Biozyme A" derived from *Aspergillus oryzae*, manufactured by Amano Enzyme Inc.; optimum pH of 5.0) was added and stirred at 50° C. for 18 hours to carryout an enzyme reaction. After completion of the reaction, an enzyme-treated starch was recovered by centrifugal filtration and blow drying. Viscosity characteristics of the obtained enzyme-treated starch were analyzed by the amylograph and the rheometer. Also, after completion of the reaction, a degradation ratio was determined using a part of the reaction solution. The results are shown in Table 2-2.

Example 2A

To 400 g of an untreated native wheat starch, 900 g of ion-exchange water was added to prepare a starch suspension. After adjusting the pH of the suspension to 5.0, 1% by weight (based on starch solid content) of α-amylase ("AMYLEX A3" derived from *Aspergillus niger*, manufactured by DANISCO; optimum pH of 5.0) was added and stirred at 50° C. for 18 hours to carry out an enzyme reaction. After completion of the reaction, an enzyme-treated starch was recovered by centrifugal filtration and blow drying. Viscosity characteristics of the obtained enzyme-treated starch were analyzed by the amylograph and the rheometer. After completion of the reaction, a degradation ratio was determined using a part of the reaction solution. The results are shown in Table 2-2.

Example 2B

To 400 g of an untreated native wheat starch, 900 g of ion-exchange water was added to prepare a starch suspension. After adjusting the pH of the suspension to 5.0, 1% by weight (based on starch solid content) of α-amylase ("Sumizyme AS" derived from *Aspergillus niger*, manufactured by SHIN NIHON CHEMICALS Corporation; optimum pH of 4.5) was added and stirred at 50° C. for 18 hours to carry out an enzyme reaction. After completion of the reaction, an enzyme-treated starch was recovered by centrifugal filtration and blow drying. Viscosity characteristics of the obtained enzyme-treated starch were analyzed by the amylograph and the rheometer. After completion of the reaction, a degradation ratio was determined using a part of the reaction solution. The results are shown in Table 2-2.

Comparative Examples 2, 3, 4-3, and 5 to 6

To 400 g of an untreated native wheat starch, 900 g of ion-exchange water was added to prepare a starch suspension. After adjusting the pH of the suspension to 5.0, 1% by weight (based on starch solid content) of α-amylase ("α-amylase 3A" derived from *Bacillus subtilis*, manufactured by HBI, Inc.; optimum pH of 5.9; Comparative Example 2), α-amylase ("Novamyl" derived from *Bacillus subtilis*, manufactured by Novo; optimum pH of 5.0; Comparative Example 3), α-amylase ("α-amylase" derived from *Bacillus amyloliquefaciens*, manufactured by Sigma-Aldrich Corporation; optimum pH of 6.0; Comparative Example 4-3), α-amylase ("TERMAMYL 120L" derived from *Bacillus licheniformis*, manufactured by Novo; optimum pH of 6.0; Comparative Example 5), or α-amylase ("Maltogenase L" derived from *Bacillus* sp., manufactured by Novo; optimum pH of 5.0; Comparative Example 6) was added and stirred at 50° C. for 18 hours to carry out an enzyme reaction. After completion of the reaction, an enzyme-treated starch was recovered by centrifugal filtration and blow drying. Viscosity characteristics of the obtained enzyme-treated starch were analyzed by the amylograph and the rheometer. After completion of the reaction, a degradation ratio was determined by a part of the reaction solution. The results are shown in Table 2-2.

Comparative Examples 4-1 and 4-2

To 400 g of an untreated native wheat starch, 900 g of ion-exchange water was added to prepare a starch suspension. After adjusting the pH of the suspension to 5.0, 0.01% by weight (based on starch solid content) of α-amylase ("α-amylase" derived from *Bacillus amyloliquefaciens*, manufactured by Sigma-Aldrich Corporation; optimum pH of 6.0) was added and stirred at 50° C. for 30 minutes to prepare a sample having a degradation ratio of about 5%. Also, using a similar amount of the enzyme, stirring was carried out at 50° C. for 1.5 hours to prepare a sample having a degradation ratio of about 10%. After completion of the reaction, an enzyme-treated starch was recovered by centrifugal filtration and blow drying. Viscosity characteristics of the obtained enzyme-treated starch were analyzed by the amylograph and the rheometer. The results are shown in Table 2-2.

Examples 3A-1 and 3A-2

To 400 g of an untreated native wheat starch, 900 g of ion-exchange water was added to prepare a starch suspension. After adjusting the pH of the suspension to 5.0, 0.1% by weight (based on starch solid content) of amyloglucosidase ("AMG" derived from *Aspergillus niger*, manufactured by Novozymes; optimum pH of 4.5) was added and stirred at 50° C. for 2 hours to prepare a sample having a degradation ratio of about 5% (Example 3A-1). Also, 0.5% by weight (based on starch solid content) of the similar enzyme was added and stirred at 50° C. for 3 hours to prepare a sample having a degradation ratio of about 10% (Example 3A-2). After completion of the reaction, an enzyme-treated starch was recovered by centrifugal filtration and blow drying. Viscosity characteristics of the obtained enzyme-treated starch were analyzed by the amylograph and the rheometer.

Example 3A-3

To 400 g of an untreated native wheat starch, 900 g of ion-exchange water was added to prepare a starch suspension. After adjusting the pH of the suspension to 5.0, 1% by weight (based on starch solid content) of amyloglucosidase ("AMG" derived from *Aspergillus niger*, manufactured by Novozymes; optimum pH of 4.5) was added and stirred at 50° C. for 18 hours to carry out an enzyme reaction. After completion of the reaction, an enzyme-treated starch was recovered by centrifugal filtration and blow drying. Viscosity characteristics of the obtained enzyme-treated starch were analyzed by the amylograph and the rheometer. After completion of the reaction, a degradation ratio was determined using a part of the reaction solution. The results are shown in Table 2-2.

Example 3B

To 400 g of an untreated native wheat starch, 900 g of ion-exchange water was added to prepare a starch suspension. After adjusting the pH of the suspension to 5.0, 1% by weight (based on starch solid content) of amyloglucosidase ("OPTIDEX L-400" derived from *Aspergillus niger*, manufactured by Genencor; optimum pH of 4.4) was added and stirred at 50° C. for 18 hours to carry out an enzyme reaction. After completion of the reaction, an enzyme-treated starch was recovered by centrifugal filtration and blow drying. Viscosity characteristics of the obtained enzyme-treated starch were analyzed by the amylograph and the rheometer. After completion of the reaction, a degradation ratio was determined using a part of the reaction solution. The results are shown in Table 2-2.

Example 3C

To 400 g of an untreated native wheat starch, 900 g of ion-exchange water was added to prepare a starch suspension. After adjusting the pH of the suspension to 5.0, 1% by weight (based on starch solid content) of amyloglucosidase ("DIAZYME X4NP" derived from *Aspergillus niger*, manufactured by DANISCO; optimum pH of 4.0) was added and stirred at 50° C. for 18 hours to carry out an enzyme reaction. After completion of the reaction, an enzyme-treated starch was recovered by centrifugal filtration and blow drying. Viscosity characteristics of the obtained enzyme-treated starch were analyzed by the amylograph and the rheometer. After completion of the reaction, a degradation ratio was determined using a part of the reaction solution. The results are shown in Table 2-2.

Example 3D

To 400 g of an untreated native wheat starch, 900 g of ion-exchange water was added to prepare a starch suspension. After adjusting the pH of the suspension to 5.0, 1% by weight (based on starch solid content) of amyloglucosidase ("glucoamylase 'Amano' SD" derived from *Aspergillus niger*, manufactured by Amano Enzyme Inc.; optimum pH of 4.5) was added and stirred at 50° C. for 18 hours to carry out an enzyme reaction. After completion of the reaction, an enzyme-treated starch was recovered by centrifugal filtration and blow drying. Viscosity characteristics of the obtained enzyme-treated starch were analyzed by the amylograph and the rheometer. After completion of the reaction, a degradation ratio was determined using a part of the reaction solution. The results are shown in Table 2-2.

Example 3E

To 400 g of an untreated native wheat starch, 900 g of ion-exchange water was added to prepare a starch suspension. After adjusting the pH of the suspension to 5.0, 1% by weight (based on starch solid content) of amyloglucosidase ("Gluczyme AF6" derived from *Rhizopus niveus*, manufactured by Amano Enzyme Inc.; optimum pH of 4.5) was added and stirred at 50° C. for 18 hours to carry out an enzyme reaction. After completion of the reaction, an enzyme-treated starch was recovered by centrifugal filtration and blow drying. Viscosity characteristics of the obtained enzyme-treated starch were analyzed by the amylograph and the rheometer. After completion of the reaction, a degradation ratio was determined using a part of the reaction solution. The results are shown in Table 2-2.

Example 3F

To 400 g of an untreated native wheat starch, 900 g of ion-exchange water was added to prepare a starch suspension. After adjusting the pH of the suspension to 5.0, 1% by weight (based on starch solid content) of amyloglucosidase ("Sumizyme" derived from *Rhizopus oryzae*, manufactured by SHIN NIHON CHEMICALS Corporation; optimum pH of 5.0) was added and stirred at 50° C. for 18 hours to carry out an enzyme reaction. After completion of the reaction, an enzyme-treated starch was recovered by centrifugal filtration and blow drying. Viscosity characteristics of the obtained enzyme-treated starch were analyzed by the amylograph and the rheometer. After completion of the reaction, a degradation ratio was determined using a part of the reaction solution. The results are shown in Table 2-2.

Comparative Example 8

To 400 g of an untreated native wheat starch, 900 g of ion-exchange water was added to prepare a starch suspension. After adjusting the pH of the suspension to 5.0, 1% by weight (based on starch solid content) of amyloglucosidase ("Reagent" derived from *Candida tsukubaensis*, manufactured by Sigma-Aldrich Corporation; optimum pH of 2.5) was added and stirred at 50° C. for 18 hours to carry out an enzyme reaction. After completion of the reaction, an enzyme-treated starch was recovered by centrifugal filtration and blow drying. Viscosity characteristics of the obtained enzyme-treated starch were analyzed by the amylograph and the rheometer. After completion of the reaction, a degradation ratio was determined using a part of the reaction solution. The results are shown in Table 2-2.

Example 4

To 400 g of an untreated native wheat starch, 900 g of ion-exchange water was added to prepare a starch suspension. After adjusting the pH of the suspension to 5.0, 0.1% by weight (based on starch solid content) of isoamylase ("Reagent" derived from *Pseudomonas amyloderamosa*, manufactured by Sigma-Aldrich Corporation; optimum pH of 3.0) was added and stirred at 50° C. for 18 hours to carry out an enzyme reaction. After completion of the reaction, an enzyme-treated starch was recovered by centrifugal filtration and blow drying. Viscosity characteristics of the obtained enzyme-treated starch were analyzed by the amylograph and the rheometer. After completion of the reaction, a degradation ratio was determined using a part of the reaction solution. The results are shown in Table 2-2.

Example 5A

To 400 g of an untreated native wheat starch, 900 g of ion-exchange water was added to prepare a starch suspension. After adjusting the pH of the suspension to 5.0, 1% by weight (based on starch solid content) of α-glucosidase ("Transglucosidase L 'Amano'" derived from *Aspergillus niger*, manufactured by Amano Enzyme Inc.; optimum pH of 5.0) was added and stirred at 50° C. for 18 hours to carry out an enzyme reaction. After completion of the reaction, an enzyme-treated starch was recovered by centrifugal filtration and blow drying. Viscosity characteristics of the obtained enzyme-treated starch were analyzed by the amylograph and the rheometer. After completion of the reaction, a degradation ratio was determined using a part of the reaction solution. The results are shown in Table 2-2.

Example 5B

To 400 g of an untreated native wheat starch, 900 g of ion-exchange water was added to prepare a starch suspension. After adjusting the pH of the suspension to 5.0, 1% by weight (based on starch solid content) of α-glucosidase ("Transglucosidase L-500" derived from *Aspergillus niger*, manufactured by Genencor; optimum pH of 5.0) was added and stirred at 50° C. for 18 hours to carry out an enzyme reaction. After completion of the reaction, an enzyme-treated starch was recovered by centrifugal filtration and blow drying. Viscosity characteristics of the obtained enzyme-treated starch were analyzed by the amylograph and the rheometer. After completion of the reaction, a degradation ratio was determined using a part of the reaction solution. The results are shown in Table 2-2.

Comparative Examples 10 and 11

To 400 g of an untreated native wheat starch, 900 g of ion-exchange water was added to prepare a starch suspension. After adjusting the pH of the suspension to 5.0, 1% by weight (based on starch solid content) of β-amylase ("OPTIMALT BBA" derived from barley, manufactured by Genencor; optimum pH of 5.0) or pullulanase ("Pullulanase" derived from *Klebsiella pneumoniae*, manufactured by Amano Enzyme Inc.; optimum pH of 6.0) was added and stirred at 50° C. for 18 hours to carry out an enzyme reaction. After completion of the reaction, an enzyme-treated starch was recovered by centrifugal filtration and blow drying. Viscosity characteristics of the obtained enzyme-treated starch were analyzed by the amylograph and the rheometer. After completion of the reaction, a degradation ratio was determined using a part of the reaction solution. The results are shown in Table 2-2.

Comparative Example 12

Viscosity characteristics were analyzed by the amylograph and the rheometer without subjecting a corn starch to an enzymatic treatment. The results are shown in Table 3-2.

Example 6

To 400 g of an untreated native corn starch, 900 g of ion-exchange water was added to prepare a starch suspension. After adjusting the pH of the suspension to 5.0, 1% by weight (based on starch solid content) of α-amylase ("Biozyme A" derived from *Aspergillus oryzae*, manufactured by Amano Enzyme Inc.; optimum pH of 5.0) was added and stirred at 50° C. for 18 hours to carryout an enzyme reaction. After completion of the reaction, an enzyme-treated starch was recovered by centrifugal filtration and blow drying. Viscosity characteristics of the obtained enzyme-treated starch were analyzed by the amylograph and the rheometer. Also, after completion of the reaction, a degradation ratio was determined using a part of the reaction solution. The results are shown in Table 3-2.

Comparative Examples 13-1 and 13-2

To 400 g of an untreated native corn starch, 900 g of ion-exchange water was added to prepare a starch suspension. After adjusting the pH of the suspension to 5.0, 0.01% by weight (based on starch solid content) (Comparative Example 13-1) of α-amylase ("Reagent" derived from *Bacillus amyloliquefaciens*, manufactured by Sigma-Aldrich Corporation; optimum pH of 6.0) was added and stirred at 50° C. for 30 minutes, or 1% by weight (based on starch solid content) (Comparative Example 13-2) of the α-amylase was added and stirred at 50° C. for 18 hours, to carryout an enzyme reaction. After completion of the reaction, an enzyme-treated starch was recovered by centrifugal filtration and blow drying. Viscosity characteristics of the obtained enzyme-treated starch were analyzed by the amylograph and the rheometer. Also, after completion of the reaction, a degradation ratio was determined by a part of the reaction solution. The results are shown in Table 3-2.

Examples 7-1 and 7-2

To 400 g of an untreated native corn starch, 900 g of ion-exchange water was added to prepare a starch suspension. After adjusting the pH of the suspension to 5.0, 0.5% by weight (based on starch solid content) (Example 7-1) of amyloglucosidase ("AMG" derived from *Aspergillus niger*, manufactured by Novozymes; optimum pH of 4.5) was added and stirred at 50° C. for 3 hours, or 1% by weight (based on starch solid content) (Example 7-2) of the amyloglucosidase was added and stirred at 50° C. for 18 hours, to carry out an enzyme reaction. After completion of the reaction, an enzyme-treated starch was recovered by centrifugal filtration and blow drying. Viscosity characteristics of the obtained enzyme-treated starch were analyzed by the amylograph and the rheometer. Also, after completion of the reaction, a degradation ratio was determined by a part of the reaction solution. The results are shown in Table 3-2.

Comparative Example 14

To 400 g of an untreated native corn starch, 900 g of ion-exchange water was added to prepare a starch suspension. After adjusting the pH of the suspension to 5.0, 1% by weight (based on starch solid content) of β-amylase ("OPTIMALT BBA" derived from barley, manufactured by Genencor; optimum pH of 5.0) was added and stirred at 50° C. for 18 hours to carry out an enzyme reaction. After completion of the reaction, an enzyme-treated starch was recovered by centrifugal filtration and blow drying. Viscosity characteristics of the obtained enzyme-treated starch were analyzed by the amylograph and the rheometer. After completion of the reaction, a degradation ratio was determined using a part of the reaction solution. The results are shown in Table 3-2.

Example 8A

To 400 g of an untreated native corn starch, 900 g of ion-exchange water was added to prepare a starch suspension. After adjusting the pH of the suspension to 5.0, 0.1% by weight (based on starch solid content) of isoamylase ("Reagent" derived from *Pseudomonas amyloderamosa*, manufactured by Sigma-Aldrich Corporation; optimum pH of 3.0) was added and stirred at 50° C. for 18 hours to carry out an enzyme reaction. After completion of the reaction, an enzyme-treated starch was recovered by centrifugal filtration and blow drying. Viscosity characteristics of the obtained enzyme-treated starch were analyzed by the amylograph and the rheometer. After completion of the reaction, a degradation ratio was determined using a part of the reaction solution. The results are shown in Table 3-2.

Example 8B

To 400 g of an untreated native corn starch, 900 g of ion-exchange water was added to prepare a starch suspension. After adjusting the pH of the suspension to 5.0, 1% by weight (based on starch solid content) of α-amylase ("AMYLEX A3" derived from *Aspergillus niger*, manufactured by DANISCO; optimum pH of 5.0) was added and stirred at 50° C. for 18 hours to carry out an enzyme reaction. After completion of the reaction, an enzyme-treated starch was recovered by centrifugal filtration and blow drying. Viscosity characteristics of the obtained enzyme-treated starch were analyzed by the amylograph and the rheometer. After completion of the reaction, a degradation ratio was determined using a part of the reaction solution. The results are shown in Table 3-2.

Example 8C

To 400 g of an untreated native corn starch, 900 g of ion-exchange water was added to prepare a starch suspension. After adjusting the pH of the suspension to 5.0, 1% by weight (based on starch solid content) of α-glucosidase ("Transglucosidase L 'Amano'" derived from *Aspergillus niger*, manufactured by Amano Enzyme Inc.; optimum pH of 5.0) was added and stirred at 50° C. for 18 hours to carry out an enzyme reaction. After completion of the reaction, an enzyme-treated starch was recovered by centrifugal filtration and blow drying. Viscosity characteristics of the obtained enzyme-treated starch were analyzed by the amylograph and the rheometer. After completion of the reaction, a degradation ratio was determined using a part of the reaction solution. The results are shown in Table 3-2.

Comparative Example 15

Viscosity characteristics were analyzed by the amylograph and the rheometer without subjecting an untreated native cassava starch to an enzymatic treatment. The results are shown in Table 4-2.

Example 9

To 400 g of an untreated native cassava starch, 900 g of ion-exchange water was added to prepare a starch suspension. After adjusting the pH of the suspension to 5.0, 1% by weight (based on starch solid content) of α-amylase ("Biozyme A" derived from *Aspergillus oryzae*, manufactured by Amano Enzyme Inc.; optimum pH of 5.0) was added and stirred at 50° C. for 18 hours to carry out an enzyme reaction. After completion of the reaction, an enzyme-treated starch was recovered by centrifugal filtration and blow drying. Viscosity characteristics of the obtained enzyme-treated starch were analyzed by the amylograph and the rheometer. After completion of the reaction, a degradation ratio was determined using a part of the reaction solution. The results are shown in Table 4-2.

Comparative Examples 16-1 and 16-2

To 400 g of an untreated native cassava starch, 900 g of ion-exchange water was added to prepare a starch suspension. After adjusting the pH of the suspension to 5.0, 0.01% by weight (based on starch solid content) (Comparative Example 16-1) of α-amylase ("Reagent" derived from *Bacillus amyloliquefaciens*, manufactured by Sigma-Aldrich Corporation; optimum pH of 6.0) was added and stirred at 50° C. for 30 minutes, or 1.0% by weight (based on starch solid content) (Comparative Example 16-2) of the α-amylase was added and stirred at 50° C. for 18 hours, to carryout an enzyme reaction. After completion of the reaction, an enzyme-treated starch was recovered by centrifugal filtration and blow drying. Viscosity characteristics of the obtained enzyme-treated starch were analyzed by the amylograph and the rheometer. Also, after completion of the reaction, a degradation ratio was determined by a part of the reaction solution. The results are shown in Table 4-2.

Examples 10-1 and 10-2

To 400 g of an untreated native cassava starch, 900 g of ion-exchange water was added to prepare a starch suspension. After adjusting the pH of the suspension to 5.0, 0.5% by weight (based on starch solid content) (Example 10-1) of amyloglucosidase ("AMG" derived from *Aspergillus niger*, manufactured by Novozymes; optimum pH of 4.5) was added and stirred at 50° C. for 3 hours, or 1% by weight (based on starch solid content) (Example 10-2) of the amyloglucosidase was added and stirred at 50° C. for 18 hours, to carry out an enzyme reaction. After completion of the reaction, an enzyme-treated starch was recovered by centrifugal filtration and blow drying. Viscosity characteristics of the obtained enzyme-treated starch were analyzed by the amylograph and the rheometer. Also, after completion of the reaction, a degradation ratio was determined by a part of the reaction solution. The results are shown in Table 4-2.

Comparative Example 17

To 400 g of an untreated native cassava starch, 900 g of ion-exchange water was added to prepare a starch suspension. After adjusting the pH of the suspension to 5.0, 1% by weight (based on starch solid content) of β-amylase ("OPTIMALT BBA" derived from barley, manufactured by Genencor; optimum pH of 5.0) was added and stirred at 50° C. for 18 hours to carry out an enzyme reaction. After completion of the reaction, an enzyme-treated starch was recovered by centrifugal filtration and blow drying. Viscosity characteristics of the obtained enzyme-treated starch were analyzed by the amylograph and the rheometer. After completion of the reaction, a degradation ratio was determined using a part of the reaction solution. The results are shown in Table 4-2.

Example 11A

To 400 g of an untreated native cassava starch, 900 g of ion-exchange water was added to prepare a starch suspension. After adjusting the pH of the suspension to 5.0, 0.1% by weight (based on starch solid content) of isoamylase ("Reagent" derived from *Pseudomonas amyloderamosa*, manufactured by Sigma-Aldrich Corporation; optimum pH of 3.0) was added and stirred at 50° C. for 18 hours to carry out an enzyme reaction. After completion of the reaction, an enzyme-treated starch was recovered by centrifugal filtration and blow drying. Viscosity characteristics of the obtained enzyme-treated starch were analyzed by the amylograph and the rheometer. After completion of the reaction, a degradation ratio was determined using a part of the reaction solution. The results are shown in Table 4-2.

Example 11B

To 400 g of an untreated native cassava starch, 900 g of ion-exchange water was added to prepare a starch suspension. After adjusting the pH of the suspension to 5.0, 1% by weight (based on starch solid content) of α-amylase ("AMYLEX A3" derived from *Aspergillus niger*, manufactured by DANISCO; optimum pH of 5.0) was added and stirred at 50° C. for 18 hours to carry out an enzyme reaction. After completion of the reaction, an enzyme-treated starch was recovered by centrifugal filtration and blow drying. Viscosity characteristics of the obtained enzyme-treated starch were analyzed by the amylograph and the rheometer. After completion of the reaction, a degradation ratio was determined using a part of the reaction solution. The results are shown in Table 4-2.

Example 11C

To 400 g of an untreated native cassava starch, 900 g of ion-exchange water was added to prepare a starch suspension. After adjusting the pH of the suspension to 5.0, 1% by weight (based on starch solid content) of α-glucosidase ("Transglucosidase L 'Amano'" derived from *Aspergillus niger*, manufactured by Amano Enzyme Inc.; optimum pH of 5.0) was added and stirred at 50° C. for 18 hours to carry out an enzyme reaction. After completion of the reaction, an enzyme-treated starch was recovered by centrifugal filtration and blow drying. Viscosity characteristics of the obtained enzyme-treated starch were analyzed by the amylograph and the rheometer. After completion of the reaction, a degradation ratio was determined using a part of the reaction solution. The results are shown in Table 4-2.

As a result, in Examples 1 to 11C, it was confirmed that a novel starch having both a high viscosity and strong gel characteristics can be prepared by subjecting to an enzymatic treatment. Further, using α-amylase derived from *Bacillus amyloliquefaciens* used in Comparative Examples 4-1 and 4-2, 13-1, 13-2, 16-1, 16-2 at a degradation ratio of 40% or less, it was impossible to prepare a starch having both a high viscosity and strong gel characteristics, which is the object of the present inventors. Therefore, it has been proved that the starch developed by the present inventors is a substance which is different from the starch prepared by Japanese Patent Gazette No. 2,615,398.

Example 12A

Method for Preparation of α-Amylase derived from *Aspergillus oryzae*

A double stranded DNA was chemically synthesized by adding an EcoRI recognition site (GAATTC) to both terminals of a base sequence of SEQ ID NO: 1 in the sequence listing. This synthetic DNA was completely cleaved by a restriction enzyme EcoRI, mixed with pYCDE1 (Method in Enzymology, 101, pp. 192-201 (1983)) which was previously completely cleaved by EcoRI, and then ligation was carried out. *E. coli* TG1 was transformed with the ligation reaction solution and a transformant into which a synthetic gene was properly introduced was selected. Plasmid pYAMY1 held by this transformant was prepared.

In accordance with the method of Ito et al. (J. bacterial., Vol. 153, 163-168 (1983)), pYAMY1 was introduced into a yeast host DBY746, and obtained a transformant capable of growing in a tryptophan-free culture medium by complementation of the tryptophan requirement. This transformant was inoculated in 100 ml of a synthetic culture medium consisting of 2% glucose, 0.67% yeast nitrogen base, 24 mg/l L-uracil, 24 mg/l L-histidine and 36 mg/l L-leucine at pH 5.7 and then cultured with shaking at 30° C. for 120 hours.

The supernatant obtained by centrifugation (at 5,000 rpm for 10 minutes) of the culture was concentrated using a hollow fiber type UF membrane module having a molecular weight cut-off of 10,000 to prepare α-amylase derived from *Aspergillus oryzae*. This α-amylase has an amino acid sequence of SEQ ID NO: 2.

Example 12B

Method for Preparation of α-Amylase derived from *Aspergillus niger*

A double stranded DNA was chemically synthesized by adding an EcoRI recognition site (GAATTC) to both terminals of a base sequence of SEQ ID NO: 3 in the sequence listing. This synthetic DNA was completely cleaved by a restriction enzyme EcoRI, mixed with pYCDE1 (Method in Enzymology, 101, pp. 192-201 (1983)) which was previously completely cleaved by EcoRI, and then ligation was carried out. *E. coli* TG1 was transformed with the ligation reaction solution and a transformant into which a synthetic gene was properly introduced was selected. Plasmid pYAMY2 held by this transformant was prepared.

In accordance with the method of Ito et al. (J. bacterial, Vol. 153, 163-168 (1983)), pYAMY2 was introduced into a yeast host DBY746, and obtained a transformant capable of growing in a tryptophan-free culture medium by complementation of the tryptophan requirement. This transformant was inoculated in 100 ml of a synthetic culture medium consisting of 2% glucose, 0.67% yeast nitrogen base, 24 mg/l L-uracil, 24 mg/l L-histidine and 36 mg/l L-leucine at pH 5.7 and then cultured with shaking at 30° C. for 120 hours.

The supernatant obtained by centrifugation (at 5,000 rpm for 10 minutes) of the culture was concentrated using a hollow fiber type UF membrane module having a molecular weight cut-off of 10,000 to prepare α-amylase derived from *Aspergillus niger*. This α-amylase has an amino acid sequence of SEQ ID NO: 4.

Example 12C

Method for Preparation of Amyloglucosidase Derived from *Aspergillus niger*

A double stranded DNA was chemically synthesized by adding an EcoRI recognition site (GAATTC) to both terminals of a base sequence of SEQ ID NO: 5 in the sequence listing. This synthetic DNA was completely cleaved by a restriction enzyme EcoRI, mixed with pYCDE1 (Method in Enzymology, 101, pp. 192-201 (1983)) which was previously completely cleaved by EcoRI, and then ligation was carried out. *E. coli* TG1 was transformed with the ligation reaction solution and a transformant into which a synthetic gene was properly introduced was selected. Plasmid pYGLU1 held by this transformant was prepared.

In accordance with the method of Ito et al. (J. bacterial, Vol. 153, 163-168 (1983)), pYGLU1 was introduced into a yeast host DBY746, and obtained a transformant capable of growing in a tryptophan-free culture medium by complementation of the tryptophan requirement. This transformant was inoculated in 100 ml of a synthetic culture medium consisting of 2% glucose, 0.67% yeast nitrogen base, 24 mg/l L-uracil, 24 mg/l L-histidine and 36 mg/l L-leucine at pH 5.7 and then cultured with shaking at 30° C. for 120 hours.

The supernatant obtained by centrifugation (at 5,000 rpm for 10 minutes) of the culture was concentrated using a hollow fiber type UF membrane module having a molecular weight cut-off of 10,000 to prepare amyloglucosidase derived from *Aspergillus niger*. This amyloglucosidase has an amino acid sequence of SEQ ID NO: 6.

Example 12D

Method for Preparation of Isoamylase Derived from *Flavobacterium* sp.

A double stranded DNA was chemically synthesized by adding an EcoRI recognition site (GAATTC) to both terminals of a base sequence of SEQ ID NO: 7 in the sequence listing. This synthetic DNA was completely cleaved by a restriction enzyme EcoRI, mixed with pYCDE1 (Method in Enzymology, 101, pp. 192-201 (1983)) which was previously completely cleaved by EcoRI, and then ligation was carried out. *E. coli* TG1 was transformed with the ligation reaction solution and a transformant into which a synthetic gene was properly introduced was selected. Plasmid pYISO1 held by this transformant was prepared.

In accordance with the method of Ito et al. (J. bacterial., Vol. 153, 163-168 (1983)), pYISO1 was introduced into a yeast host DBY746, and obtained a transformant capable of growing in a tryptophan-free culture medium by complementation of the tryptophan requirement. This transformant was inoculated in 100 ml of a synthetic culture medium consisting of 2% glucose, 0.67% yeast nitrogen base, 24 mg/l L-uracil, 24 mg/l L-histidine and 36 mg/l L-leucine at pH 5.7 and then cultured with shaking at 30° C. for 120 hours.

The supernatant obtained by centrifugation (at 5,000 rpm for 10 minutes) of the culture was concentrated using a hollow fiber type UF membrane module having a molecular weight cut-off of 10,000 to prepare isoamylase derived from *Flavobacterium* sp. This isoamylase has an amino acid sequence of SEQ ID NO: 8.

Example 12E

Method for Preparation of Isoamylase Derived from *Pseudomonas Amyloderamosa*

A double stranded DNA was chemically synthesized by adding an EcoRI recognition site (GAATTC) to both terminals of a base sequence of SEQ ID NO: 9 in the sequence listing. This synthetic DNA was completely cleaved by a restriction enzyme EcoRI, mixed with pYCDE1 (Method in Enzymology, 101, pp. 192-201 (1983)) which was previously completely cleaved by EcoRI, and then ligation was carried out. *E. coli* TG1 was transformed with the ligation reaction solution and a transformant into which a synthetic gene was properly introduced was selected. Plasmid pYISO2 held by this transformant was prepared.

In accordance with the method of Ito et al. (J. bacterial., Vol. 153, 163-168 (1983)), pYISO2 was introduced into a yeast host DBY746, and obtained a transformant capable of growing in a tryptophan-free culture medium by complementation of the tryptophan requirement. This transformant was inoculated in 100 ml of a synthetic culture medium consisting of 2% glucose, 0.67% yeast nitrogen base, 24 mg/l L-uracil, 24 mg/l L-histidine and 36 mg/l L-leucine at pH 5.7 and then cultured with shaking at 30° C. for 120 hours.

The supernatant obtained by centrifugation (at 5,000 rpm for 10 minutes) of the culture was concentrated using a hollow fiber type UF membrane module having a molecular weight cut-off of 10,000 to prepare isoamylase derived from *Pseudomonas amyloderamosa*. This isoamylase has an amino acid sequence of SEQ ID NO: 10.

Example 12A-1

To 400 g of an untreated native wheat starch, 900 g of ion-exchange water was added to prepare a starch suspension. After adjusting the pH of the suspension to 5.0, 1% by weight (based on starch solid content) of α-amylase (derived from *Aspergillus oryzae*) prepared in Example 12A was added and stirred at 50° C. for 18 hours to carryout an enzyme reaction. After completion of the reaction, an enzyme-treated starch was recovered by centrifugal filtration and blow drying. Viscosity characteristics of the obtained enzyme-treated starch were analyzed by the amylograph and the rheometer. After completion of the reaction, a degradation ratio was determined using a part of the reaction solution. The results are shown in Table 5-2 below.

Example 12B-1

To 400 g of an untreated native wheat starch, 900 g of ion-exchange water was added to prepare a starch suspension. After adjusting the pH of the suspension to 5.0, 1% by weight (based on starch solid content) of α-amylase (derived from *Aspergillus niger*) prepared in Example 12B was added and stirred at 50° C. for 18 hours to carry out an enzyme reaction. After completion of the reaction, an enzyme-treated starch was recovered by centrifugal filtration and blow drying. Viscosity characteristics of the obtained enzyme-treated starch were analyzed by the amylograph and the rheometer. After completion of the reaction, a degradation ratio was determined using a part of the reaction solution. The results are shown in Table 5-2 below.

Example 12C-1

To 400 g of an untreated native wheat starch, 900 g of ion-exchange water was added to prepare a starch suspension. After adjusting the pH of the suspension to 5.0, 1% by weight (based on starch solid content) of amyloglucosidase (derived from *Aspergillus niger*) prepared in Example 12C was added and stirred at 50° C. for 18 hours to carry out an enzyme reaction. After completion of the reaction, an enzyme-treated starch was recovered by centrifugal filtration and blow drying. Viscosity characteristics of the obtained enzyme-treated starch were analyzed by the amylograph and the rheometer. After completion of the reaction, a degradation ratio was determined using a part of the reaction solution. The results are shown in Table 5-2 below.

Example 12D-1

To 400 g of an untreated native wheat starch, 900 g of ion-exchange water was added to prepare a starch suspension. After adjusting the pH of the suspension to 5.0, 1% by weight (based on starch solid content) of isoamylase (derived from *Flavobacterium* sp.) prepared in Example 12D was added and stirred at 50° C. for 18 hours to carry out an enzyme reaction. After completion of the reaction, an enzyme-treated starch was recovered by centrifugal filtration and blow drying. Viscosity characteristics of the obtained enzyme-treated starch were analyzed by the amylograph and the rheometer. After completion of the reaction, a degradation ratio was determined using a part of the reaction solution. The results are shown in Table 5-2 below.

Example 12E-1

To 400 g of an untreated native wheat starch, 900 g of ion-exchange water was added to prepare a starch suspension. After adjusting the pH of the suspension to 5.0, 1% by weight (based on starch solid content) of isoamylase (derived from *Pseudomonas amyloderamosa*) prepared in Example 12E was added and stirred at 50° C. for 18 hours to carry out an enzyme reaction. After completion of the reaction, an enzyme-treated starch was recovered by centrifugal filtration and blow drying. Viscosity characteristics of the obtained enzyme-treated starch were analyzed by the amylograph and the rheometer. After completion of the reaction, a degradation ratio was determined using a part of the reaction solution. The results are shown in Table 5-2 below.

TABLE 2-1

Summary of Names, Origins and Product Names of Enzymes used for Wheat Starch

| Example | Name | Origins | Product name (Manufacturer) |
|---|---|---|---|
| Comp. Ex. 1 | — | — | Untreated wheat starch |
| Example 1-1 | α-amylase | *Aspergillus oryzae* | Biozyme A (Amano Enzyme) |
| Example 1-2 | α-amylase | *Aspergillus oryzae* | Biozyme A (Amano Enzyme) |
| Example 1-3 | α-amylase | *Aspergillus oryzae* | Biozyme A (Amano Enzyme) |
| Example 2A | α-amylase | *Aspergillus niger* | AMYLEX A3 (DANISCO) |
| Example 2B | α-amylase | *Aspergillus niger* | Sumizyme AS (SHIN NIHON CHEMICALS Corporation) |
| Comp. Ex. 2 | α-amylase | *Bacillus subtilis* | α-amylase 3A (HBI) |
| Comp. Ex. 3 | α-amylase | *Bacillus subtilis* | Novamyl (Novo) |
| Comp. Ex. 4-1 | α-amylase | *Bacillus amyloliquefaciens* | Reagent (Sigma-Aldrich Corporation) |
| Comp. Ex. 4-2 | α-amylase | *Bacillus amyloliquefaciens* | Reagent (Sigma-Aldrich Corporation) |
| Comp. Ex. 4-3 | α-amylase | *Bacillus amyloliquefaciens* | Reagent (Sigma-Aldrich Corporation) |
| Comp. Ex. 5 | α-amylase | *Bacillus licheniformis* | TERMAMYL 120L (Novo) |
| Comp. Ex. 6 | α-amylase | *Bacillus* sp. | Maltogenase L (Novo) |
| Example 3A-1 | amyloglucosidase | *Aspergillus niger* | AMG (Novo) |
| Example 3A-2 | amyloglucosidase | *Aspergillus niger* | AMG (Novo) |
| Example 3A-3 | amyloglucosidase | *Aspergillus niger* | AMG (Novo) |
| Example 3B | amyloglucosidase | *Aspergillus niger* | OPTIDEX L-400 (Genencor) |
| Example 3C | amyloglucosidase | *Aspergillus niger* | DIAZYME X4NP (DANISCO) |
| Example 3D | amyloglucosidase | *Aspergillus niger* | Glucoamylase "Amano" SD (Amano Enzyme) |
| Example 3E | amyloglucosidase | *Rhizopus niveus* | Gluczyme AF6 (Amano Enzyme) |
| Example 3F | amyloglucosidase | *Rhizopus oryzae* | Sumizyme (SHIN NIHON CHEMICALS Corporation) |
| Comp. Ex. 8 | amyloglucosidase | *Candida tsukubaensis* | Reagent (Sigma-Aldrich Corporation) |
| Example 4 | isoamylase | *Pseudamonas amyloderamosa* | Reagent (Sigma-Aldrich Corporation) |
| Example 5A | α-glucosidase | *Aspergillus niger* | Transglucosidase L "Amano" (Amano Enzyme) |
| Example 5B | α-glucosidase | *Aspergillus niger* | Transglucosidase L-500 (Genencor) |
| Comp. Ex. 10 | β-amylase | Barley | OPTIMALT BBA (Genencor) |
| Comp. Ex. 11 | pullulanase | *Klebsiella pneumoniae* | Pullulanase (Amano Enzyme) |
| Example 13-1 | CGTase | *Bacillus licheniformis* | Toruzyme 3.0L (Novo) |
| Example 13-2 | CGTase | *Paenibacillus macerans* (*Bacillus macerans*) | Cyclodextrin glucanotransferase "Amano" (Amano Enzyme) |

Comp. Ex. = Comparative Example

TABLE 2-2

Table 2-2: Summary of Results of Wheat Starch (Starch Concentration for Amylograph: 8.5%)

| Example | Degradation ratio (%) | Maximum viscosity Measured value (BU) | Maximum viscosity Relative % (%) | Breakdown viscosity (BU) | Rupture stress Measured value (g) | Rupture stress Relative % (%) | Young's modulus Measured value (dyn/cm$^2$) | Young's modulus Relative % (%) | Evaluation results |
|---|---|---|---|---|---|---|---|---|---|
| Comp. Ex. 1 | — | 621 | 100 | 126 | 141 | 100 | 4,601,665 | 100 | — |
| Example 1-1 | 5 | 672 | 108 | 188 | 167 | 118 | 5,188,263 | 113 | Usable |
| Example 1-2 | 8 | 707 | 114 | 221 | 185 | 131 | 5,490,949 | 119 | Usable |
| Example 1-3 | 19 | 738 | 119 | 279 | 206 | 146 | 5,533,540 | 120 | Usable |
| Example 2A | 15 | 880 | 142 | 365 | 211 | 150 | 5,465,779 | 119 | Usable |
| Example 2B | 14 | 839 | 135 | 374 | 165 | 117 | 5,484,457 | 119 | Usable |
| Comp. Ex. 2 | 33 | 398 | 64 | 241 | 15 | 11 | 637,600 | 14 | Not usable |
| Comp. Ex. 3 | 24 | 14 | 2 | 8 | Not measurable since gel is not formed because of being too soft | | | | Not usable |
| Comp. Ex. 4-1 | 5 | 148 | 24 | 118 | Not measurable since gel is not formed because of being too soft | | | | Not usable |
| Comp. Ex. 4-2 | 13 | 172 | 28 | 142 | Not measurable since gel is not formed because of being too soft | | | | Not usable |
| Comp. Ex. 4-3 | 46 | 658 | 106 | 302 | 34 | 24 | 1,260,110 | 27 | Not usable |
| Comp. Ex. 5 | 29 | 535 | 86 | 271 | 37 | 26 | 1,493,271 | 32 | Not usable |
| Comp. Ex. 6 | 20 | 70 | 11 | 33 | 25 | 18 | 834,422 | 18 | Not usable |
| Example 3A-1 | 4 | 641 | 103 | 165 | 218 | 155 | 5,520,234 | 120 | Usable |
| Example 3A-2 | 15 | 719 | 116 | 229 | 263 | 187 | 5,890,552 | 128 | Usable |
| Example 3A-3 | 29 | 727 | 117 | 267 | 311 | 221 | 6,356,475 | 138 | Usable |
| Example 3B | 20 | 858 | 138 | 385 | 307 | 218 | 6,731,469 | 146 | Usable |
| Example 3C | 26 | 873 | 141 | 394 | 313 | 222 | 6,489,069 | 141 | Usable |
| Example 3D | 20 | 867 | 140 | 369 | 242 | 172 | 5,998,440 | 130 | Usable |
| Example 3E | 42 | 806 | 130 | 407 | 283 | 201 | 5,581,328 | 121 | Usable |
| Example 3F | 43 | 808 | 130 | 403 | 286 | 203 | 5,941,241 | 129 | Usable |
| Comp. Ex. 8 | 5 | 736 | 119 | 263 | 119 | 84 | 4,096,046 | 89 | Not usable |
| Example 4 | 6 | 828 | 133 | 300 | 297 | 211 | 6,987,728 | 152 | Usable |
| Example 5A | 4 | 746 | 120 | 291 | 166 | 118 | 5,142,993 | 112 | Usable |
| Example 5B | 5 | 554 | 89 | 274 | 180 | 128 | 6,418,528 | 139 | Usable |
| Comp. Ex. 10 | 7 | 757 | 122 | 256 | 145 | 103 | 4,385,924 | 95 | Not usable |
| Comp. Ex. 11 | 4 | 601 | 97 | 245 | 140 | 99 | 4,534,673 | 99 | Not usable |
| Example 13-1 | 14 | 444 | 71 | 422 | 161 | 114 | 5,136,339 | 112 | Usable |
| Example 13-2 | 12 | 475 | 76 | 460 | 159 | 113 | 5,291,915 | 115 | Usable |

Comp. Ex. = Comparative Example

TABLE 3-1

Summary of Names, Origins and Product Names of Enzymes used for Corn Starch

| Example | Name | Origins | Product name (Manufacturer) |
|---|---|---|---|
| Comp. Ex. 12 | — | — | Untreated corn starch |
| Example 6 | α-amylase | *Aspergillus oryzae* | Biozyme A (Amano Enzyme) |
| Comp. Ex. 13-1 | α-amylase | *Bacillus amyloliquefaciens* | Reagent (Sigma-Aldrich Corporation) |
| Comp. Ex. 13-2 | α-amylase | *Bacillus amyloliquefaciens* | Reagent (Sigma-Aldrich Corporation) |
| Example 7-1 | amyloglucosidase | *Aspergillus niger* | AMG (Novo) |
| Example 7-2 | amyloglucosidase | *Aspergillus niger* | AMG (Novo) |
| Comp. Ex. 14 | β-amylase | Barley | OPTIMALT BBA (Genencor) |
| Example 8A | isoamylase | *Pseudomonas amyloderamosa* | Reagent (Sigma-Aldrich Corporation) |
| Example 8B | α-amylase | *Aspergillus niger* | AMYLEX A3 (DANISCO) |
| Example 8C | α-glucosidase | *Aspergillus niger* | Transglucosidase L "Amano" (Amano Enzyme) |
| Example 14 | CGTase | *Bacillus licheniformis* | Toruzyme 3.0L (Novo) |

Comp. Ex. = Comparative Example

TABLE 3-2

Table 3-2: Summary of Results of Corn Starch (Starch Concentration for Amylograph: 7.0%)

| Example | Degradation ratio (%) | Maximum viscosity Measured value (BU) | Maximum viscosity Relative % (%) | Breakdown viscosity (BU) | Rupture stress Measured value (g) | Rupture stress Relative % (%) | Young's modulus Measured value (dyn/cm$^2$) | Young's modulus Relative % (%) | Evaluation results |
|---|---|---|---|---|---|---|---|---|---|
| Comp. Ex. 12 | — | 476 | 100 | 182 | 171 | 100 | 5,603,029 | 100 | — |
| Example 6 | 8 | 425 | 89 | 161 | 230 | 135 | 6,054,798 | 108 | Usable |
| Comp. Ex. 13-1 | 11 | 414 | 87 | 162 | 56 | 33 | 2,434,858 | 43 | Not usable |
| Comp. Ex. 13-2 | 40 | 383 | 80 | 141 | 153 | 90 | 4,318,913 | 77 | Not usable |

TABLE 3-2-continued

Table 3-2: Summary of Results of Corn Starch (Starch Concentration for Amylograph: 7.0%)

| Example | Degradation ratio (%) | Maximum viscosity Measured value (BU) | Maximum viscosity Relative % (%) | Breakdown viscosity (BU) | Rupture stress Measured value (g) | Rupture stress Relative % (%) | Young's modulus Measured value (dyn/cm$^2$) | Young's modulus Relative % (%) | Evaluation results |
|---|---|---|---|---|---|---|---|---|---|
| Example 7-1 | 11 | 455 | 96 | 153 | 381 | 223 | 7,805,888 | 139 | Usable |
| Example 7-2 | 33 | 432 | 91 | 170 | 348 | 204 | 6,219,387 | 111 | Usable |
| Comp. Ex. 14 | 1 | 477 | 100 | 152 | 183 | 107 | 5,582,293 | 100 | Not usable |
| Example 8A | 1 | 445 | 93 | 163 | 216 | 126 | 6,304,730 | 113 | Usable |
| Example 8B | 23 | 414 | 87 | 176 | 297 | 174 | 5,910,873 | 105 | Usable |
| Example 8C | 1 | 451 | 95 | 163 | 220 | 129 | 6,731,402 | 120 | Usable |
| Example 14 | 7 | 285 | 60 | 273 | 222 | 130 | 6,546,236 | 117 | Usable |

Comp. Ex. = Comparative Example

TABLE 4-1

Summary of Names, Origins and Product Names of Enzymes used for Cassava Starch

| Example | Name | Origins | Product name (Manufacturer) |
|---|---|---|---|
| Comp. Ex. 15 | — | — | Untreated cassava starch |
| Example 9 | α-amylase | *Aspergillus oryzae* | Biozyme A (Amano Enzyme) |
| Comp. Ex. 16-1 | α-amylase | *Bacillus amyloliquefaciens* | Reagent (Sigma-Aldrich Corporation) |
| Comp. Ex. 16-2 | α-amylase | *Bacillus amyloliquefaciens* | Reagent (Sigma-Aldrich Corporation) |
| Example 10-1 | amyloglucosidase | *Aspergillus niger* | AMG (Novo) |
| Example 10-2 | amyloglucosidase | *Aspergillus niger* | AMG (Novo) |
| Comp. Ex. 17 | β-amylase | Barley | OPTIMALT BBA (Genencor) |
| Example 11A | isoamylase | *Pseudomonas amyloderamosa* | Reagent (Sigma-Aldrich Corporation) |
| Example 11B | α-amylase | *Aspergillus niger* | AMYLEX A3(DANISCO) |
| Example 11C | α-glucosidase | *Aspergillus niger* | Transglucosidase L "Amano" (Amano Enzyme) |
| Example 15 | CGTase | *Bacillus licheniformis* | Toruzyme 3.0L(Novo) |

Comp. Ex. = Comparative Example

TABLE 4-2

Table 4-2: Summary of Results of Cassava Starch (Starch Concentration for Amylograph: 6.0%)

| Example | Degradation ratio (%) | Maximum viscosity Measured value (BU) | Maximum viscosity Relative % (%) | Breakdown viscosity (BU) | Rupture stress Measured value (g) | Rupture stress Relative % (%) | Young's modulus Measured value (dyn/cm$^2$) | Young's modulus Relative % (%) | Evaluation results |
|---|---|---|---|---|---|---|---|---|---|
| Comp. Ex. 15 | — | 757 | 100 | 509 | 51 | 100 | 472,273 | 100 | — |
| Example 9 | 6 | 737 | 97 | 434 | 60 | 118 | 567,949 | 120 | Usable |
| Comp. Ex. 16-1 | 11 | 271 | 36 | 256 | 21 | 41 | 225,310 | 48 | Not usable |
| Comp. Ex. 16-2 | 34 | 112 | 15 | 109 | Not measurable since gel is not formed because of being too soft | | | | Not usable |
| Example 10-1 | 11 | 704 | 93 | 419 | 71 | 139 | 715,243 | 151 | Usable |
| Example 10-2 | 28 | 660 | 87 | 388 | 115 | 225 | 1,390,964 | 295 | Usable |
| Comp. Ex. 17 | 2 | 755 | 100 | 440 | 52 | 102 | 494,672 | 105 | Not usable |
| Example 11A | 2 | 642 | 85 | 377 | 75 | 147 | 701,944 | 149 | Usable |
| Example 11B | 16 | 561 | 74 | 328 | 89 | 175 | 969,841 | 205 | Usable |
| Example 11C | 2 | 638 | 84 | 374 | 70 | 137 | 663,407 | 140 | Usable |
| Example 15 | 7 | 533 | 70 | 529 | 92 | 180 | 2,342,930 | 496 | Usable |

Comp. Ex. = Comparative Example

TABLE 5-1

Summary of Names, Origins and Product Names of Enzymes used when Enzyme prepared by Genetic Recombination is reacted with Wheat Starch

| Example | Name | Origins | Product name (Manufacturer) |
|---|---|---|---|
| Comparative Example 1 | — | — | Untreated wheat starch |
| Example 12A-1 | α-amylase | *Aspergillus oryzae* | SEQ ID NO: 2 |
| Example 12B-1 | α-amylase | *Aspergillus niger* | SEQ ID NO: 4 |
| Example 12C-1 | amyloglucosidase | *Aspergillus niger* | SEQ ID NO: 6 |
| Example 12D-1 | isoamylase | *Flavobacterium* sp. | SEQ ID NO: 8 |
| Example 12E-1 | isoamylase | *Pseudomonas amyloderamosa* | SEQ ID NO: 10 |

TABLE 5-2

Table 5-2: Summary of Results when Enzyme prepared by Genetic Recombination is reacted with Wheat Starch (Starch Concentration for Amylograph: 8.5%)

| Example | Degradation ratio (%) | Maximum viscosity Measured value (BU) | Maximum viscosity Relative % (%) | Breakdown viscosity (BU) | Rupture stress Measured value (g) | Rupture stress Relative % (%) | Young's modulus Measured value (dyn/cm$^2$) | Young's modulus Relative % (%) | Evaluation results |
|---|---|---|---|---|---|---|---|---|---|
| Comparatve Example 1 | — | 621 | 100 | 81 | 141 | 100 | 4,601,665 | 100 | — |
| Example 12A-1 | 25 | 785 | 126 | 403 | 252 | 179 | 5,785,782 | 126 | Usable |
| Example 12B-1 | 15 | 797 | 128 | 309 | 281 | 199 | 6,712,299 | 146 | Usable |
| Example 12C-1 | 26 | 806 | 130 | 407 | 378 | 268 | 6,973,739 | 152 | Usable |
| Example 12D-1 | 6 | 781 | 126 | 306 | 285 | 202 | 6,425,189 | 140 | Usable |
| Example 12E-1 | 6 | 775 | 125 | 297 | 263 | 187 | 6,483,006 | 141 | Usable |

Trial Production Examples

Next, the present invention will be described in more detail by way of Trial Production Examples, but the present invention is not limited to the following Trial Production Example. Unless otherwise specified, "parts" means "parts by mass".

Trial Production Example 1

Preparation of Cookie

Among the formulations shown in Table 10 below, salt-free butter and shortening were put in a mixer and then well mixed. Furthermore, white soft sugar and common salt were added, well mixed, and then ammonium hydrogen carbonate previously dissolved in water was added and well mixed. Finally, a powder sample obtained by previously mixing soft wheat flour, a starch and baking soda (sodium hydrogen carbonate) was added, followed by well mixing until a mass of a dough was formed. The mass of the dough was spread thinly using a rolling pin, cut using a mold and then baked in an oven (at 200° C. for 15 minutes) to prepare cookies.

TABLE 10

| Formulation (Parts) | Comparative Trial Production Example 1-1 | Comparative Trial Production Example 1-2 | Comparative Trial Production Example 1-3 | Comparative Trial Production Example 1-4 | Trial Production Example 1-1 | Trial Production Example 1-2 |
|---|---|---|---|---|---|---|
| Soft wheat flour | 150 | 150 | 150 | 150 | 150 | 150 |
| Chemically unmodified cassava starch Note (4) | 150 | — | — | — | — | — |
| Chemically modified cassava starch 1 Note (1) | — | 150 | — | — | — | — |
| Chemically modified cassava starch 2 Note (2) | — | — | 150 | — | — | — |
| Chemically modified cassava starch 3 Note (3) | — | — | — | 150 | — | — |
| Starch prepared in Example 9 | — | — | — | — | 150 | — |
| Starch prepared in Example 10-2 | — | — | — | — | — | 150 |
| White soft sugar | 120 | 120 | 120 | 120 | 120 | 120 |
| Salt-free butter | 60 | 60 | 60 | 60 | 60 | 60 |
| Shortening | 60 | 60 | 60 | 60 | 60 | 60 |
| Ammonium hydrogen carbonate | 3 | 3 | 3 | 3 | 3 | 3 |
| Baking soda | 3 | 3 | 3 | 3 | 3 | 3 |
| Common salt | 1 | 1 | 1 | 1 | 1 | 1 |
| Water | 34 | 34 | 34 | 34 | 34 | 34 |

Note (1)

Chemically modified cassava starch 1: "RK-08", manufactured by GLICO FOODS CO., LTD.

Note (2)

Chemically modified cassava starch 2: "CHEMISTAR 280", manufactured by GLICO FOODS CO., LTD. "CHEMISTAR" is a registered trademark of GLICO FOODS CO., LTD.

Note (3)

Chemically modified cassava starch 3: "CHEMISTAR 300S", manufactured by GLICO FOODS CO., LTD. "CHEMISTAR" is a registered trademark of GLICO FOODS CO., LTD.

Note (4)

Chemically unmodified cassava starch: untreated native cassava starch.

The obtained cookies showed the following results. That is, both the cookies of Trial Production Examples 1-1 and 1-2, in which any one of the starches prepared in Examples 9 and 10-2 was added, were soft and had texture with nice melt in mouth as compared with the cookies of Comparative Trial Production Examples 1 to 4, which were hard and crunchy, and also had texture with poor melt in mouth. In particular, the cookies of Trial Production Examples 1-1 and 1-2 had very light texture and were readily edible. Regarding the dough at the time of shaping, both the doughs of Trial Production Examples 1-1 and 1-2 were very dry and non-sticky as compared with the doughs of Comparative Trial Production Examples 1-1 to 1-4, and did not stick to hands, rolling pin and the like, and also showed very nice operability.

Trial Production Example 2

Preparation of Sponge Cake

Among the formulations shown in Table 11 below, whole egg and granulated sugar were warmed to around a body temperature while mixing using a hand mixer. Furthermore, the mixture was stirred by a hand mixer until the mixture become to a mixture that has a viscosity, fine bubbles and wholly whitish state. To the mixture, a powder sample obtained by previously mixing soft wheat flour, a starch and wheat gluten was added through sieving, followed by mixing using a spatula. Finally, a mixture of melted butter and milk was added and mixed. The obtained mixture was poured into a mold and then baked in an oven (at 200° C. for 15 minutes, then at 190° C. for 18 minutes) to prepare a sponge cake.

The obtained sponge cakes showed the following results. That is, all the sponge cakes of Trial Production Example 2-1 to 2-4, in which any one of the starches prepared in Examples 1-3, 2A, 3A-3 and 5A was added, showed nice swelling after baking and had a large volume, and also had soft and puffy nice texture as compared with the sponge cakes of Comparative Trial Production Example 2-1 and Comparative Trial Production Example 2-2.

Trial Production Example 3

Preparation of Custard Cream

Among the formulations shown in Table 12 below, granulated sugar was added to egg yolk beaten well by a beater, followed by mixing by the beater. To the mixture, a powder sample obtained by previously mixing soft wheat flour and a starch was added through sieving, followed by mixing. Furthermore, warmed milk was added and mixed with them, the mixture was filtered and put in a pan, and then heated. The mixture was stirred by a wooden spatula until the mixture become to a mixture that has a viscosity and a smooth state. Finally, butter, a food color and vanilla essence were added and mixed with them to prepare a custard cream.

TABLE 12

| Formulation (Parts) | Comparative Trial Production Example 3-1 | Comparative Trial Production Example 3-2 | Trial Production Example 3-1 | Trial Production Example 3-2 |
|---|---|---|---|---|
| Milk | 300 | 300 | 300 | 300 |
| Egg yolk | 35 | 35 | 35 | 35 |
| Granulated sugar | 60 | 60 | 60 | 60 |
| Soft wheat flour | 10 | 10 | 10 | 10 |
| Chemically unmodified wheat starch Note (3) | 10 | — | — | — |

TABLE 11

| Formulation (Parts) | Comparative Trial Production Example 2-1 | Comparative Trial Production Example 2-2 | Trial Production Example 2-1 | Trial Production Example 2-2 | Trial Production Example 2-3 | Trial Production Example 2-4 |
|---|---|---|---|---|---|---|
| Soft wheat flour | 50 | 50 | 50 | 50 | 50 | 50 |
| Chemically unmodified wheat starch Note (3) | 40 | — | — | — | — | — |
| Chemically modified wheat starch Note (1) | — | 40 | — | — | — | — |
| Starch prepared in Example 1-3 | — | — | 40 | — | — | — |
| Starch prepared in Example 2A | — | — | — | 40 | — | — |
| Starch prepared in Example 3A-3 | — | — | — | — | 40 | — |
| Starch prepared in Example 5A | — | — | — | — | — | 40 |
| Wheat gluten Note (2) | 4.5 | 4.5 | 4.5 | 4.5 | 4.5 | 4.5 |
| Whole egg | 170 | 170 | 170 | 170 | 170 | 170 |
| Granulated sugar | 100 | 100 | 100 | 100 | 100 | 100 |
| Salt-free butter | 35 | 35 | 35 | 35 | 35 | 35 |
| Milk | 25 | 25 | 25 | 25 | 25 | 25 |

Note (1)
Chemically modified wheat starch: "MIDSOL 1020", manufactured by GLICO FOODS CO., LTD.

Note (2)
Wheat gluten: "FinegluVP", manufactured by GLICO FOODS CO., LTD. "Fineglu" is a registered trademark of GLICO FOODS CO., LTD.

Note (3)
Chemically unmodified wheat starch: untreated native wheat starch.

TABLE 12-continued

| Formulation (Parts) | Comparative Trial Production Example 3-1 | Comparative Trial Production Example 3-2 | Trial Production Example 3-1 | Trial Production Example 3-2 |
|---|---|---|---|---|
| Chemically modified wheat starch [Note (1)] | — | 10 | — | — |
| Starch prepared in Example 1-3 | — | — | 10 | — |
| Starch prepared in Example 3A-3 | — | — | — | 10 |
| Salt-free butter | 15 | 15 | 15 | 15 |
| KUCHINA COLOR 400LS [Note (2)] | appropriate amount | appropriate amount | appropriate amount | appropriate amount |
| Vanilla essence | appropriate amount | appropriate amount | appropriate amount | appropriate amount |

Note (1)
Chemically modified wheat starch: "MIDSOL 1020", manufactured by GLICO FOODS CO., LTD.

Note (2)
KUCHINA COLOR 400LS: Gardenia yellow food color. "KUCHINA COLOR" is a registered trademark of GLICO FOODS CO., LTD.

Note (3)
Chemically unmodified wheat starch: Untreated native wheat starch.

The obtained custard creams showed the following results. That is, both the custard creams of Trial Production Example 3-1 and 3-2, in which any one of starches prepared in Examples 1-3 and 3A-3 was added, had appropriate body and shape retention, and had nice melt in mouth and smooth texture. On the other hand, the custard cream of Comparative Trial Production Example 3-1 had gel-like physical properties and heavy texture, and also had poor melt in mouth and poor smoothness. Also, the custard cream of Comparative Trial Production Example 3-2 had poor body and shape retention, and had texture with stickiness and poor melt in mouth.

Trial Production Example 4

Preparation of Milk Pudding

Among the formulations shown in Table 13 below, granulated sugar was added to milk and mixed well using a wooden spatula to dissolve the granulated sugar. To the mixture, a starch sample was added and mixed well using the wooden spatula. The mixture was heated while stirring by the wooden spatula until the mixture become to a mixture having a viscosity and a smooth state. The mixture was filled in a jelly cup and quenched in an ice bath to prepare a milk pudding.

TABLE 13

| Formulation (Parts) | Comparative Trial Production Example 4-1 | Comparative Trial Production Example 4-2 | Trial Production Example 4-1 | Trial Production Example 4-2 |
|---|---|---|---|---|
| Milk | 170 | 170 | 170 | 170 |
| Granulated sugar | 10 | 10 | 10 | 10 |
| Chemically unmodified wheat starch [Note (2)] | 10 | — | — | — |
| Chemically Modified wheat starch [Note (1)] | — | 10 | — | — |
| Starch prepared in Example 1-3 | — | — | 10 | — |
| Starch prepared in Example 3A-3 | — | — | — | 10 |

Note (1)
Chemically modified wheat starch: "MIDSOL 1020", manufactured by GLICO FOODS CO., LTD.

Note (2)
Chemically unmodified wheat starch: Untreated native wheat starch.

The obtained milk puddings showed the following results. That is, both the milk puddings of Trial Production Examples 4-1 and 4-2, in which any one of the starches prepared in Examples 1-3 and 3A-3 was added, had sticky and chewy and also had nice melt in mouth and smooth texture. On the other hand, the milk pudding of Comparative Trial Production Example 4-1 was sticky but had texture with hard yogurt-like hardness and was therefore inferior in both melt in mouth and smoothness as compared with those of Trial Production Examples. Also, the milk pudding of Comparative Trial Production Example 4-2 was not firmly gelled and had a texture with stickiness, and also had poor melt in mouth.

Trial Production Example 5

Preparation of Kudzu Starch Cake

Among the formulations shown in Table 14 below, a mixture of a starch sample and white soft sugar was added to water and white soft sugar was dissolved by well mixing using a wooden spatula. The mixture was heated while stirring using the wooden spatula until the mixture become a pasty mixture with a viscosity and a transparency state. The mixture was poured into a mold and quenched in an ice bath to prepare a kudzu starch cake.

TABLE 14

| Formulation (Parts) | Comparative Trial Production Example 5-1 | Comparative Trial Production Example 5-2 | Comparative Trial Production Example 5-3 | Trial Production Example 5-1 | Trial Production Example 5-2 | Trial Production Example 5-3 | Trial Production Example 5-4 |
|---|---|---|---|---|---|---|---|
| Fermented wheat starch | 56 | — | — | — | — | — | — |
| Chemically unmodified wheat starch [Note (2)] | — | 56 | — | — | — | — | — |
| Chemically modified wheat starch [Note (1)] | — | — | 56 | — | — | — | — |
| Starch prepared in Example 1-3 | — | — | — | 56 | — | — | — |
| Starch prepared in Example 2A | — | — | — | — | 56 | — | — |
| Starch prepared in Example 3A-3 | — | — | — | — | — | 56 | — |
| Starch prepared in Example 5A | — | — | — | — | — | — | 56 |

TABLE 14-continued

| Formulation (Parts) | Comparative Trial Production Example 5-1 | Comparative Trial Production Example 5-2 | Comparative Trial Production Example 5-3 | Trial Production Example 5-1 | Trial Production Example 5-2 | Trial Production Example 5-3 | Trial Production Example 5-4 |
|---|---|---|---|---|---|---|---|
| White soft sugar | 32 | 32 | 32 | 32 | 32 | 32 | 32 |
| Water | 280 | 280 | 280 | 280 | 280 | 280 | 280 |

Note (1)
Chemically modified wheat starch: "MIDSOL 1020", manufactured by GLICO FOODS CO., LTD.
Note (2)
Chemically unmodified wheat starch: Untreated native wheat starch.

The obtained kudzu starch cakes showed the following results. That is, all the kudzu starch cakes of Trial Production Example 5-1 to 5-4, in which any one of the starches prepared in Examples 1-3, 2A, 3A-3 and 5A was added, had a appropriate hardness and brittleness, and had appropriate viscoelasticity and sticky texture. As compared with a kudzu starch cake so called in the Kanto area in Comparative Trial Production Example 5-1, in which a fermented wheat starch obtained by fermenting for a long period, for example, one or more years was used, the kudzu starch cakes having the identical texture could be prepared without requiring fermentation for a long period in Trial Production Examples. Furthermore, the obtained kudzu starch cakes had nice flavor without having peculiar flavor derived from a fermented wheat starch and fermentation odor. On the other hand, the kudzu starch cake of Comparative Trial Production Example 5-2 was hard and brittle, and had texture with stickiness in the mouth. Also, the kudzu starch cake of Comparative Trial Production Example 5-3 had soft and brittle texture and showed texture far different from that of the kudzu starch cake so called in the Kanto area, together with those of Comparative Trial Production Example 5-2 and Comparative Trial Production Example 5-3.

Trial Production Example 6

Preparation of Goma-dofu

Among the formulation shown in Table 15 below, a starch sample was added to water and the mixture was heated while stirring using a wooden spatula until the mixture become a pasty mixture with a viscosity and a transparency state. A sesame paste was added to them and mixed well. The mixture was filled in a container and then cooled to obtain a goma-dofu.

TABLE 15

| Formulation (Parts) | Comparative Trial Production Example 6-1 | Comparative Trial Production Example 6-2 | Trial Production Example 6-1 | Trial Production Example 6-2 |
|---|---|---|---|---|
| Sesame paste | 50 | 50 | 50 | 50 |
| Chemically unmodified wheat starch Note (2) | 30 | — | — | — |
| Chemically modified wheat starch Note (1) | — | 30 | — | — |
| Starch prepared in Example 1-3 | — | — | 30 | — |
| Starch prepared in Example 3A-3 | — | — | — | 30 |
| Water | 300 | 300 | 300 | 300 |

Note (1)
Chemically modified wheat starch: "MIDSOL 1020", manufactured by GLICO FOODS CO., LTD.
Note (2)
Chemically unmodified wheat starch: Untreated native wheat starch.

The obtained goma-dofus showed the following results. That is, both the goma-dofus of Trial Production Examples 6-1 and 6-2, in which anyone of starches prepared in Examples 1-3 and 3A-3 was added, had appropriately sticky texture and appropriate crispy sensation in contrast to a texture with rich elasticity like texture obtained by the addition of a kudzu powder, and had readily edible texture with less stickiness and sticking in the mouth. Thus, it could be expected for the obtained goma-dofu to be applied to foods for advanced aged persons, for example. On the other hand, the goma-dofu of Comparative Trial Production Example 6-1 has soft and strong sticky texture and the goma-dofu of Comparative Trial Production Example 6-2 had hard and brittle texture, but had neither elasticity nor sticky texture, and thus both goma-dofus of Comparative Trial Production Example 6-1 and Comparative Trial Production Example 6-2 were inferior in deliciousness and ease of eating.

Trial Production Example 7

Preparation of Kamaboko

Among the formulations shown in Table 16 below, a fish paste, common salt, sugar, monosodiumglutamate and potassium sorbate were put in a (silent) mixer and well mixed until the mixture had a viscosity. In order to inhibit a temperature rise of the fish paste, a half amount of moisture with ice was added to them and mixed. Then, egg white, Mirin and a starch previously suspended in the remaining water with ice were added to them and mixed well until a homogeneous mixture was obtained. Indication of the temperature of the fish paste after mixing was within a range from 10 to 15° C. The mixed fish paste was deaerated and filled in a cage. After filling, the cage filled with a mixed fish paste was subjected to a sterilization step (at 90° C. for 40 minutes) and cooled to prepare a kamaboko.

TABLE 16

| Formulation (Parts) | Comparative Trial Production Example 7-1 | Comparative Trial Production Example 7-2 | Comparative Trial Production Example 7-3 | Trial Production Example 7-1 | Trial Production Example 7-2 |
|---|---|---|---|---|---|
| Fish paste | 100 | 100 | 100 | 100 | 100 |
| Chemically unmodified wheat starch Note (3) | 15 | — | — | — | — |
| Chemically modified wheat starch 1 Note (1) | — | 15 | — | — | — |
| Chemically modified wheat starch 2 Note (2) | — | — | 15 | — | — |
| Starch prepared in Example 1-3 | — | — | — | 15 | — |
| Starch prepared in Example 3A-3 | — | — | — | — | 15 |
| Common salt | 3 | 3 | 3 | 3 | 3 |
| Sugar | 2.5 | 2.5 | 2.5 | 2.5 | 2.5 |
| Egg white | 5 | 5 | 5 | 5 | 5 |
| Mirin | 4 | 4 | 4 | 4 | 4 |
| Monosodium glutamate | 0.5 | 0.5 | 0.5 | 0.5 | 0.5 |
| Potassium sorbate | 0.3 | 0.3 | 0.3 | 0.3 | 0.3 |
| Water with ice | 40 | 40 | 40 | 40 | 40 |

Note (1)
Chemically modified wheat starch 1: "MIDSOL 1020", manufactured by GLICO FOODS CO., LTD.
Note (2)
Chemically modified wheat starch 2: "Ginrin", manufactured by GLICO FOODS CO., LTD. "Ginrin" is a registered trademark of GLICO FOODS CO., LTD.
Note (3)
Chemically unmodified wheat starch: Untreated native wheat starch.

On the next day of production and after one week, the obtained kamabokos were subjected to a sensory test. The kamaboko of Comparative Trial Production Example 7-1 had texture with slightly poor elasticity and also had no good chewiness. The kamaboko of Comparative Trial Production Example 7-2 had hardness but had stiff texture, and also retrogradation of the starch arose in a sensory test after refrigeration for one week, and thus the kamaboko showed dry and tasteless texture with water separation. The kamaboko of Comparative Trial Production Example 7-3 was less likely to cause change with time due to retrogradation because of the structure of the starch, but showed greasy texture with poor elasticity. As compared with these Comparative Trial Production Examples, both the kamabokos of Trial Production Examples 7-1 and 7-2, in which any one of the starches prepared in Examples 1-3 and 3A-3 was added, had elasticity with nice chewiness and also caused less change with time.

Trial Production Example 8

Preparation of Glaze for Mitarashi Dango

Among the formulation shown in Table 17 below, a starch sample was previously suspended in a part of water. The total amount of white soft sugar, dark soy sauce, Mirin, starch syrup and the remaining water were put in a pan and then mixed well by a wooden spatula. Furthermore, the starch sample previously suspended in water was added to them and heated while stirring using the wooden spatula. The mixture was heated until the mixture becomes a pasty mixture with a viscosity and a transparency state, to prepare a glaze for mitarashi dango.

TABLE 17

| Formulation (Parts) | Comparative Trial Production Example 8-1 | Comparative Trial Production Example 8-2 | Trial Production Example 8-1 | Trial Production Example 8-2 |
|---|---|---|---|---|
| White soft sugar | 95 | 95 | 95 | 95 |
| Dark soy sauce | 80 | 80 | 80 | 80 |
| Mirin | 35 | 35 | 35 | 35 |
| Starch syrup | 8 | 8 | 8 | 8 |
| Chemically unmodified cassava starch Note (2) | 10 | — | — | — |
| Chemically modified cassava starch Note (1) | — | 10 | — | — |
| Starch prepared in Example 9 | — | — | 10 | — |
| Starch prepared in Example 10-2 | — | — | — | 10 |
| Water | 70 | 70 | 70 | 70 |

Note (1)
Chemically modified cassava starch: "RK-08", manufactured by GLICO FOODS CO., LTD.
Note (2)
Chemically unmodified cassava starch: Untreated native cassava starch.

The obtained glaze for mitarashi dango showed the following results. That is, both the glazes for mitarashi dango of Trial Production Example 8-1 and 8-2, in which any one of the starches prepared in Examples 9 and 10-2 was added, had nice body and shape retention, and were less likely to drop because of nice adhesion onto the dango, and also had less stickiness and thread-forming sensation and had smooth texture. On the other hand, the glaze for mitarashi dango of Comparative Trial Production Example 8-1 had gel-like physical properties and heavy texture, and also had poor melt in mouth and no smoothness. The glaze for mitarashi dango of Comparative Trial Production Example 8-2 had poor body and poor shape retention and caused dropping because of poor adhesion onto a dango, and also had texture with stickiness and poor melt in mouth. For example, in freezing distribution of a split and broiled eel, in order to prevent a salsa for the split and broiled eel from dropping at the time of thawing, a salsa having a high viscosity and nice body and shape retention may be sometimes used in the final step of baking. However there is a problem that the salsa having a high viscosity usually has strong stickiness or in a gel-like form, and also has jellied fish-like physical properties and heavy texture. Use of the enzyme-treated starch in the present invention makes it possible to prepare a split and broiled fish which is less likely to drop because of nice adhesion onto the eel and the like, and has less stickiness and thread-forming sensation, and has smooth texture.

Trial Production Example 9

Preparation of Fruit Sauce

Among the formulations shown in Table 18 below, a starch sample was previously suspended in a part of water. Fruit puree, white soft sugar, lemon juice and the total amount of the remaining water were put in a pan and heated with stirring using the wooden spatula. Furthermore, the starch sample previously suspended in water was added to them. The mixture was heated until the mixture become a pasty mixture with a viscosity and a transparency state to prepare a fruit sauce.

TABLE 18

| Formulation (Parts) | Comparative Trial Production Example 9-1 | Comparative Trial Production Example 9-2 | Trial Production Example 9-1 | Trial Production Example 9-2 |
|---|---|---|---|---|
| Fruit puree | 100 | 100 | 100 | 100 |
| White soft sugar | 10 | 10 | 10 | 10 |
| Chemically unmodified cassava starch [Note (2)] | 3 | — | — | — |
| Chemically modified cassava starch [Note (1)] | — | 3 | — | — |
| Starch prepared in Example 9 | — | — | 3 | — |
| Starch prepared in Example 10-2 | — | — | — | 3 |
| Lemon juice | 2 | 2 | 2 | 2 |
| Water | 10 | 10 | 10 | 10 |

Note (1)
Chemically modified cassava starch: "RK-08", manufactured by GLICO FOODS CO., LTD.
Note (2)
Chemically unmodified cassava starch: Untreated native cassava starch.

The obtained fruit sauces showed the following results. That is, both the fruit sauces of Trial Production Example 9-1 and 9-2, in which any one of the starches prepared in Examples 9 and 10-2 was added, had nice body and shape retention, and had nice adhesion onto a food such as dessert, and had less stickiness and thread-forming sensation, and smooth texture. On the other hand, the fruit sauce of Comparative Trial Production Example 9-1 had gel-like physical properties and heavy texture, and also had poor melt in mouth and no smoothness. The fruit sauce of Comparative Trial Production Example 9-2 had poor body and poor shape retention, and caused dropping because of poor adhesion onto a food such as dessert, and also had texture with stickiness, and poor melt in mouth.

Trial Production Example 10

Preparation of Dressing

Among the formulations shown in Table 19 below, white soft sugar and a starch sample which are previously mixed in powder state was added to water, and heated with stirring at 90° C. for 10 minutes. Brewed vinegar, common salt, lemon juice, and seasonings including monosodium glutamate and the like were added and further heated with stirring for 5 minutes. After cooling it to room temperature, egg yolk was added to them and mixed well. Using a homomixer manufactured by Tokushu Kika Kogyo Co., Ltd. (Now in the name of: PRIMIX Corporation), salad oil was slowly added dropwise while mixing with stirring at 8,000 rpm. After dropwise addition of the entire amount of salad oil, the mixture was mixed with stirring at 8,000 rpm further for 5 minutes to prepare a dressing.

TABLE 19

| Formulation (Parts) | Comparative Trial Production Example 10-1 | Comparative Trial Production Example 10-2 | Trial Production Example 10-1 | Trial Production Example 10-2 |
|---|---|---|---|---|
| Salad oil | 38 | 38 | 38 | 38 |
| Brewed vinegar (acidity: 4.2) | 10 | 10 | 10 | 10 |
| Egg yolk | 5 | 5 | 5 | 5 |
| White soft sugar | 5 | 5 | 5 | 5 |
| Common Salt | 3 | 3 | 3 | 3 |
| Lemon juice | 2 | 2 | 2 | 2 |
| Chemically unmodified cassava starch [Note (2)] | 2.5 | — | — | — |
| Chemically modified cassava starch [Note (1)] | — | 2.5 | — | — |
| Starch prepared in Example 9 | — | — | 2.5 | — |
| Starch prepared in Example 10-2 | — | — | — | 2.5 |
| Monosodium glutamate | 0.2 | 0.2 | 0.2 | 0.2 |
| Pepper | Suitable amount | Suitable amount | Suitable amount | Suitable amount |
| Mustard | Suitable amount | Suitable amount | Suitable amount | Suitable amount |
| Water | 33.8 | 33.8 | 33.8 | 33.8 |

Note (1)
Chemically modified cassava starch: "RK-08", manufactured by GLICO FOODS CO., LTD.
Note (2)
Chemically unmodified cassava starch: Untreated native cassava starch.

The obtained dressings showed the following results. That is, both the dressings of Trial Production Examples 10-1 and 10-2, in which each of the starches prepared in Examples 9 and 10-2 was added, had nice body and nice shape retention, and were less likely to drop because of nice adhesion onto vegetables and the like, and caused less stickiness and thread-forming sensation, and had smooth texture. On the other hand, the dressing of Comparative Trial Production Example 10-1 had gel-like physical properties and heavy texture, and also had poor melt in mouth and no smoothness. Also, the dressing of Comparative Trial Production Example 10-2 had poor body and poor shape retention and caused dropping because of poor adhesion onto vegetables and the like, and also had texture with stickiness, and poor melt in mouth.

Trial Production Example 11

Preparation of Batter for Deep-Fried Food

Among the formulations shown in Table 20 below, soft wheat flour and a starch sample previously mixed in a powder state were suspended in cold water and mixed well to prepare a batter for deep-fried food.

TABLE 20

| Formulation (Parts) | Comparative Trial Production Example 11-1 | Comparative Trial Production Example 11-2 | Trial Production Example 11-1 | Trial Production Example 11-2 |
|---|---|---|---|---|
| Soft wheat flour | 150 | 95 | 95 | 95 |
| Chemically unmodified cassava starch [Note (2)] | 30 | — | — | — |
| Chemically modified cassava starch [Note (1)] | — | 30 | — | — |
| Starch prepared in Example 9 | — | — | 30 | — |
| Starch prepared in Example 10-2 | — | — | — | 30 |
| Cold water | 230 | 230 | 230 | 230 |

Note (1)
Chemically modified cassava starch: "RK-08", manufactured by GLICO FOODS CO., LTD.

Note (2)
Chemically unmodified cassava starch: Untreated native cassava starch.

The obtained batters for deep-fried food showed the following results. That is, both the tempuras obtained by dipping ingredients such as prawn in the batters for deep-fried food of Trial Production Examples 11-1 and 11-2, in which the starch prepared in Example 9 or 10-2 was added, thereby coating the ingredients with the batters, and frying in oil, or the fried foods obtained by dipping ingredients such as prawn in the batters for deep-fried food of Trial Production Examples 11-1 and 11-2, in which the starch prepared in Example 9 or 10-2 was added, thereby coating the ingredients with the batters, further coating this with a bread crumbs and frying in oil, had a crispy and light texture. On the other hand, tempuras and fried foods, in which the batters for deep-fried food of Comparative Trial Production Example 11-1 and Comparative Trial Production Example 11-2 were used, had poor crispy texture, and hardly made users feel lightness.

Trial Production Example 12

Preparation of Sausage

Among the formulations shown in Table 21 below, pork arm meat was put in a silent cutter, while cutting the pork arm meat at a high speed, casein sodium, common salt, white soft sugar, a seasoning, a pickle solution, a pork powder, spice, potassium sorbate, a pH adjusting agent and a food color were added and mixed well. When the mixture was formed into a paste, water with ice and lard were added and cutting was continued. Finally, a starch sample was added to them and mixed well to give a homogeneous paste. The paste was filled in a casing and then sterilized at 80° C. for 40 minutes to prepare a sausage by cooling with running water.

TABLE 21

| Formulation (Parts) | Comparative Trial Production Example 12-1 | Comparative Trial Production Example 12-2 | Trial Production Example 12-1 | Trial Production Example 12-2 |
|---|---|---|---|---|
| Pork arm meat | 60 | 60 | 60 | 60 |
| Lard | 10 | 10 | 10 | 10 |
| Casein sodium | 1 | 1 | 1 | 1 |
| Chemically unmodified cassava starch [Note (3)] | 3 | — | — | — |
| Chemically modified cassava starch [Note (1)] | — | 3 | — | — |
| Starch prepared in Example 9 | — | — | 3 | — |
| Starch prepared in Example 10-2 | — | — | — | 3 |
| Water with ice | 25 | 25 | 25 | 25 |
| Common salt | 1.4 | 1.4 | 1.4 | 1.4 |
| White soft sugar | 1 | 1 | 1 | 1 |
| Seasoning | 0.3 | 0.3 | 0.3 | 0.3 |
| pickle solution | 0.5 | 0.5 | 0.5 | 0.5 |
| Pork powder | 1 | 1 | 1 | 1 |
| Spice | 0.5 | 0.5 | 0.5 | 0.5 |
| Potassium sorbate | 0.15 | 0.15 | 0.15 | 0.15 |
| pH adjusting agent | 0.15 | 0.15 | 0.15 | 0.15 |
| Creation Color RC [Note (2)] | appropriate amount | appropriate amount | appropriate amount | appropriate amount |

Note (1)
Chemically modified cassava starch: "RK-08", manufactured by GLICO FOODS CO., LTD.

Note (2)
Creation Color RC: Cochineal food color. "Creation" is a registered trademark of GLICO FOODS CO., LTD.

Note (3)
Chemically unmodified cassava starch: Untreated native cassava starch.

On the next day of production and after one week, the obtained sausages were subjected to a sensory test. The sausage of Comparative Trial Production Example 12-1 had texture with slightly poor elasticity and had no good chewiness. The sausage of Comparative Trial Production Example 12-2 had hardness but had stiff texture, and retrogradation of the starch arose in a sensory test after refrigeration for one week, and thus the sausage showed dry and tasteless texture with water separation. As compared with those of these Comparative Trial Production Examples, both the sausages of Trial Production Examples 12-1 and 12-2, in which the starch prepared in Example 9 or 10-2 was added, had elasticity with nice chewiness and also caused less change with time.

Trial Production Example 13

Preparation of Raw Udon

To a powder mixture obtained by mixing a starch, medium wheat flour and a powdered gluten in the following ratio in accordance with the formulation shown in Table 22 below, water for kneading obtained by dissolving 2 parts of common salt in 40 parts of water was added, followed by kneading in a vacuum mixer for 12 minutes. Using a noodle making machine, the obtained kneaded mixture was subjected to compound and rolling to obtain a noodle strip, which was cut using a cutting-tooth No. 10 to obtain a raw udon.

TABLE 22

| Formulation (Parts) | Comparative Trial Production Example 13-1 | Comparative Trial Production Example 13-2 | Comparative Trial Production Example 13-3 | Trial Production Example 13-1 |
|---|---|---|---|---|
| Wheat flour | 80 | 80 | 80 | 80 |
| Chemically unmodified cassava starch [Note (3)] | 20 | — | — | — |

TABLE 22-continued

| Formulation (Parts) | Comparative Trial Production Example 13-1 | Comparative Trial Production Example 13-2 | Comparative Trial Production Example 13-3 | Trial Production Example 13-1 |
|---|---|---|---|---|
| Chemically modified cassava starch 1 Note (1) | — | 20 | — | — |
| Chemically modified cassava starch 2 Note (2) | — | — | 20 | — |
| Starch prepared in Example 10-2 | — | — | — | 20 |
| Powdered gluten | 2 | 2 | 2 | 2 |
| Salt | 2 | 2 | 2 | 2 |
| Water | 40 | 40 | 40 | 40 |

Note (1)

Chemically modified cassava starch 1: "CHEMISTAR 280", manufactured by GLICO FOODS CO., LTD. "CHEMISTAR" is a registered trademark of GLICO FOODS CO., LTD.

Note (2)

Chemically modified cassava starch 2: "RK-08", manufactured by GLICO FOODS CO., LTD.

Note (3)

Chemically unmodified cassava starch: Untreated native cassava starch.

The obtained raw udon was boiled in boiling water for 10 minutes and dipped in a hot soup, and then texture was evaluated. The udon of Comparative Trial Production Example 13-1 and Comparative Trial Production Example 13-2 was poor in elasticity and texture was hardly improved. Regarding the udon of Comparative Trial Production Example 13-3, a slight effect of imparting elasticity was recognized. However, rigid hardness was merely imparted and this effect may have a bad effect on noodles. On the other hand, regarding the udon of Trial Production Example 13-1, the effect of imparting sticky texture with excellent chewiness was recognized.

Trial Production Example 14

Preparation of Jelly Candy

In accordance with the formulations shown in Table 23 below, white sugar, starch syrup, a starch and water were mixed with stirring in the following ratio, the mixture was dissolved by heating up to Bx (Brix) 75. The obtained solution was filled in a mold, and left at normal temperature for 24 hours. After confirming that the solution has been solidified, it was removed from the mold to obtain a jelly candy.

TABLE 23

| Formulation (Parts) | Comparative Trial Production Example 14-1 | Comparative Trial Production Example 14-2 | Trial Production Example 14-1 | Trial Production Example 14-2 |
|---|---|---|---|---|
| Sugar | 34 | 34 | 34 | 34 |
| Starch syrup | 30 | 30 | 30 | 30 |
| Chemically unmodified cassava starch Note (2) | 21 | — | — | — |
| Chemically modified cassava starch Note (1) | — | 21 | — | — |
| Starch prepared in Example 9 | — | — | 21 | — |
| Starch prepared in Example 10-2 | — | — | — | 21 |
| Water | 15 | 15 | 15 | 15 |

Note (1)

Chemically modified cassava starch: "CHEMISTAR 300S" manufactured by GLICO FOODS CO., LTD. "CHEMISTAR" is a registered trademark of GLICO FOODS CO., LTD.

Note (2)

Chemically unmodified cassava starch: Untreated native cassava starch.

The obtained jelly candies showed the following results. That is, both the jelly candies of Trial Production Example 14-1 and 14-2 had appropriate viscoelasticity and nice melt texture in mouth. On the other hand, the jelly candy of Comparative Trial Production Example 14-1 had strong elastic sensation, and the jelly candy of Comparative Trial Production Example 14-2 had strong sticky textures, but both the jelly candies had strong pasty sensation and poor melt in mouth.

Trial Production Example 15

Preparation of Frozen Dessert

In accordance with the formulation shown in Table 24 below, while raw materials and water were mixed with stirring in the following ratio, the mixture was dissolved by heating up to Bx (Brix) 40. The obtained solution was put in an ice cream maker and cooled with stirring for 35 minutes. The obtained materials was transferred to a container and then frozen to obtain a frozen dessert.

TABLE 24

| Formulation (Parts) | Comparative Trial Production Example 15-1 | Comparative Trial Production Example 15-2 | Trial Production Example 15-1 | Trial Production Example 15-2 |
|---|---|---|---|---|
| Starch syrup | 18 | 18 | 18 | 18 |
| Granulated sugar | 12 | 12 | 12 | 12 |
| Fresh cream | 12 | 12 | 12 | 12 |
| Vegetable oil and fat | 6 | 6 | 6 | 6 |
| Chemically unmodified cassava starch Note (2) | 2.4 | — | — | — |
| Chemically modified cassava starch Note (1) | — | 2.4 | — | — |
| Starch prepared in Example 9 | — | — | 2.4 | — |
| Starch prepared in Example 10-2 | — | — | — | 2.4 |
| Guar gum | 0.4 | 0.4 | 0.4 | 0.4 |
| Emulsifier | 0.2 | 0.2 | 0.2 | 0.2 |
| Water | 49 | 49 | 49 | 49 |

Note (1)

Chemically modified cassava starch: "CHEMISTAR 300S", manufactured by GLICO FOODS CO., LTD. "CHEMISTAR" is a registered trademark of GLICO FOODS CO., LTD.

Note (2)

Chemically unmodified cassava starch: Untreated native cassava starch.

The obtained frozen desserts showed the following results. That is, both the frozen desserts of Trial Production Examples 15-1 and 15-2 had appropriate viscoelasticity and sticky texture, and had nice melt texture in mouth. On the other hand, the frozen dessert of Comparative Trial Production Example 15-1 had sticky texture and the frozen dessert of Comparative Trial Production Example 15-2 also had sticky texture and spinnability. However, both the frozen desserts had strong pasty sensation and poor melt in mouth.

Example 13-1

To 400 g of an untreated native wheat starch, 900 g of ion-exchange water was added to prepare a starch suspension. After adjusting the pH of the suspension to 5.0, 1% by weight (based on starch solid content) of cyclodextrin glucanotransferase ("Toruzyme 3.0 L" derived from *Bacillus licheniformis*, manufactured by Novo; optimum pH of 6.0) was added and stirred at 50° C. for 18 hours to carry out an enzyme reaction. After completion of the reaction, an enzyme-treated starch was recovered by centrifugal filtration and blow drying. Viscosity characteristics of the obtained enzyme-treated starch were analyzed by the amylograph and the rheometer. Also, after completion of the reaction, a degradation ratio was determined by a part of a reaction solution. The results are shown in Table 2-2. As a result, the setback viscosity of it was 7.0 (BU).

Example 13-2

To 400 g of an untreated native wheat starch, 900 g of ion-exchange water was added to prepare a starch suspension. After adjusting the pH of the suspension to 6.0, 1% by weight (based on starch solid content) of cyclodextrin glucanotransferase (Cyclodextrin Cycrodextrin glucanotransferase "Amano" derived from *Paenibacillus macerans* (*Bacillus macerans*), manufactured by Amano Enzyme) was added and stirred at 50° C. for 18 hours to carry out an enzyme reaction. After completion of the reaction, an enzyme-treated starch was recovered by centrifugal filtration and blow drying. Viscosity characteristics of the obtained enzyme-treated starch were analyzed by the amylograph and the rheometer. Also, after completion of the reaction, a degradation ratio was determined by a part of a reaction solution. The results are shown in Table 2-2.

Example 14

To 400 g of an untreated native corn starch, 900 g of ion-exchange water was added to prepare a starch suspension. After adjusting the pH of the suspension to 5.0, 1% by weight (based on starch solid content) of cyclodextrin glucanotransferase ("Toruzyme 3.0 L" derived from *Bacillus licheniformis*, manufactured by Novo; optimum pH of 6.0) was added and stirred at 50° C. for 18 hours to carry out an enzyme reaction. After completion of the reaction, an enzyme-treated starch was recovered by centrifugal filtration and blow drying. Viscosity characteristics of the obtained enzyme-treated starch were analyzed by the amylograph and the rheometer. Also, after completion of the reaction, a degradation ratio was determined by a part of a reaction solution. The results are shown in Table 3-2. As a result, the setback viscosity of it was 0 (BU).

Example 15

To 400 g of an untreated native cassava starch, 900 g of ion-exchange water was added to prepare a starch suspension. After adjusting the pH of the suspension to 5.0, 1% by weight (based on starch solid content) of cyclodextrin glucanotransferase ("Toruzyme 3.0 L" derived from *Bacillus licheniformis*, manufactured by Novo; optimum pH of 6.0) was added and stirred at 50° C. for 18 hours to carry out an enzyme reaction. After completion of the reaction, an enzyme-treated starch was recovered by centrifugal filtration and blow drying. Viscosity characteristics of the obtained enzyme-treated starch were analyzed by the amylograph and the rheometer. Also, after completion of the reaction, a degradation ratio was determined by a part of a reaction solution. The results are shown in Table 4-2. As a result, the setback viscosity of it was 2 (BU).

Comparative Example 18

To 500 g of an untreated native cassava starch, 750 g of an aqueous 6.7% (w/w) sodium sulfate solution was added to prepare a starch suspension. After adjusting the pH of the suspension to 8.5, 7.36 g of a vinyl acetate monomer was added and stirred at 30° C. for 40 minutes to allow a reaction proceed. After 40 minutes, the pH of the suspension was adjusted to 6.0 and the reaction was terminated. After completion of the reaction, starch acetate was recovered by centrifugal filtration and blow drying. Viscosity characteristics of the obtained starch acetate were analyzed by the amylograph and the rheometer.

Comparative Example 19

To 500 g of an untreated native cassava starch, 785 g of an aqueous 11% (w/w) sodium sulfate solution was added to prepare a starch suspension. After adjusting the pH of the suspension to 11.0, 24 g of propylene oxide was added and stirred at 42° C. for 16 hours to allow a reaction proceed. After 16 hours, the pH of the suspension was adjusted to 6.0 and the reaction was terminated. After completion of the reaction, a hydroxypropyl starch was recovered by centrifugal filtration and blow drying. Viscosity characteristics of the obtained hydroxypropyl starch were analyzed by the amylograph and the rheometer.

Comparative Example 20

To 500 g of an untreated native cassava starch, 750 g of an aqueous 6.7% (w/w) sodium sulfate solution was added to prepare a starch suspension. After adjusting the pH of the suspension to 11.0, 10 µl of phosphorus oxychloride was added and stirred at 30° C. for 1 hour to allow a reaction proceed. After 1 hour, the pH of the suspension was adjusted to 6.0 and the reaction was terminated. After completion of the reaction, a distarch phosphate was recovered by centrifugal filtration and blow drying. Viscosity characteristics of the obtained distarch phosphate were analyzed by the amylograph and the rheometer.

Comparative Example 21

To 500 g of an untreated native cassava starch, 910 g of an aqueous 10% (w/w) sodium sulfate solution was added to prepare a starch suspension. After adjusting the pH of the suspension to 11.0, 16 g of propylene oxide was added and stirred at 42° C. for 16 hours to allow an etherification reaction proceed. After 16 hours, the temperature of the starch suspension was adjusted to 30° C., 5 µl of phosphorus oxychloride was added and stirred at 30° C. for 1 hour to carry out a crosslinking reaction proceed. After 1 hour, the pH of the suspension was adjusted to 6.0 and the entire reaction was terminated. After completion of the reaction, a hydroxypropyl distarch phosphate was recovered by centrifugal filtration and blow drying. Viscosity characteristics of the obtained hydroxypropyl distarch phosphate were analyzed by the amylograph and the rheometer.

Example 16

To 4 Kg of an untreated native cassava starch, 9 Kg of ion-exchange water was added to prepare a starch suspension. After adjusting the pH of the suspension to 5.0, 1% by weight (based on starch solid content) of amyloglucosidase ("OPTIDEX L-400" derived from *Aspergillus niger*, manufactured by Genencor; optimum pH of 4.4) was added and stirred at 50° C. for 18 hours to carry out an enzyme reaction. After completion of the reaction, an enzyme-treated starch was recovered by centrifugal filtration and blow drying. It is noted that the degradation ratio of the obtained sample was 21%.

Example 17

To 400 g of the starch acetate prepared in Comparative Example 18, 900 g of ion-exchange water was added to prepare a starch suspension. After adjusting the pH of the suspension to 5.0, 1% by weight (based on starch solid content) of amyloglucosidase ("OPTIDEX L-400" derived from *Aspergillus niger*, manufactured by Genencor; optimum pH of 4.4) was added and stirred at 50° C. for 18 hours to carry out an enzyme reaction. After completion of the reaction, an enzyme-treated starch was recovered by centrifugal filtration and blow drying. Viscosity characteristics of the obtained enzyme-treated starch were analyzed by the amylograph and the rheometer. After completion of the reaction, a degradation ratio was determined using a part of the reaction solution.

Example 18

To 400 g of the starch acetate prepared in Comparative Example 18, 900 g of ion-exchange water was added to prepare a starch suspension. After adjusting the pH of the suspension to 5.0, 1% by weight (based on starch solid content) of α-amylase ("AMYLEX A3" derived from *Aspergillus niger*, manufactured by DANISCO; optimum pH of 5.0) was added and stirred at 50° C. for 18 hours to carryout an enzyme reaction. After completion of the reaction, an enzyme-treated starch was recovered by centrifugal filtration and blow drying. Viscosity characteristics of the obtained enzyme-treated starch were analyzed by the amylograph and the rheometer. Also, after completion of the reaction, a degradation ratio was determined using a part of the reaction solution.

Example 19

To 400 g of the hydroxypropyl starch prepared in Comparative Example 19, 900 g of ion-exchange water was added to prepare a starch suspension. After adjusting the pH of the suspension to 5.0, 1% by weight (based on starch solid content) of amyloglucosidase ("OPTIDEX L-400" derived from *Aspergillus niger*, manufactured by Genencor; optimum pH of 4.4) was added and stirred at 50° C. for 18 hours to carry out an enzyme reaction. After completion of the reaction, an enzyme-treated starch was recovered by centrifugal filtration and blow drying. Viscosity characteristics of the obtained enzyme-treated starch were analyzed by the amylograph and the rheometer. Also, after completion of the reaction, a degradation ratio was determined using a part of the reaction solution.

Example 20

To 400 g of the hydroxypropyl starch prepared in Comparative Example 19, 900 g of ion-exchange water was added to prepare a starch suspension. After adjusting the pH of the suspension to 5.0, 1% by weight (based on starch solid content) of α-amylase ("AMYLEX A3" derived from *Aspergillus niger*, manufactured by DANISCO; optimum pH of 5.0) was added and stirred at 50° C. for 18 hours to carry out an enzyme reaction. After completion of the reaction, an enzyme-treated starch was recovered by centrifugal filtration and blow drying. Viscosity characteristics of the obtained enzyme-treated starch were analyzed by the amylograph and the rheometer. Also, after completion of the reaction, a degradation ratio was determined using a part of the reaction solution.

Example 21

To 400 g of the distarch phosphate prepared in Comparative Example 20, 900 g of ion-exchange water was added to prepare a starch suspension. After adjusting the pH of the suspension to 5.0, 1% by weight (based on starch solid content) of amyloglucosidase ("OPTIDEX L-400" derived from *Aspergillus niger*, manufactured by Genencor; optimum pH of 4.4) was added and stirred at 50° C. for 18 hours to carry out an enzyme reaction. After completion of the reaction, an enzyme-treated starch was recovered by centrifugal filtration and blow drying. Viscosity characteristics of the obtained enzyme-treated starch were analyzed by the amylograph and the rheometer. Also, after completion of the reaction, a degradation ratio was determined using a part of the reaction solution.

Example 22

To 400 g of the distarch phosphate prepared in Comparative Example 20, 900 g of ion-exchange water was added to prepare a starch suspension. After adjusting the pH of the suspension to 5.0, 1% by weight (based on starch solid content) of α-amylase ("AMYLEX A3" derived from *Aspergillus niger*, manufactured by DANISCO; optimum pH of 5.0) was added and stirred at 50° C. for 18 hours to carry out an enzyme reaction. After completion of the reaction, an enzyme-treated starch was recovered by centrifugal filtration and blow drying. Viscosity characteristics of the obtained enzyme-treated starch were analyzed by the amylograph and the rheometer. Also, after completion of the reaction, a degradation ratio was determined using a part of the reaction solution.

Example 23

To 400 g of the hydroxypropyl distarch phosphate prepared in Comparative Example 21, 900 g of ion-exchange water was added to prepare a starch suspension. After adjusting the pH of the suspension to 5.0, 1% by weight (based on starch solid content) of amyloglucosidase ("OPTIDEX L-400" derived from *Aspergillus niger*, manufactured by Genencor; optimum pH of 4.4) was added and stirred at 50° C. for 18 hours to carry out an enzyme reaction. After completion of the reaction, an enzyme-treated starch was recovered by centrifugal filtration and blow drying. Viscosity characteristics of the obtained enzyme-treated starch were analyzed by the amylograph and the rheometer. Also, after completion of the reaction, a degradation ratio was determined using a part of the reaction solution.

Example 24

To 400 g of the hydroxypropyl distarch phosphate prepared in Comparative Example 21, 900 g of ion-exchange water was added to prepare a starch suspension. After adjusting the pH of the suspension to 5.0, 1% by weight (based on starch solid content) of α-amylase ("AMYLEX A3" derived from *Aspergillus niger*, manufactured by DANISCO; optimum pH of 5.0) was added and stirred at 50° C. for 18 hours to carry out an enzyme reaction. After completion of the reaction, an enzyme-treated starch was recovered by centrifugal filtration and blow drying. Viscosity characteristics of the obtained enzyme-treated starch were analyzed by the amylograph and the rheometer. Also, after completion of the reaction, a degradation ratio was determined using a part of the reaction solution.

Example 25

To 500 g of the enzyme-treated starch prepared in Example 16, 750 g of an aqueous 6.7% (w/w) sodium sulfate solution was added to prepare a starch suspension. After adjusting the pH of the suspension to 8.5, 7.36 g of a vinyl acetate monomer was added and stirred at 30° C. for 40 minutes to carry out a reaction. After 40 minutes, the pH of the suspension was adjusted to 6.0 and the reaction was terminated. After completion of the reaction, an acetic acid enzyme-treated starch was recovered by centrifugal filtration and blow drying. Viscosity characteristics of the obtained acetic acid enzyme-treated starch were analyzed by the amylograph and the rheometer. Also, after completion of the reaction, a degradation ratio was determined by apart of the reaction solution.

Example 26

To 500 g of the enzyme-treated starch prepared in Example 16, 785 g of an aqueous 11% (w/w) sodium sulfate solution was added to prepare a starch suspension. After adjusting the pH of the suspension to 11.0, 24 g of propylene oxide was added and stirred at 42° C. for 16 hours to carry out a reaction. After 16 hours, the pH of the suspension was adjusted to 6.0 and the reaction was terminated. After completion of the reaction, a hydroxypropyl enzyme-treated starch was recovered by centrifugal filtration and blow drying. Viscosity characteristics of the obtained hydroxypropyl enzyme-treated starch were analyzed by the amylograph and the rheometer. Also, after completion of the reaction, a degradation ratio was determined by a part of the reaction solution.

Example 27

To 500 g of the enzyme-treated starch prepared in Example 16, 750 g of an aqueous 6.7% (w/w) sodium sulfate solution was added to prepare a starch suspension. After adjusting the pH of the suspension to 11.0, 10 µl of phosphorus oxychloride was added and stirred at 30° C. for 1 hour to carry out a reaction. After 1 hour, the pH of the suspension was adjusted to 6.0 and the reaction was terminated. After completion of the reaction, an enzyme-treated distarch phosphate was recovered by centrifugal filtration and blow drying. Viscosity characteristics of the obtained enzyme-treated distarch phosphate were analyzed by the amylograph and the rheometer. Also, after completion of the reaction, a degradation ratio was determined by a part of the reaction solution.

Example 28

To 500 g of the enzyme-treated starch prepared in Example 16, 910 g of an aqueous 10% (w/w) sodium sulfate solution was added to prepare a starch suspension. After adjusting the pH of the suspension to 11.0, 16 g of propylene oxide was added and stirred at 42° C. for 16 hours to carry out an etherification reaction. After 16 hours, the temperature of the starch suspension was adjusted to 30° C. and 5 µl of phosphorus oxychloride was added and stirred at 30° C. for 1 hour to carry out a crosslinking reaction. After 1 hour, the pH of the suspension was adjusted to 6.0 and the entire reaction was terminated. After completion of the reaction, an enzyme-treated hydroxypropyl distarch phosphate was recovered by centrifugal filtration and blow drying. Viscosity characteristics of the obtained enzyme-treated hydroxypropyl distarch phosphate were analyzed by the amylograph and the rheometer. Also, after completion of the reaction, a degradation ratio was determined by a part of the reaction solution.

The measurement results of Comparative Examples 18 to 21 and Examples 17 to 28 are shown in Table 25-2. It is noted that in an analysis by the rheometer of the present starch which used the chemical modification and the enzymatic treatment in combination, after refrigeration storage at 5° C. for 16 hours the gel did not have the hardness sufficient for the measurement. Therefore, it was difficult to compare physical properties of the gels. Therefore, confirmation was carried out after refrigeration storage at 5° C. for 21 days. The details are as follows.

A starch paste was prepared so that the concentration of the starch was 20% by weight on the dry matter basis, and then filled in a Krehalon casing having a folding width of 45 mm. This starch paste filled in the casing was heated to 90° C. at 1° C./min and maintained at 90° C. for 30 minutes. Then, the starch paste was left to cool in a constant-temperature water bath at 20° C. for 30 minutes, and then it was cooled to 5° C. in a refrigerator. After cooling, it was refrigerated at 5° C. for 21 days, then it was left at room temperature (about 25° C.) for 4 hours to return the temperature of it to room temperature, and then the measurement was carried out with a rheometer (RT-2010J-CW) manufactured by Rheotech Inc. The measurement was carried out under the measurement conditions of the rheometer: a test item: a rupture test; a height of a sample: 25 mm; and a movement rate (rupture rate) of a sample: 6 cm/min, using an adapter of a spherical jig for measurement viscosity φ5 (diameter: 5 mm, area: 19.635 $mm^2$). At the measurement, the hardness of the starch gel was evaluated by a rupture stress (g) and a Young's modulus ($dyn/cm^2$).

TABLE 25-1

Summary of Names, Origins and Product Names of Enzymes used for Chemical Modification and Enzymatic Treatment in combination

| Example | Name of enzyme | Origin | Kind of chemical modification |
|---|---|---|---|
| Comp. Ex. 18 | — | — | Acetylation |
| Example 17 | amyloglucosidase | *Aspergillus niger* | Acetylation |
| Example 18 | α-amylase | *Aspergillus niger* | Acetylation |
| Example 25 | amyloglucosidase | *Aspergillus niger* | Acetylation |
| Comp. Ex. 19 | — | — | Hydroxypropylation |
| Example 19 | amyloglucosidase | *Aspergillus niger* | Hydroxypropylation |

TABLE 25-1-continued

Summary of Names, Origins and Product Names of Enzymes used for
Chemical Modification and Enzymatic Treatment in combination

| Example | Name of enzyme | Origin | Kind of chemical modification |
|---|---|---|---|
| Example 20 | α-amylase | *Aspergillus niger* | Hydroxypropylation |
| Example 26 | amyloglucosidase | *Aspergillus niger* | Hydroxypropylation |
| Comp. Ex. 20 | — | — | Phosphate crosslinking |
| Example 21 | amyloglucosidase | *Aspergillus niger* | Phosphate crosslinking |
| Example 22 | α-amylase | *Aspergillus niger* | Phosphate crosslinking |
| Example 27 | amyloglucosidase | *Aspergillus niger* | Phosphate crosslinking |
| Comp. Ex. 21 | — | — | Hydroxypropylation phosphate crosslinking |
| Example 23 | amyloglucosidase | *Aspergillus niger* | Hydroxypropylation phosphate crosslinking |
| Example 24 | α-amylase | *Aspergillus niger* | Hydroxypropylation phosphate crosslinking |
| Example 28 | amyloglucosidase | *Aspergillus niger* | Hydroxypropylation phosphate crosslinking |
| Comp. Ex. 22 | — | — | Oxidized starch |
| Example 29 | amyloglucosidase | *Aspergillus niger* | Oxidized starch |
| Example 30 | α-amylase | *Aspergillus niger* | Oxidized starch |
| Comp. Ex. 23 | — | — | (Bleached starch) |
| Example 31 | amyloglucosidase | *Aspergillus niger* | (Bleached starch) |
| Example 32 | α-amylase | *Aspergillus niger* | (Bleached starch) |

Comp. Ex. = Comparative Example

TABLE 25-2

Table 25-2: Summary of combined use of chemical modification and
enzymatic treatment (Starch Concentration for Amylograph: 6.0%)

| | | Maximum viscosity | | | Rupture stress | | Young's modulus | |
|---|---|---|---|---|---|---|---|---|
| Example | Degradation ratio (%) | Measured value (BU) | Relative % (%) | Breakdown viscosity (BU) | Measured value (g) | Relative % (%) | Measured value (dyn/cm$^2$) | Relative % (%) |
| Comp. Ex. 18 | — | 895 | 100 | 606 | 121 | 100 | 2,499,026 | 100 |
| Example 17 | 7 | 727 | 81 | 433 | 145 | 120 | 2,923,860 | 117 |
| Example 18 | 9 | 693 | 77 | 429 | 142 | 117 | 3,023,821 | 121 |
| Example 25 | 21 | 797 | 89 | 472 | 215 | 178 | 4,169,554 | 167 |
| Comp. Ex. 19 | — | 1004 | 100 | 670 | 33 | 100 | 373,715 | 100 |
| Example 19 | 20 | 845 | 84 | 550 | 47 | 142 | 483,149 | 129 |
| Example 20 | 21 | 661 | 66 | 470 | 43 | 130 | 669,986 | 179 |
| Example 26 | 21 | 824 | 82 | 525 | 71 | 215 | 573,625 | 153 |
| Comp. Ex. 20 | — | 903 | 100 | 0 | 170 | 100 | 3,943,691 | 100 |
| Example 21 | 21 | 908 | 101 | 0 | 283 | 166 | 5,319,388 | 135 |
| Example 22 | 15 | 871 | 96 | 0 | 337 | 198 | 7,529,620 | 191 |
| Example 27 | 21 | 898 | 99 | 0 | 554 | 326 | 10,027,924 | 254 |
| Comp. Ex. 21 | — | 769 | 100 | 403 | 31 | 100 | 250,328 | 100 |
| Example 23 | 19 | 740 | 96 | 413 | 45 | 145 | 391,117 | 156 |
| Example 24 | 21 | 524 | 68 | 356 | 64 | 206 | 1,218,285 | 487 |
| Example 28 | 21 | 784 | 102 | 207 | 125 | 403 | 1,497,293 | 598 |
| Comp. Ex. 22 | — | 317 | 100 | 227 | 91 | 100 | 4,468,130 | 100 |
| Example 29 | 7 | 419 | 132 | 324 | 119 | 131 | 5,953,997 | 133 |
| Example 30 | 9 | 411 | 130 | 315 | 101 | 111 | 5,048,987 | 113 |
| Comp. Ex. 23 | — | 715 | 100 | 181 | 137 | 100 | 4,494,603 | 100 |
| Example 31 | 22 | 673 | 94 | 138 | 224 | 164 | 5,293,378 | 118 |
| Example 32 | 31 | 630 | 88 | 143 | 237 | 173 | 6,764,052 | 150 |

* Degradation ratios in Examples 25 to 28 each refer to a degradation ratio of an enzyme-treated starch used as a base material.

It was confirmed that when the chemical modification and the enzymatic treatment are used in combination, particularly when the distarch phosphate is subjected to the enzymatic treatment, gel forming ability can be enhanced while maintaining a maximum viscosity. This is an extremely excellent advantage as compared with the fact that when phosphate crosslinking is increased in a conventional chemical modification, the gel becomes harder but the maximum viscosity drastically decreases, thus leading to the cause of powderiness. It was also confirmed for not only the distarch phosphate but also other chemically modified starches that, by carrying out an enzymatic treatment, it is possible to enhance gel forming ability while relatively maintaining the viscosity as compared with a conventional chemically modified starch.

Comparative Example 22

Oxidized Starch

To 500 g of an untreated native cassava starch, 750 g of ion-exchange water was added to prepare a starch suspension. After adjusting the pH of the suspension to 10.0, 2.5 g of sodium hypochlorite whose effective chlorine amount is 10% was added and stirred at 30° C. for 2 hours to carry out a reaction, while maintaining the pH of the suspension at 10.0. After 2 hours, the pH of the suspension was adjusted to 6.0 and then 2 g of sodium hydrogen sulfite was added. Immediately after stirring, the pH of the suspension was adjusted to 6.0 and the reaction was terminated. After completion of the reaction, the oxidized starch was recovered by centrifugal filtration and blow drying. Viscosity characteristics of the obtained oxidized starch were analyzed by the amylograph and the rheometer.

Comparative Example 23

Bleached Starch

To 500 g of an untreated native cassava starch, 700 g of ion-exchange water was added to prepare a starch suspension. After adjusting the pH of the suspension to 11.0, 2.5 g of sodium hypochlorite whose effective chlorine amount is 10% was added and stirred at 30° C. for 5 minutes while maintaining the pH of the suspension at 11. Then, 0.25 g of sodium metabisulfite was added and stirred for 10 minutes, the pH of the suspension was adjusted to 6.0 and the reaction was terminated. After completion of the reaction, the bleached starch was recovered by centrifugal filtration and blow drying. Viscosity characteristics of the obtained bleached starch were analyzed by the amylograph and the rheometer.

Example 29

In the Case where an Oxidized Starch was Treated with an Amyloglucosidase

To 400 g of the oxidized starch prepared in Comparative Example 22, 900 g of ion-exchange water was added to prepare a starch suspension. After adjusting the pH of the suspension to 5.0, 1% by weight (based on starch solid content) of amyloglucosidase ("OPTIDEX L-400" derived from *Aspergillus niger*, manufactured by Genencor; optimum pH of 4.4) was added and stirred at 50° C. for 18 hours to carry out an enzyme reaction. After completion of the reaction, an enzyme-treated starch was recovered by centrifugal filtration and blow drying. Viscosity characteristics of the obtained enzyme-treated starch were analyzed by the amylograph and the rheometer. Also, after completion of the reaction, a degradation ratio was determined using a part of the reaction solution.

Example 30

In the Case where an Oxidized Starch was Treated with an α-Amylase

To 400 g of the oxidized starch prepared in Comparative Example 22, 900 g of ion-exchange water was added to prepare a starch suspension. After adjusting the pH of the suspension to 5.0, 1% by weight (based on starch solid content) of α-amylase ("AMYLEX A3" derived from *Aspergillus niger*, manufactured by DANISCO; optimum pH of 5.0) was added and stirred at 50° C. for 18 hours to carry out an enzyme reaction. After completion of the reaction, an enzyme-treated starch was recovered by centrifugal filtration and blow drying. Viscosity characteristics of the obtained enzyme-treated starch were analyzed by the amylograph and the rheometer. Also, after completion of the reaction, a degradation ratio was determined using a part of the reaction solution.

Example 31

In the Case where a Bleached Starch was Treated with an Amyloglucosidase

To 400 g of the bleached starch prepared in Comparative Example 23, 900 g of ion-exchange water was added to prepare a starch suspension. After adjusting the pH of the suspension to 5.0, 1% by weight (based on starch solid content) of amyloglucosidase ("OPTIDEX L-400" derived from *Aspergillus niger*, manufactured by Genencor; optimum pH of 4.4) was added and stirred at 50° C. for 18 hours to carry out an enzyme reaction. After completion of the reaction, an enzyme-treated starch was recovered by centrifugal filtration and blow drying. Viscosity characteristics of the obtained enzyme-treated starch were analyzed by the amylograph and the rheometer. Also, after completion of the reaction, a degradation ratio was determined using a part of the reaction solution.

Example 32

In the Case where a Bleached Starch was Treated with an α-Amylase

To 400 g of the bleached starch prepared in Comparative Example 23, 900 g of ion-exchange water was added to prepare a starch suspension. After adjusting the pH of the suspension to 5.0, 1% by weight (based on starch solid content) of α-amylase ("AMYLEX A3" derived from *Aspergillus niger*, manufactured by DANISCO; optimum pH of 5.0) was added and stirred at 50° C. for 18 hours to carry out an enzyme reaction. After completion of the reaction, an enzyme-treated starch was recovered by centrifugal filtration and blow drying. Viscosity characteristics of the obtained enzyme-treated starch were analyzed by the amylograph and the rheometer. Also, after completion of the reaction, a degradation ratio was determined using a part of the reaction solution. The measurement results of Comparative Examples 22 to 23 and Examples 29 to 32 are shown in Table 25-2.

Comparative Example 24

To 2 kg of an untreated native corn starch, ion-exchange water was added thereby adjusting the water content to 21%. The resultant was filled in a 3 L glass beaker in a state where blank space was as small as possible, and the upper portion was covered with an aluminum foil, and then heated at 120° C. for 15 minutes to carry out a heat-moisture treatment. After completion of the heat-moisture treatment, the heat-moisture-treated starch was recovered by blow drying.

Example 33

To 4 Kg of an untreated native corn starch, 9 Kg of ion-exchange water was added to prepare a starch suspension. After adjusting the pH of the suspension to 5.0, 1% by weight (based on starch solid content) of amyloglucosidase ("OPTIDEX L-400" derived from *Aspergillus niger*, manufactured by Genencor; optimum pH of 4.4) was added and stirred at 50° C. for 18 hours to carry out an enzyme reaction. After completion of the reaction, an enzyme-treated starch was recovered by centrifugal filtration and blow drying. It is noted that the degradation ratio of the obtained sample was 34%.

Example 34

To 4 Kg of an untreated native corn starch, 9 Kg of ion-exchange water was added to prepare a starch suspension. After adjusting the pH of the suspension to 5.0, 1% by weight (based on starch solid content) of α-amylase ("AMYLEX A3" derived from *Aspergillus niger*, manufactured by DANISCO; optimum pH of 5.0) was added and stirred at 50° C. for 18 hours to carry out an enzyme reaction. After completion of the reaction, an enzyme-treated starch was recovered by centrifugal filtration and blow drying. It is noted that the degradation ratio of the obtained sample was 28%.

Example 35

To 400 g of the heat-moisture-treated starch prepared in Comparative Example 24, 900 g of ion-exchange water was added to prepare a starch suspension. After adjusting the pH of the suspension to 5.0, 1% by weight (based on starch solid content) of amyloglucosidase ("OPTIDEX L-400" derived from *Aspergillus niger*, manufactured by Genencor; optimum pH of 4.4) was added and stirred at 50° C. for 18 hours to carry out an enzyme reaction. After completion of the reaction, an enzyme-heat-moisture-treated starch was recovered by centrifugal filtration and blow drying. Viscosity characteristics of the obtained enzyme-heat-moisture-treated starch were analyzed by the amylograph and the rheometer. Also, after completion of the reaction, a degradation ratio was determined using a part of the reaction solution.

Example 36

To 400 g of the heat-moisture-treated starch prepared in Comparative Example 24, 900 g of ion-exchange water was added to prepare a starch suspension. After adjusting the pH of the suspension to 5.0, 1% by weight (based on starch solid content) of α-amylase ("AMYLEX A3" derived from *Aspergillus niger*, manufactured by DANISCO; optimum pH of 5.0) was added and stirred at 50° C. for 18 hours to carry out an enzyme reaction. After completion of the reaction, an enzyme-heat-moisture-treated starch was recovered by centrifugal filtration and blow drying. Viscosity characteristics of the obtained enzyme-heat-moisture-treated starch were analyzed by the amylograph and the rheometer. Also, after completion of the reaction, a degradation ratio was determined using a part of the reaction solution.

Example 37

To 400 g of the enzyme-treated starch prepared in Example 33, ion-exchange water was added thereby adjusting the water content to 21%. The resultant was filled in a 1 L glass beaker in a state where blank space was as small as possible, and the upper portion was covered with an aluminum foil, and then heated at 120° C. for 15 minutes to carry out a heat-moisture treatment. After completion of the heat-moisture treatment, the heat-moisture-enzyme-treated starch was recovered by blow drying. Viscosity characteristics of the obtained heat-moisture-enzyme-treated starch were analyzed by the amylograph and the rheometer. Also, after completion of the reaction, a degradation ratio was determined by a part of the reaction solution.

Example 38

To 400 g of the enzyme-treated starch prepared in Example 34, ion-exchange water was added thereby adjusting the water content to 20%. The resultant was filled in a 1 L glass beaker in a state where blank space was as small as possible, and the upper portion was covered with an aluminum foil, and then heated at 120° C. for 15 minutes to carry out a heat-moisture treatment. After completion of the heat-moisture treatment, the heat-moisture-enzyme-treated starch was recovered by blow drying. Viscosity characteristics of the obtained heat-moisture-enzyme-treated starch were analyzed by the amylograph and the rheometer. Also, after completion of the reaction, a degradation ratio was determined by a part of the reaction solution. The measurement results of Comparative Example 24 and Examples 35 to 38 are shown in Table 26-2.

TABLE 26-1

Summary of Names, Origins and Product Names of Enzymes Used for a Treatment of a Heat-moisture-treated Starch

| Example | Name of enzyme | Origin | Product name of enzyme (manufacture) |
|---|---|---|---|
| Comparative Example 24 | — | — | Untreated corn starch |
| Example 35 | amyloglucosidase | *Aspergillus niger* | OPTIDEX L-400 (Genencor) |
| Example 36 | α-amylase | *Aspergillus niger* | AMYLEX A3 (DANISCO) |
| Example 37 | amyloglucosidase | *Aspergillus niger* | OPTIDEX L-400 (Genencor) |
| Example 38 | α-amylase | *Aspergillus niger* | AMYLEX A3 (DANISCO) |

TABLE 26-2

| | | Maximum viscosity | | | Next Day | | | |
| | | | | | Rupture stress | | Young's modulus | |
| Example | Degradation ratio (%) | Measured value (BU) | Relative % (%) | Breakdown viscosity (BU) | Measured value (g) | Relative % (%) | Measured value (dyn/cm$^2$) | Relative % (%) |
|---|---|---|---|---|---|---|---|---|
| Comparative Example 24 | — | 401 | 100 | 108 | 230 | 100 | 6,091,460 | 100 |
| Example 35 | 39 | 351 | 88 | 96 | 439 | 191 | 6,566,419 | 108 |
| Example 36 | 33 | 351 | 88 | 91 | 436 | 190 | 6,788,705 | 111 |
| Example 37 | 34 | 327 | 82 | 74 | 420 | 182 | 6,690,934 | 110 |
| Example 38 | 28 | 349 | 87 | 79 | 428 | 186 | 7,132,581 | 117 |

* Degradation ratios in Examples 37 and 38 each refer to a degradation ratio of enzyme-treated starch used as a base material.

As described above, the present invention has been exemplified using a preferred embodiment of the present invention, but the present invention should not be construed to be limited to this embodiment. It is understood that the present invention should be construed for its scope only by the claims. It is understood that those skilled in the art can practice an equivalent range based on the description of the invention and the technical common knowledge, from the description of the specific preferable embodiment of the present invention. It is understood that patents, patent applications and publications cited in the present specification should be herein incorporated by reference for the content thereof as if the contents themselves were specifically described in the present specification.

INDUSTRIAL APPLICABILITY

As described above, the present invention provides various industrial advantages by using an enzyme having characteristics capable of increasing a maximum viscosity of a starch.

According to the present invention, it becomes possible to provide a food having new textures which could not be obtained by a conventional chemically unmodified starch and a chemically modified starch. For example, use of the enzyme-treated cassava starch in the present invention makes it possible to prepare a cookie which is very light and soft and has texture with nice melt in mouth, and to provide a cookie having readily edible texture which is also suited for persons of advanced age and infants. In addition, since the dough at the time of shaping a cookie is very dry and not sticky, the water addition amount at the time of preparing the dough can be further increased, thus making it possible to increase a yield factor. Furthermore, for a food such as kudzu starch cake so-called in the Kanto area, which requires long time and much labor heretofore because the preparation of a wheat starch as a raw material requires a fermentation process for a long period such as one or more years, use of an enzyme-treated wheat starch of the present invention makes it possible to easily prepare a kudzu starch cake so-called in the Kanto area which does not have fermentation odor derived from a fermented wheat starch and has nice flavor, without requiring such long time and much labor.

Furthermore, when the enzyme-treated cassava starch of the present invention is used in noodles, for example, raw udon, the texture improving effect of impairing sticky texture with rich chewiness is recognized, and no adverse influence was exerted on factors of the quality of noodles, such as "slippery and smooth" and "sogginess". Thus, it has been found that the addition of this enzyme-treated starch easily improve the texture of the noodle to those favored by Japanese.

The invention claimed is:

1. A method of producing a starch gel-containing food, the method comprising the steps of:
   treating starch granules with an enzyme at a temperature of about 10° C. or higher and about 70° C. or lower to obtain enzyme-treated starch granules having improved gel forming ability;
   removing a carbohydrate produced by enzymatic hydrolysis from the enzyme-treated starch granules;
   mixing a food material, the enzyme-treated starch granules and water to obtain a mixture;
   heating the mixture thereby gelatinizing the enzyme-treated starch granules in the mixture; and
   cooling the mixture containing the gelatinized enzyme-treated starch granules thereby gelling the starch granules to obtain a starch gel-containing food, wherein
   the enzyme is selected from the group consisting of α-amylase derived from *Aspergillus oryzae* or *Aspergillus niger*; amyloglucosidase derived from *Aspergillus niger*, *Rhizopus niveus* or *Rhizopus oryzae*; α-glucosidase derived from *Aspergillus niger*; isoamylase derived from *Flavobacterium* sp. or *Pseudomonas amyloderamosa*; and cyclodextrin glucanotransferase derived from *Bacillus licheniformis* or *Paenibacillus macerans* (*Bacillus macerans*), provided that said starch granule is not a starch granule of high amylose starch containing 30% or more amylose.

2. A method of producing a starch gel-containing food, the method comprising the steps of:
   treating starch granules with an enzyme at a temperature of about 10° C. or higher and about 70° C. or lower to obtain enzyme-treated starch granules having improved gel forming ability;
   removing a carbohydrate produced by enzymatic hydrolysis from the enzyme-treated starch granules;
   mixing a food material, the enzyme-treated starch granules and water to obtain a mixture;
   heating the mixture thereby gelatinizing the enzyme-treated starch granules in the mixture; and
   cooling the mixture containing the gelatinized enzyme-treated starch granules thereby gelling the starch granules to obtain a starch gel-containing food, wherein: (1) the enzyme is encoded by a nucleic acid molecule which is capable of hybridizing under stringent conditions with a nucleic acid molecule consisting of a base sequence complementary to a base sequence of SEQ ID NO: 1, 3, 5, 7, or 9, and has a starch hydrolysis activity;

wherein the stringent conditions are hybridization in a solution containing 50% formamide, 5×SSC (750 mM NaCl, 75 mM trisodium citrate), 50 mM sodium phosphate (pH 7.6), 5×Denhardt's solution (0.2% BSA, 0.2% Ficoll 400 and 0.2% polyvinylpyrrolidone), 10% dextran sulfate and 20 µg/ml denatured sheared salmon sperm DNA at 65° C., and subsequent washing under the condition of 65° C. using an SSC solution having a 0.1 to 2-fold concentration (a composition of an SSC solution having a 1-fold concentration is 150 mM sodium chloride and 15 mM sodium citrate), provided that said starch granule is not a starch granule of high amylose starch containing 30% or more amylose.

3. A method of producing a starch gel-containing food, the method comprising the steps of:

treating starch granules with an enzyme at a temperature of about 10° C. or higher and about 70° C. or lower to obtain enzyme-treated starch granules having improved gel forming ability;

removing a carbohydrate produced by enzymatic hydrolysis from the enzyme-treated starch granules;

mixing a food material, the enzyme-treated starch granules and water to obtain a mixture;

heating the mixture thereby gelatinizing the enzyme-treated starch granules in the mixture; and cooling the mixture containing the gelatinized enzyme-treated starch granules thereby gelling the starch granules to obtain a starch gel-containing food, wherein:

(1) the enzyme has an amino acid sequence having at least 95% or more of sequence identity with an amino acid sequence of SEQ ID NO: 2, 4, 6, 8, or 10, and has a starch hydrolysis activity, provided that said starch granule is not a starch granule of high amylose starch containing 30% or more amylose.

4. The method according to claim 1, wherein the starch granules are starch granules of an untreated starch, a physically treated starch or a chemically modified starch.

5. The method according to claim 1, wherein the starch granules are starch granules of an untreated starch, and the starch granules have been neither chemically modified nor physically treated in any stage until the starch gel-containing food is obtained by the method.

6. The method according to claim 1, wherein the starch granules are starch granules of an untreated starch or a physically treated starch, the method further comprises the step of chemically modifying the enzyme-treated starch, and the chemically modified enzyme-treated starch is mixed with the food material and water.

7. The method according to claim 1, wherein the starch granules are starch granules of an untreated starch or a chemically modified starch, the method further comprises the step of physically treating the enzyme-treated starch, and the physically treated enzyme-treated starch is mixed with the food material and water.

8. A starch gel-containing food produced by the method according to claim 1.

9. The food according to claim 8, wherein the food is a high moisture content type food and the amount of moisture of the food is more than 40 g and less than 95 g per 100 g of the edible portion.

10. The food according to claim 8, wherein the food is selected from the group consisting of traditional Japanese-style confectioneries, fat- or oil-containing foods, gelatinous foods, fish meat and animal meat processed foods, salsa and sauces, and noodles.

11. The food according to claim 8, wherein the food is a low moisture content type food and the amount of moisture of the food is 1 g or more and 40 g or less per 100 g of the edible portion.

12. The food according to claim 8, wherein the food is selected from the group consisting of baked foods, Western-style confectioneries, and fried foods.

13. The food according to claim 8, wherein the starch is derived from cassaya, corn or wheat.

14. The method according to claim 2, wherein the starch granules are starch granules of an untreated starch, a physically treated starch or a chemically modified starch.

15. The method according to claim 2, wherein the starch granules are starch granules of an untreated starch, and the starch granules have been neither chemically modified nor physically treated in any stage until the starch gel-containing food is obtained by the method.

16. The method according to claim 2, wherein the starch granules are starch granules of an untreated starch or a physically treated starch, the method further comprises the step of chemically modifying the enzyme-treated starch, and the chemically modified enzyme-treated starch is mixed with the food material and water.

17. The method according to claim 2, wherein the starch granules are starch granules of an untreated starch or a chemically modified starch, the method further comprises the step of physically treating the enzyme-treated starch, and the physically treated enzyme-treated starch is mixed with the food material and water.

18. A starch gel-containing food produced by the method according to claim 2.

19. The food according to claim 18, wherein the food is a high moisture content type food and the amount of moisture of the food is more than 40 g and less than 95 g per 100 g of the edible portion.

20. The food according to claim 18, wherein the food is selected from the group consisting of traditional Japanese-style confectioneries, fat- or oil-containing foods, gelatinous foods, fish meat and animal meat processed foods, salsa and sauces, and noodles.

21. The food according to claim 18, wherein the food is a low moisture content type food and the amount of moisture of the food is 1 g or more and 40 g or less per 100 g of the edible portion.

22. The food according to claim 18, wherein the food is selected from the group consisting of baked foods, Western-style confectioneries, and fried foods.

23. The food according to claim 18, wherein the starch is derived from cassaya, corn or wheat.

24. The method according to claim 3, wherein the starch granules are starch granules of an untreated starch, a physically treated starch or a chemically modified starch.

25. The method according to claim 3, wherein the starch granules are starch granules of an untreated starch, and the starch granules have been neither chemically modified nor physically treated in any stage until the starch gel-containing food is obtained by the method.

26. The method according to claim 3, wherein the starch granules are starch granules of an untreated starch or a physically treated starch, the method further comprises the step of chemically modifying the enzyme-treated starch, and the chemically modified enzyme-treated starch is mixed with the food material and water.

27. The method according to claim 3, wherein the starch granules are starch granules of an untreated starch or a chemically modified starch, the method further comprises the step of physically treating the enzyme-treated starch, and the physically treated enzyme-treated starch is mixed with the food material and water.

28. A starch gel-containing food produced by the method according to claim 3.

29. The food according to claim 28, wherein the food is a high moisture content type food and the amount of moisture of the food is more than 40 g and less than 95 g per 100 g of the edible portion.

30. The food according to claim 28, wherein the food is selected from the group consisting of traditional Japanese-style confectioneries, fat- or oil-containing foods, gelatinous foods, fish meat and animal meat processed foods, salsa and sauces, and noodles.

31. The food according to claim 28, wherein the food is a low moisture content type food and the amount of moisture of the food is 1 g or more and 40 g or less per 100 g of the edible portion.

32. The food according to claim 28, wherein the food is selected from the group consisting of baked foods, Western-style confectioneries, and fried foods.

33. The food according to claim 28, wherein the starch is derived from cassaya, corn or wheat.

34. The method according to claim 1, wherein the enzyme-treated starch granules can form a gel having a rupture stress higher than that of the starch granules before the treatment with the enzyme when measured by a rheometer.

35. The method according to claim 2, wherein the enzyme-treated starch granules can form a gel having a rupture stress higher than that of the starch granules before the treatment with the enzyme when measured by a rheometer.

36. The method according to claim 3, wherein the enzyme-treated starch granules can form a gel having a rupture stress higher than that of the starch granules before the treatment with the enzyme when measured by a rheometer.

* * * * *

```
                        SEQUENCE LISTING

<160> NUMBER OF SEQ ID NOS: 14

<210> SEQ ID NO 1
<211> LENGTH: 1848
<212> TYPE: DNA
<213> ORGANISM: Aspergillus oryzae
<220> FEATURE:
<221> NAME/KEY: CDS
<222> LOCATION: (1)..(1848)

<400> SEQUENCE: 1 atg cct tcc aag gtc aca cag tat ctg acc ggt gtt cca cac acc gac        48
Met Pro Ser Lys Val Thr Gln Tyr Leu Thr Gly Val Pro His Thr Asp
1               5                   10                  15 tgc ttg ggt acc gaa gca gtt gat acg tct att gaa gta gaa cgg cgc        96
Cys Leu Gly Thr Glu Ala Val Asp Thr Ser Ile Glu Val Glu Arg Arg
            20                  25                  30 atg atg acg cat ccg tcc tat att tgg cta tac ctg tca gaa aat cag       144
Met Met Thr His Pro Ser Tyr Ile Trp Leu Tyr Leu Ser Glu Asn Gln
        35                  40                  45 ctt ttt ctt gtt ggg tat ttt cat cag ttt cac ttc gta gcc tct cat       192
Leu Phe Leu Val Gly Tyr Phe His Gln Phe His Phe Val Ala Ser His
    50                  55                  60 agc ggc ttt ctt tct att caa gcc atc aat gtt acc cat tcc atc ctg       240
Ser Gly Phe Leu Ser Ile Gln Ala Ile Asn Val Thr His Ser Ile Leu
65                  70                  75                  80 gtt tct ctt act tct cta ttc aca agc ggt cgg tct gtg gat act aaa       288
Val Ser Leu Thr Ser Leu Phe Thr Ser Gly Arg Ser Val Asp Thr Lys
                85                  90                  95 tac gtg gtt aaa ata gaa gag gca cag cat ctt act aaa ctc cca tca       336
Tyr Val Val Lys Ile Glu Glu Ala Gln His Leu Thr Lys Leu Pro Ser
            100                 105                 110 tgg gat acc cct gac aat tcg ctc atg cta caa ggt ttt gaa tgg cat       384
Trp Asp Thr Pro Asp Asn Ser Leu Met Leu Gln Gly Phe Glu Trp His
        115                 120                 125 gtt cca gat gat caa ggg cat tgg aaa cgt ctt caa cgc tca cta gtg       432
Val Pro Asp Asp Gln Gly His Trp Lys Arg Leu Gln Arg Ser Leu Val
    130                 135                 140 agt cta aaa tcg att ggt gtc gac agt att tgg att cca ccg gga tgt       480
Ser Leu Lys Ser Ile Gly Val Asp Ser Ile Trp Ile Pro Pro Gly Cys
145                 150                 155                 160
```

-continued

| | | |
|---|---|---|
| aaa gca atg aac cct tcc ggt aat ggc tat gac atc tat gat cta tac<br>Lys Ala Met Asn Pro Ser Gly Asn Gly Tyr Asp Ile Tyr Asp Leu Tyr<br>165　　　　　　　　170　　　　　　　　175 | | 528 |
| gac cta gga gaa ttc gac cag aag gga tca cga tct aca aaa tgg ggc<br>Asp Leu Gly Glu Phe Asp Gln Lys Gly Ser Arg Ser Thr Lys Trp Gly<br>　　　180　　　　　　　　185　　　　　　　　190 | | 576 |
| agc aag aca gaa ctc caa tca cta gct tgc tct gcg cgg aat ctc ggg<br>Ser Lys Thr Glu Leu Gln Ser Leu Ala Cys Ser Ala Arg Asn Leu Gly<br>195　　　　　　　　200　　　　　　　　205 | | 624 |
| att ggc att tgc tgg gat gca gtt ctt aac cac aaa gct ggt gcg gat<br>Ile Gly Ile Cys Trp Asp Ala Val Leu Asn His Lys Ala Gly Ala Asp<br>210　　　　　　　　215　　　　　　　　220 | | 672 |
| tat aca gaa cgg ttt tcg gct gta aaa gtg gac cca aaa gac cgc agt<br>Tyr Thr Glu Arg Phe Ser Ala Val Lys Val Asp Pro Lys Asp Arg Ser<br>225　　　　　　　　230　　　　　　　　235　　　　　　　　240 | | 720 |
| gtt gaa atc ttc gct gca agg gag att gaa ggc tgg gtt gga ttc agt<br>Val Glu Ile Phe Ala Ala Arg Glu Ile Glu Gly Trp Val Gly Phe Ser<br>　　　245　　　　　　　　250　　　　　　　　255 | | 768 |
| ttc ccg ggc cgt ggc ggc ata tat agt tct atg aaa tat agc tgg cat<br>Phe Pro Gly Arg Gly Gly Ile Tyr Ser Ser Met Lys Tyr Ser Trp His<br>　　　260　　　　　　　　265　　　　　　　　270 | | 816 |
| cat ttc agc ggc gtt gac tgg gat gaa gct cgg aag aaa aat gcg ata<br>His Phe Ser Gly Val Asp Trp Asp Glu Ala Arg Lys Lys Asn Ala Ile<br>　　　275　　　　　　　　280　　　　　　　　285 | | 864 |
| tac aga gtt gct agc aaa cga tgg tct gat gat gtg gcc cac gag aag<br>Tyr Arg Val Ala Ser Lys Arg Trp Ser Asp Asp Val Ala His Glu Lys<br>290　　　　　　　　295　　　　　　　　300 | | 912 |
| gga aac tat gac tat ctt atg ttc gcc gac cta gat tat tcc aac cta<br>Gly Asn Tyr Asp Tyr Leu Met Phe Ala Asp Leu Asp Tyr Ser Asn Leu<br>305　　　　　　　　310　　　　　　　　315　　　　　　　　320 | | 960 |
| gaa gtt cag aag gac gtt ctc cga tgg gga gaa tgg ata gga agc caa<br>Glu Val Gln Lys Asp Val Leu Arg Trp Gly Glu Trp Ile Gly Ser Gln<br>　　　325　　　　　　　　330　　　　　　　　335 | | 1008 |
| tta cct ctc tgg ggt atg agg tta gat gca agc aaa cac tac tcg gct<br>Leu Pro Leu Trp Gly Met Arg Leu Asp Ala Ser Lys His Tyr Ser Ala<br>　　　340　　　　　　　　345　　　　　　　　350 | | 1056 |
| gat ttc cag aag aaa ttt gtc aat cac gtt cga gca act gtc ggg ccg<br>Asp Phe Gln Lys Lys Phe Val Asn His Val Arg Ala Thr Val Gly Pro<br>　　　355　　　　　　　　360　　　　　　　　365 | | 1104 |
| cag att ttc ttc gtt gca gag tat tgg agc ggc gat gtc agg gtt ctt<br>Gln Ile Phe Phe Val Ala Glu Tyr Trp Ser Gly Asp Val Arg Val Leu<br>370　　　　　　　　375　　　　　　　　380 | | 1152 |
| atg cat tac cta cag aag atg gat tac cag ctg tct ctg ttc gat gca<br>Met His Tyr Leu Gln Lys Met Asp Tyr Gln Leu Ser Leu Phe Asp Ala<br>385　　　　　　　　390　　　　　　　　395　　　　　　　　400 | | 1200 |
| ccc tta gtc ggg cgc ttc tcg agg atc tcg cgc acg gga gaa gat ctt<br>Pro Leu Val Gly Arg Phe Ser Arg Ile Ser Arg Thr Gly Glu Asp Leu<br>　　　405　　　　　　　　410　　　　　　　　415 | | 1248 |
| cgc gag atc ttc gat gat acg ctg gta ggg aac aag cct gca cac gca<br>Arg Glu Ile Phe Asp Asp Thr Leu Val Gly Asn Lys Pro Ala His Ala<br>　　　420　　　　　　　　425　　　　　　　　430 | | 1296 |
| att act cta gtt atg aat cat gac acg gta aga gag aga cag tcc cta<br>Ile Thr Leu Val Met Asn His Asp Thr Val Arg Glu Arg Gln Ser Leu<br>　　　435　　　　　　　　440　　　　　　　　445 | | 1344 |
| gag gct cca att gca tca ttc ttc aag cca ctc gcc tat gca tta att<br>Glu Ala Pro Ile Ala Ser Phe Phe Lys Pro Leu Ala Tyr Ala Leu Ile<br>450　　　　　　　　455　　　　　　　　460 | | 1392 |
| cta ctc cga gac aag ggg cag ccg tgt ata ttt tat gga gac ctt tac<br>Leu Leu Arg Asp Lys Gly Gln Pro Cys Ile Phe Tyr Gly Asp Leu Tyr<br>465　　　　　　　　470　　　　　　　　475　　　　　　　　480 | | 1440 |

```
ggt atc aga cgc ggc gtc aaa aat ccc atg act cca tcc tgt ggc gga    1488
Gly Ile Arg Arg Gly Val Lys Asn Pro Met Thr Pro Ser Cys Gly Gly
                485                 490                 495 aag ctt cca gtt ctt gca cgg gct cgt aag ctt tat gct tac ggc gaa    1536
Lys Leu Pro Val Leu Ala Arg Ala Arg Lys Leu Tyr Ala Tyr Gly Glu
        500                 505                 510 caa tgc gac tat ttt gat caa gcc aat tgc atc gga ttc gtc cgt tat    1584
Gln Cys Asp Tyr Phe Asp Gln Ala Asn Cys Ile Gly Phe Val Arg Tyr
            515                 520                 525 ggc aac ttg cat cac ccg tcc ggt cta gca tgc atc atg agc aac ggg    1632
Gly Asn Leu His His Pro Ser Gly Leu Ala Cys Ile Met Ser Asn Gly
        530                 535                 540 ggt gcg tct cag aaa cgt atg tac gtc gga cgg agc cat gcc aag gag    1680
Gly Ala Ser Gln Lys Arg Met Tyr Val Gly Arg Ser His Ala Lys Glu
545                 550                 555                 560 cga tgg aca gac att ttg ggg tgg cat cca aag aca gtt atc atc gat    1728
Arg Trp Thr Asp Ile Leu Gly Trp His Pro Lys Thr Val Ile Ile Asp
                565                 570                 575 aag aaa ggt tat ggg ata ttt cct gtt tct gca atg cag gtt agt gtc    1776
Lys Lys Gly Tyr Gly Ile Phe Pro Val Ser Ala Met Gln Val Ser Val
            580                 585                 590 tgg gtg aac tcg gcc gca gaa gcg aga gaa agt ctt caa gag cct ttc    1824
Trp Val Asn Ser Ala Ala Glu Ala Arg Glu Ser Leu Gln Glu Pro Phe
        595                 600                 605 gag gag aag att tac gag aat tga                                    1848
Glu Glu Lys Ile Tyr Glu Asn
    610                 615

<210> SEQ ID NO 2
<211> LENGTH: 615
<212> TYPE: PRT
<213> ORGANISM: Aspergillus oryzae

<400> SEQUENCE: 2

Met Pro Ser Lys Val Thr Gln Tyr Leu Thr Gly Val Pro His Thr Asp
1               5                   10                  15

Cys Leu Gly Thr Glu Ala Val Asp Thr Ser Ile Glu Val Glu Arg Arg
            20                  25                  30

Met Met Thr His Pro Ser Tyr Ile Trp Leu Tyr Leu Ser Glu Asn Gln
        35                  40                  45

Leu Phe Leu Val Gly Tyr Phe His Gln Phe His Phe Val Ala Ser His
    50                  55                  60

Ser Gly Phe Leu Ser Ile Gln Ala Ile Asn Val Thr His Ser Ile Leu
65                  70                  75                  80

Val Ser Leu Thr Ser Leu Phe Thr Ser Gly Arg Ser Val Asp Thr Lys
                85                  90                  95

Tyr Val Val Lys Ile Glu Glu Ala Gln His Leu Thr Lys Leu Pro Ser
            100                 105                 110

Trp Asp Thr Pro Asp Asn Ser Leu Met Leu Gln Gly Phe Glu Trp His
        115                 120                 125

Val Pro Asp Asp Gln Gly His Trp Lys Arg Leu Gln Arg Ser Leu Val
    130                 135                 140

Ser Leu Lys Ser Ile Gly Val Asp Ser Ile Trp Ile Pro Pro Gly Cys
145                 150                 155                 160

Lys Ala Met Asn Pro Ser Gly Asn Gly Tyr Asp Ile Tyr Asp Leu Tyr
                165                 170                 175

Asp Leu Gly Glu Phe Asp Gln Lys Gly Ser Arg Ser Thr Lys Trp Gly
            180                 185                 190
```

```
Ser Lys Thr Glu Leu Gln Ser Leu Ala Cys Ser Ala Arg Asn Leu Gly
    195                 200                 205

Ile Gly Ile Cys Trp Asp Ala Val Leu Asn His Lys Ala Gly Ala Asp
210                 215                 220

Tyr Thr Glu Arg Phe Ser Ala Val Lys Val Asp Pro Lys Asp Arg Ser
225                 230                 235                 240

Val Glu Ile Phe Ala Ala Arg Glu Ile Glu Gly Trp Val Gly Phe Ser
                245                 250                 255

Phe Pro Gly Arg Gly Gly Ile Tyr Ser Ser Met Lys Tyr Ser Trp His
                260                 265                 270

His Phe Ser Gly Val Asp Trp Asp Glu Ala Arg Lys Lys Asn Ala Ile
            275                 280                 285

Tyr Arg Val Ala Ser Lys Arg Trp Ser Asp Val Ala His Glu Lys
            290                 295                 300

Gly Asn Tyr Asp Tyr Leu Met Phe Ala Asp Leu Asp Tyr Ser Asn Leu
305                 310                 315                 320

Glu Val Gln Lys Asp Val Leu Arg Trp Gly Glu Trp Ile Gly Ser Gln
                325                 330                 335

Leu Pro Leu Trp Gly Met Arg Leu Asp Ala Ser Lys His Tyr Ser Ala
                340                 345                 350

Asp Phe Gln Lys Lys Phe Val Asn His Val Arg Ala Thr Val Gly Pro
            355                 360                 365

Gln Ile Phe Phe Val Ala Glu Tyr Trp Ser Gly Asp Val Arg Val Leu
            370                 375                 380

Met His Tyr Leu Gln Lys Met Asp Tyr Gln Leu Ser Leu Phe Asp Ala
385                 390                 395                 400

Pro Leu Val Gly Arg Phe Ser Arg Ile Ser Arg Thr Gly Glu Asp Leu
                405                 410                 415

Arg Glu Ile Phe Asp Asp Thr Leu Val Gly Asn Lys Pro Ala His Ala
            420                 425                 430

Ile Thr Leu Val Met Asn His Asp Thr Val Arg Glu Arg Gln Ser Leu
            435                 440                 445

Glu Ala Pro Ile Ala Ser Phe Phe Lys Pro Leu Ala Tyr Ala Leu Ile
    450                 455                 460

Leu Leu Arg Asp Lys Gly Gln Pro Cys Ile Phe Tyr Gly Asp Leu Tyr
465                 470                 475                 480

Gly Ile Arg Arg Gly Val Lys Asn Pro Met Thr Pro Ser Cys Gly Gly
                485                 490                 495

Lys Leu Pro Val Leu Ala Arg Ala Lys Leu Tyr Ala Tyr Gly Glu
            500                 505                 510

Gln Cys Asp Tyr Phe Asp Gln Ala Asn Cys Ile Gly Phe Val Arg Tyr
            515                 520                 525

Gly Asn Leu His His Pro Ser Gly Leu Ala Cys Ile Met Ser Asn Gly
    530                 535                 540

Gly Ala Ser Gln Lys Arg Met Tyr Val Gly Arg Ser His Ala Lys Glu
545                 550                 555                 560

Arg Trp Thr Asp Ile Leu Gly Trp His Pro Lys Thr Val Ile Ile Asp
                565                 570                 575

Lys Lys Gly Tyr Gly Ile Phe Pro Val Ser Ala Met Gln Val Ser Val
            580                 585                 590

Trp Val Asn Ser Ala Ala Glu Ala Arg Glu Ser Leu Gln Glu Pro Phe
            595                 600                 605
```

```
                     Glu Glu Lys Ile Tyr Glu Asn
                         610                 615

<210> SEQ ID NO 3
<211> LENGTH: 1497
<212> TYPE: DNA
<213> ORGANISM: Aspergillus niger
<220> FEATURE:
<221> NAME/KEY: CDS
<222> LOCATION: (1)..(1497)

<400> SEQUENCE: 3 atg gtc gcg tgg tgg tct cta ttt ctg tac ggc ctt cag gtc gcg gca      48
Met Val Ala Trp Trp Ser Leu Phe Leu Tyr Gly Leu Gln Val Ala Ala
1               5                   10                  15 cct gct ttg gct gca acg cct gcg gac tgg cga tcg caa tcc att tat      96
Pro Ala Leu Ala Ala Thr Pro Ala Asp Trp Arg Ser Gln Ser Ile Tyr
            20                  25                  30 ttc ctc ctc acg gat cga ttt gca agg acg gat ggg tcg acg act gcg     144
Phe Leu Leu Thr Asp Arg Phe Ala Arg Thr Asp Gly Ser Thr Thr Ala
        35                  40                  45 act tgt aat act gcg gat cag aaa tac tgt ggt gga aca tgg cag ggc     192
Thr Cys Asn Thr Ala Asp Gln Lys Tyr Cys Gly Gly Thr Trp Gln Gly
    50                  55                  60 atc atc gac aag ttg gac tat atc cag gga atg ggc ttc aca gcc atc     240
Ile Ile Asp Lys Leu Asp Tyr Ile Gln Gly Met Gly Phe Thr Ala Ile
65                  70                  75                  80 tgg atc acc ccc gtt aca gcc cag ctg ccc cag acc acc gca tat gga     288
Trp Ile Thr Pro Val Thr Ala Gln Leu Pro Gln Thr Thr Ala Tyr Gly
                85                  90                  95 gat gcc tac cat ggc tac tgg cag cag gat ata tac tct ctg aac gaa     336
Asp Ala Tyr His Gly Tyr Trp Gln Gln Asp Ile Tyr Ser Leu Asn Glu
            100                 105                 110 aac tac ggc act gca gat gac ttg aag gcg ctc tct tcg gcc ctt cat     384
Asn Tyr Gly Thr Ala Asp Asp Leu Lys Ala Leu Ser Ser Ala Leu His
        115                 120                 125 gag agg ggg atg tat ctt atg gtc gat gtg gtt gct aac cat atg ggc     432
Glu Arg Gly Met Tyr Leu Met Val Asp Val Val Ala Asn His Met Gly
    130                 135                 140 tat gat gga gcg ggt agc tca gtc gat tac agt gtg ttt aaa ccg ttc     480
Tyr Asp Gly Ala Gly Ser Ser Val Asp Tyr Ser Val Phe Lys Pro Phe
145                 150                 155                 160 agt tcc caa gac tac ttc cac ccg ttc tgt ttc att caa aac tat gaa     528
Ser Ser Gln Asp Tyr Phe His Pro Phe Cys Phe Ile Gln Asn Tyr Glu
                165                 170                 175 gat cag act cag gtt gag gat tgc tgg cta gga gat aac act gtc tcc     576
Asp Gln Thr Gln Val Glu Asp Cys Trp Leu Gly Asp Asn Thr Val Ser
            180                 185                 190 ttg cct gat ctc gat acc acc aag gat gtg gtc aag aat gaa tgg tac     624
Leu Pro Asp Leu Asp Thr Thr Lys Asp Val Val Lys Asn Glu Trp Tyr
        195                 200                 205 gac tgg gtg gga tca ttg gta tcg aac tac tcc att gac ggc ctc cgt     672
Asp Trp Val Gly Ser Leu Val Ser Asn Tyr Ser Ile Asp Gly Leu Arg
    210                 215                 220 atc gac aca gta aaa cac gtc cag aag gac ttc tgg ccc ggg tac aac     720
Ile Asp Thr Val Lys His Val Gln Lys Asp Phe Trp Pro Gly Tyr Asn
225                 230                 235                 240 aaa gcc gca ggc gtg tac tgt atc ggc gag gtg ctc gac ggt gat ccg     768
Lys Ala Ala Gly Val Tyr Cys Ile Gly Glu Val Leu Asp Gly Asp Pro
                245                 250                 255 gcc tac act tgt ccc tac cag aac gtc atg gac ggc gta ctg aac tat     816
```

```
                Ala Tyr Thr Cys Pro Tyr Gln Asn Val Met Asp Gly Val Leu Asn Tyr
                                260                 265                 270 ccc att tac tat cca ctc ctc aac gcc ttc aag tca acc tcc ggc agc        864
Pro Ile Tyr Tyr Pro Leu Leu Asn Ala Phe Lys Ser Thr Ser Gly Ser
            275                 280                 285 atg gac gac ctc tac aac atg atc aac acc gtc aaa tcc gac tgt cca        912
Met Asp Asp Leu Tyr Asn Met Ile Asn Thr Val Lys Ser Asp Cys Pro
        290                 295                 300 gac tca aca ctc ctg ggc aca ttc gtc gag aac cac gac aac cca cgg        960
Asp Ser Thr Leu Leu Gly Thr Phe Val Glu Asn His Asp Asn Pro Arg
305                 310                 315                 320 ttc gct tct tac acc aac gac ata gcc ctc gcc aag aac gtc gca gca       1008
Phe Ala Ser Tyr Thr Asn Asp Ile Ala Leu Ala Lys Asn Val Ala Ala
                325                 330                 335 ttc atc atc ctc aac gac gga atc ccc atc atc tac gcc ggc caa gaa       1056
Phe Ile Ile Leu Asn Asp Gly Ile Pro Ile Ile Tyr Ala Gly Gln Glu
            340                 345                 350 cag cac tac gcc ggc gga aac gac ccc gcg aac cgc gaa gca acc tgg       1104
Gln His Tyr Ala Gly Gly Asn Asp Pro Ala Asn Arg Glu Ala Thr Trp
        355                 360                 365 ctc tcg ggc tac ccg acc gac agc gag ctg tac aag tta att gcc tcc       1152
Leu Ser Gly Tyr Pro Thr Asp Ser Glu Leu Tyr Lys Leu Ile Ala Ser
370                 375                 380 gcg aac gca atc cgg aac tat gcc att agc aaa gat aca gga ttc gtg       1200
Ala Asn Ala Ile Arg Asn Tyr Ala Ile Ser Lys Asp Thr Gly Phe Val
385                 390                 395                 400 acc tac aag aac tgg ccc atc tac aaa gac gac aca acg atc gcc atg       1248
Thr Tyr Lys Asn Trp Pro Ile Tyr Lys Asp Asp Thr Thr Ile Ala Met
                405                 410                 415 cgc aag ggc aca gat ggg tcg cag atc gtg act atc ttg tcc aac aag       1296
Arg Lys Gly Thr Asp Gly Ser Gln Ile Val Thr Ile Leu Ser Asn Lys
            420                 425                 430 ggt gct tcg ggt gat tcg tat acc ctc tcc ttg agt ggt gcg ggt tac       1344
Gly Ala Ser Gly Asp Ser Tyr Thr Leu Ser Leu Ser Gly Ala Gly Tyr
        435                 440                 445 aca gcc ggc cag caa ttg acg gag gtc att ggc tgc acg acc gtg acg       1392
Thr Ala Gly Gln Gln Leu Thr Glu Val Ile Gly Cys Thr Thr Val Thr
450                 455                 460 gtt ggt tcg gat gga aat gtg cct gtt cct atg gca ggt ggg cta cct       1440
Val Gly Ser Asp Gly Asn Val Pro Val Pro Met Ala Gly Gly Leu Pro
465                 470                 475                 480 agg gta ttg tat ccg act gag aag ttg gca ggt agc aag atc tgt agt       1488
Arg Val Leu Tyr Pro Thr Glu Lys Leu Ala Gly Ser Lys Ile Cys Ser
                485                 490                 495 agc tcg tga                                                           1497
Ser Ser <210> SEQ ID NO 4
<211> LENGTH: 498
<212> TYPE: PRT
<213> ORGANISM: Aspergillus niger

<400> SEQUENCE: 4

Met Val Ala Trp Trp Ser Leu Phe Leu Tyr Gly Leu Gln Val Ala Ala
1               5                   10                  15

Pro Ala Leu Ala Ala Thr Pro Ala Asp Trp Arg Ser Gln Ser Ile Tyr
            20                  25                  30

Phe Leu Leu Thr Asp Arg Phe Ala Arg Thr Asp Gly Ser Thr Thr Ala
        35                  40                  45
```

```
Thr Cys Asn Thr Ala Asp Gln Lys Tyr Cys Gly Gly Thr Trp Gln Gly
    50                  55                  60

Ile Ile Asp Lys Leu Asp Tyr Ile Gln Gly Met Gly Phe Thr Ala Ile
65                  70                  75                  80

Trp Ile Thr Pro Val Thr Ala Gln Leu Pro Gln Thr Thr Ala Tyr Gly
                85                  90                  95

Asp Ala Tyr His Gly Tyr Trp Gln Gln Asp Ile Tyr Ser Leu Asn Glu
                100                 105                 110

Asn Tyr Gly Thr Ala Asp Asp Leu Lys Ala Leu Ser Ser Ala Leu His
            115                 120                 125

Glu Arg Gly Met Tyr Leu Met Val Asp Val Val Ala Asn His Met Gly
        130                 135                 140

Tyr Asp Gly Ala Gly Ser Ser Val Asp Tyr Ser Val Phe Lys Pro Phe
145                 150                 155                 160

Ser Ser Gln Asp Tyr Phe His Pro Phe Cys Phe Ile Gln Asn Tyr Glu
                165                 170                 175

Asp Gln Thr Gln Val Glu Asp Cys Trp Leu Gly Asp Asn Thr Val Ser
            180                 185                 190

Leu Pro Asp Leu Asp Thr Thr Lys Asp Val Val Lys Asn Glu Trp Tyr
        195                 200                 205

Asp Trp Val Gly Ser Leu Val Ser Asn Tyr Ser Ile Asp Gly Leu Arg
    210                 215                 220

Ile Asp Thr Val Lys His Val Gln Lys Asp Phe Trp Pro Gly Tyr Asn
225                 230                 235                 240

Lys Ala Ala Gly Val Tyr Cys Ile Gly Glu Val Leu Asp Gly Asp Pro
                245                 250                 255

Ala Tyr Thr Cys Pro Tyr Gln Asn Val Met Asp Gly Val Leu Asn Tyr
            260                 265                 270

Pro Ile Tyr Tyr Pro Leu Leu Asn Ala Phe Lys Ser Thr Ser Gly Ser
        275                 280                 285

Met Asp Asp Leu Tyr Asn Met Ile Asn Thr Val Lys Ser Asp Cys Pro
    290                 295                 300

Asp Ser Thr Leu Leu Gly Thr Phe Val Glu Asn His Asp Asn Pro Arg
305                 310                 315                 320

Phe Ala Ser Tyr Thr Asn Asp Ile Ala Leu Ala Lys Asn Val Ala Ala
                325                 330                 335

Phe Ile Ile Leu Asn Asp Gly Ile Pro Ile Ile Tyr Ala Gly Gln Glu
            340                 345                 350

Gln His Tyr Ala Gly Gly Asn Asp Pro Ala Asn Arg Glu Ala Thr Trp
        355                 360                 365

Leu Ser Gly Tyr Pro Thr Asp Ser Glu Leu Tyr Lys Leu Ile Ala Ser
    370                 375                 380

Ala Asn Ala Ile Arg Asn Tyr Ala Ile Ser Lys Asp Thr Gly Phe Val
385                 390                 395                 400

Thr Tyr Lys Asn Trp Pro Ile Tyr Lys Asp Asp Thr Thr Ile Ala Met
                405                 410                 415

Arg Lys Gly Thr Asp Gly Ser Gln Ile Val Thr Ile Leu Ser Asn Lys
            420                 425                 430

Gly Ala Ser Gly Asp Ser Tyr Thr Leu Ser Leu Ser Gly Ala Gly Tyr
        435                 440                 445

Thr Ala Gly Gln Gln Leu Thr Glu Val Ile Gly Cys Thr Thr Val Thr
    450                 455                 460

Val Gly Ser Asp Gly Asn Val Pro Val Pro Met Ala Gly Gly Leu Pro
```

```
                465                 470                 475                 480
Arg Val Leu Tyr Pro Thr Glu Lys Leu Ala Gly Ser Lys Ile Cys Ser
                    485                 490                 495

Ser Ser

<210> SEQ ID NO 5
<211> LENGTH: 1923
<212> TYPE: DNA
<213> ORGANISM: Aspergillus niger
<220> FEATURE:
<221> NAME/KEY: CDS
<222> LOCATION: (1)..(1923)

<400> SEQUENCE: 5 atg tcg ttc cga tct cta ctc gcc ctg agc ggc ctc gtc tgc aca ggg      48
Met Ser Phe Arg Ser Leu Leu Ala Leu Ser Gly Leu Val Cys Thr Gly
1               5                   10                  15 ttg gca aat gtg att tcc aag cgc gcg acc ttg gat tca tgg ttg agc      96
Leu Ala Asn Val Ile Ser Lys Arg Ala Thr Leu Asp Ser Trp Leu Ser
            20                  25                  30 aac gaa gcg acc gtg gct cgt act gcc atc ctg aat aac atc ggg gcg     144
Asn Glu Ala Thr Val Ala Arg Thr Ala Ile Leu Asn Asn Ile Gly Ala
        35                  40                  45 gac ggt gct tgg gtg tcg ggc gcg gac tct ggc att gtc gtt gct agt     192
Asp Gly Ala Trp Val Ser Gly Ala Asp Ser Gly Ile Val Val Ala Ser
    50                  55                  60 ccc agc acg gat aac ccg gac tac ttc tac acc tgg act cgc gac tct     240
Pro Ser Thr Asp Asn Pro Asp Tyr Phe Tyr Thr Trp Thr Arg Asp Ser
65                  70                  75                  80 ggt ctc gtc ctc aag acc ctc gtc gat ctc ttc cga aat gga gat acc     288
Gly Leu Val Leu Lys Thr Leu Val Asp Leu Phe Arg Asn Gly Asp Thr
                85                  90                  95 agt ctc ctc tcc acc att gag aac tac atc tcc gcc cag gca att gtc     336
Ser Leu Leu Ser Thr Ile Glu Asn Tyr Ile Ser Ala Gln Ala Ile Val
            100                 105                 110 cag ggt atc agt aac ccc tct ggt gat ctg tcc agc ggc gct ggt ctc     384
Gln Gly Ile Ser Asn Pro Ser Gly Asp Leu Ser Ser Gly Ala Gly Leu
        115                 120                 125 ggt gaa ccc aag ttc aat gtc gat gag act gcc tac act ggt tct tgg     432
Gly Glu Pro Lys Phe Asn Val Asp Glu Thr Ala Tyr Thr Gly Ser Trp
    130                 135                 140 gga cgg ccg cag cga gat ggt ccg gct ctg aga gca act gct atg atc     480
Gly Arg Pro Gln Arg Asp Gly Pro Ala Leu Arg Ala Thr Ala Met Ile
145                 150                 155                 160 ggc ttc ggg cag tgg ctg ctt gac aat ggc tac acc agc acc gca acg     528
Gly Phe Gly Gln Trp Leu Leu Asp Asn Gly Tyr Thr Ser Thr Ala Thr
                165                 170                 175 gac att gtt tgg ccc ctc gtt agg aac gac ctg tcg tat gtg gct caa     576
Asp Ile Val Trp Pro Leu Val Arg Asn Asp Leu Ser Tyr Val Ala Gln
            180                 185                 190 tac tgg aac cag aca gga tat gat ctc tgg gaa gaa gtc aat ggc tcg     624
Tyr Trp Asn Gln Thr Gly Tyr Asp Leu Trp Glu Glu Val Asn Gly Ser
        195                 200                 205 tct ttc ttt acg att gct gtg caa cac cgc gcc ctt gtc gaa ggt agt     672
Ser Phe Phe Thr Ile Ala Val Gln His Arg Ala Leu Val Glu Gly Ser
    210                 215                 220 gcc ttc gcg acg gcc gtg ggc tcg tcc tgc tcc tgg tgt gat tct cag     720
Ala Phe Ala Thr Ala Val Gly Ser Ser Cys Ser Trp Cys Asp Ser Gln
225                 230                 235                 240 gca ccc gaa att ctc tgc tac ctg cag tcc ttc tgg acc ggc agc ttc     768
```

```
                  Ala Pro Glu Ile Leu Cys Tyr Leu Gln Ser Phe Trp Thr Gly Ser Phe
                                  245                 250                 255 att ctg gcc aac ttc gat agc agc cgt tcc ggc aag gac gca aac acc        816
Ile Leu Ala Asn Phe Asp Ser Ser Arg Ser Gly Lys Asp Ala Asn Thr
            260                 265                 270 ctc ctg gga agc atc cac acc ttt gat cct gag gcc gca tgc gac gac        864
Leu Leu Gly Ser Ile His Thr Phe Asp Pro Glu Ala Ala Cys Asp Asp
                275                 280                 285 tcc acc ttc cag ccc tgc tcc ccg cgc gcg ctc gcc aac cac aag gag        912
Ser Thr Phe Gln Pro Cys Ser Pro Arg Ala Leu Ala Asn His Lys Glu
290                 295                 300 gtt gta gac tct ttc cgc tca atc tat acc ctc aac gat ggt ctc agt        960
Val Val Asp Ser Phe Arg Ser Ile Tyr Thr Leu Asn Asp Gly Leu Ser
305                 310                 315                 320 gac agc gag gct gtt gcg gtg ggt cgg tac cct gag gac acg tac tac       1008
Asp Ser Glu Ala Val Ala Val Gly Arg Tyr Pro Glu Asp Thr Tyr Tyr
                325                 330                 335 aac ggc aac ccg tgg ttc ctg tgc acc ttg gct gcc gca gag cag ttg       1056
Asn Gly Asn Pro Trp Phe Leu Cys Thr Leu Ala Ala Ala Glu Gln Leu
            340                 345                 350 tac gat gct cta tac cag tgg gac aag cag ggg tcg ttg gag gtc aca       1104
Tyr Asp Ala Leu Tyr Gln Trp Asp Lys Gln Gly Ser Leu Glu Val Thr
                355                 360                 365 gat gtg tcg ctg gac ttc ttc aag gca ctg tac agc gat gct gct act       1152
Asp Val Ser Leu Asp Phe Phe Lys Ala Leu Tyr Ser Asp Ala Ala Thr
370                 375                 380 ggc acc tac tct tcg tcc agt tcg act tat agt agc att gta gat gcc       1200
Gly Thr Tyr Ser Ser Ser Ser Thr Tyr Ser Ser Ile Val Asp Ala
385                 390                 395                 400 gtg aag act ttc gcc gat ggc ttc gtc tct att gtg gaa act cac gcc       1248
Val Lys Thr Phe Ala Asp Gly Phe Val Ser Ile Val Glu Thr His Ala
                405                 410                 415 gca agc aac ggc tcc atg tcc gag caa tac gac aag tct gat ggc gag       1296
Ala Ser Asn Gly Ser Met Ser Glu Gln Tyr Asp Lys Ser Asp Gly Glu
            420                 425                 430 cag ctt tcc gct cgc gac ctg acc tgg tct tat gct gct ctg ctg acc       1344
Gln Leu Ser Ala Arg Asp Leu Thr Trp Ser Tyr Ala Ala Leu Leu Thr
                435                 440                 445 gcc aac aac cgt cgt aac tcc gtc gtg cct gct tct tgg ggc gag acc       1392
Ala Asn Asn Arg Arg Asn Ser Val Val Pro Ala Ser Trp Gly Glu Thr
450                 455                 460 tct gcc agc agc gtg ccc ggc acc tgt gcg gcc aca tct gcc att ggt       1440
Ser Ala Ser Ser Val Pro Gly Thr Cys Ala Ala Thr Ser Ala Ile Gly
465                 470                 475                 480 acc tac agc agt gtg act gtc acc tcg tgg ccg agt atc gtg gct act       1488
Thr Tyr Ser Ser Val Thr Val Thr Ser Trp Pro Ser Ile Val Ala Thr
                485                 490                 495 ggc ggc acc act acg acg gct acc ccc act gga tcc ggc agc gtg acc       1536
Gly Gly Thr Thr Thr Thr Ala Thr Pro Thr Gly Ser Gly Ser Val Thr
            500                 505                 510 tcg acc agc aag acc acc gcg act gct agc aag acc agc acc agt acg       1584
Ser Thr Ser Lys Thr Thr Ala Thr Ala Ser Lys Thr Ser Thr Ser Thr
                515                 520                 525 tca tca acc tcc tgt acc act ccc acc gcc gtg gct gtg act ttc gat       1632
Ser Ser Thr Ser Cys Thr Thr Pro Thr Ala Val Ala Val Thr Phe Asp
530                 535                 540 ctg aca gct acc acc acc tac ggc gag aac atc tac ctg gtc gga tcg       1680
Leu Thr Ala Thr Thr Thr Tyr Gly Glu Asn Ile Tyr Leu Val Gly Ser
545                 550                 555                 560
```

| | | | | | | | | | | | | | | | | |
|---|---|---|---|---|---|---|---|---|---|---|---|---|---|---|---|---|
| atc | tct | cag | ctg | ggt | gac | tgg | gaa | acc | agc | gac | ggc | ata | gct | ctg | agt | 1728 |
| Ile | Ser | Gln | Leu | Gly | Asp | Trp | Glu | Thr | Ser | Asp | Gly | Ile | Ala | Leu | Ser | |
| | | | | 565 | | | | 570 | | | | | 575 | | | |
| gct | gac | aag | tac | act | tcc | agc | gac | ccg | ctc | tgg | tat | gtc | act | gtg | act | 1776 |
| Ala | Asp | Lys | Tyr | Thr | Ser | Ser | Asp | Pro | Leu | Trp | Tyr | Val | Thr | Val | Thr | |
| | 580 | | | | | 585 | | | | | 590 | | | | | |
| ctg | ccg | gct | ggt | gag | tcg | ttt | gag | tac | aag | ttt | atc | cgc | att | gag | agc | 1824 |
| Leu | Pro | Ala | Gly | Glu | Ser | Phe | Glu | Tyr | Lys | Phe | Ile | Arg | Ile | Glu | Ser | |
| | | 595 | | | | | 600 | | | | | 605 | | | | |
| gat | gac | tcc | gtg | gag | tgg | gag | agt | gat | ccc | aac | cga | gaa | tac | acc | gtt | 1872 |
| Asp | Asp | Ser | Val | Glu | Trp | Glu | Ser | Asp | Pro | Asn | Arg | Glu | Tyr | Thr | Val | |
| 610 | | | | | 615 | | | | | 620 | | | | | | |
| cct | cag | gcg | tgc | gga | acg | tcg | acc | gcg | acg | gtg | act | gac | acc | tgg | cgg | 1920 |
| Pro | Gln | Ala | Cys | Gly | Thr | Ser | Thr | Ala | Thr | Val | Thr | Asp | Thr | Trp | Arg | |
| 625 | | | | 630 | | | | | 635 | | | | | | 640 | |
| tag | | | | | | | | | | | | | | | | 1923 |

<210> SEQ ID NO 6
<211> LENGTH: 640
<212> TYPE: PRT
<213> ORGANISM: Aspergillus niger

<400> SEQUENCE: 6

Met Ser Phe Arg Ser Leu Leu Ala Leu Ser Gly Leu Val Cys Thr Gly
1               5                   10                  15

Leu Ala Asn Val Ile Ser Lys Arg Ala Thr Leu Asp Ser Trp Leu Ser
            20                  25                  30

Asn Glu Ala Thr Val Ala Arg Thr Ala Ile Leu Asn Asn Ile Gly Ala
        35                  40                  45

Asp Gly Ala Trp Val Ser Gly Ala Asp Ser Gly Ile Val Val Ala Ser
    50                  55                  60

Pro Ser Thr Asp Asn Pro Asp Tyr Phe Tyr Thr Trp Thr Arg Asp Ser
65                  70                  75                  80

Gly Leu Val Leu Lys Thr Leu Val Asp Leu Phe Arg Asn Gly Asp Thr
                85                  90                  95

Ser Leu Leu Ser Thr Ile Glu Asn Tyr Ile Ser Ala Gln Ala Ile Val
            100                 105                 110

Gln Gly Ile Ser Asn Pro Ser Gly Asp Leu Ser Ser Gly Ala Gly Leu
        115                 120                 125

Gly Glu Pro Lys Phe Asn Val Asp Glu Thr Ala Tyr Thr Gly Ser Trp
    130                 135                 140

Gly Arg Pro Gln Arg Asp Gly Pro Ala Leu Arg Ala Thr Ala Met Ile
145                 150                 155                 160

Gly Phe Gly Gln Trp Leu Leu Asp Asn Gly Tyr Thr Ser Thr Ala Thr
                165                 170                 175

Asp Ile Val Trp Pro Leu Val Arg Asn Asp Leu Ser Tyr Val Ala Gln
            180                 185                 190

Tyr Trp Asn Gln Thr Gly Tyr Asp Leu Trp Glu Glu Val Asn Gly Ser
        195                 200                 205

Ser Phe Phe Thr Ile Ala Val Gln His Arg Ala Leu Val Glu Gly Ser
    210                 215                 220

Ala Phe Ala Thr Ala Val Gly Ser Ser Cys Ser Trp Cys Asp Ser Gln
225                 230                 235                 240

Ala Pro Glu Ile Leu Cys Tyr Leu Gln Ser Phe Trp Thr Gly Ser Phe
                245                 250                 255

Ile Leu Ala Asn Phe Asp Ser Ser Arg Ser Gly Lys Asp Ala Asn Thr

```
                260                 265                 270
Leu Leu Gly Ser Ile His Thr Phe Asp Pro Glu Ala Ala Cys Asp Asp
            275                 280                 285

Ser Thr Phe Gln Pro Cys Ser Pro Arg Ala Leu Ala Asn His Lys Glu
            290                 295                 300

Val Val Asp Ser Phe Arg Ser Ile Tyr Thr Leu Asn Asp Gly Leu Ser
305                 310                 315                 320

Asp Ser Glu Ala Val Ala Val Gly Arg Tyr Pro Glu Asp Thr Tyr Tyr
                325                 330                 335

Asn Gly Asn Pro Trp Phe Leu Cys Thr Leu Ala Ala Ala Glu Gln Leu
            340                 345                 350

Tyr Asp Ala Leu Tyr Gln Trp Asp Lys Gln Gly Ser Leu Glu Val Thr
            355                 360                 365

Asp Val Ser Leu Asp Phe Phe Lys Ala Leu Tyr Ser Ala Ala Ala Thr
370                 375                 380

Gly Thr Tyr Ser Ser Ser Ser Thr Tyr Ser Ser Ile Val Asp Ala
385                 390                 395                 400

Val Lys Thr Phe Ala Asp Gly Phe Val Ser Ile Val Glu Thr His Ala
                405                 410                 415

Ala Ser Asn Gly Ser Met Ser Glu Gln Tyr Asp Lys Ser Asp Gly Glu
            420                 425                 430

Gln Leu Ser Ala Arg Asp Leu Thr Trp Ser Tyr Ala Ala Leu Leu Thr
            435                 440                 445

Ala Asn Asn Arg Arg Asn Ser Val Val Pro Ala Ser Trp Gly Glu Thr
450                 455                 460

Ser Ala Ser Ser Val Pro Gly Thr Cys Ala Ala Thr Ser Ala Ile Gly
465                 470                 475                 480

Thr Tyr Ser Ser Val Thr Val Thr Ser Trp Pro Ser Ile Val Ala Thr
                485                 490                 495

Gly Gly Thr Thr Thr Thr Ala Thr Pro Thr Gly Ser Gly Ser Val Thr
            500                 505                 510

Ser Thr Ser Lys Thr Thr Ala Thr Ala Ser Lys Thr Ser Thr Ser Thr
            515                 520                 525

Ser Ser Thr Ser Cys Thr Thr Pro Thr Ala Val Ala Val Thr Phe Asp
530                 535                 540

Leu Thr Ala Thr Thr Thr Tyr Gly Glu Asn Ile Tyr Leu Val Gly Ser
545                 550                 555                 560

Ile Ser Gln Leu Gly Asp Trp Glu Thr Ser Asp Gly Ile Ala Leu Ser
                565                 570                 575

Ala Asp Lys Tyr Thr Ser Ser Asp Pro Leu Trp Tyr Val Thr Val Thr
            580                 585                 590

Leu Pro Ala Gly Glu Ser Phe Glu Tyr Lys Phe Ile Arg Ile Glu Ser
            595                 600                 605

Asp Asp Ser Val Glu Trp Glu Ser Asp Pro Asn Arg Glu Tyr Thr Val
610                 615                 620

Pro Gln Ala Cys Gly Thr Ser Thr Ala Thr Val Thr Asp Thr Trp Arg
625                 630                 635                 640

<210> SEQ ID NO 7
<211> LENGTH: 2334
<212> TYPE: DNA
<213> ORGANISM: Flavobacterium sp.
<220> FEATURE:
<221> NAME/KEY: CDS
<222> LOCATION: (1)..(2334)
```

<400> SEQUENCE: 7

```
atg gac cca cac gcc ccg cag cgg caa cga agc ggg cag cgc ttg cgc        48
Met Asp Pro His Ala Pro Gln Arg Gln Arg Ser Gly Gln Arg Leu Arg
1               5                   10                  15 gcc ctc gcc ctg gcc gcg ctg gcc tgc gcg ctg agc ccg gcc cac gcc        96
Ala Leu Ala Leu Ala Ala Leu Ala Cys Ala Leu Ser Pro Ala His Ala
                20                  25                  30 gcc atc gat gcg cag cag ctc ggc gcg cgc tac gac gcc gcc cag gcc       144
Ala Ile Asp Ala Gln Gln Leu Gly Ala Arg Tyr Asp Ala Ala Gln Ala
            35                  40                  45 aac ctc gcg ttc cgg gtc tat tcc tcg cgc gcg acc cgc gtc gag gtg       192
Asn Leu Ala Phe Arg Val Tyr Ser Ser Arg Ala Thr Arg Val Glu Val
    50                  55                  60 ttc ctg tac aag aac ccg acc ggc tcg cag gaa gtc gcg cgg ctg gcg       240
Phe Leu Tyr Lys Asn Pro Thr Gly Ser Gln Glu Val Ala Arg Leu Ala
65                  70                  75                  80 ctg agc aag gac ccg gcg acc cag gtg tgg tcg ctg tcg ctg ccg acc       288
Leu Ser Lys Asp Pro Ala Thr Gln Val Trp Ser Leu Ser Leu Pro Thr
                85                  90                  95 agc acg atc aag aac acc tac ggc atc acc ggc gcc gtc tac tac ggt       336
Ser Thr Ile Lys Asn Thr Tyr Gly Ile Thr Gly Ala Val Tyr Tyr Gly
            100                 105                 110 tac cgc gcc tgg ggc ccg aac tgg ccc tac gat gcg gcc tgg acc aag       384
Tyr Arg Ala Trp Gly Pro Asn Trp Pro Tyr Asp Ala Ala Trp Thr Lys
        115                 120                 125 ggc agc gcc acc ggc ttc gtc agc gac gtc gac aac gcc ggc aac cgt       432
Gly Ser Ala Thr Gly Phe Val Ser Asp Val Asp Asn Ala Gly Asn Arg
    130                 135                 140 ttc aat ccg aac aag ctg ctg ctc gac ccc tac gcg cgc gag atc agc       480
Phe Asn Pro Asn Lys Leu Leu Leu Asp Pro Tyr Ala Arg Glu Ile Ser
145                 150                 155                 160 cag gac ccg aac acc gcg acc tgc gcc gac ggc acc atc tac gcc acc       528
Gln Asp Pro Asn Thr Ala Thr Cys Ala Asp Gly Thr Ile Tyr Ala Thr
                165                 170                 175 ggc gcc gcg cac cgc aac aag gac agc ggc ctg tgc gcg agc aag ggc       576
Gly Ala Ala His Arg Asn Lys Asp Ser Gly Leu Cys Ala Ser Lys Gly
            180                 185                 190 atc gcg ctg gcc gcg gac gcg acc tcg gtc ggc agc aag ccg acc cgc       624
Ile Ala Leu Ala Ala Asp Ala Thr Ser Val Gly Ser Lys Pro Thr Arg
        195                 200                 205 gcg ctc aag gac gag gtg atc tac gaa gtg cac gtg cgc ggc ctg acc       672
Ala Leu Lys Asp Glu Val Ile Tyr Glu Val His Val Arg Gly Leu Thr
    210                 215                 220 cgc aac gac gac agc gtg ccc gcg gcc gaa cgc ggc acc tac aag ggc       720
Arg Asn Asp Asp Ser Val Pro Ala Ala Glu Arg Gly Thr Tyr Lys Gly
225                 230                 235                 240 gcc gcg cgc aag gcc gcc gcg ttg gcc gcg ctc ggc gtc acc gcg gtc       768
Ala Ala Arg Lys Ala Ala Ala Leu Ala Ala Leu Gly Val Thr Ala Val
                245                 250                 255 gag ttc ctg ccg gtg cag gaa acc cag aac gac cag aac gat gtc gat       816
Glu Phe Leu Pro Val Gln Glu Thr Gln Asn Asp Gln Asn Asp Val Asp
            260                 265                 270 ccc aat tcc acc gcg ggc gac aac tac tgg ggc tac atg acc ctc aac       864
Pro Asn Ser Thr Ala Gly Asp Asn Tyr Trp Gly Tyr Met Thr Leu Asn
        275                 280                 285 tac ttc gcc ccg gac cgc cgc tac gcc tac gac aag tcg gcc ggc ggg       912
Tyr Phe Ala Pro Asp Arg Arg Tyr Ala Tyr Asp Lys Ser Ala Gly Gly
    290                 295                 300
```

-continued

| | | |
|---|---|---|
| ccg acc cgc gaa tgg aag gcg atg gtc aag gcc ttc cac gac gcc ggc<br>Pro Thr Arg Glu Trp Lys Ala Met Val Lys Ala Phe His Asp Ala Gly<br>305                         310                       315                    320 | 960 | |
| atc aag gtc tac atc gac gtg gtc tac aac cac acc ggc gaa ggc ggc<br>Ile Lys Val Tyr Ile Asp Val Val Tyr Asn His Thr Gly Glu Gly Gly<br>325                      330                     335 | 1008 | |
| ccg tgg agc ggc acc gac ggg ctc agc gtc tac aac ctg ctc tcg ttc<br>Pro Trp Ser Gly Thr Asp Gly Leu Ser Val Tyr Asn Leu Leu Ser Phe<br>340                      345                     350 | 1056 | |
| cgc ggc ctc gac aac ccg gcc tac tac tcg ctg agc agc gat tac aag<br>Arg Gly Leu Asp Asn Pro Ala Tyr Tyr Ser Leu Ser Ser Asp Tyr Lys<br>355                      360                     365 | 1104 | |
| tat ccg tgg gac aac acc ggc gtc ggc ggc aac tac aac acc cgc cat<br>Tyr Pro Trp Asp Asn Thr Gly Val Gly Gly Asn Tyr Asn Thr Arg His<br>370                      375                     380 | 1152 | |
| ccc atc gcc cag aac ctg atc gtc gac tcg ctg gcg tac tgg cgc gac<br>Pro Ile Ala Gln Asn Leu Ile Val Asp Ser Leu Ala Tyr Trp Arg Asp<br>385                         390                     395                    400 | 1200 | |
| gcg ctc ggc gta gac ggt ttc cgc ttc gat ctg gcc tcg gtg ctc ggc<br>Ala Leu Gly Val Asp Gly Phe Arg Phe Asp Leu Ala Ser Val Leu Gly<br>                        405                     410                     415 | 1248 | |
| aac agc tgc cag cac ggc tgc ttc aac ttc gac aag aac gac tcg ggc<br>Asn Ser Cys Gln His Gly Cys Phe Asn Phe Asp Lys Asn Asp Ser Gly<br>         420                     425                     430 | 1296 | |
| aac gcg ctc aac cgc atc gtc gcc gag ctg ccg ccg cgc ccg gcc gcg<br>Asn Ala Leu Asn Arg Ile Val Ala Glu Leu Pro Pro Arg Pro Ala Ala<br>         435                     440                     445 | 1344 | |
| ggc ggc gcc ggc gcg gac ctg atc gcc gaa ccc tgg gcg atc ggc ggc<br>Gly Gly Ala Gly Ala Asp Leu Ile Ala Glu Pro Trp Ala Ile Gly Gly<br>450                         455                     460 | 1392 | |
| aac tcc tac cag gtc ggc ggc ttc ccg gcc ggc tgg gcc gag tgg aac<br>Asn Ser Tyr Gln Val Gly Gly Phe Pro Ala Gly Trp Ala Glu Trp Asn<br>465                      470                     475                    480 | 1440 | |
| ggc ctc tac cgc gac gcg ctg cgc aag aag cag aac aag ctc ggc gtg<br>Gly Leu Tyr Arg Asp Ala Leu Arg Lys Lys Gln Asn Lys Leu Gly Val<br>                       485                     490                     495 | 1488 | |
| gaa acg gtc acc ccc ggc acc ctg gcc acg cgc ttc gcc ggc tcc aac<br>Glu Thr Val Thr Pro Gly Thr Leu Ala Thr Arg Phe Ala Gly Ser Asn<br>                500                     505                     510 | 1536 | |
| gac ctg tac ggc gac gac ggc cgc aag ccg tgg cat tcg atc aac ttc<br>Asp Leu Tyr Gly Asp Asp Gly Arg Lys Pro Trp His Ser Ile Asn Phe<br>                515                     520                     525 | 1584 | |
| gtg gtc gcc cac gac ggc ttc acc ctc aac gac ctg tac gcc tac aac<br>Val Val Ala His Asp Gly Phe Thr Leu Asn Asp Leu Tyr Ala Tyr Asn<br>530                         535                     540 | 1632 | |
| gac aag cag aac aac cag ccg tgg ccg tac ggg ccg tcc gac ggc ggc<br>Asp Lys Gln Asn Asn Gln Pro Trp Pro Tyr Gly Pro Ser Asp Gly Gly<br>545                      550                     555                    560 | 1680 | |
| gag gac cac aac ctg agc tgg aac cag ggc ggc atc gtc gcc gag cag<br>Glu Asp His Asn Leu Ser Trp Asn Gln Gly Gly Ile Val Ala Glu Gln<br>                    565                     570                     575 | 1728 | |
| cgc aag gcc gcg cgc acc gga ctg gcg ttg ctg atg ctc agc gcc ggc<br>Arg Lys Ala Ala Arg Thr Gly Leu Ala Leu Leu Met Leu Ser Ala Gly<br>                    580                     585                     590 | 1776 | |
| gtg ccg atg atc acc ggc ggc gac gag gcg ctg cgc acc cag ttc ggc<br>Val Pro Met Ile Thr Gly Gly Asp Glu Ala Leu Arg Thr Gln Phe Gly<br>         595                     600                     605 | 1824 | |
| aac aac aac acc tac aac ctg gat tcg gcg gcc aac tgg ctg tac tgg<br>Asn Asn Asn Thr Tyr Asn Leu Asp Ser Ala Ala Asn Trp Leu Tyr Trp<br>610                         615                     620 | 1872 | |

-continued

```
agc cgc agc gcg ctc gag gcc gac cac gag acc tac acc aag cgc ctg      1920
Ser Arg Ser Ala Leu Glu Ala Asp His Glu Thr Tyr Thr Lys Arg Leu
625                 630                 635                 640 atc gcg ttc cgc aag gcg cac ccg gcg ctg cgc ccg gcg aac ttc tat      1968
Ile Ala Phe Arg Lys Ala His Pro Ala Leu Arg Pro Ala Asn Phe Tyr
                645                 650                 655 tcg gcc agc gac acc aac ggc aac gtg atg gag cag ttg cgc tgg ttc      2016
Ser Ala Ser Asp Thr Asn Gly Asn Val Met Glu Gln Leu Arg Trp Phe
            660                 665                 670 aag ccc gac ggc gcg cag gcc gac agc gcc tac ttc aac ggc gcc gac      2064
Lys Pro Asp Gly Ala Gln Ala Asp Ser Ala Tyr Phe Asn Gly Ala Asp
        675                 680                 685 aac cac gcc ctg gcc tgg cgc atc gac ggc agc gag ttc ggc gac agc      2112
Asn His Ala Leu Ala Trp Arg Ile Asp Gly Ser Glu Phe Gly Asp Ser
    690                 695                 700 gcc agc gcg atc tac gtc gcc tac aac ggc tgg tcc ggc gcg gtc gac      2160
Ala Ser Ala Ile Tyr Val Ala Tyr Asn Gly Trp Ser Gly Ala Val Asp
705                 710                 715                 720 ttc aag ctg ccg tgg ccg ggc acc ggc aag cag tgg tac cgg gtc acc      2208
Phe Lys Leu Pro Trp Pro Gly Thr Gly Lys Gln Trp Tyr Arg Val Thr
                725                 730                 735 gat acc gcg acc tgg aac gaa ggc ccc aac gcg gtg gcg ctg ccc ggc      2256
Asp Thr Ala Thr Trp Asn Glu Gly Pro Asn Ala Val Ala Leu Pro Gly
            740                 745                 750 agc gag acc ctg atc ggc ggc gag aac acc gtc tac ggc atg cag gcg      2304
Ser Glu Thr Leu Ile Gly Gly Glu Asn Thr Val Tyr Gly Met Gln Ala
        755                 760                 765 cgc tcg ctg ctg ttg ctg atc gcg aag tga                              2334
Arg Ser Leu Leu Leu Leu Ile Ala Lys
    770                 775

<210> SEQ ID NO 8
<211> LENGTH: 777
<212> TYPE: PRT
<213> ORGANISM: Flavobacterium sp.

<400> SEQUENCE: 8

Met Asp Pro His Ala Pro Gln Arg Gln Arg Ser Gly Gln Arg Leu Arg
1               5                   10                  15

Ala Leu Ala Leu Ala Ala Leu Ala Cys Ala Leu Ser Pro Ala His Ala
                20                  25                  30

Ala Ile Asp Ala Gln Gln Leu Gly Ala Arg Tyr Asp Ala Ala Gln Ala
            35                  40                  45

Asn Leu Ala Phe Arg Val Tyr Ser Ser Arg Ala Thr Arg Val Glu Val
        50                  55                  60

Phe Leu Tyr Lys Asn Pro Thr Gly Ser Gln Glu Val Ala Arg Leu Ala
65                  70                  75                  80

Leu Ser Lys Asp Pro Ala Thr Gln Val Trp Ser Leu Ser Leu Pro Thr
                85                  90                  95

Ser Thr Ile Lys Asn Thr Tyr Gly Ile Thr Gly Ala Val Tyr Tyr Gly
                100                 105                 110

Tyr Arg Ala Trp Gly Pro Asn Trp Pro Tyr Asp Ala Ala Trp Thr Lys
            115                 120                 125

Gly Ser Ala Thr Gly Phe Val Ser Asp Val Asp Asn Ala Gly Asn Arg
        130                 135                 140

Phe Asn Pro Asn Lys Leu Leu Leu Asp Pro Tyr Ala Arg Glu Ile Ser
145                 150                 155                 160
```

```
Gln Asp Pro Asn Thr Ala Thr Cys Ala Asp Gly Thr Ile Tyr Ala Thr
            165                 170                 175
Gly Ala Ala His Arg Asn Lys Asp Ser Gly Leu Cys Ala Ser Lys Gly
        180                 185                 190
Ile Ala Leu Ala Ala Asp Ala Thr Ser Val Gly Ser Lys Pro Thr Arg
            195                 200                 205
Ala Leu Lys Asp Glu Val Ile Tyr Glu Val His Val Arg Gly Leu Thr
    210                 215                 220
Arg Asn Asp Asp Ser Val Pro Ala Ala Glu Arg Gly Thr Tyr Lys Gly
225                 230                 235                 240
Ala Ala Arg Lys Ala Ala Leu Ala Ala Leu Gly Val Thr Ala Val
                245                 250                 255
Glu Phe Leu Pro Val Gln Glu Thr Gln Asn Asp Gln Asn Asp Val Asp
            260                 265                 270
Pro Asn Ser Thr Ala Gly Asp Asn Tyr Trp Gly Tyr Met Thr Leu Asn
        275                 280                 285
Tyr Phe Ala Pro Asp Arg Arg Tyr Ala Tyr Asp Lys Ser Ala Gly Gly
    290                 295                 300
Pro Thr Arg Glu Trp Lys Ala Met Val Lys Ala Phe His Asp Ala Gly
305                 310                 315                 320
Ile Lys Val Tyr Ile Asp Val Val Tyr Asn His Thr Gly Glu Gly Gly
                325                 330                 335
Pro Trp Ser Gly Thr Asp Gly Leu Ser Val Tyr Asn Leu Leu Ser Phe
            340                 345                 350
Arg Gly Leu Asp Asn Pro Ala Tyr Tyr Ser Leu Ser Ser Asp Tyr Lys
        355                 360                 365
Tyr Pro Trp Asp Asn Thr Gly Val Gly Gly Asn Tyr Asn Thr Arg His
    370                 375                 380
Pro Ile Ala Gln Asn Leu Ile Val Asp Ser Leu Ala Tyr Trp Arg Asp
385                 390                 395                 400
Ala Leu Gly Val Asp Gly Phe Arg Phe Asp Leu Ala Ser Val Leu Gly
                405                 410                 415
Asn Ser Cys Gln His Gly Cys Phe Asn Phe Asp Lys Asn Asp Ser Gly
            420                 425                 430
Asn Ala Leu Asn Arg Ile Val Ala Glu Leu Pro Pro Arg Pro Ala Ala
        435                 440                 445
Gly Gly Ala Gly Ala Asp Leu Ile Ala Glu Pro Trp Ala Ile Gly Gly
    450                 455                 460
Asn Ser Tyr Gln Val Gly Gly Phe Pro Ala Gly Trp Ala Glu Trp Asn
465                 470                 475                 480
Gly Leu Tyr Arg Asp Ala Leu Arg Lys Lys Gln Asn Lys Leu Gly Val
                485                 490                 495
Glu Thr Val Thr Pro Gly Thr Leu Ala Thr Arg Phe Ala Gly Ser Asn
            500                 505                 510
Asp Leu Tyr Gly Asp Gly Arg Lys Pro Trp His Ser Ile Asn Phe
        515                 520                 525
Val Val Ala His Asp Gly Phe Thr Leu Asn Asp Leu Tyr Ala Tyr Asn
    530                 535                 540
Asp Lys Gln Asn Asn Gln Pro Trp Pro Tyr Gly Pro Ser Asp Gly Gly
545                 550                 555                 560
Glu Asp His Asn Leu Ser Trp Asn Gln Gly Gly Ile Val Ala Glu Gln
                565                 570                 575
Arg Lys Ala Ala Arg Thr Gly Leu Ala Leu Leu Met Leu Ser Ala Gly
```

```
                    580                 585                 590
        Val Pro Met Ile Thr Gly Gly Asp Glu Ala Leu Arg Thr Gln Phe Gly
                595                 600                 605

Asn Asn Asn Thr Tyr Asn Leu Asp Ser Ala Ala Asn Trp Leu Tyr Trp
            610                 615                 620

Ser Arg Ser Ala Leu Glu Ala Asp His Glu Thr Tyr Thr Lys Arg Leu
        625                 630                 635                 640

Ile Ala Phe Arg Lys Ala His Pro Ala Leu Arg Pro Ala Asn Phe Tyr
                        645                 650                 655

Ser Ala Ser Asp Thr Asn Gly Asn Val Met Glu Gln Leu Arg Trp Phe
                    660                 665                 670

Lys Pro Asp Gly Ala Gln Ala Asp Ser Ala Tyr Phe Asn Gly Ala Asp
                675                 680                 685

Asn His Ala Leu Ala Trp Arg Ile Asp Gly Ser Glu Phe Gly Asp Ser
            690                 695                 700

Ala Ser Ala Ile Tyr Val Ala Tyr Asn Gly Trp Ser Gly Ala Val Asp
        705                 710                 715                 720

Phe Lys Leu Pro Trp Pro Gly Thr Gly Lys Gln Trp Tyr Arg Val Thr
                        725                 730                 735

Asp Thr Ala Thr Trp Asn Glu Gly Pro Asn Ala Val Ala Leu Pro Gly
                    740                 745                 750

Ser Glu Thr Leu Ile Gly Gly Glu Asn Thr Val Tyr Gly Met Gln Ala
                755                 760                 765

Arg Ser Leu Leu Leu Leu Ile Ala Lys
            770                 775

<210> SEQ ID NO 9
<211> LENGTH: 2316
<212> TYPE: DNA
<213> ORGANISM: Pseudomonas amyloderamosa
<220> FEATURE:
<221> NAME/KEY: CDS
<222> LOCATION: (1)..(2316)

<400> SEQUENCE: 9 atg aag tgc cca aag att ctc ggc gcg ctg ctt ggc tgc gcg gtg ctc       48
Met Lys Cys Pro Lys Ile Leu Gly Ala Leu Leu Gly Cys Ala Val Leu
1               5                   10                  15 gct ggt gtg ccc gca atg ccg gcg cat gcg gcc atc aac agc atg agc       96
Ala Gly Val Pro Ala Met Pro Ala His Ala Ala Ile Asn Ser Met Ser
                20                  25                  30 ctg ggc gcg agc tac gac gcg caa cag gcc aac atc acc ttt cgc gtt      144
Leu Gly Ala Ser Tyr Asp Ala Gln Gln Ala Asn Ile Thr Phe Arg Val
            35                  40                  45 tac tcc tcg cag gcc acg cgc atc gtg ctg tac ctc tat tcg gca ggt      192
Tyr Ser Ser Gln Ala Thr Arg Ile Val Leu Tyr Leu Tyr Ser Ala Gly
        50                  55                  60 tac ggt gtg cag gag tcg gcc acc tac acg ctg agc cca gcg ggc agt      240
Tyr Gly Val Gln Glu Ser Ala Thr Tyr Thr Leu Ser Pro Ala Gly Ser
65                  70                  75                  80 ggt gta tgg gcg gtg acg gtg ccg gtg tcg tcg atc aag gcg gcc ggc      288
Gly Val Trp Ala Val Thr Val Pro Val Ser Ser Ile Lys Ala Ala Gly
                85                  90                  95 atc acg ggg gcg gtg tac tac ggg tat cgc gcc tgg ggg ccg aat tgg      336
Ile Thr Gly Ala Val Tyr Tyr Gly Tyr Arg Ala Trp Gly Pro Asn Trp
                100                 105                 110 cct tat gcc agc aac tgg ggc aag ggt tcg cag gcg ggc tgt gtt tcc      384
Pro Tyr Ala Ser Asn Trp Gly Lys Gly Ser Gln Ala Gly Cys Val Ser
```

```
                115                 120                 125
gac gtc gac gcc aac ggc gac cgc ttc aat ccc aac aaa ctg ttg ttg      432
Asp Val Asp Ala Asn Gly Asp Arg Phe Asn Pro Asn Lys Leu Leu Leu
        130                 135                 140 gac ccc tac gcg cag gaa gtg agc cag gat ccg ctg aac ccg tcc aac      480
Asp Pro Tyr Ala Gln Glu Val Ser Gln Asp Pro Leu Asn Pro Ser Asn
145                 150                 155                 160 cag aac ggc aac gtg ttc gcc tct gcg cac tat cgc acc acc gac agt      528
Gln Asn Gly Asn Val Phe Ala Ser Ala His Tyr Arg Thr Thr Asp Ser
                165                 170                 175 ggc atc tat gca ccc aag ggt gtc gtg ctg gtg ccc agt acg caa agt      576
Gly Ile Tyr Ala Pro Lys Gly Val Val Leu Val Pro Ser Thr Gln Ser
        180                 185                 190 acc ggc acc aaa ccc aca cgc gcg cag aag gat gat gtg atc tac gag      624
Thr Gly Thr Lys Pro Thr Arg Ala Gln Lys Asp Asp Val Ile Tyr Glu
195                 200                 205 gtg cat gtg cgc ggc ttc acc gag cag gac acc tct atc cct gcg cag      672
Val His Val Arg Gly Phe Thr Glu Gln Asp Thr Ser Ile Pro Ala Gln
        210                 215                 220 tat cgc ggc acc tat tac ggt gca ggg ctc aag gcc agt tac ctc gcc      720
Tyr Arg Gly Thr Tyr Tyr Gly Ala Gly Leu Lys Ala Ser Tyr Leu Ala
225                 230                 235                 240 agc ctg ggc gtg acc gcg gtg gaa ttc ctg ccg gtg cag gaa acg cag      768
Ser Leu Gly Val Thr Ala Val Glu Phe Leu Pro Val Gln Glu Thr Gln
                245                 250                 255 aat gat gcg aac gat gtg gtt ccc aat tca gat gcc aac cag aac tac      816
Asn Asp Ala Asn Asp Val Val Pro Asn Ser Asp Ala Asn Gln Asn Tyr
        260                 265                 270 tgg ggc tac atg acc gag aac tac ttc tcg ccg gat cgc cgc tat gcc      864
Trp Gly Tyr Met Thr Glu Asn Tyr Phe Ser Pro Asp Arg Arg Tyr Ala
        275                 280                 285 tac aac aag gcg gct ggc ggt ccc acg gcg gag ttc cag gcg atg gtg      912
Tyr Asn Lys Ala Ala Gly Gly Pro Thr Ala Glu Phe Gln Ala Met Val
290                 295                 300 cag gcg ttt cac aac gca ggc atc aag gtc tac atg gat gtg gtc tac      960
Gln Ala Phe His Asn Ala Gly Ile Lys Val Tyr Met Asp Val Val Tyr
305             310                 315                 320 aac cac acc gcc gaa ggc ggc acc tgg acc agc agt gat ccc acc acg     1008
Asn His Thr Ala Glu Gly Gly Thr Trp Thr Ser Ser Asp Pro Thr Thr
                325                 330                 335 gcc acc att tat tcg tgg cgc ggc ttg gac aat gcc acg tac tac gag     1056
Ala Thr Ile Tyr Ser Trp Arg Gly Leu Asp Asn Ala Thr Tyr Tyr Glu
        340                 345                 350 ctg acc tcg ggc aac caa tac ttc tac gac aac acg ggc att ggc gcg     1104
Leu Thr Ser Gly Asn Gln Tyr Phe Tyr Asp Asn Thr Gly Ile Gly Ala
        355                 360                 365 aac ttc aat acg tac aac acg gtg gcg cag aac ctt atc gtc gac tcg     1152
Asn Phe Asn Thr Tyr Asn Thr Val Ala Gln Asn Leu Ile Val Asp Ser
370                 375                 380 gtg gcg tat tgg gcg aac acg atg ggc gtg gat ggc ttt cgc ttc gac     1200
Val Ala Tyr Trp Ala Asn Thr Met Gly Val Asp Gly Phe Arg Phe Asp
385                 390                 395                 400 ctt gct tcc gtg ctc ggc aac agt tgc ctc aat gcc gta cac gcg tcc     1248
Leu Ala Ser Val Leu Gly Asn Ser Cys Leu Asn Ala Val His Ala Ser
                405                 410                 415 gcg ccc aat tgc ccg aac ggt ggt tat aac ttc gac gcg gcg gat agc     1296
Ala Pro Asn Cys Pro Asn Gly Gly Tyr Asn Phe Asp Ala Ala Asp Ser
        420                 425                 430 aac gta gcg atc aac cgc atc cta cgc gag ttc acg gtg cgc ccg gcg     1344
```

```
                Asn Val Ala Ile Asn Arg Ile Leu Arg Glu Phe Thr Val Arg Pro Ala
                            435                 440                 445 gcg ggc ggc acg gtc tgg atc tgt ttg cgg aac ctt ggg cca tcg gcg        1392
Ala Gly Gly Thr Val Trp Ile Cys Leu Arg Asn Leu Gly Pro Ser Ala
450                 455                 460 gca act cgt acc agc tgg gtg gat tcc cgc agg gtg gtc cga gtg gaa        1440
Ala Thr Arg Thr Ser Trp Val Asp Ser Arg Arg Val Val Arg Val Glu
465                 470                 475                 480 tgg tct gtt ccg cga cag ctg cgg cag gcg cag aac gag ctg ggt agc        1488
Trp Ser Val Pro Arg Gln Leu Arg Gln Ala Gln Asn Glu Leu Gly Ser
                485                 490                 495 atg acc atc tat gtg acg cag gat gcg aat gat ttc tcc ggt tcg tcc        1536
Met Thr Ile Tyr Val Thr Gln Asp Ala Asn Asp Phe Ser Gly Ser Ser
500                 505                 510 aat ctg ttc cag tcc agt ggg cgg tcg ccg tgg aac tcg atc aac ttt        1584
Asn Leu Phe Gln Ser Ser Gly Arg Ser Pro Trp Asn Ser Ile Asn Phe
            515                 520                 525 atc gac gtg cat gac ggc atg acg ttg aag gac gtg tac tcc tgc aac        1632
Ile Asp Val His Asp Gly Met Thr Leu Lys Asp Val Tyr Ser Cys Asn
530                 535                 540 ggc gcc aac aac agt cag gcg tcg tac ggg ccg tcg gat ggc ggc acg        1680
Gly Ala Asn Asn Ser Gln Ala Ser Tyr Gly Pro Ser Asp Gly Gly Thr
545                 550                 555                 560 agc acc aat tac agt tgg gat cag ggc atg tcg gcg gga acg ggt gcc        1728
Ser Thr Asn Tyr Ser Trp Asp Gln Gly Met Ser Ala Gly Thr Gly Ala
                565                 570                 575 gcg gtc gac cag cgt cga gcg gca cga acg ggc atg gcc ttc gag atg        1776
Ala Val Asp Gln Arg Arg Ala Ala Arg Thr Gly Met Ala Phe Glu Met
            580                 585                 590 ttg tcc gcg ggc acg ccg ttg atg cag ggc ggc gac gaa tac ctg cgc        1824
Leu Ser Ala Gly Thr Pro Leu Met Gln Gly Gly Asp Glu Tyr Leu Arg
595                 600                 605 acg ctc cag tgc aac aac aat gcc tac aac ctc gac tcc agc gcc aac        1872
Thr Leu Gln Cys Asn Asn Asn Ala Tyr Asn Leu Asp Ser Ser Ala Asn
610                 615                 620 tgg ctt acc tat agc tgg acc acc gat caa tcg aac ttc tac acc ttc        1920
Trp Leu Thr Tyr Ser Trp Thr Thr Asp Gln Ser Asn Phe Tyr Thr Phe
625                 630                 635                 640 gcg caa cgc ctc att cgt tcc gca agg cac atc ccg ctt cgc ccg tcg        1968
Ala Gln Arg Leu Ile Arg Ser Ala Arg His Ile Pro Leu Arg Pro Ser
                645                 650                 655 agc tgg tac agc ggc agc cag ttg acg tgg tat cag ccc agt gga gcc        2016
Ser Trp Tyr Ser Gly Ser Gln Leu Thr Trp Tyr Gln Pro Ser Gly Ala
            660                 665                 670 gtg gcg gac agc aac tac tgg aac aac acc agc aac tac gcc att gcc        2064
Val Ala Asp Ser Asn Tyr Trp Asn Asn Thr Ser Asn Tyr Ala Ile Ala
675                 680                 685 tac gcc atc aat ggg cct tcg ctg ggc gac agc aat tcc atc tat gtc        2112
Tyr Ala Ile Asn Gly Pro Ser Leu Gly Asp Ser Asn Ser Ile Tyr Val
690                 695                 700 gct tac aac ggt tgg tcg agc agc gtg act ttc acc ttg cct gcg cca        2160
Ala Tyr Asn Gly Trp Ser Ser Ser Val Thr Phe Thr Leu Pro Ala Pro
705                 710                 715                 720 ccg tca ggc acg cag tgg tat cgc gtc acg gat acc tgc gac tgg aac        2208
Pro Ser Gly Thr Gln Trp Tyr Arg Val Thr Asp Thr Cys Asp Trp Asn
                725                 730                 735 gat ggc gcc agt acg ttt gtt gca ccg ggc agc gag aca ttg atc ggc        2256
Asp Gly Ala Ser Thr Phe Val Ala Pro Gly Ser Glu Thr Leu Ile Gly
            740                 745                 750
```

-continued

| | | | | | | | | | | | | |
|---|---|---|---|---|---|---|---|---|---|---|---|---|
| ggc | gcg | ggc | acc | acc | tat | ggg | caa | tgc | ggt | caa | tcg | ctg ctg ctg ttg | 2304 |
| Gly | Ala | Gly | Thr | Thr | Tyr | Gly | Gln | Cys | Gly | Gln | Ser | Leu Leu Leu Leu |
| | 755 | | | | | 760 | | | | | 765 | |

| | | | | |
|---|---|---|---|---|
| atc | tcc | aag | tag | 2316 |
| Ile | Ser | Lys | | |
| | 770 | | | |

<210> SEQ ID NO 10
<211> LENGTH: 771
<212> TYPE: PRT
<213> ORGANISM: Pseudomonas amyloderamosa

<400> SEQUENCE: 10

Met Lys Cys Pro Lys Ile Leu Gly Ala Leu Leu Gly Cys Ala Val Leu
1               5                   10                  15

Ala Gly Val Pro Ala Met Pro Ala His Ala Ala Ile Asn Ser Met Ser
                20                  25                  30

Leu Gly Ala Ser Tyr Asp Ala Gln Gln Ala Asn Ile Thr Phe Arg Val
            35                  40                  45

Tyr Ser Ser Gln Ala Thr Arg Ile Val Leu Tyr Leu Tyr Ser Ala Gly
        50                  55                  60

Tyr Gly Val Gln Glu Ser Ala Thr Tyr Thr Leu Ser Pro Ala Gly Ser
65                  70                  75                  80

Gly Val Trp Ala Val Thr Val Pro Val Ser Ser Ile Lys Ala Ala Gly
                85                  90                  95

Ile Thr Gly Ala Val Tyr Tyr Gly Tyr Arg Ala Trp Gly Pro Asn Trp
            100                 105                 110

Pro Tyr Ala Ser Asn Trp Gly Lys Gly Ser Gln Ala Gly Cys Val Ser
        115                 120                 125

Asp Val Asp Ala Asn Gly Asp Arg Phe Asn Pro Asn Lys Leu Leu Leu
130                 135                 140

Asp Pro Tyr Ala Gln Glu Val Ser Gln Asp Pro Leu Asn Pro Ser Asn
145                 150                 155                 160

Gln Asn Gly Asn Val Phe Ala Ser Ala His Tyr Arg Thr Thr Asp Ser
                165                 170                 175

Gly Ile Tyr Ala Pro Lys Gly Val Val Leu Val Pro Ser Thr Gln Ser
            180                 185                 190

Thr Gly Thr Lys Pro Thr Arg Ala Gln Lys Asp Asp Val Ile Tyr Glu
        195                 200                 205

Val His Val Arg Gly Phe Thr Glu Gln Asp Thr Ser Ile Pro Ala Gln
210                 215                 220

Tyr Arg Gly Thr Tyr Tyr Gly Ala Gly Leu Lys Ala Ser Tyr Leu Ala
225                 230                 235                 240

Ser Leu Gly Val Thr Ala Val Glu Phe Leu Pro Val Gln Glu Thr Gln
                245                 250                 255

Asn Asp Ala Asn Asp Val Val Pro Asn Ser Asp Ala Asn Gln Asn Tyr
            260                 265                 270

Trp Gly Tyr Met Thr Glu Asn Tyr Phe Ser Pro Asp Arg Arg Tyr Ala
        275                 280                 285

Tyr Asn Lys Ala Ala Gly Gly Pro Thr Ala Glu Phe Gln Ala Met Val
290                 295                 300

Gln Ala Phe His Asn Ala Gly Ile Lys Val Tyr Met Asp Val Val Tyr
305                 310                 315                 320

Asn His Thr Ala Glu Gly Gly Thr Trp Thr Ser Ser Asp Pro Thr Thr
                325                 330                 335

-continued

```
Ala Thr Ile Tyr Ser Trp Arg Gly Leu Asp Asn Ala Thr Tyr Tyr Glu
                340                 345                 350

Leu Thr Ser Gly Asn Gln Tyr Phe Tyr Asp Asn Thr Gly Ile Gly Ala
                355                 360                 365

Asn Phe Asn Thr Tyr Asn Thr Val Ala Gln Asn Leu Ile Val Asp Ser
            370                 375                 380

Val Ala Tyr Trp Ala Asn Thr Met Gly Val Asp Gly Phe Arg Phe Asp
385                 390                 395                 400

Leu Ala Ser Val Leu Gly Asn Ser Cys Leu Asn Ala Val His Ala Ser
                405                 410                 415

Ala Pro Asn Cys Pro Asn Gly Gly Tyr Asn Phe Asp Ala Ala Asp Ser
            420                 425                 430

Asn Val Ala Ile Asn Arg Ile Leu Arg Glu Phe Thr Val Arg Pro Ala
            435                 440                 445

Ala Gly Gly Thr Val Trp Ile Cys Leu Arg Asn Leu Gly Pro Ser Ala
            450                 455                 460

Ala Thr Arg Thr Ser Trp Val Asp Ser Arg Val Val Arg Val Glu
465                 470                 475                 480

Trp Ser Val Pro Arg Gln Leu Arg Gln Ala Gln Asn Glu Leu Gly Ser
                485                 490                 495

Met Thr Ile Tyr Val Thr Gln Asp Ala Asn Asp Phe Ser Gly Ser Ser
                500                 505                 510

Asn Leu Phe Gln Ser Ser Gly Arg Ser Pro Trp Asn Ser Ile Asn Phe
            515                 520                 525

Ile Asp Val His Asp Gly Met Thr Leu Lys Asp Val Tyr Ser Cys Asn
530                 535                 540

Gly Ala Asn Asn Ser Gln Ala Ser Tyr Gly Pro Ser Asp Gly Gly Thr
545                 550                 555                 560

Ser Thr Asn Tyr Ser Trp Asp Gln Gly Met Ser Ala Gly Thr Gly Ala
                565                 570                 575

Ala Val Asp Gln Arg Arg Ala Ala Arg Thr Gly Met Ala Phe Glu Met
                580                 585                 590

Leu Ser Ala Gly Thr Pro Leu Met Gln Gly Gly Asp Glu Tyr Leu Arg
            595                 600                 605

Thr Leu Gln Cys Asn Asn Asn Ala Tyr Asn Leu Asp Ser Ser Ala Asn
            610                 615                 620

Trp Leu Thr Tyr Ser Trp Thr Thr Asp Gln Ser Asn Phe Tyr Thr Phe
625                 630                 635                 640

Ala Gln Arg Leu Ile Arg Ser Ala Arg His Ile Pro Leu Arg Pro Ser
                645                 650                 655

Ser Trp Tyr Ser Gly Ser Gln Leu Thr Trp Tyr Gln Pro Ser Gly Ala
                660                 665                 670

Val Ala Asp Ser Asn Tyr Trp Asn Asn Thr Ser Asn Tyr Ala Ile Ala
            675                 680                 685

Tyr Ala Ile Asn Gly Pro Ser Leu Gly Asp Ser Asn Ser Ile Tyr Val
            690                 695                 700

Ala Tyr Asn Gly Trp Ser Ser Val Thr Phe Thr Leu Pro Ala Pro
705                 710                 715                 720

Pro Ser Gly Thr Gln Trp Tyr Arg Val Thr Asp Thr Cys Asp Trp Asn
                725                 730                 735

Asp Gly Ala Ser Thr Phe Val Ala Pro Gly Ser Glu Thr Leu Ile Gly
            740                 745                 750

Gly Ala Gly Thr Thr Tyr Gly Gln Cys Gly Gln Ser Leu Leu Leu Leu
```

<210> SEQ ID NO 11
<211> LENGTH: 2598
<212> TYPE: DNA
<213> ORGANISM: Aspergillus niger
<220> FEATURE:
<221> NAME/KEY: CDS
<222> LOCATION: (1)..(2598)

<400> SEQUENCE: 11

| | | | | | | | | | | | | | | | | |
|---|---|---|---|---|---|---|---|---|---|---|---|---|---|---|---|---|
| atg | ttg | ggg | tct | ttg | ctt | tta | ctc | tta | ccc | ctt | gtg | ggc | gct | gct | gtc | 48 |
| Met | Leu | Gly | Ser | Leu | Leu | Leu | Leu | Leu | Pro | Leu | Val | Gly | Ala | Ala | Val | |
| 1 | | | | 5 | | | | | 10 | | | | | 15 | | |

| att | gga | ccc | agg | gca | aac | agt | cag | agt | tgc | cca | ggg | tat | aag | gcg | tcc | 96 |
|---|---|---|---|---|---|---|---|---|---|---|---|---|---|---|---|---|
| Ile | Gly | Pro | Arg | Ala | Asn | Ser | Gln | Ser | Cys | Pro | Gly | Tyr | Lys | Ala | Ser | |
| | | | 20 | | | | | 25 | | | | | 30 | | | |

| aac | gtc | caa | aag | cag | gct | agg | tca | ctg | act | gcg | gat | ctg | act | cta | gct | 144 |
|---|---|---|---|---|---|---|---|---|---|---|---|---|---|---|---|---|
| Asn | Val | Gln | Lys | Gln | Ala | Arg | Ser | Leu | Thr | Ala | Asp | Leu | Thr | Leu | Ala | |
| | 35 | | | | | 40 | | | | | 45 | | | | | |

| ggt | acg | cct | tgt | aat | agc | tat | ggc | aag | gat | ttg | gaa | gac | ctc | aag | ctg | 192 |
|---|---|---|---|---|---|---|---|---|---|---|---|---|---|---|---|---|
| Gly | Thr | Pro | Cys | Asn | Ser | Tyr | Gly | Lys | Asp | Leu | Glu | Asp | Leu | Lys | Leu | |
| 50 | | | | | 55 | | | | | 60 | | | | | | |

| ctt | gtg | gaa | tat | cag | act | gat | gaa | cgg | tta | cat | gtt | atg | atc | tac | gat | 240 |
|---|---|---|---|---|---|---|---|---|---|---|---|---|---|---|---|---|
| Leu | Val | Glu | Tyr | Gln | Thr | Asp | Glu | Arg | Leu | His | Val | Met | Ile | Tyr | Asp | |
| 65 | | | | | 70 | | | | | 75 | | | | | 80 | |

| gcc | gac | gag | gaa | gtc | tat | caa | gtt | cct | gaa | tca | gtc | ctt | cct | cgc | gtg | 288 |
|---|---|---|---|---|---|---|---|---|---|---|---|---|---|---|---|---|
| Ala | Asp | Glu | Glu | Val | Tyr | Gln | Val | Pro | Glu | Ser | Val | Leu | Pro | Arg | Val | |
| | | | | 85 | | | | | 90 | | | | | 95 | | |

| ggt | agt | gac | gag | gac | tct | gag | gac | agt | gtt | ttg | gaa | ttt | gac | tat | gtg | 336 |
|---|---|---|---|---|---|---|---|---|---|---|---|---|---|---|---|---|
| Gly | Ser | Asp | Glu | Asp | Ser | Glu | Asp | Ser | Val | Leu | Glu | Phe | Asp | Tyr | Val | |
| | | | 100 | | | | | 105 | | | | | 110 | | | |

| gaa | gaa | ccg | ttt | tca | ttc | acc | atc | tcc | aag | gga | gat | gag | gtc | ctg | ttt | 384 |
|---|---|---|---|---|---|---|---|---|---|---|---|---|---|---|---|---|
| Glu | Glu | Pro | Phe | Ser | Phe | Thr | Ile | Ser | Lys | Gly | Asp | Glu | Val | Leu | Phe | |
| | | 115 | | | | | 120 | | | | | 125 | | | | |

| gac | tct | tcg | gca | tca | cca | cta | gtt | ttt | cag | tcg | caa | tat | gtg | aac | ctt | 432 |
|---|---|---|---|---|---|---|---|---|---|---|---|---|---|---|---|---|
| Asp | Ser | Ser | Ala | Ser | Pro | Leu | Val | Phe | Gln | Ser | Gln | Tyr | Val | Asn | Leu | |
| | 130 | | | | | 135 | | | | | 140 | | | | | |

| cgc | acc | tgg | ttg | ccc | gat | gat | ccc | tat | gtg | tat | ggt | ctc | gga | gag | cat | 480 |
|---|---|---|---|---|---|---|---|---|---|---|---|---|---|---|---|---|
| Arg | Thr | Trp | Leu | Pro | Asp | Asp | Pro | Tyr | Val | Tyr | Gly | Leu | Gly | Glu | His | |
| 145 | | | | | 150 | | | | | 155 | | | | | 160 | |

| tct | gac | cct | atg | cgc | ttg | cca | aca | tac | aat | tac | acg | cgg | acc | ctt | tgg | 528 |
|---|---|---|---|---|---|---|---|---|---|---|---|---|---|---|---|---|
| Ser | Asp | Pro | Met | Arg | Leu | Pro | Thr | Tyr | Asn | Tyr | Thr | Arg | Thr | Leu | Trp | |
| | | | | 165 | | | | | 170 | | | | | 175 | | |

| aac | cgc | gac | gcg | tat | ggc | act | cca | aac | aac | acc | aac | ttg | tac | ggt | agt | 576 |
|---|---|---|---|---|---|---|---|---|---|---|---|---|---|---|---|---|
| Asn | Arg | Asp | Ala | Tyr | Gly | Thr | Pro | Asn | Asn | Thr | Asn | Leu | Tyr | Gly | Ser | |
| | | | 180 | | | | | 185 | | | | | 190 | | | |

| cat | cct | gtc | tac | tat | gat | cac | cgt | gga | aag | tcc | gga | act | tat | gga | gtc | 624 |
|---|---|---|---|---|---|---|---|---|---|---|---|---|---|---|---|---|
| His | Pro | Val | Tyr | Tyr | Asp | His | Arg | Gly | Lys | Ser | Gly | Thr | Tyr | Gly | Val | |
| | | 195 | | | | | 200 | | | | | 205 | | | | |

| ttc | ctg | ctg | aac | tct | aat | ggt | atg | gac | atc | aag | atc | aac | caa | acg | aca | 672 |
|---|---|---|---|---|---|---|---|---|---|---|---|---|---|---|---|---|
| Phe | Leu | Leu | Asn | Ser | Asn | Gly | Met | Asp | Ile | Lys | Ile | Asn | Gln | Thr | Thr | |
| | 210 | | | | | 215 | | | | | 220 | | | | | |

| gat | gga | aag | cag | tac | ttg | gaa | tac | aat | ctt | ctc | ggc | ggt | gtt | ctg | gac | 720 |
|---|---|---|---|---|---|---|---|---|---|---|---|---|---|---|---|---|
| Asp | Gly | Lys | Gln | Tyr | Leu | Glu | Tyr | Asn | Leu | Leu | Gly | Gly | Val | Leu | Asp | |
| 225 | | | | | 230 | | | | | 235 | | | | | 240 | |

| ttc | tac | ttc | ttc | tac | gga | gaa | gat | cct | aag | caa | gcg | agc | atg | gaa | tac | 768 |
|---|---|---|---|---|---|---|---|---|---|---|---|---|---|---|---|---|
| Phe | Tyr | Phe | Phe | Tyr | Gly | Glu | Asp | Pro | Lys | Gln | Ala | Ser | Met | Glu | Tyr | |
| | | | | 245 | | | | | 250 | | | | | 255 | | |

| | | | | | | | | | | | | | | | | |
|---|---|---|---|---|---|---|---|---|---|---|---|---|---|---|---|---|
| tca | aag | att | gtc | ggt | ctc | ccg | gca | atg | cag | agt | tac | tgg | act | ttc | ggc | 816 |
| Ser | Lys | Ile | Val | Gly | Leu | Pro | Ala | Met | Gln | Ser | Tyr | Trp | Thr | Phe | Gly | |
| | | | 260 | | | | | 265 | | | | | 270 | | | |
| gta | tgc | ccc | cca | ccc | cct | aat | ccc | ata | aca | gtc | cga | gtt | gtg | gtc | tac | 864 |
| Val | Cys | Pro | Pro | Pro | Pro | Asn | Pro | Ile | Thr | Val | Arg | Val | Val | Val | Tyr | |
| | | 275 | | | | | 280 | | | | | 285 | | | | |
| aac | tac | agc | cag | gca | aag | att | cct | ctg | gag | acg | atg | tgg | aca | gat | atc | 912 |
| Asn | Tyr | Ser | Gln | Ala | Lys | Ile | Pro | Leu | Glu | Thr | Met | Trp | Thr | Asp | Ile | |
| | 290 | | | | | 295 | | | | | 300 | | | | | |
| gac | tac | atg | gac | aag | aga | agg | gtg | ttt | acc | ctt | gat | cct | cag | agg | ttc | 960 |
| Asp | Tyr | Met | Asp | Lys | Arg | Arg | Val | Phe | Thr | Leu | Asp | Pro | Gln | Arg | Phe | |
| 305 | | | | | 310 | | | | | 315 | | | | | 320 | |
| ccg | ctc | gaa | aag | atg | cgg | gag | ttg | gta | acc | tac | ctg | cac | aat | cat | gat | 1008 |
| Pro | Leu | Glu | Lys | Met | Arg | Glu | Leu | Val | Thr | Tyr | Leu | His | Asn | His | Asp | |
| | | | | 325 | | | | | 330 | | | | | 335 | | |
| cag | cat | tac | att | gtc | atg | gtt | gac | ccg | gct | gtg | agc | gta | agc | aat | aac | 1056 |
| Gln | His | Tyr | Ile | Val | Met | Val | Asp | Pro | Ala | Val | Ser | Val | Ser | Asn | Asn | |
| | | | 340 | | | | | 345 | | | | | 350 | | | |
| acg | gca | tat | atc | acc | ggc | gtg | aga | gac | gat | gtt | ttc | ctt | cac | aat | cag | 1104 |
| Thr | Ala | Tyr | Ile | Thr | Gly | Val | Arg | Asp | Asp | Val | Phe | Leu | His | Asn | Gln | |
| | | 355 | | | | | 360 | | | | | 365 | | | | |
| aac | ggt | agc | cta | tac | gag | ggt | gct | gtt | tgg | cct | ggt | gtc | act | gtt | ttc | 1152 |
| Asn | Gly | Ser | Leu | Tyr | Glu | Gly | Ala | Val | Trp | Pro | Gly | Val | Thr | Val | Phe | |
| | 370 | | | | | 375 | | | | | 380 | | | | | |
| cca | gac | tgg | ttc | aat | gag | ggt | act | cag | gat | tac | tgg | act | gcg | caa | ttt | 1200 |
| Pro | Asp | Trp | Phe | Asn | Glu | Gly | Thr | Gln | Asp | Tyr | Trp | Thr | Ala | Gln | Phe | |
| 385 | | | | | 390 | | | | | 395 | | | | | 400 | |
| caa | cag | ttc | ttt | gat | ccc | aag | tcc | gga | gtc | gat | att | gac | gcc | ctg | tgg | 1248 |
| Gln | Gln | Phe | Phe | Asp | Pro | Lys | Ser | Gly | Val | Asp | Ile | Asp | Ala | Leu | Trp | |
| | | | | 405 | | | | | 410 | | | | | 415 | | |
| att | gac | atg | aac | gaa | gcc | tcc | aat | ttc | tgc | cct | tat | cct | tgt | ctg | gac | 1296 |
| Ile | Asp | Met | Asn | Glu | Ala | Ser | Asn | Phe | Cys | Pro | Tyr | Pro | Cys | Leu | Asp | |
| | | | 420 | | | | | 425 | | | | | 430 | | | |
| cca | gcg | gca | tac | gcg | atc | tcc | gcc | gac | ctc | cca | ccg | gca | gca | cca | cct | 1344 |
| Pro | Ala | Ala | Tyr | Ala | Ile | Ser | Ala | Asp | Leu | Pro | Pro | Ala | Ala | Pro | Pro | |
| | | | 435 | | | | | 440 | | | | | 445 | | | |
| gtt | cgg | cca | agc | agc | ccg | atc | cca | ctg | ccc | gga | ttc | ccc | gcg | gac | ttt | 1392 |
| Val | Arg | Pro | Ser | Ser | Pro | Ile | Pro | Leu | Pro | Gly | Phe | Pro | Ala | Asp | Phe | |
| | | 450 | | | | | 455 | | | | | 460 | | | | |
| cag | cct | tcg | tct | aag | cga | tct | gtt | aaa | aga | gcg | caa | gga | gat | aaa | ggg | 1440 |
| Gln | Pro | Ser | Ser | Lys | Arg | Ser | Val | Lys | Arg | Ala | Gln | Gly | Asp | Lys | Gly | |
| 465 | | | | | 470 | | | | | 475 | | | | | 480 | |
| aag | aag | gtt | ggg | ttg | ccc | aat | cgc | aac | ctc | act | gac | ccg | ccc | tac | acc | 1488 |
| Lys | Lys | Val | Gly | Leu | Pro | Asn | Arg | Asn | Leu | Thr | Asp | Pro | Pro | Tyr | Thr | |
| | | | | 485 | | | | | 490 | | | | | 495 | | |
| att | cgg | aat | gcc | gca | ggt | gtc | ctt | agt | atg | agc | act | atc | gag | acg | gat | 1536 |
| Ile | Arg | Asn | Ala | Ala | Gly | Val | Leu | Ser | Met | Ser | Thr | Ile | Glu | Thr | Asp | |
| | | | 500 | | | | | 505 | | | | | 510 | | | |
| ctc | att | cat | gcg | ggt | gaa | ggg | tat | gcc | gag | tat | gat | act | cac | aat | ctc | 1584 |
| Leu | Ile | His | Ala | Gly | Glu | Gly | Tyr | Ala | Glu | Tyr | Asp | Thr | His | Asn | Leu | |
| | | 515 | | | | | 520 | | | | | 525 | | | | |
| tat | gga | aca | agg | tta | gtg | atg | agc | tct | gct | tcc | cgc | acg | gct | atg | cag | 1632 |
| Tyr | Gly | Thr | Arg | Leu | Val | Met | Ser | Ser | Ala | Ser | Arg | Thr | Ala | Met | Gln | |
| | 530 | | | | | 535 | | | | | 540 | | | | | |
| gcc | cgc | cgt | ccc | gat | gtg | agg | cct | ttg | gtc | atc | act | cgc | agt | acg | ttt | 1680 |
| Ala | Arg | Arg | Pro | Asp | Val | Arg | Pro | Leu | Val | Ile | Thr | Arg | Ser | Thr | Phe | |
| 545 | | | | | 550 | | | | | 555 | | | | | 560 | |
| gca | ggc | gct | gga | gca | cac | gta | gga | cac | tgg | ctg | ggc | gac | aac | ttt | agc | 1728 |
| Ala | Gly | Ala | Gly | Ala | His | Val | Gly | His | Trp | Leu | Gly | Asp | Asn | Phe | Ser | |

-continued

|     | 565 |     |     |     | 570 |     |     |     | 575 |     |     |     |      |
|---|---|---|---|---|---|---|---|---|---|---|---|---|---|
| gat | tgg | gtt | cac | tac | cgg | atc | tcc | atc | gcg | cag | atc | ctc | tcc ttc gcg | 1776 |
| Asp | Trp | Val | His | Tyr | Arg | Ile | Ser | Ile | Ala | Gln | Ile | Leu | Ser Phe Ala |
|     |     |     | 580 |     |     |     |     | 585 |     |     |     |     | 590 |

```
gat tgg gtt cac tac cgg atc tcc atc gcg cag atc ctc tcc ttc gcg    1776
Asp Trp Val His Tyr Arg Ile Ser Ile Ala Gln Ile Leu Ser Phe Ala
            580                 585                 590 tcc atg ttc cag att cca atg gtc ggg gct gac gtg tgt ggg ttt ggt    1824
Ser Met Phe Gln Ile Pro Met Val Gly Ala Asp Val Cys Gly Phe Gly
        595                 600                 605 agc aac acg acg gag gaa ttg tgt gcc cga tgg gcg tca ctt ggt gcc    1872
Ser Asn Thr Thr Glu Glu Leu Cys Ala Arg Trp Ala Ser Leu Gly Ala
610                 615                 620 ttc tat acg ttc tac cgc aat cat aac gag ctg ggc gac ata tcg caa    1920
Phe Tyr Thr Phe Tyr Arg Asn His Asn Glu Leu Gly Asp Ile Ser Gln
625                 630                 635                 640 gag ttc tac cgc tgg cct acg gtt gcc gag tcc gcg cgt aag gcc att    1968
Glu Phe Tyr Arg Trp Pro Thr Val Ala Glu Ser Ala Arg Lys Ala Ile
                645                 650                 655 gac atc cgg tac aag ctc ctc gat tat atc tac act gct ctt cac cgg    2016
Asp Ile Arg Tyr Lys Leu Leu Asp Tyr Ile Tyr Thr Ala Leu His Arg
        660                 665                 670 caa agc cag acc ggc gag cca ttc ctg cag cct caa ttc tac ctg tac    2064
Gln Ser Gln Thr Gly Glu Pro Phe Leu Gln Pro Gln Phe Tyr Leu Tyr
675                 680                 685 cct gag gat tcg aac acc ttt gcg aac gac cgg cag ttc ttc tat ggt    2112
Pro Glu Asp Ser Asn Thr Phe Ala Asn Asp Arg Gln Phe Phe Tyr Gly
690                 695                 700 gac gcc ctt ctt gtc agc ccc gtg ttg aat gag gga tcc acc tca gtc    2160
Asp Ala Leu Leu Val Ser Pro Val Leu Asn Glu Gly Ser Thr Ser Val
705                 710                 715                 720 gac gca tac ttc ccg gac gac atc ttc tac gat tgg tac aca ggg gca    2208
Asp Ala Tyr Phe Pro Asp Asp Ile Phe Tyr Asp Trp Tyr Thr Gly Ala
                725                 730                 735 gtg gtg cgt ggg cac gga gaa aac atc acg ctc agc aac atc aac atc    2256
Val Val Arg Gly His Gly Glu Asn Ile Thr Leu Ser Asn Ile Asn Ile
        740                 745                 750 acc cac atc cct ctg cac atc cgc ggt gga aat atc ata cct gtc agg    2304
Thr His Ile Pro Leu His Ile Arg Gly Gly Asn Ile Ile Pro Val Arg
755                 760                 765 aca tcc agc ggc atg aca acc act gag gtt cgt aag cag ggc ttc gag    2352
Thr Ser Ser Gly Met Thr Thr Thr Glu Val Arg Lys Gln Gly Phe Glu
770                 775                 780 ctg atc atc gcg cca gac ttg gat gac acc gca tcg ggc agt cta tat    2400
Leu Ile Ile Ala Pro Asp Leu Asp Asp Thr Ala Ser Gly Ser Leu Tyr
785                 790                 795                 800 ttg gat gat gga gac tcg ttg aac ccg tca tct gtg aca gag ctc gag    2448
Leu Asp Asp Gly Asp Ser Leu Asn Pro Ser Ser Val Thr Glu Leu Glu
                805                 810                 815 ttc acg tac agc aaa ggg gag ttg cac gtg aag ggt aca ttc gga cag    2496
Phe Thr Tyr Ser Lys Gly Glu Leu His Val Lys Gly Thr Phe Gly Gln
        820                 825                 830 aag gcc gtc ccc aag gtg gag aaa tgt acc ttg ctg ggg aag tca gca    2544
Lys Ala Val Pro Lys Val Glu Lys Cys Thr Leu Leu Gly Lys Ser Ala
835                 840                 845 cgg acg ttc aag ggc ttt gca ctc gat gcg ccg gtg aac ttt aag ctg    2592
Arg Thr Phe Lys Gly Phe Ala Leu Asp Ala Pro Val Asn Phe Lys Leu
850                 855                 860 aag tag                                                            2598
Lys
865
```

```
<210> SEQ ID NO 12
<211> LENGTH: 865
<212> TYPE: PRT
<213> ORGANISM: Aspergillus niger

<400> SEQUENCE: 12
```

| | | | | | | | | | | | | | | |
|---|---|---|---|---|---|---|---|---|---|---|---|---|---|---|
| Met | Leu | Gly | Ser | Leu | Leu | Leu | Leu | Pro | Leu | Val | Gly | Ala | Ala | Val |
| 1 | | | | 5 | | | | | 10 | | | | | 15 |
| Ile | Gly | Pro | Arg | Ala | Asn | Ser | Gln | Ser | Cys | Pro | Gly | Tyr | Lys | Ala | Ser |
| | | | 20 | | | | | 25 | | | | | 30 | | |
| Asn | Val | Gln | Lys | Gln | Ala | Arg | Ser | Leu | Thr | Ala | Asp | Leu | Thr | Leu | Ala |
| | | | 35 | | | | | 40 | | | | | 45 | | |
| Gly | Thr | Pro | Cys | Asn | Ser | Tyr | Gly | Lys | Asp | Leu | Glu | Asp | Leu | Lys | Leu |
| | 50 | | | | | 55 | | | | | 60 | | | | |
| Leu | Val | Glu | Tyr | Gln | Thr | Asp | Glu | Arg | Leu | His | Val | Met | Ile | Tyr | Asp |
| 65 | | | | | 70 | | | | | 75 | | | | | 80 |
| Ala | Asp | Glu | Glu | Val | Tyr | Gln | Val | Pro | Glu | Ser | Val | Leu | Pro | Arg | Val |
| | | | | 85 | | | | | 90 | | | | | 95 | |
| Gly | Ser | Asp | Glu | Asp | Ser | Glu | Asp | Ser | Val | Leu | Glu | Phe | Asp | Tyr | Val |
| | | | 100 | | | | | 105 | | | | | 110 | | |
| Glu | Glu | Pro | Phe | Ser | Phe | Thr | Ile | Ser | Lys | Gly | Asp | Glu | Val | Leu | Phe |
| | | | 115 | | | | | 120 | | | | | 125 | | |
| Asp | Ser | Ser | Ala | Ser | Pro | Leu | Val | Phe | Gln | Ser | Gln | Tyr | Val | Asn | Leu |
| | 130 | | | | | 135 | | | | | 140 | | | | |
| Arg | Thr | Trp | Leu | Pro | Asp | Asp | Pro | Tyr | Val | Tyr | Gly | Leu | Gly | Glu | His |
| 145 | | | | | 150 | | | | | 155 | | | | | 160 |
| Ser | Asp | Pro | Met | Arg | Leu | Pro | Thr | Tyr | Asn | Tyr | Thr | Arg | Thr | Leu | Trp |
| | | | | 165 | | | | | 170 | | | | | 175 | |
| Asn | Arg | Asp | Ala | Tyr | Gly | Thr | Pro | Asn | Asn | Thr | Asn | Leu | Tyr | Gly | Ser |
| | | | 180 | | | | | 185 | | | | | 190 | | |
| His | Pro | Val | Tyr | Tyr | Asp | His | Arg | Gly | Lys | Ser | Gly | Thr | Tyr | Gly | Val |
| | | | 195 | | | | | 200 | | | | | 205 | | |
| Phe | Leu | Leu | Asn | Ser | Asn | Gly | Met | Asp | Ile | Lys | Ile | Asn | Gln | Thr | Thr |
| | 210 | | | | | 215 | | | | | 220 | | | | |
| Asp | Gly | Lys | Gln | Tyr | Leu | Glu | Tyr | Asn | Leu | Leu | Gly | Val | Leu | Asp |
| 225 | | | | | 230 | | | | | 235 | | | | | 240 |
| Phe | Tyr | Phe | Phe | Tyr | Gly | Glu | Asp | Pro | Lys | Gln | Ala | Ser | Met | Glu | Tyr |
| | | | | 245 | | | | | 250 | | | | | 255 | |
| Ser | Lys | Ile | Val | Gly | Leu | Pro | Ala | Met | Gln | Ser | Tyr | Trp | Thr | Phe | Gly |
| | | | 260 | | | | | 265 | | | | | 270 | | |
| Val | Cys | Pro | Pro | Pro | Asn | Pro | Ile | Thr | Val | Arg | Val | Val | Tyr |
| | | | 275 | | | | | 280 | | | | | 285 | | |
| Asn | Tyr | Ser | Gln | Ala | Lys | Ile | Pro | Leu | Glu | Thr | Met | Trp | Thr | Asp | Ile |
| | 290 | | | | | 295 | | | | | 300 | | | | |
| Asp | Tyr | Met | Asp | Lys | Arg | Arg | Val | Phe | Thr | Leu | Asp | Pro | Gln | Arg | Phe |
| 305 | | | | | 310 | | | | | 315 | | | | | 320 |
| Pro | Leu | Glu | Lys | Met | Arg | Glu | Leu | Val | Thr | Tyr | Leu | His | Asn | His | Asp |
| | | | | 325 | | | | | 330 | | | | | 335 | |
| Gln | His | Tyr | Ile | Val | Met | Val | Asp | Pro | Ala | Val | Ser | Val | Ser | Asn | Asn |
| | | | 340 | | | | | 345 | | | | | 350 | | |
| Thr | Ala | Tyr | Ile | Thr | Gly | Val | Arg | Asp | Asp | Val | Phe | Leu | His | Asn | Gln |
| | | | 355 | | | | | 360 | | | | | 365 | | |
| Asn | Gly | Ser | Leu | Tyr | Glu | Gly | Ala | Val | Trp | Pro | Gly | Val | Thr | Val | Phe |
| | 370 | | | | | 375 | | | | | 380 | | | | |

-continued

```
Pro Asp Trp Phe Asn Glu Gly Thr Gln Asp Tyr Trp Thr Ala Gln Phe
385                 390                 395                 400

Gln Gln Phe Phe Asp Pro Lys Ser Gly Val Asp Ile Asp Ala Leu Trp
            405                 410                 415

Ile Asp Met Asn Glu Ala Ser Asn Phe Cys Pro Tyr Pro Cys Leu Asp
        420                 425                 430

Pro Ala Ala Tyr Ala Ile Ser Ala Asp Leu Pro Pro Ala Ala Pro Pro
                435                 440                 445

Val Arg Pro Ser Ser Pro Ile Pro Leu Pro Gly Phe Pro Ala Asp Phe
450                 455                 460

Gln Pro Ser Ser Lys Arg Ser Val Lys Arg Ala Gln Gly Asp Lys Gly
465                 470                 475                 480

Lys Lys Val Gly Leu Pro Asn Arg Asn Leu Thr Asp Pro Pro Tyr Thr
                485                 490                 495

Ile Arg Asn Ala Ala Gly Val Leu Ser Met Ser Thr Ile Glu Thr Asp
                500                 505                 510

Leu Ile His Ala Gly Glu Gly Tyr Ala Glu Tyr Asp Thr His Asn Leu
            515                 520                 525

Tyr Gly Thr Arg Leu Val Met Ser Ser Ala Ser Arg Thr Ala Met Gln
530                 535                 540

Ala Arg Arg Pro Asp Val Arg Pro Leu Val Ile Thr Arg Ser Thr Phe
545                 550                 555                 560

Ala Gly Ala Gly Ala His Val Gly His Trp Leu Gly Asp Asn Phe Ser
                565                 570                 575

Asp Trp Val His Tyr Arg Ile Ser Ile Ala Gln Ile Leu Ser Phe Ala
                580                 585                 590

Ser Met Phe Gln Ile Pro Met Val Gly Ala Asp Val Cys Gly Phe Gly
            595                 600                 605

Ser Asn Thr Thr Glu Glu Leu Cys Ala Arg Trp Ala Ser Leu Gly Ala
            610                 615                 620

Phe Tyr Thr Phe Tyr Arg Asn His Asn Glu Leu Gly Asp Ile Ser Gln
625                 630                 635                 640

Glu Phe Tyr Arg Trp Pro Thr Val Ala Glu Ser Ala Arg Lys Ala Ile
                645                 650                 655

Asp Ile Arg Tyr Lys Leu Leu Asp Tyr Ile Tyr Thr Ala Leu His Arg
            660                 665                 670

Gln Ser Gln Thr Gly Glu Pro Phe Leu Gln Pro Gln Phe Tyr Leu Tyr
        675                 680                 685

Pro Glu Asp Ser Asn Thr Phe Ala Asn Asp Arg Gln Phe Phe Tyr Gly
690                 695                 700

Asp Ala Leu Leu Val Ser Pro Val Leu Asn Glu Gly Ser Thr Ser Val
705                 710                 715                 720

Asp Ala Tyr Phe Pro Asp Asp Ile Phe Tyr Asp Trp Tyr Thr Gly Ala
            725                 730                 735

Val Val Arg Gly His Gly Glu Asn Ile Thr Leu Ser Asn Ile Asn Ile
                740                 745                 750

Thr His Ile Pro Leu His Ile Arg Gly Gly Asn Ile Ile Pro Val Arg
            755                 760                 765

Thr Ser Ser Gly Met Thr Thr Thr Glu Val Arg Lys Gln Gly Phe Glu
            770                 775                 780

Leu Ile Ile Ala Pro Asp Leu Asp Asp Thr Ala Ser Gly Ser Leu Tyr
785                 790                 795                 800

Leu Asp Asp Gly Asp Ser Leu Asn Pro Ser Ser Val Thr Glu Leu Glu
```

```
                    805                 810                 815
Phe Thr Tyr Ser Lys Gly Glu Leu His Val Lys Gly Thr Phe Gly Gln
            820                 825                 830

Lys Ala Val Pro Lys Val Glu Lys Cys Thr Leu Leu Gly Lys Ser Ala
        835                 840                 845

Arg Thr Phe Lys Gly Phe Ala Leu Asp Ala Pro Val Asn Phe Lys Leu
    850                 855                 860

Lys
865

<210> SEQ ID NO 13
<211> LENGTH: 2502
<212> TYPE: DNA
<213> ORGANISM: Paenibacillus macerans
<220> FEATURE:
<221> NAME/KEY: CDS
<222> LOCATION: (35)..(2176)
<220> FEATURE:
<221> NAME/KEY: sig_peptide
<222> LOCATION: (35)..(115)
<220> FEATURE:
<221> NAME/KEY: mat_peptide
<222> LOCATION: (116)..(2176)

<400> SEQUENCE: 13
gatcggcaga acatttgaga ggagaggtag gaca atg aaa tcg cgg tac aaa cgt       55
                                      Met Lys Ser Arg Tyr Lys Arg
                                             -25 ttg acc tcc ctg gcg ctt tcg ctg agt atg gcg ttg ggg att tca ctg       103
Leu Thr Ser Leu Ala Leu Ser Leu Ser Met Ala Leu Gly Ile Ser Leu
-20                 -15                 -10                 -5 ccc gca tgg gca tca ccc gat acg agc gtg gac aac aag gtc aat ttc       151
Pro Ala Trp Ala Ser Pro Asp Thr Ser Val Asp Asn Lys Val Asn Phe
        -1  1                   5                  10 agt acg gac gtc atc tat cag att gtg acc gac cgc ttc gcg gac ggg       199
Ser Thr Asp Val Ile Tyr Gln Ile Val Thr Asp Arg Phe Ala Asp Gly
        15                  20                  25 gac agg acg aac aat ccg gcg ggg gat gcg ttc agc ggc gac cga tcc       247
Asp Arg Thr Asn Asn Pro Ala Gly Asp Ala Phe Ser Gly Asp Arg Ser
    30                  35                  40 aat ttg aag ctc tat ttc ggg gga gac tgg cag ggg att atc gac aag       295
Asn Leu Lys Leu Tyr Phe Gly Gly Asp Trp Gln Gly Ile Ile Asp Lys
45                  50                  55                  60 att aac gac ggt tat ttg acc ggc atg ggc gtc acc gcc ctc tgg ata       343
Ile Asn Asp Gly Tyr Leu Thr Gly Met Gly Val Thr Ala Leu Trp Ile
                65                  70                  75 tcc caa cct gtg gaa aat atc acc tcc gtc atc aag tat tcc ggc gtt       391
Ser Gln Pro Val Glu Asn Ile Thr Ser Val Ile Lys Tyr Ser Gly Val
            80                  85                  90 aac aat acg tct tat cac ggt tac tgg gcg agg gat ttt aag caa acc       439
Asn Asn Thr Ser Tyr His Gly Tyr Trp Ala Arg Asp Phe Lys Gln Thr
        95                 100                 105 aac gac gct ttc ggg gat ttt gcc gat ttt caa aat ctg att gat acg       487
Asn Asp Ala Phe Gly Asp Phe Ala Asp Phe Gln Asn Leu Ile Asp Thr
    110                 115                 120 ctc acg ctc ata aca tca agg tcg gat cga ctt cgc ccc caa cca cac       535
Leu Thr Leu Ile Thr Ser Arg Ser Asp Arg Leu Arg Pro Gln Pro His
125                 130                 135                 140 gtc tcc ggc cga gca ggg acg aac ccc ggc ttc gcc gag aac ggt gcg       583
Val Ser Gly Arg Ala Gly Thr Asn Pro Gly Phe Ala Glu Asn Gly Ala
                145                 150                 155
```

```
ctg tat gat aac ggt tcg ctg ctc ggc gcc tac agc aat gat acg gcc       631
Leu Tyr Asp Asn Gly Ser Leu Leu Gly Ala Tyr Ser Asn Asp Thr Ala
            160                 165                 170 ggc ctt ttc cat cat aac ggg ggg acc gat ttt tcc acg att gaa gac       679
Gly Leu Phe His His Asn Gly Gly Thr Asp Phe Ser Thr Ile Glu Asp
            175                 180                 185 ggt att tac aag aac ctc tac gac ctg gcg gac atc aac cat aac aac       727
Gly Ile Tyr Lys Asn Leu Tyr Asp Leu Ala Asp Ile Asn His Asn Asn
            190                 195                 200 aac gct atg gac gct tat ttt aaa agc gct atc gac ctt tgg ctc ggc       775
Asn Ala Met Asp Ala Tyr Phe Lys Ser Ala Ile Asp Leu Trp Leu Gly
205             210                 215                 220 atg ggt gtg gac ggg att cgt ttt gac gcg gtg aag cag tat cct ttc       823
Met Gly Val Asp Gly Ile Arg Phe Asp Ala Val Lys Gln Tyr Pro Phe
                225                 230                 235 ggc tgg caa aaa agc ttc gtt tcc tcg att tac ggc ggc gat cat ccg       871
Gly Trp Gln Lys Ser Phe Val Ser Ser Ile Tyr Gly Gly Asp His Pro
                240                 245                 250 gta ttt acg ttc ggg gaa tgg tat ctt ggc gcg gat caa acc gac gga       919
Val Phe Thr Phe Gly Glu Trp Tyr Leu Gly Ala Asp Gln Thr Asp Gly
            255                 260                 265 gac aac att aaa ttc gcc aac gaa agc ggg atg aac ctg ctg gac ttt       967
Asp Asn Ile Lys Phe Ala Asn Glu Ser Gly Met Asn Leu Leu Asp Phe
270             275                 280 gaa tac gcg cag gaa gtg cgc gaa gtg ttc cgg gac aaa acg gaa acg      1015
Glu Tyr Ala Gln Glu Val Arg Glu Val Phe Arg Asp Lys Thr Glu Thr
285             290                 295                 300 atg aag gat ctc tat gag gtg ctg gcc agc acg gag tcg caa tac gac      1063
Met Lys Asp Leu Tyr Glu Val Leu Ala Ser Thr Glu Ser Gln Tyr Asp
                305                 310                 315 tac atc aac aat atg gtg acc ttc atc gac aac cat gat atg gac cgg      1111
Tyr Ile Asn Asn Met Val Thr Phe Ile Asp Asn His Asp Met Asp Arg
            320                 325                 330 ttc cag gtt gcc ggt tcc ggt acg cgg gcg acc gag caa gcg ttg gcg      1159
Phe Gln Val Ala Gly Ser Gly Thr Arg Ala Thr Glu Gln Ala Leu Ala
            335                 340                 345 ctg acg ctg act tcc cgc ggc gtg cca gcc atc tac tac ggc acg gag      1207
Leu Thr Leu Thr Ser Arg Gly Val Pro Ala Ile Tyr Tyr Gly Thr Glu
350             355                 360 cag tac atg acc ggc gat ggc gac ccc aac aac cgg gcg atg atg acc      1255
Gln Tyr Met Thr Gly Asp Gly Asp Pro Asn Asn Arg Ala Met Met Thr
365             370                 375                 380 tcg ttt aat acc ggg acg acg gct tat aaa gtg att cag gca ttg gcg      1303
Ser Phe Asn Thr Gly Thr Thr Ala Tyr Lys Val Ile Gln Ala Leu Ala
                385                 390                 395 ccg ctg cgt aaa tcc aat ccg gcc atc gct tat ggg acg acg aca gag      1351
Pro Leu Arg Lys Ser Asn Pro Ala Ile Ala Tyr Gly Thr Thr Thr Glu
                400                 405                 410 cgc tgg gtt aac aac gat gtg ttg att att gaa cgc aaa ttc ggc agc      1399
Arg Trp Val Asn Asn Asp Val Leu Ile Ile Glu Arg Lys Phe Gly Ser
            415                 420                 425 agc gcc gct ttg gtg gcg att aat cga aac tcg tcc gct gct tat ccg      1447
Ser Ala Ala Leu Val Ala Ile Asn Arg Asn Ser Ser Ala Ala Tyr Pro
            430                 435                 440 att tcg ggt ctg ttg agt tcg ctg ccg gcg ggc act tat tcg gat gta      1495
Ile Ser Gly Leu Leu Ser Ser Leu Pro Ala Gly Thr Tyr Ser Asp Val
445             450                 455                 460 ttg aac gga ctc tta aac ggc aac tcc att acc gtg ggc agc ggc ggc      1543
Leu Asn Gly Leu Leu Asn Gly Asn Ser Ile Thr Val Gly Ser Gly Gly
                465                 470                 475
```

```
gcc gtc acc aac ttt acg ctg gcg gcc ggc ggc acg gcg gta tgg cag      1591
Ala Val Thr Asn Phe Thr Leu Ala Ala Gly Gly Thr Ala Val Trp Gln
            480                 485                 490 tac aca gcg ccg gaa acg tcg ccg gcg atc ggc aat gtg ggt ccc acc      1639
Tyr Thr Ala Pro Glu Thr Ser Pro Ala Ile Gly Asn Val Gly Pro Thr
        495                 500                 505 atg ggc cag ccg ggg aat ata gtg acg att gac ggg cgc ggc ttt ggc      1687
Met Gly Gln Pro Gly Asn Ile Val Thr Ile Asp Gly Arg Gly Phe Gly
    510                 515                 520 ggc acg gcg ggc acg gtt tat ttc ggg acg acg gcg gtg acc ggc tcc      1735
Gly Thr Ala Gly Thr Val Tyr Phe Gly Thr Thr Ala Val Thr Gly Ser
525                 530                 535                 540 ggc atc gta agc tgg gag gac acg cag att aag gcg gtc ata ccg aag      1783
Gly Ile Val Ser Trp Glu Asp Thr Gln Ile Lys Ala Val Ile Pro Lys
                545                 550                 555 gtc gcg gcg ggc aaa acg ggc gta tcg gtc aaa acg tcg tcc ggc acc      1831
Val Ala Ala Gly Lys Thr Gly Val Ser Val Lys Thr Ser Ser Gly Thr
            560                 565                 570 gcc agc aat aca ttc aaa agc ttc aat gta ctg acg ggg gat cag gtc      1879
Ala Ser Asn Thr Phe Lys Ser Phe Asn Val Leu Thr Gly Asp Gln Val
        575                 580                 585 acg gtg cgt ttc ctg gtc aat caa gcc aat acc aat tac gga aca aat      1927
Thr Val Arg Phe Leu Val Asn Gln Ala Asn Thr Asn Tyr Gly Thr Asn
    590                 595                 600 gtt tat ctt gtc ggc aac gcc gcc gag ctc ggc acc tgg gac ccg aac      1975
Val Tyr Leu Val Gly Asn Ala Ala Glu Leu Gly Thr Trp Asp Pro Asn
605                 610                 615                 620 aaa gcg att ggg ccg atg tac aat cag gtg atc gcc aag tac ccg tcc      2023
Lys Ala Ile Gly Pro Met Tyr Asn Gln Val Ile Ala Lys Tyr Pro Ser
                625                 630                 635 tgg tat tac gat gtc agc gtg ccg gcg ggg aca aag ctg gat ttt aaa      2071
Trp Tyr Tyr Asp Val Ser Val Pro Ala Gly Thr Lys Leu Asp Phe Lys
            640                 645                 650 ttt att aaa aag ggc ggt ggt acg gtg act tgg gaa ggc ggg ggc aac      2119
Phe Ile Lys Lys Gly Gly Gly Thr Val Thr Trp Glu Gly Gly Gly Asn
        655                 660                 665 cat acg tac acg acg ccg gcc agc ggc gta ggg acg gtg acg gtg gac      2167
His Thr Tyr Thr Thr Pro Ala Ser Gly Val Gly Thr Val Thr Val Asp
    670                 675                 680 tgg caa aat taagcggcta agcggccggc ctgaacgaga ggcatccggc             2216
Trp Gln Asn
685 aaaaaactgc ggcggccggc agttaaagtc gacgtgcaaa cgtgccgggg aggattgtga   2276 aatacaggtg cgggatccag gagaacaaaa acgatttttt gaggaaagtt ataaattatt   2336 ttccgaacga tatggcaagc aaaatattgc ttatgcaaca gttcataatg atgagcaaac   2396 ccctcacatg catttaggtg ttgtgcctat gcgtgatgga aaatgcaagg aaaaaatgtg   2456 tttaatcgtc aagactgtta tggctacagt aatcccgagc atatga                 2502

<210> SEQ ID NO 14
<211> LENGTH: 714
<212> TYPE: PRT
<213> ORGANISM: Paenibacillus macerans

<400> SEQUENCE: 14

Met Lys Ser Arg Tyr Lys Arg Leu Thr Ser Leu Ala Leu Ser Leu Ser
        -25                 -20                 -15

Met Ala Leu Gly Ile Ser Leu Pro Ala Trp Ala Ser Pro Asp Thr Ser
```

-continued

```
                -10             -5              -1  1           5
Val Asp Asn Lys Val Asn Phe Ser Thr Asp Val Ile Tyr Gln Ile Val
                10              15              20

Thr Asp Arg Phe Ala Asp Gly Asp Arg Thr Asn Asn Pro Ala Gly Asp
                25              30              35

Ala Phe Ser Gly Asp Arg Ser Asn Leu Lys Leu Tyr Phe Gly Gly Asp
                40              45              50

Trp Gln Gly Ile Ile Asp Lys Ile Asn Asp Gly Tyr Leu Thr Gly Met
55              60              65

Gly Val Thr Ala Leu Trp Ile Ser Gln Pro Val Glu Asn Ile Thr Ser
70              75              80              85

Val Ile Lys Tyr Ser Gly Val Asn Asn Thr Ser Tyr His Gly Tyr Trp
                90              95              100

Ala Arg Asp Phe Lys Gln Thr Asn Asp Ala Phe Gly Asp Phe Ala Asp
                105             110             115

Phe Gln Asn Leu Ile Asp Thr Leu Thr Leu Ile Thr Ser Arg Ser Asp
                120             125             130

Arg Leu Arg Pro Gln Pro His Val Ser Gly Arg Ala Gly Thr Asn Pro
                135             140             145

Gly Phe Ala Glu Asn Gly Ala Leu Tyr Asp Asn Gly Ser Leu Leu Gly
150             155             160             165

Ala Tyr Ser Asn Asp Thr Ala Gly Leu Phe His His Asn Gly Gly Thr
                170             175             180

Asp Phe Ser Thr Ile Glu Asp Gly Ile Tyr Lys Asn Leu Tyr Asp Leu
                185             190             195

Ala Asp Ile Asn His Asn Asn Asn Ala Met Asp Ala Tyr Phe Lys Ser
                200             205             210

Ala Ile Asp Leu Trp Leu Gly Met Gly Val Asp Gly Ile Arg Phe Asp
                215             220             225

Ala Val Lys Gln Tyr Pro Phe Gly Trp Gln Lys Ser Phe Val Ser Ser
230             235             240             245

Ile Tyr Gly Gly Asp His Pro Val Phe Thr Phe Gly Glu Trp Tyr Leu
                250             255             260

Gly Ala Asp Gln Thr Asp Gly Asp Asn Ile Lys Phe Ala Asn Glu Ser
                265             270             275

Gly Met Asn Leu Leu Asp Phe Glu Tyr Ala Gln Glu Val Arg Glu Val
                280             285             290

Phe Arg Asp Lys Thr Glu Thr Met Lys Asp Leu Tyr Glu Val Leu Ala
                295             300             305

Ser Thr Glu Ser Gln Tyr Asp Tyr Ile Asn Asn Met Val Thr Phe Ile
310             315             320             325

Asp Asn His Asp Met Asp Arg Phe Gln Val Ala Gly Ser Gly Thr Arg
                330             335             340

Ala Thr Glu Gln Ala Leu Ala Leu Thr Leu Thr Ser Arg Gly Val Pro
                345             350             355

Ala Ile Tyr Tyr Gly Thr Glu Gln Tyr Met Thr Gly Asp Gly Asp Pro
                360             365             370

Asn Asn Arg Ala Met Met Thr Ser Phe Asn Thr Gly Thr Thr Ala Tyr
                375             380             385

Lys Val Ile Gln Ala Leu Ala Pro Leu Arg Lys Ser Asn Pro Ala Ile
390             395             400             405

Ala Tyr Gly Thr Thr Thr Glu Arg Trp Val Asn Asn Asp Val Leu Ile
                410             415             420
```

-continued

```
Ile Glu Arg Lys Phe Gly Ser Ser Ala Ala Leu Val Ala Ile Asn Arg
            425                 430                 435

Asn Ser Ser Ala Ala Tyr Pro Ile Ser Gly Leu Leu Ser Ser Leu Pro
        440                 445                 450

Ala Gly Thr Tyr Ser Asp Val Leu Asn Gly Leu Leu Asn Gly Asn Ser
        455                 460                 465

Ile Thr Val Gly Ser Gly Gly Ala Val Thr Asn Phe Thr Leu Ala Ala
470                 475                 480                 485

Gly Gly Thr Ala Val Trp Gln Tyr Thr Ala Pro Glu Thr Ser Pro Ala
                490                 495                 500

Ile Gly Asn Val Gly Pro Thr Met Gly Gln Pro Gly Asn Ile Val Thr
                505                 510                 515

Ile Asp Gly Arg Gly Phe Gly Gly Thr Ala Gly Thr Val Tyr Phe Gly
            520                 525                 530

Thr Thr Ala Val Thr Gly Ser Gly Ile Val Ser Trp Glu Asp Thr Gln
        535                 540                 545

Ile Lys Ala Val Ile Pro Lys Val Ala Ala Gly Lys Thr Gly Val Ser
550                 555                 560                 565

Val Lys Thr Ser Ser Gly Thr Ala Ser Asn Thr Phe Lys Ser Phe Asn
                570                 575                 580

Val Leu Thr Gly Asp Gln Val Thr Val Arg Phe Leu Val Asn Gln Ala
            585                 590                 595

Asn Thr Asn Tyr Gly Thr Asn Val Tyr Leu Val Gly Asn Ala Ala Glu
        600                 605                 610

Leu Gly Thr Trp Asp Pro Asn Lys Ala Ile Gly Pro Met Tyr Asn Gln
        615                 620                 625

Val Ile Ala Lys Tyr Pro Ser Trp Tyr Asp Val Ser Val Pro Ala
630                 635                 640                 645

Gly Thr Lys Leu Asp Phe Lys Phe Ile Lys Lys Gly Gly Gly Thr Val
            650                 655                 660

Thr Trp Glu Gly Gly Gly Asn His Thr Tyr Thr Thr Pro Ala Ser Gly
                665                 670                 675

Val Gly Thr Val Thr Val Asp Trp Gln Asn
            680                 685
```